US009180197B2

(12) United States Patent
Dadey

(10) Patent No.: US 9,180,197 B2
(45) Date of Patent: *Nov. 10, 2015

(54) SUSTAINED DELIVERY FORMULATIONS OF RISPERIDONE COMPOUNDS

(71) Applicant: Indivior UK Limited, Slough (GB)

(72) Inventor: Eric Dadey, Furlong, PA (US)

(73) Assignee: Indivior UK Limited, Slough (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/490,034

(22) Filed: Sep. 18, 2014

(65) Prior Publication Data

US 2015/0099767 A1    Apr. 9, 2015

Related U.S. Application Data

(63) Continuation of application No. 12/602,058, filed as application No. PCT/US2008/001928 on Feb. 13, 2008.

(60) Provisional application No. 60/940,340, filed on May 25, 2007.

(51) Int. Cl.
| | |
|---|---|
| *A61K 47/34* | (2006.01) |
| *A61K 9/00* | (2006.01) |
| *A61K 31/519* | (2006.01) |
| *A61K 47/22* | (2006.01) |
| *A61K 47/32* | (2006.01) |

(52) U.S. Cl.
CPC .............. *A61K 47/34* (2013.01); *A61K 9/0024* (2013.01); *A61K 31/519* (2013.01); *A61K 47/22* (2013.01); *A61K 47/32* (2013.01)

(58) Field of Classification Search
CPC ... A61K 47/34; A61K 9/0024; A61K 31/519; A61K 47/22; A61K 47/32
USPC ............................ 514/259.41; 424/400, 422
See application file for complete search history.

(56) References Cited

U.S. PATENT DOCUMENTS

| | | | |
|---|---|---|---|
| 4,804,663 | A | 2/1989 | Kennis et al. |
| 4,938,763 | A | 7/1990 | Dunn et al. |
| 5,278,201 | A | 1/1994 | Dunn et al. |
| 5,324,519 | A | 6/1994 | Dunn et al. |
| 5,453,425 | A | 9/1995 | Francois et al. |
| 5,616,587 | A | 4/1997 | Francois et al. |
| 5,648,093 | A | 7/1997 | Gole et al. |
| 5,688,801 | A | 11/1997 | Mesens et al. |
| 5,702,716 | A | 12/1997 | Dunn et al. |
| 5,744,153 | A | 4/1998 | Yewey et al. |
| 5,770,231 | A | 6/1998 | Mesens et al. |
| 5,792,477 | A | 8/1998 | Rickey |
| 5,916,598 | A | 6/1999 | Rickey et al. |
| 5,945,115 | A | 8/1999 | Dunn et al. |
| 5,965,168 | A | 10/1999 | Mesens et al. |
| 5,990,194 | A | 11/1999 | Dunn et al. |
| 6,110,503 | A | 8/2000 | Ri-Key et al. |
| 6,110,921 | A | 8/2000 | Mesens et al. |
| 6,143,314 | A | 11/2000 | Chandrashekar et al. |
| 6,194,006 | B1 | 2/2001 | Lyon |
| 6,224,905 | B1 | 5/2001 | Lawrence et al. |
| 6,261,583 | B1 | 7/2001 | Dunn et al. |
| 6,264,987 | B1 | 7/2001 | Wright et al. |
| 6,368,632 | B1 | 4/2002 | Mesens et al. |
| 6,379,703 | B1 | 4/2002 | Lyons et al. |
| 6,379,704 | B2 | 4/2002 | Wright et al. |
| 6,403,114 | B1 | 6/2002 | Rickey et al. |
| 6,461,631 | B1 | 10/2002 | Dunn et al. |
| 6,528,080 | B2 | 3/2003 | Dunn et al. |
| 6,534,092 | B2 | 3/2003 | Wright et al. |
| 6,565,874 | B1 | 5/2003 | Dunn et al. |
| 6,596,316 | B2 | 7/2003 | Lyons et al. |
| 6,630,155 | B1 | 10/2003 | Chandrashekar et al. |
| RE39,181 | E | 7/2006 | Francois et al. |
| 8,221,778 | B2 | 7/2012 | Siegel et al. |
| 8,329,203 | B2 | 12/2012 | Siegel et al. |
| 8,486,455 | B2 | 7/2013 | Dunn et al. |
| 8,802,127 | B2 | 8/2014 | Siegel et al. |
| 2003/0004100 | A1 | 1/2003 | Dasch et al. |
| 2005/0032781 | A1 | 2/2005 | Ehrich |
| 2006/0002979 | A1* | 1/2006 | Ashammakhi et al. ....... 424/426 |
| 2007/0077304 | A1 | 4/2007 | Luk et al. |
| 2010/0266655 | A1 | 10/2010 | Dadey |
| 2010/0292195 | A1 | 11/2010 | Dadey et al. |

FOREIGN PATENT DOCUMENTS

| | | |
|---|---|---|
| EP | 0537559 A1 | 4/1993 |
| JP | 5286850 A | 11/1993 |

(Continued)

OTHER PUBLICATIONS

Anonymous, "Form 10-K QLT Inc.", Internet Article, [online]. [retrieved May 14, 2009]. Retrieved from the Internet: <IJRL: http://www.gltinc.com/QLTincl_downloadslinvestment/10K-2006.pdf>, (Mar. 1, 2007), 71 pgs.

(Continued)

*Primary Examiner* — Blessing M Fubara

(74) *Attorney, Agent, or Firm* — Mintz Levin Cohn Ferris Glovsky and Popeo, P.C.

(57) ABSTRACT

The present invention relates to a risperidone sustained release delivery system for treatment of medical conditions relating delusional psychosis, schizophrenia, bipolar disorder, psychotic depression, obsessive-compulsion disorder, Tourette syndrome, and autistic spectrum disorders. The sustained release delivery system includes a flowable composition containing risperidone, a metabolite, or a prodrug thereof and an implant containing risperidone, a metabolite, or a prodrug thereof. The flowable composition may be injected into tissue whereupon it coagulates to become the solid or gel, monolithic implant. The flowable composition includes a biodegradable, thermoplastic polymer, an organic liquid, and risperidone, a metabolite, or a prodrug thereof.

7 Claims, 28 Drawing Sheets

(56) References Cited

FOREIGN PATENT DOCUMENTS

| JP | 9511741 A | 11/1997 |
|---|---|---|
| JP | 2002528403 A | 9/2002 |
| JP | 2002537221 A | 11/2002 |
| JP | 2004510807 A | 4/2008 |
| JP | 2009510116 A | 3/2009 |
| JP | 2010506965 A | 3/2010 |
| JP | 2010519218 A | 6/2010 |
| JP | 2003514006 A | 4/2013 |
| WO | WO-95/27481 A1 | 10/1995 |
| WO | WO-00/06117 A1 | 2/2000 |
| WO | WO-00/24374 A1 | 5/2000 |
| WO | WO-01/35929 A2 | 5/2001 |
| WO | WO-02/30393 A2 | 4/2002 |
| WO | WO-2007/041410 A2 | 4/2007 |
| WO | WO 2007/041410 A2 * | 4/2007 |
| WO | WO-2008/045516 A1 | 4/2008 |
| WO | WO-2008/100532 A1 | 8/2008 |
| WO | WO-2008/153611 A2 | 12/2008 |

OTHER PUBLICATIONS

Anonymous, "U.S Securities and Exchange Commission", QLT Inc., 10-K Title Page, [online]. [retrieved May 14, 2009]. Retrieved from the Internet: <URL: http://www.sec.gov/Archivesledgaridata1827809/000094523407000108/0000945234-07-000108-ndex.idea.htm>, (Mar. 1, 2007), 1 pg.

"U.S. Appl. No. 14/490,082, Non Final Office Action mailed Oct. 10, 2014", 12 pgs.

"Application Serial No. MX/a/2009/012781, Voluntary Amendment filed", 11 pgs.

"Australian Application Serial No. 2008262545, Examiner Report mailed Oct. 15, 2012", 5 pgs.

"Australian Application Serial No. 2008262545, Response filed May 27, 2013 to Examiner Report mailed Oct. 15, 2012", 26 pgs.

"Australian Application Serial No. 2008262545, Response filed Nov. 13, 2013 to Examiner Report mailed Jun. 19, 2013", 21 pgs.

"Australian Application Serial No. 2008262545, Examiner Report mailed Jun. 19, 2013", 5 pgs.

"Canadian Application Serial No. 2,687,979, Office Action mailed May 7, 2014", 4 pgs.

"Chinese Application Serial No. 200880100394.0, Office Action mailed Jul. 25, 2012", 25 pgs.

"Chinese Application Serial No. 200880100394.0, Response filed Oct. 9, 2012 to Office Action mailed Jul. 25, 2012", CN Response Only, 12 pgs.

"Chinese Application Serial No. 200880100394.0, Office Action mailed Apr. 2, 2013", 10 pgs.

"Chinese Application Serial No. 200880100394.0, Response filed Mar. 9, 2012 to Office Action mailed Oct. 25, 2011", 16 pgs.

"Chinese Application Serial No. 200880100394.0, Response filed Jun. 17, 2013 to Office Action mailed Apr. 2, 2013", (w/ English Translation of Amended Claims), 19 pgs.

"Chinese Application Serial No. 200880100394.0, Decision on Rejection mailed Sep. 3, 2013", (w/ English Translation), 11 pgs.

"Chinese Application Serial No. 200880100394.0, Request for Reexamination filed Dec. 18, 2013 in response to Decision on Rejection mailed Sep. 3, 2013", (w/ English Translation), 11 pgs.

"European Application Serial No. 08725543.6, Communication Noting Loss of Rights pursuant to Rule 112(1) CPC mailed Nov. 17, 2010", 2 pgs.

"European Application Serial No. 08725543.6, Office Action mailed Mar. 31, 2010", 5 pgs.

"European Application Serial No. 08725543.6, Response filed Jan. 17, 2011 to Noting Loss of Rights mailed Nov. 17, 2010 and Office Action mailed Mar. 31, 2010", 16 pgs.

"European Application Serial No. 08725543.6, Office Action mailed Feb. 6, 2013", 10 pgs.

European Application Serial No. 08725543.6, Summons to Attend Oral Proceedings mailed Jun. 13, 2014, 7 pgs.

"European Application Serial No. 08725543.6, Response filed Jul. 11, 2013 to Office Action mailed Feb. 6, 2013", 20 pgs.

"Gel: From Wikipedia, the free encyclopedia", [online]. [retrieved on Jul. 23, 2013]. Retrieved from the Internet: <URL: http://en.wikipedia.org/wiki/Gel>, (2013), 5 pgs.

"International Application Serial No. PCTIUS2008/001928, International Preliminary Report on Patentability mailed Dec. 10, 2009", 11 pgs.

"International Application Serial No. PCT/US2008/001928, International Search Report Jun. 10, 2009" 4 pgs. International Application Serial No. PCT/US2008/001928, Written Opinion mailed Jun. 10, 2009,10 pgs.

"Japanese Application Serial No. 2010-509326, Office Action mailed Jan. 22, 2013", 10 pgs.

"Japanese Application Serial No. 2010-509326, Response filed Apr. 18, 2013 to Office Action mailed Jan. 22, 2013", 21 pgs.

"Japanese Application Serial No. 2010-509326, Office Action mailed May 14, 2013", (w/ English Translation), 4 pgs.

"Mexican Application Serial No. MX/a/2009/012781, Response filed Feb. 28, 2013 to Office Action mailed Nov. 21, 2012", 15 pgs.

"Mexican Application Serial No. MX/a/2009/012781, Office Action mailed Nov. 21, 2012".

"Mexican Application Serial No. MX/a/2009/012781, Office Action mailed Mar. 5, 2014", 4 pgs.

"Mexican Application Serial No. MX/a/2009/012781, Office Action mailed Jun. 24, 2013". (w/ English Summary), 7 pgs.

"Mexican Application Serial No. MX/a/2009/012781, Response filed Nov. 4, 2013 to Office Action mailed Jun. 24, 2013",17 pgs.

New Zealand Application Serial No. 581862, First Examiner Report mailed Oct. 19, 2010, 3 pgs.

"New Zealand Application Serial No. 581862, Office Action mailed Feb. 9, 2012", 2 pgs.

"New Zealand Application Serial No. 581862, Response filed May 10, 2012 to Office Action mailed Feb. 9, 2012", 12 pgs.

New Zealand Application Serial No. 581862, Response filed May 10, 2012 to Office Action mailed Feb. 9, 2012, 12 pages.

"New Zealand Application Serial No. 597621, Response filed Apr. 30, 2013 to Examiner Report mailed Jan. 20, 2012", 11 pgs.

New Zealand Application Serial No. 611649, Response filed Jan. 16, 2014 to First Examination Report mailed Jun. 11, 2013, 4 pgs.

"New Zealand Application Serial No. 611649, Response filed Mar. 21, 2014 to Subsequent Examiners Report mailed Feb. 5, 2014", 2 pgs.

"New Zealand Application Serial No. 611649, Subsequent Examiners Report mailed Feb. 5, 2014", 2 pgs.

"New Zealand Application Serial No. 611649, Third Examination Report mailed Apr. 7, 2014", 1 pg.

"New Zealand Application Serial No. 597621, Examiner Report mailed May 16, 2013", 2 pgs.

"New Zealand Application Serial No. 597621, Response filed Jun. 7, 2013 to Examiner Report mailed May 16, 2013", 7 pgs.

"New Zealand Application Serial No. 581862, Response filed Jan. 18, 2012 to Office Action mailed Oct. 19, 2010", 30 pgs.

"New Zealand Application Serial No. 597621, Examiner Report mailed Jan. 20, 2012", 3 pgs.

Packhaeuser, C. B, et al., "In situ forming parenteral drug delivery systems: an overview", Eur J Pharm Biopharm., 58(2), (Sep. 2004), 445-55.

"New Zealand Application Serial No. 611649, First Examination Report mailed Jun. 11, 2013", 3 pgs.

Stroup, T. S, et al., "Effectiveness of Olanzapine, Quetiapine, Risperidone, and Ziprasidone in Patients With Chronic Schizophrenia Following Discontinuation of a Previous Atypical Antipsychotic," Am J Psychiatry, 163(4), Apr. 2006, 611-22.

Tserki et al. ("Biodegradable aliphatic polyesters. Part II. Synthesis and characterization of chain extended poly(butylene succinate-co-butylene adipate" in Polymer Degradation and Stability 91 (2006) 377-384).

Xia et al. ("Uniform biodegradable microparticle systems for controlled release" in J. Controlled Release Jul. 18, 2002; (82(1): 137-147).

(56) References Cited

OTHER PUBLICATIONS

"Form 10-K QLT Inc.", <URL:http://www.oltinc.com/QLTincidownloads/investment110k-2006.pdf>, (2006), 137 pgs.

QLT Inc./BC, "Form 10-K—Annual Report pursuant to Section 13 and 15(d)", (filed on Mar. 1 2007), 436 pgs.

"Form 10-K QLT Inc.", <URL:http://www.oltinc.com/QLTincidownloads/investment 10k-2006.pdf>, (2006), 137 pages.

* cited by examiner

SUSTAINED DELIVERY FORMULATIONS OF RISPERIDONE COMPOUNDS

RELATED APPLICATIONS

This application is a continuation of U.S. patent application Ser. No. 12/602,058, filed Jun. 30, 2010, which is a U.S. National-Stage entry under 35 U.S.C. §371 based on International Application No. PCT/US2008/001928, filed 13 Feb. 2008, and published in English as WO 2008/153611 A2 on 18 Dec. 2008, which designates the United States of America, and claims priority under 35 U.S.C. §119(e) to U.S. Application Ser. No. 60/940,340, filed May 25, 2007, each of which is incorporated herein by reference in its entirety.

FIELD OF THE INVENTION

This disclosure relates to a risperidone sustained release delivery system for treatment of diseases ameliorated by risperidone compounds. The sustained release delivery system includes a flowable composition containing risperidone, a metabolite, or a prodrug thereof and an implant containing risperidone, a metabolite, or a prodrug thereof.

BACKGROUND OF THE INVENTION

Risperidone (also known as 4-[2-[4-(6-fluorobenzo[d]isoxazol-3-yl)-1-piperidyl]ethyl]-3-methyl-2,6-diazabicyclo[4.4.0]deca-1,3-dien-5-one and marketed under the trade name RISPERDAL®) is an atypical antipsychotic medication. The chemical structure of risperidone is shown in formula (1).

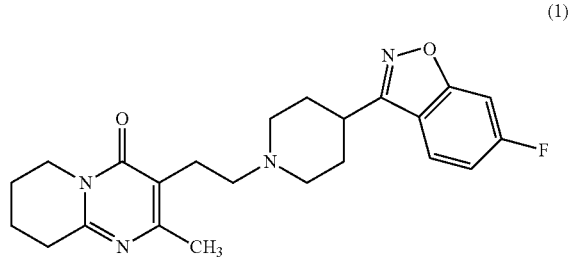 [SMILES: Cc1nc2n(c(=O)c1CCN1CCC(c3noc4cc(F)ccc34)CC1)CCCC2]

(1)

Risperidone is most often used to treat delusional psychosis (including schizophrenia), but risperidone is also used to treat some forms of bipolar disorder, psychotic depression, obsessive-compulsion disorder, and Tourette syndrome. Risperidone is also used in low doses for treating autistic spectrum disorders. Risperidone's therapeutic activity in schizophrenia is believed to be mediated through a combination of dopamine Type 2 ($D_2$) and serotonin Type 2 ($5HT_2$) receptor antagonism.

Currently, the commercial sustained-release product of an atypical psychotic is RISPERDAL® CONSTA® marketed by Janssen, L.P. RISPERDAL® CONSTA® is an intramuscular microsphere formulation and is intended to deliver therapeutic levels of risperidone for two weeks. However, due to the inherent lag phase of most microsphere products, the patient is required to supplement the first 21 days of RISPERDAL® CONSTA® treatment with daily doses of risperidone. Approximately three weeks after a single intramuscular injection of RISPERDAL® CONSTA® and concurrent daily doses of oral risperidone, the microspheres release sufficient risperidone in the systemic circulation that the patient can discontinue supplementation with daily doses of the oral therapy.

The primary limitation of liposomes and microspheres used in sustained-release delivery systems is, typically, the limited amount of drug that can be entrapped in the dosage form. The amount of space available to entrap drug is restricted by the structure of the particulate. Further, the size of the injection is limited by the discomfort of the patient.

Other sustained-release delivery systems such as solid, biodegradable rods, or nondegradable reservoirs typically require surgical implantation. Furthermore, for the nondegradable delivery systems, a second surgical procedure is required to remove the empty reservoir.

There is a continuing need to develop products providing increased bioavailability of risperidone. In particular, there is a need to develop sustained release formulations of risperidone that do not suffer from low bioavailability, poor release kinetics, injection site toxicity, relatively large volume injections, and inconveniently short duration of release.

SUMMARY OF THE INVENTION

The present invention is directed to a risperidone sustained release delivery system capable of delivering risperidone, a metabolite, or a prodrug thereof for a duration of about 14 days to about 3 months. The risperidone sustained release delivery system includes a flowable composition and a gel or solid implant for the sustained release of risperidone, a metabolite, or a prodrug thereof. The implant is produced from the flowable composition. The risperidone sustained release delivery system provides in situ 1-month and 3-month release profiles characterized by an exceptionally high bioavailability and minimal risk of permanent tissue damage and typically no risk of muscle necrosis.

Several direct comparisons between the risperidone sustained release delivery system and RISPERDAL® CONSTA® have been conducted. In addition, the sustained release delivery system provides blood levels in the therapeutic range immediately after injection, whereas RISPERDAL® CONSTA® product has exhibited the characteristic lag phase prior to the release of risperidone.

In one embodiment, a risperidone sustained release delivery system is provided. This delivery system includes a flowable composition and a controlled, sustained release implant. The flowable composition includes a biodegradable thermoplastic polymer, a biocompatible, polar, aprotic organic liquid, and risperidone, a metabolite, or a prodrug thereof. The flowable composition may be transformed into the implant by contact with water, body fluid, or other aqueous medium. In one embodiment, the flowable composition is injected into the body whereupon it transforms in situ into the solid or gel implant.

The thermoplastic polymer of the flowable composition and implant is at least substantially insoluble in an aqueous medium or body fluid, or typically completely insoluble in those media. The thermoplastic polymer may be a homopolymer, a copolymer, or a terpolymer of repeating monomeric units linked by such groups as ester groups, anhydride groups, carbonate groups, amide groups, urethane groups, urea groups, ether groups, esteramide groups, acetal groups, ketal groups, orthocarbonate groups, and any other organic functional group that can be hydrolyzed by enzymatic or hydrolytic reaction (i.e., is biodegradable by this hydrolytic action). The thermoplastic polymer may be a polyester that may be composed of units of about one or more hydroxycarboxylic acid residues, or diol and dicarboxylic acid residues, wherein the distribution of differing residues may be random, block, paired, or sequential. The polyester may be a combination of about one or more diols and about one or more dicarboxylic acids. The hydroxy carboxylic acid or acids may also be in the form of dimers.

When the biodegradable thermoplastic polymer is a polyester, the polyesters include, for example, a polylactide, a polyglycolide, a polycaprolactone, a copolymer thereof, a terpolymer thereof, or any combination thereof, optionally incorporating a third mono-alcohol or polyol component. More preferably, the biodegradable thermoplastic polyester is a polylactide, a polyglycolide, a copolymer thereof, a terpolymer thereof, or a combination thereof, optionally incorporating a third mono-alcohol or polyol component. More preferably, the suitable biodegradable thermoplastic polyester is about 50/50 poly(lactide-co-glycolide) (hereinafter PLG) having a carboxy terminal group or is a 75/25 or a 85/15 PLG with a carboxy terminal group or such a PLG formulated with about one or more mono-alcohol or polyol units. When a mono-alcohol or polyol is incorporated into the polyester, the mono-alcohol or polyol constitutes a third covalent component of the polymer chain. When a mono-alcohol is incorporated, the carboxy terminus of the polyester is esterified with the mono-alcohol. When a polyol is incorporated, it chain extends and optionally branches the polyester. The polyol functions as a polyester polymerization point with the polyester chains extending from multiple hydroxyl moieties of the polyol, and those hydroxyl moieties are esterified by a carboxyl group of the polyester chain. For an embodiment employing a diol, the polyester is linear with polyester chains extending from both esterified hydroxy groups. For an embodiment employing a triol or higher polyol, the polyester may be linear or may be branched with polyester chains extending from the esterified hydroxy groups. Suitable polyols include, for example, aliphatic and aromatic diols, saccharides such as glucose, lactose, maltose, sorbitol, triols such as glycerol, fatty alcohols, and the like, tetraols, pentaols, hexaols, and the like.

The biodegradable thermoplastic polymer can be present in any suitable amount, provided the biodegradable thermoplastic polymer is at least substantially insoluble in aqueous medium or body fluid. The biodegradable thermoplastic polymer is present in about 10 wt. % to about 95 wt. % of the flowable composition, preferably present in about 20 wt. % to about 70 wt. % of the flowable composition or more preferably is present in about 30 wt. % to about 60 wt. % of the flowable composition. Preferably, the biodegradable thermoplastic polymer has an average molecular weight of about 10,000 Daltons (Da) to about 45,000 Daltons, or more preferably about 15,000 Daltons to about 40,000 Daltons.

The biodegradable thermoplastic polymer may also be a non-hydrolyzed PLG low-burst copolymer polyester material having a weight average molecular weight of about 10 kilodaltons (kDa) to about 50 kilodaltons, a polydispersity index of about 1.4 to about 2.0, and from which a copolymer fraction characterized by a weight average molecular weight of about 4 kDa to about 10 kDa and a polydispersity index of about 1.4 to about 2.5 has been removed.

The flowable composition also includes a biocompatible, polar aprotic organic liquid. The biocompatible polar aprotic liquid can be an amide, an ester, a carbonate, a ketone, an ether, a sulfonyl, or any other organic compound that is liquid at ambient temperature, is polar and is aprotic. The biocompatible polar aprotic organic liquid may be very slightly soluble to completely soluble in all proportions in body fluid. While the organic liquid generally should have similar solubility profiles in aqueous medium and body fluid, body fluid is typically more lipophilic than aqueous medium. Consequently, some organic liquids that are insoluble in aqueous medium should be at least slightly soluble in body fluid. These examples of organic liquid are included within the definition of organic liquids.

Preferably, the biocompatible polar aprotic liquid comprises N-methyl-2-pyrrolidone, 2-pyrrolidone, N,N-dimethylformamide, dimethyl sulfoxide, propylene carbonate, caprolactam, triacetin, or any combination thereof. More preferably, the biocompatible polar aprotic liquid is N-methyl-2-pyrrolidone. Preferably, the polar aprotic organic liquid is present in about 10 wt. % to about 90 wt. % of the composition or is present in about 30 wt. % to about 70 wt. % of the composition.

The risperidone, a metabolite, or a prodrug thereof is present in at least about 0.001 wt. % concentration in the flowable composition with the upper limit being the limit of dispersibility of the risperidone, a metabolite, or a prodrug thereof within the flowable composition. Preferably, the concentration is about 0.5 wt. % to about 50 wt. % of the flowable composition or more preferably about 1 wt. % to about 30 wt. % of the flowable composition.

The risperidone, a metabolite, or a prodrug thereof in the flowable composition may be in the form of a salt and the salt gegenion may be derived from a pharmaceutically acceptable organic or inorganic acid, or preferably the gegenion may be a polycarboxylic acid.

Preferably, the flowable composition is formulated as an injectable delivery system. The flowable composition preferably has a volume of about 0.20 mL to about 2.0 mL or preferably about 0.30 mL to about 1.0 mL. The injectable composition is preferably formulated for administration about once per month, about once per three months, or about once per four months, to about once per six months. Preferably, the flowable composition is a liquid or a gel composition, suitable for injection into a patient. The flowable composition may have the property of production of minimal tissue necrosis when injected subcutaneously.

Excipients, release modifiers, plasticizers, pore forming agents, gelation liquids, non-active extenders, and other ingredients may also be included within the risperidone sustained release delivery system. Upon administration of the flowable composition, some of these additional ingredients, such as gelation liquids and release modifiers should remain with the implant, while others, such as pore forming agents should separately disperse and/or diffuse along with the organic liquid.

In one embodiment, a method is provided for forming a flowable composition for use as a controlled release implant. The method includes mixing, in any order, a biodegradable thermoplastic polymer, a biocompatible polar aprotic liquid, and risperidone, a metabolite, or a prodrug thereof. The biodegradable thermoplastic polymer may be at least substantially insoluble in aqueous medium or body fluid. These ingredients, their properties, and preferred amounts are as disclosed above. The mixing is performed for a sufficient period of time effective to form the flowable composition for use as a controlled release implant. Preferably, the biocompatible thermoplastic polymer and the biocompatible polar aprotic organic liquid are mixed together to form a mixture and the mixture is combined with the risperidone, a metabolite, or a prodrug thereof to form the flowable composition. Preferably, the flowable composition is a solution or dispersion, especially preferably a solution, of the risperidone, a metabolite, or a prodrug thereof and biodegradable thermoplastic polymer in the organic liquid. The flowable composition preferably includes an effective amount of a biodegradable thermoplastic polymer, an effective amount of a biocompatible polar aprotic organic liquid, and an effective amount of risperidone, a metabolite, or a prodrug thereof. These ingredients, the preferred ingredients, their properties, and preferred amounts are as disclosed above.

In one embodiment, a biodegradable implant formed in situ, in a patient is provided, by the steps including: injecting a flowable composition including a biodegradable thermoplastic polymer that is at least substantially insoluble in body fluid, a biocompatible polar aprotic organic liquid; and risperidone, a metabolite, or a prodrug thereof into the body of the patient, and allowing the biocompatible polar aprotic liquid to dissipate to produce a solid or gel biodegradable implant. The flowable composition includes an effective amount of the biodegradable thermoplastic polymer, an effective amount of the biocompatible polar aprotic liquid, and an effective amount of risperidone, a metabolite, or a prodrug thereof and the solid implant releases an effective amount of risperidone, a metabolite, or a prodrug thereof over time as the solid implant biodegrades in the patient and optionally the patient is a human.

In one embodiment, a method is provided of forming a biodegradable implant in situ, in a living patient. The method includes injecting the flowable composition including a biodegradable thermoplastic polymer that is at least substantially insoluble in body fluid, a biocompatible polar aprotic organic liquid, and risperidone, a metabolite, or a prodrug thereof within the body of a patient and allowing the biocompatible polar aprotic organic liquid to dissipate to produce a solid or gel biodegradable implant. Preferably, the biodegradable solid or gel implant releases an effective amount of risperidone, a metabolite, or a prodrug thereof by diffusion, erosion, or a combination of diffusion and erosion as the solid or gel implant biodegrades in the patient.

In one embodiment, a method is provided of treating or preventing mammalian diseases that are ameliorated, cured, or prevented by risperidone, a metabolite, or a prodrug thereof. The method includes administering, to a patient (preferably a human patient) in need of such treatment or prevention, an effective amount of a flowable composition including a biodegradable thermoplastic polymer that is at least substantially insoluble in body fluid, a biocompatible polar aprotic organic liquid, and risperidone, a metabolite, or a prodrug thereof.

In one embodiment, a kit is provided. The kit includes a first container and a second container. The first container includes a composition of the biodegradable thermoplastic polymer and the biocompatible polar aprotic organic liquid. The biodegradable thermoplastic polymer may be at least substantially insoluble in aqueous medium or body fluid. The second container includes risperidone, a metabolite, or a prodrug thereof. These ingredients, their properties, and preferred amounts are as disclosed above. Preferably, the first container is a syringe and the second container is a syringe. In addition, the risperidone, a metabolite, or a prodrug thereof may be lyophilized. The kit can preferably include, for example, instructions. Preferably, the first container can be connected to the second container. More preferably, the first container and the second container are each configured to be directly connected to each other.

In one embodiment, a solid or gel implant is provided. The solid or gel implant is composed of at least the biocompatible thermoplastic polymer and risperidone, a metabolite, or a prodrug thereof and is substantially insoluble in body fluid. The biodegradable thermoplastic polymer may be at least substantially insoluble in aqueous medium or body fluid. While risperidone, a metabolite, or a prodrug thereof itself has at least some solubility in body fluid, its isolation within the substantially insoluble implant allows for its slow, sustained release into the body.

The solid implant has a solid matrix or a solid microporous matrix while the gel implant has a gelatinous matrix. The matrix can be a core surrounded by a skin. The implant may be solid and microporous. When microporous, the core preferably contains pores of diameters from about 1 to about 1000 microns. When microporous, the skin preferably contains pores of smaller diameters than those of the core pores. In addition, the skin pores are preferably of a size such that the skin is functionally non-porous in comparison with the core.

The solid or gel implant can optionally include, for example, one or more biocompatible organic substances which may function as an excipient as described above, or which may function as a plasticizer, a sustained release profile modifier, emulsifier, and/or isolation carrier for risperidone, a metabolite, or a prodrug thereof.

The biocompatible organic liquid may also serve as an organic substance of the implant and/or may provide an additional function such as a plasticizer, a modifier, an emulsifier, or an isolation carrier. There may be two or more organic liquids present in the flowable composition such that the primary organic liquid acts as a mixing, solubilizing, or dispersing agent, and the supplemental organic liquid or liquids provide additional functions within the flowable composition and the implant. Alternatively, there may be one organic liquid which at least may act as a mixing, solubilizing, or dispersing agent for the other components, and may provide additional functions as well. As second or additional components, additional kinds of biodegradable organic liquids typically are combined with the flowable composition and may remain with the implant as the administered flowable composition coagulates.

When serving as a plasticizer, the biocompatible organic substance provides such properties as flexibility, softness, moldability, and drug release variation to the implant. When serving as a modifier, the biocompatible organic substance also provides the property of risperidone release variation to the implant. Typically, the plasticizer increases the rate of risperidone, a metabolite, or a prodrug thereof release while the modifier slows the rate of risperidone, a metabolite, or a prodrug thereof release. Also, there can be structural overlap between these two kinds of organic substances functioning as plasticizers and rate modifiers.

When serving as an emulsifier, the biocompatible organic substance at least in part enables a uniform mixture of the risperidone, a metabolite, or a prodrug thereof within the flowable composition and within the implant.

When serving as an isolation carrier, the biocompatible organic substance should function to encapsulate, isolate, or otherwise surround molecules or nanoparticles of the risperidone, a metabolite, or a prodrug thereof so as to prevent its burst at least in part, and to isolate the risperidone, a metabolite, or a prodrug thereof from degradation by other components of the flowable composition and implant.

The amount of biocompatible organic substance optionally remaining in the solid or gel implant is preferably minor, such as from about 0 wt. % (or an almost negligible amount) to about 20 wt. % of the composition. In addition, the amount of biocompatible organic substance optionally present in the solid or gel implant preferably decreases over time.

The solid implant may also include, for example, a biocompatible organic liquid that is very slightly soluble to completely soluble in all proportions in body fluid and at least partially dissolves at least a portion of the thermoplastic polyester, and optionally the amount of biocompatible organic liquid is less than about 5 wt. % of the total weight of the implant, and optionally the amount of biocompatible organic liquid decreases over time.

The solid implant may also include, for example, a core that contains pores of diameters from about 1 to about 1000 microns, and optionally the skin contains pores of smaller diameters than those of the core pores, and optionally the skin pores are of a size such that the skin is functionally non-porous in comparison with the core.

In one embodiment, a flowable composition having a substantially linear cumulative release profile is provided.

In one embodiment, a method is provided for treatment of a patient having a medical condition including administering to the patient an effective amount of risperidone, a metabolite, or a prodrug thereof in combination with an at least substantially water-insoluble biodegradable thermoplastic polymer and a biocompatible, polar, aprotic organic liquid, wherein the mental condition comprises delusional psychosis, schizophrenia, bipolar disorder, psychotic depression, obsessive-compulsion disorder, Tourette syndrome, autistic spectrum disorders, or any combination thereof. This method of treatment may include, for example, combination therapy with another known pharmaceutical compound designated for treatment of the malcondition.

In one embodiment, a method is provided for treating a patient having a medical condition comprising administering to the patient a flowable composition to provide a biodegradable implant comprising risperidone, a metabolite, or a prodrug thereof and a biodegradable polymer, wherein the implant releases delivers therapeutically effective dosage from about 1 to about 16 milligrams (mg) of risperidone, a metabolite, or a prodrug thereof per day, or preferably from about 1 to about 5 milligrams (mg) of risperidone, a metabolite, or a prodrug thereof per day.

The therapeutically effective dosage of risperidone, a metabolite, or a prodrug thereof may be achieved within about two days after administration of the implant, or preferably, within about one day after administration of the implant.

The therapeutically effective dosage of risperidone, a metabolite, or a prodrug thereof may be delivered for at least about 15 days after administration of the implant, or preferably for at least about 30 days after administration of the implant, or preferably for at least about 45 days after administration of the implant, or preferably for at least about 60 days after administration of the implant.

The medical condition may include, for example, delusional psychosis, schizophrenia, bipolar disorder, psychotic depression, obsessive-compulsion disorder, Tourette syndrome, and autistic spectrum disorders. The individual may be a human.

DEFINITIONS

Figure 1:
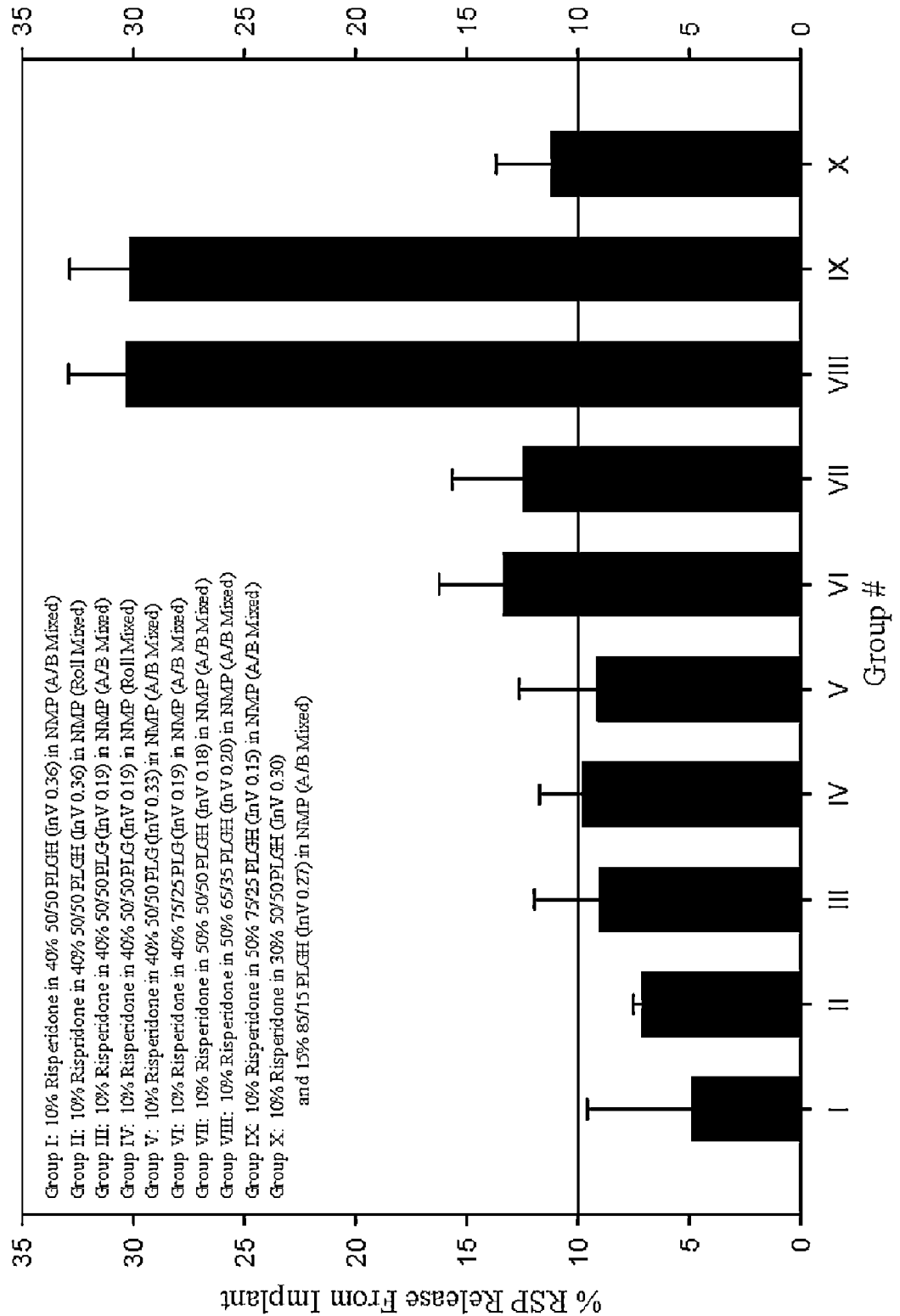
FIG. 1 illustrates the 24-hour release of risperidone from selected ATRIGEL® formulations in rats.

The words and phrases presented in this patent application have their ordinary meanings to one of skill in the art unless otherwise indicated. Such ordinary meanings can be obtained by reference to their use in the art and by reference to general and scientific dictionaries such as WEBSTER'S NEW WORLD DICTIONARY, Simon & Schuster, New York, N.Y., 1995, THE AMERICAN HERITAGE DICTIONARY OF THE ENGLISH LANGUAGE, Houghton Mifflin, Boston Mass., 1981, and HAWLEY'S CONDENSED CHEMICAL DICTIONARY, 14$^{th}$ edition, Wiley Europe, 2002.

The following explanations of certain terms are meant to be illustrative rather than exhaustive. These terms have their ordinary meanings given by usage in the art and in addition include the following explanations.

As used herein, the term "and/or" means any one of the items, any combination of the items, or all of the items with which this term is associated.

As used herein, the singular forms "a," "an," and "the" include plural reference unless the context clearly dictates otherwise. Thus, for example, a reference to "a formulation" includes a plurality of such formulations, so that a formulation of compound X includes formulations of compound X.

As used herein, the term "acceptable salts" refer to derivatives wherein the parent compound is modified by making acid or base salts thereof. Suitable acceptable salts include, but are not limited to, mineral or organic acid salts of basic residues such as amines; alkali or organic salts of acidic residues such as carboxylic acids; and the like. The acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Specifically, the acceptable salts can include, for example, those salts that naturally occur in vivo in a mammal.

As used herein, the term "biocompatible" means that the material, substance, compound, molecule, polymer, or system to which it applies should not cause severe toxicity, severe adverse biological reaction, or lethality in an animal to which it is administered at reasonable doses and rates.

As used herein, the term "biodegradable" means that the material, substance, compound, molecule, polymer, or system is cleaved, oxidized, hydrolyzed, or otherwise broken down by hydrolytic, enzymatic, or another mammalian biological process for metabolism to chemical units that can be assimilated or eliminated by the mammalian body.

As used herein, the term "bioerodible" means that the material, substance, compound, molecule, polymer, or system is biodegraded or mechanically removed by a mammalian biological process so that new surface is exposed.

As used herein, the term "therapeutically effective amount" is intended to include an amount of risperidone, a metabolite, or a prodrug thereof, a pharmaceutically acceptable salt thereof, a derivative thereof, or any combination of those useful to treat or prevent the underlying disorder or disease, or to treat the symptoms associated with the underlying disorder or disease in a host. Synergy, as described, for example, by Chou and Talalay, *Adv. Enzyme Regul.* 22, 27-55 (1984), occurs when the effect of risperidone, a metabolite, or a prodrug thereof, a pharmaceutically acceptable salt thereof, or a derivative thereof when administered in combination is greater than the additive effect of the risperidone, a metabolite, or a prodrug thereof, pharmaceutically acceptable salt thereof, or a derivative thereof when administered alone as a single agent. In general, a synergistic effect is most clearly demonstrated at suboptimal concentrations of the risperidone, a metabolite, or a prodrug thereof, a pharmaceutically acceptable salt thereof, or derivative thereof. Synergy can be in terms of lower cytotoxicity, increased activity, or some other beneficial effect of the combination compared with the individual components.

As used herein, the term "flowable" refers to the ability of the "flowable" composition to be transported under pressure into the body of a patient. For example, the flowable composition can have a low viscosity like water, and be injected with the use of a syringe, beneath the skin of a patient. The flowable composition can alternatively have a high viscosity as in a gel and can be placed into a patient through a high pressure transport device such as a high pressure syringe, cannula, needle, and the like. The ability of the composition to be injected into a patient should typically depend upon the viscosity of the composition. The composition should therefore have a suitable viscosity ranging from low like water to high like a gel, such that the composition can be forced through the transport device (e.g., syringe) into the body of a patient.

As used herein, the term "gel" refers to a substance having a gelatinous, jelly-like, or colloidal properties. See, e.g., CONCISE CHEMICAL AND TECHNICAL DICTIONARY, $4^{th}$ Edition, Chemical Publishing Co., Inc., p. 567, New York, N.Y. (1986).

As used herein, the term "liquid" refers to a substance that undergoes continuous deformation under a shearing stress. See, e.g., CONCISE CHEMICAL AND TECHNICAL DICTIONARY, $4^{th}$ Edition, Chemical Publishing Co., Inc., p. 707, New York, N.Y. (1986).

As used herein, the term "patient" refers to a warm-blooded animal, and preferably a mammal, such as, for example, a cat, dog, horse, cow, pig, mouse, rat, or primate, including a human.

As used herein, the term "polymer" refers to a molecule of one or more repeating monomeric residue units covalently bonded together by one or more repeating chemical functional groups. The term includes all polymeric forms such as linear, branched, star, random, block, graft, and the like. It includes homopolymers formed from a single monomer, copolymer formed from two or more monomers, terpolymers formed from three or more polymers, and polymers formed from more than three monomers. Differing forms of a polymer may also have more than one repeating, covalently bonded functional group. The term may also refer to substantially linear polyesters, also referred to herein as "PLG copolymers," predominantly formed of monomeric lactate and glycolate hydroxyacids, or lactide and glycolide dimeric hydroxyacids, and include, for example, compositions referred to in the art as poly(lactate-glycolate), poly(lactate (co)glycolate), poly(lactide-glycolide), poly(lactide (co)glycolide), PLG, PLGH, and the like, with the understanding that additional moieties may be included, such as core/initiator groups (for example, diols, hydroxyacids, and the like), capping groups (for example, esters of terminal carboxyl groups, and the like) and other pendant groups or chain extension groups covalently linked to or within a polyester backbone, including groups that cross-link the substantially linear polyester molecular chains, without departing from the meaning assigned herein. PLG copolymers, as the term is used herein, includes molecular chains with terminal hydroxyl groups, terminal carboxyl groups (i.e., acid-terminated, sometimes termed PLGH) and terminal ester groups (i.e., capped).

As used herein, the term "polyester" refers to polymers containing monomeric repeats, at least in part, of the linking group: —OC(=O)— or —C(=O)O—.

As used herein, the terms "skin" and "core" of a skin and core matrix mean that a cross section of the matrix should present a discernable delineation between an outer surface and the inner portion of the matrix. The outer surface is the skin and the inner portion is the core.

As used herein, the term "thermoplastic" as applied to a polymer means that the polymer repeatedly should melt upon heating and should solidify upon cooling. It signifies that no or a slight degree of cross-linking between polymer molecules is present. It is to be contrasted with the term "thermoset" which indicates that the polymer should set or substantially cross-link upon heating or upon application of a similar reactive process and should no longer undergo melt-solidification cycles upon heating and cooling.

As used herein, the terms "treating," "treat," or "treatment" includes (i) preventing a pathologic condition (e.g., schizophrenia) from occurring (e.g., prophylaxis); (ii) inhibiting the pathologic condition (e.g., schizophrenia) or arresting its development; and (iii) relieving the pathologic condition (e.g., relieving the symptoms associated with schizophrenia).

DESCRIPTION OF THE INVENTION

The present invention is directed to a risperidone sustained release delivery system. The sustained release delivery system includes a flowable composition and a gel or solid implant. The delivery system provides an in situ sustained release of risperidone, a metabolite, or a prodrug thereof. The flowable composition accomplishes the sustained release through its use to produce the implant. The implant has a low implant volume and provides a long term delivery of risperidone, a metabolite, or a prodrug thereof. The flowable composition enables subcutaneous formation of the implant in situ and causes little or no tissue necrosis. The in situ implant exhibits superior results relative to the RISPERDAL® CONSTA® product in that the implant delivers higher and longer lasting blood levels of the risperidone compared with the RISPERDAL® CONSTA® product. The in situ implant provides therapeutic plasma risperidone, a metabolite, or a prodrug thereof levels immediately after injection and maintains steady-state plasma levels from four to six weeks. Further, the in situ implant does not require supplemental daily oral doses of RISPERDAL® for the first twenty-one days, as required with the RISPERDAL® CONSTA® product.

Another advantage is that the in situ implant should provide greater patience compliance. RISPERDAL® CONSTA® is administered as a 2.0 mL intramuscular injection, whereas one embodiment is injected into the subcutaneous space with a volume of injection of about 0.80 mL. It is postulated that patients should prefer a smaller subcutaneous injection (bout 0.80 mL) over a larger (about 2.0 mL) intramuscular injection.

Another advantage of one embodiment includes a simple manufacturing process and delivery system. For example, the risperidone, a metabolite, or a prodrug thereof is filled into a syringe, the syringe is sealed, and the entire drug substance syringe is terminally sterilized by gamma irradiation. The biodegradable polymer used is dissolved in N-methyl-2-pyrrolidinone and filled in a second syringe. The syringe is sealed and the delivery system is terminally sterilized by gamma irradiation. At the time of injection, the syringes are coupled through the luer-lock connection and the product is constituted by cycling the components between the two syringes. In this way, the drug is incorporated into the delivery system and very little is lost to the device.

In contrast, the RISPERDAL® CONSTA® product is made by a microsphere formation and encapsulation process, before being injected into the patient.

The flowable composition is a combination of a biodegradable, at least substantially water-insoluble thermoplastic polymer, a biocompatible polar aprotic organic liquid and risperidone, a metabolite, or a prodrug thereof. The polar, aprotic organic liquid has a solubility in body fluid ranging from practically insoluble to completely soluble in all proportions. Preferably, the thermoplastic polymer is a thermoplastic polyester of about one or more hydroxycarboxylic acids or about one or more diols and dicarboxylic acids. Especially preferably, the thermoplastic polymer is a polyester of about one or more hydroxylcarboxyl dimers such as lactide, glycolide, dicaprolactone, and the like.

The specific and preferred biodegradable thermoplastic polymers and polar aprotic solvents; the concentrations of thermoplastic polymers, polar aprotic organic liquids, and risperidone, a metabolite, or a prodrug thereof; the molecular weights of the thermoplastic polymer; and the weight or mole ranges of components of the solid implant described herein are exemplary. They do not exclude other biodegradable thermoplastic polymers and polar aprotic organic liquids; other concentrations of thermoplastic polymers, polar aprotic liquids, and risperidone, a metabolite, or a prodrug thereof; other molecular weights of the thermoplastic polymer; and other components within the solid implant.

In one embodiment, a flowable composition suitable for use in providing a controlled sustained release implant is provided, a method for forming the flowable composition, a method for using the flowable composition, the biodegradable sustained release solid or gel implant that is formed from the flowable composition, a method of forming the biodegradable implant in situ, a method for treating disease through use of the biodegradable implant and a kit that includes the flowable composition. The flowable composition may preferably be used to provide a biodegradable or bioerodible microporous in situ formed implant in animals.

The flowable composition is composed of a biodegradable thermoplastic polymer in combination with a biocompatible polar aprotic organic liquid and risperidone, a metabolite, or a prodrug thereof. The biodegradable thermoplastic polymer is substantially insoluble in aqueous medium and/or in body fluid, biocompatible, and biodegradable and/or bioerodible within the body of a patient. The flowable composition may be administered as a liquid or gel into tissue and forms an implant in situ. Alternatively, the implant may be formed ex vivo by combining the flowable composition with an aqueous medium. In this embodiment, the preformed implant may be surgically administered to the patient. In either embodiment, the thermoplastic polymer coagulates or solidifies to form the solid or gel implant upon the dissipation, dispersement, or leaching of the organic liquid from the flowable composition when the flowable composition contacts a body fluid, an aqueous medium, or water. The coagulation or solidification entangles and entraps the other components of the flowable composition such as risperidone, a metabolite, or a prodrug thereof excipients, organic substances, and the like, so that they become dispersed within the gelled or solidified implant matrix. The flowable composition is biocompatible and the polymer matrix of the implant does not cause substantial tissue irritation or necrosis at the implant site. The implant delivers a sustained level of risperidone, a metabolite, or a prodrug thereof to the patient. Preferably, the flowable composition can be a liquid or a gel, suitable for injection in a patient (e.g., human).

One embodiment surprisingly improves the bioavailability of a sustained release formulation of risperidone, a metabolite, or a prodrug thereof. In addition, one embodiment provides: (a) relatively low volume injections; (b) improved local tissue tolerance at the injection site; (c) an opportunity to use a subcutaneous injection rather than an intramuscular injection; and (d) less frequent injections compared to other products.

By comparison to formulations derived from other sustained release drug delivery technologies, the risperidone sustained release delivery system should provide: (a) superior release kinetics with minimal burst; (b) increased duration of drug release with less frequent injections; (c) markedly improved bioavailability; (d) improved local tissue tolerance due to a small injection volume, and (e) the ability to use of a subcutaneous injection rather than intramuscular injection. Taken together, these features make a highly beneficial risperidone sustained release delivery system.

Biodegradable Thermoplastic Polymer

The flowable composition is produced by combining a solid, biodegradable thermoplastic polymer, risperidone, a metabolite, or a prodrug thereof and a biocompatible polar aprotic organic liquid. The flowable composition can be administered by a syringe and needle to a patient in need of treatment. Any suitable biodegradable thermoplastic polymer can be employed, provided that the biodegradable thermoplastic polymer is at least substantially insoluble in body fluid.

The biocompatible, biodegradable, thermoplastic polymer can be made from a variety of monomers which form polymer chains or monomeric units joined together by linking groups. The thermoplastic polymer is composed of a polymer chain or backbone containing monomeric units joined by such linking groups as ester, amide, urethane, anhydride, carbonate, urea, esteramide, acetal, ketal, or orthocarbonate groups as well as any other organic functional group that can be hydrolyzed by enzymatic or hydrolytic reaction (i.e., is biodegradable by this hydrolytic action). The thermoplastic polymer is typically formed by reaction of starting monomers containing the reactant groups that should form the backbone linking groups. For example, alcohols and carboxylic acids should form ester linking groups. Isocyanates and amines or alcohols should respectively form urea or urethane linking groups.

Any aliphatic, aromatic, or arylalkyl starting monomer having the specified functional groups can be used to make the thermoplastic polymers, provided that the polymers and their degradation products are biocompatible. The monomer or monomers used in forming the thermoplastic polymer may be of a single or multiple identity. The resultant thermoplastic polymer should be a homopolymer formed from one monomer, or one set of monomers such as when a diol and diacid are used, or a copolymer, terpolymer, or multi-polymer formed from two or more, or three or more, or more than three monomers or sets of monomers. The biocompatibility specifications of such starting monomers are known in the art.

The thermoplastic polymers are substantially insoluble in aqueous media and body fluids, preferably completely insoluble in such media and fluids. They are also capable of dissolving or dispersing in selected organic liquids having a water solubility ranging from completely soluble in all proportions to water insoluble. The thermoplastic polymers also are biocompatible.

When used in the flowable composition, the thermoplastic polymer in combination with the organic liquid provides a viscosity of the flowable composition that varies from low viscosity, similar to that of water, to a high viscosity, similar to that of a paste, depending on the molecular weight and concentration of the thermoplastic polymer. Typically, the polymeric composition includes about 10 wt. % to about 95 wt. %, more preferably about 20 wt. % to about 70 wt. %, most preferably about 30 wt. % to about 60 wt. %, of a thermoplastic polymer.

In one embodiment, the biodegradable, biocompatible thermoplastic polymer can be a linear polymer, it can be a branched polymer, or it can be a combination thereof. Any option is available according to one embodiment. To provide a branched thermoplastic polymer, some fraction of one of the starting monomers may be at least trifunctional, and preferably multifunctional. This multifunctional character provides at least some branching of the resulting polymer chain. For example, when the polymer chosen contains ester linking groups along its polymer backbone, the starting monomers normally should be hydroxycarboxylic acids, cyclic dimers of hydroxycarboxylic acids, cyclic trimers of hydroxycarboxylic acids, diols, or dicarboxylic acids. Thus, to provide a branched thermoplastic polymer, some fraction of a starting monomer that is at least multifunctional, such as a triol or a tricarboxylic acid is included within the combination of monomers being polymerized to form the thermoplastic polymer. In addition, the polymers may incorporate more than one multifunctional unit per polymer molecule, and typically many multifunctional units depending on the stoichiometry of the polymerization reaction. The polymers may also optionally incorporate at least about one multifunctional unit per polymer molecule. A so-called star or branched polymer is formed when about one multifunctional unit is incorporated in a polymer molecule.

The preferred thermoplastic polyester may be formed from such monomers as hydroxycarboxylic acids or dimers thereof. Alternatively, a thermoplastic polyester may be formed from a dicarboxylic acid and a diol. A branching monomer such as a dihydroxycarboxylic acid would be included with the first kind of starting monomer, or a triol and/or a tricarboxylic acid would be included with the second kind of starting monomer if a branched polyester were desired. Similarly, a triol, tetraol, pentaol, or hexaol such as sorbitol or glucose can be included with the first kind of starting monomer if a branched or star polyester were desired. The same rationale would apply to polyamides. A triamine and/or triacid would be included with starting monomers of a diamine and dicarboxylic acid. An amino dicarboxylic acid, diamino carboxylic acid, or a triamine would be included with the second kind of starting monomer, amino acid. Any aliphatic, aromatic, or arylalkyl starting monomer having the specified functional groups can be used to make the branched thermoplastic polymers, provided that the polymers and their degradation products are biocompatible. The biocompatibility specifications of such starting monomers are known in the art.

The monomers used to make the biocompatible thermoplastic polymers should produce polymers or copolymers that are thermoplastic, biocompatible, and biodegradable. Suitable thermoplastic, biocompatible, biodegradable polymers suitable for use as the biocompatible thermoplastic branched polymers include, for example, polyesters, polylactides, polyglycolides, polycaprolactones, polyanhydrides, polyamides, polyurethanes, polyesteramides, polydioxanones, polyacetals, polyketals, polycarbonates, polyorthocarbonates, polyorthoesters, polyphosphoesters, polyphosphazenes, polyhydroxybutyrates, polyhydroxyvalerates, polyalkylene oxalates, polyalkylene succinates, poly(malic acid), poly (amino acids), and copolymers, terpolymers, combinations, or mixtures of the above materials. Suitable examples of such biocompatible, biodegradable, thermoplastic polymers are disclosed, e.g., in U.S. Pat. Nos. 4,938,763, 5,278,201, 5,324, 519, 5,702,716, 5,744,153, 5,990,194, 6,461,631, and 6,565, 874.

The polymer composition can also include, for example, polymer blends of the polymers with other biocompatible polymers, so long as they do not interfere undesirably with the biodegradable characteristics of the composition. Blends of the polymer with such other polymers may offer even greater flexibility in designing the precise release profile desired for targeted drug delivery or the precise rate of biodegradability desired for implants.

The preferred biocompatible thermoplastic polymers or copolymers are those which have a lower degree of crystallization and are more hydrophobic. These polymers and copolymers are more soluble in the biocompatible organic liquids than highly crystalline polymers such as polyglycolide, which has a high degree of hydrogen-bonding. Preferred materials with the desired solubility parameters are polylactides, polycaprolactones, and copolymers of these with glycolide so as to provide more amorphous regions to enhance solubility. Generally, the biocompatible, biodegradable thermoplastic polymer is substantially soluble in the organic liquid so that solutions, dispersions, or mixtures up to about 50-60 wt. % solids can be made. Preferably, the polymers are typically completely soluble in the organic liquid so that solutions, dispersions, or mixtures up to about 85-98 wt. % solids can be made. The polymers also are at least substantially insoluble in water so that less than about 0.1 g of polymer per mL of water should dissolve or disperse in water. Preferably, the polymers are typically completely insoluble in water so that less than about 0.001 g of polymer per mL of water should dissolve or disperse in water. At this preferred level, the flowable composition with a completely water miscible organic liquid should almost immediately transform to the solid implant.

The polymer composition can also include, for example, a biocompatible, biodegradable PLG low-burst copolymer material adapted for use in a controlled release formulation, the low-burst copolymer material being characterized by a weight average molecular weight of about 10 kilodaltons to about 50 kilodaltons and a polydispersity index of about 1.4 to about 2.0, and being further characterized by having separated there from a copolymer fraction characterized by a weight average molecular weight of about 4 kDa to about 10 kDa and a polydispersity index of about 1.4 to about 2.5 (hereinafter the "removed copolymer fraction"). The PLG low-burst copolymer material is prepared from a starting PLG copolymer material without a step of hydrolysis of a higher molecular weight PLG copolymer material, by dissolving the starting copolymer material, which is not a product of hydrolysis of a higher molecular weight PLG copolymer material, in a solvent, precipitating the low-burst copolymer material with a non-solvent. This process, as applied to a starting material that has never been subjected to hydrolysis, separates out an amount of the removed copolymer fraction effective to confer desirable controlled release properties including low initial burst upon the copolymer. These materials, also known as PLGHp, are disclosed in copending and commonly-assigned U.S. patent application Ser. No. 60/901, 435, filed Feb. 15, 2007, entitled "LOW-BURST POLYMERS AND METHODS TO PRODUCE POLYMERS," which is hereby incorporated by reference.

Optionally, the delivery system may also contain a combination of a non-polymeric material and an amount of a thermoplastic polymer. The combination of non-polymeric material and thermoplastic polymer may be adjusted and designed to provide a more coherent risperidone sustained release delivery system.

Non-polymeric materials useful are those that are biocompatible, substantially insoluble in water and body fluids, and biodegradable and/or bioerodible within the body of an animal. The non-polymeric material is capable of being at least partially solubilized in an organic liquid. In the flowable composition containing some organic liquid or other additive, the non-polymeric materials are also capable of coagulating or solidifying to form a solid or gel implant upon the dissipation, dispersement or leaching of the organic liquid component from the flowable composition upon contact of the flowable composition with a body fluid. The matrix of all embodiments of the implant including a non-polymeric material should have a consistency ranging from gelatinous to impressionable and moldable, to a hard, dense solid.

Non-polymeric materials that can be used in the delivery system generally include, for example, any having the foregoing characteristics. Suitable useful non-polymeric materials include, for example, sterols such as cholesterol, stigmasterol, beta-sistosterol, and estradiol; cholestery esters such as cholesteryl stearate, $C_{18}$-$C_{36}$ mono-, di-, and tricylglycerides such as glyceryl monooleate, glyceryl monolinoleate, glyceryl monolaurate, glyceryl monodocosanoate, glyceryl monomyristate, glyceryl monodicenoate, glyceryl dipalmitate, glyceryl didocosanoate, glyceryl dimyristate, glyceryl tridocosanoate, glyceryl trimyristate, glyceryl tridecenoate, glyceryl tristearate, and mixtures thereof; sucrose fatty acid esters such as sucrose distearate and sucrose palmitate; sorbitan fatty acid esters such as sorbitan monostearate, sorbitan monopalmitate, and sorbitan tristearate; $C_{16}$-$C_{18}$ fatty alcohols such as cetyl alcohol, myristyl alcohol, stearyl alcohol, and cetostearyl alcohol; esters of fatty alcohols and fatty acids such as cetyl palmitate and cetearyl palmitate; anhydrides of fatty acids such as stearic anhydride; phospholipids including phosphatidylcholine (lecithin), phosphatidylserine, phosphatidylethanolamine, phosphatidylinositol, and lysoderivatives thereof; sphingosine and derivatives thereof; spingomyelins such as stearyl, palmitoyl, and tricosanyl sphingomyelins; ceramides such as stearyl and palmitoyl ceramides; glycosphingolipids; lanolin and lanolin alcohols; and combinations and mixtures thereof. Preferred non-polymeric materials include, for example, cholesterol, glyceryl monostearate, glyceryl tristearate, stearic acid, stearic anhydride, glyceryl monooleate, glyceryl monolinoleate, and acetylated monoglycerides.

The polymeric and non-polymeric materials may be selected and/or combined to control the rate of biodegradation, bioerosion, and/or bioabsorption within the implant site. Generally, the implant matrix should breakdown over a period from about 1 week to about 12 months, preferably over a period of about 1 week to about 4 months.

Thermoplastic Polymer Molecular Weight

The molecular weight of the polymer can affect the rate of risperidone, a metabolite, or a prodrug thereof release from the implant. Under these conditions, as the molecular weight of the polymer increases, the rate of risperidone, a metabolite, or a prodrug thereof release from the system decreases. This phenomenon can be advantageously used in the formulation of systems for the controlled release of risperidone, a metabolite, or a prodrug thereof. For relatively quick release of risperidone, a metabolite, or a prodrug thereof, low molecular weight polymers can be chosen to provide the desired release rate. For release of risperidone, a metabolite, or a prodrug thereof over a relatively long period of time, a higher polymer molecular weight can be chosen. Accordingly, a risperidone sustained release delivery system can be produced with an optimum polymer molecular weight range for the release of risperidone, a metabolite, or a prodrug thereof over a selected length of time.

The molecular weight of a polymer can be varied by any of a variety of methods. The choice of method is typically determined by the type of polymer composition. For example, if a thermoplastic polyester is used that is biodegradable by hydrolysis, the molecular weight can be varied by controlled hydrolysis, such as in a steam autoclave. Typically, the degree of polymerization can be controlled, for example, by varying the number and type of reactive groups and the reaction times.

The control of molecular weight and/or inherent viscosity of the thermoplastic polymer is a factor involved in the formation and performance of the implant. In general, thermoplastic polymers with higher molecular weight and higher inherent viscosity should provide an implant with a slower degradation rate and therefore a longer duration. Changes and fluxuations of the molecular weight of the thermoplastic polymer following the compounding of the delivery system should result in the formation of an implant that shows a degradation rate and duration substantially different from the degradation rate and duration desired or predicted.

The useful thermoplastic polymers may have average molecular weights ranging from about 1 kiloDalton (kDa) to about 1,000 kDa, preferably from about 2 kDa to about 500 kDa, more preferably from about 5 kDa to about 200 kDa, and most preferably from about 5 kDa to about 100 kDa. The molecular weight may also be indicated by the inherent viscosity (abbreviated as "I.V.", units are in deciliters/gram). Generally, the inherent viscosity of the thermoplastic polymer is a measure of its molecular weight and degradation time (e.g., a thermoplastic polymer with a high inherent viscosity has a higher molecular weight and longer degradation time). Preferably, the thermoplastic polymer has a molecular weight, as shown by the inherent viscosity, from about 0.05 dL/g to about 2.0 dL/g (as measured in chloroform), more preferably from about 0.10 dL/g to about 1.5 dL/g.

Characteristics of Preferred Polyester

The preferred thermoplastic biodegradable polymer of the flowable composition is a polyester. Generally, the polyester may be composed of units of about one or more hydroxycarboxylic acid residues wherein the distribution of differing units may be random, block, paired, or sequential. Alternatively, the polyester may be composed of units of about one or more diols and about one or more dicarboxylic acids. The distribution should depend upon the starting materials used to synthesize the polyester and upon the process for synthesis. An example of a polyester composed of differing paired units distributed in block or sequential fashion is a poly(lactide-co-glycolide). An example of a polyester composed of differing unpaired units distributed in random fashion is poly(lactic acid-co-glycolic acid). Suitable biodegradable thermoplastic polyesters include, for example, polylactides, polyglycolides, polycaprolactones, copolymers thereof, terpolymers thereof, and any combinations thereof. Preferably, the suitable biodegradable thermoplastic polyester is a polylactide, a polyglycolide, a copolymer thereof, a terpolymer thereof, or a combination thereof.

The terminal groups of the poly(DL-lactide-co-glycolide) can either be hydroxyl, carboxyl, or ester depending upon the method of polymerization. Polycondensation of lactic or glycolic acid should provide a polymer with terminal hydroxyl and carboxyl groups. Ring-opening polymerization of the cyclic lactide or glycolide monomers with water, lactic acid, or glycolic acid should provide polymers with these same terminal groups. However, ring-opening of the cyclic monomers with a monofunctional alcohol such as methanol, ethanol, or 1-dodecanol should provide a polymer with about one hydroxyl group and about one ester terminal group. Ring-opening polymerization of the cyclic monomers with a polyol such as glucose, 1,6-hexanediol, or polyethylene glycol should provide a polymer with hydroxyl terminal groups. Such a polymerization of dimers of hydroxycarboxylic acids and a polyol is a chain extension of the polymer. The polyol acts as a central condensation point with the polymer chain growing from the hydroxyl groups incorporated as ester moieties of the polymer. The polyol may be a diol, triol, tetraol, pentaol, or hexaol of about 2 to about 30 carbons in length. Examples include saccharides, reduced saccharides such as sorbitol, diols such as hexane-1,6-diol, triols such as glycerol or reduced fatty acids, and similar polyols. Generally, the polyesters copolymerized with alcohols or polyols should provide longer duration implants.

The type, molecular weight, and amount of the preferred biodegradable thermoplastic polyester present in the flowable composition should typically depend upon the desired properties of the controlled sustained release implant. For example, the type, molecular weight, and amount of biodegradable thermoplastic polyester can influence the length of time in which the risperidone, a metabolite, or a prodrug thereof is released from the controlled sustained release implant. Specifically, in one embodiment, the composition can be used to formulate a one month sustained release delivery system of risperidone, a metabolite, or a prodrug thereof. In such an embodiment, the biodegradable thermoplastic polyester can be a 50/50, 55/45, 75/25, 85/15, 90/10, or 95/5 poly(DL-lactide-co-glycolide) having a carboxy terminal group, preferably a 50/50 poly(DL-lactide-co-glycolide) having a carboxy terminal group; can be present in about 20 wt. % to about 70 wt. % of the composition; and can have an average molecular weight of about 10,000 Daltons to about 45,000 Daltons, or preferably about 15,000 Daltons to about 40,000 Daltons.

In one embodiment, the flowable composition can be formulated to provide a three month sustained release delivery system of risperidone, a metabolite, or a prodrug thereof. In such an embodiment, the biodegradable thermoplastic polyester can be a 50/50, 55/45, 75/25, 85/15, 90/10, or 95/5 poly(DL-lactide-co-glycolide) without a carboxy terminal group; preferably be a 75/25 poly(DL-lactide-co-glycolide) without a carboxy terminal group; can be present in about 20 wt. % to about 70 wt. % of the composition; and can have an average molecular weight of about 10,000 Daltons to about 45,000 Daltons, or preferably about 15,000 Daltons to about 40,000 Daltons; or can be an 85/15 poly(DL-lactide-co-glycolide) containing a 1,6-hexane diol chain extender, at a weight percentage of about 20 wt. % to about 70 wt. % of the flowable composition and at an average molecular weight of about 10,000 Daltons to about 45,000 Daltons or preferably about 15,000 Daltons to about 40,000 Daltons. Any polyester that has a terminal carboxyl group can optionally be extended with a diol moiety.

In one embodiment, the flowable composition can be formulated to provide a three month sustained release delivery system of risperidone, a metabolite, or a prodrug thereof. In such an embodiment, the biodegradable thermoplastic polymer may be a non-hydrolyzed PLG low-burst copolymer polyester material having a weight average molecular weight of about 10 kilodaltons to about 50 kilodaltons, a polydispersity index of about 1.4 to about 2.0, and from which a copolymer fraction characterized by a weight average molecular weight of about 4 kDa to about 10 kDa and a polydispersity index of about 1.4 to about 2.5 has been removed.

Polar Aprotic Organic Solvent

Organic liquids suitable for use in the flowable composition are biocompatible and display a range of solubilities in aqueous medium, body fluid, or water. That range includes complete insolubility at all concentrations upon initial contact, to complete solubility at all concentrations upon initial contact between the organic liquid and the aqueous medium, body fluid, or water.

While the solubility or insolubility of the organic liquid in water can be used as a solubility guide, its water solubility or insolubility in body fluid typically should vary from its solubility or insolubility in water. Relative to water, body fluid contains physiologic salts, lipids, proteins, and the like, and should have a differing solvating ability for organic liquids. This phenomenon is similar to the classic "salting out" characteristic displayed by saline relative to water. Body fluid displays similar variability relative to water but in contrast to a "salting out" factor, body fluid typically has a higher solvating ability for most organic liquids than water. This higher ability is due in part to the greater lipophilic character of body fluid relative to water, and also in part to the dynamic character of body fluid. In a living organism, body fluid is not static but rather moves throughout the organism. In addition, body fluid is purged or cleansed by tissues of the organism so that body fluid contents are removed. As a result, body fluid in living tissue should remove, solvate, or dissipate organic liquids that are utterly insoluble in water.

Pursuant to the foregoing understanding of the solubility differences among water, aqueous media, and body fluid, the organic liquid may be completely insoluble to completely soluble in water when the two are initially combined. Preferably the organic liquid is at least slightly soluble, more preferably moderately soluble, especially more preferably highly soluble, and most preferably soluble at all concentrations in water. The corresponding solubilities of the organic liquids in aqueous media and body fluid should tend to track the trends indicated by the water solubilities. In body fluid, the solubilities of the organic liquids should tend to be higher than those in water.

When an organic liquid that is insoluble to slightly soluble in body fluid is used in any of the embodiments of the sustained release delivery system, it should allow water to permeate into the implanted delivery system over a period of time ranging from seconds to weeks or months. This process may decrease or increase the delivery rate of the risperidone, a metabolite, or a prodrug thereof and in the case of the flowable composition, it should affect the rate of coagulation or solidification. When an organic liquid that is moderately soluble to very soluble in body fluid is used in any of the embodiments of the delivery system, it should diffuse into body fluid over a period of minutes to days. The diffusion rate may decrease or increase the delivery rate of the risperidone, a metabolite, or a prodrug thereof. When highly soluble organic liquids are used, they should diffuse from the delivery system over a period of seconds to hours. Under some circumstances, this rapid diffusion is responsible at least in part for the so-called burst effect. The burst effect is a short-lived but rapid release of risperidone, a metabolite, or a prodrug thereof upon implantation of the delivery system followed by a long-lived, slow release of risperidone, a metabolite, or a prodrug thereof.

Organic liquids used in the delivery system include, for example, aliphatic, aryl, and arylalkyl; linear, cyclic, and branched organic compounds that are liquid or at least flowable at ambient and physiological temperature and contain such functional groups as alcohols, alkoxylated alcohols, ketones, ethers, polymeric ethers, amides, esters, carbonates, sulfoxides, sulfones, any other functional group that is compatible with living tissue, and any combination thereof. The organic liquid preferably is a polar aprotic, or polar protic organic solvent. Preferably, the organic liquid has a molecular weight in the range of about 30 to about 1000.

Preferred biocompatible organic liquids that are at least slightly soluble in aqueous or body fluid include, for example, N-methyl-2-pyrrolidone, 2-pyrrolidone; ($C_1$-$C_{15}$) alcohols, diols, triols, and tetraols such as ethanol, glycerin, propylene glycol, and butanol; ($C_3$-$C_{15}$) alkyl ketones such as acetone, diethyl ketone, and methyl ethyl ketone; ($C_3$-$C_{15}$) esters and alkyl esters of mono-, di-, and tricarboxylic acids such as 2-ethyoxyethyl acetate, ethyl acetate, methyl acetate, ethyl lactate, ethyl butyrate, diethyl malonate, diethyl glutonate, tributyl citrate, diethyl succinate, tributyrin, isopropyl myristate, dimethyl adipate, dimethyl succinate, dimethyl oxalate, dimethyl citrate, triethyl citrate, acetyl tributyl citrate, and glyceryl triacetate; ($C_1$-$C_{15}$) amides such as dimethylformamide, dimethylacetamide, and caprolactam; ($C_3$-$C_{20}$) ethers such as tetrahydrofuran or solketal; tweens, triacetin, decylmethylsulfoxide, dimethyl sulfoxide, oleic acid, 1-dodecylazacycloheptan-2-one, N-methyl-2-pyrrolidone, esters of carbonic acid and alkyl alcohols such as propylene carbonate, ethylene carbonate, and dimethyl carbonate; alkyl ketones such as acetone and methyl ethyl ketone; alcohols such as solketal, glycerol formal, and glycofurol; dialkylamides such as dimethylformamide, dimethylacetamide, dimethylsulfoxide, and dimethylsulfone; lactones such as epsilon-caprolactone and butyrolactone; cyclic alkyl amides such as caprolactam; triacetin and diacetin; aromatic amides such as N,N-dimethyl-m-toluamide; and mixtures and combinations thereof. Preferred solvents include, for example, N-methyl-2-pyrrolidone, 2-pyrrolidone, dimethylsulfoxide, ethyl lactate, propylene carbonate, solketal, triacetin, glycerol formal, isopropylidene glycol, and glycofurol.

Other preferred organic liquids are benzyl alcohol, benzyl benzoate, dipropylene glycol, tributyrin, ethyl oleate, glycerin, glycofural, isopropyl myristate, isopropyl palmitate, oleic acid, polyethylene glycol, propylene carbonate, and triethyl citrate. The most preferred solvents are N-methyl-2-pyrrolidone, 2-pyrrolidone, dimethyl sulfoxide, triacetin, and propylene carbonate because of their solvating ability and their compatibility.

The type and amount of biocompatible organic liquid present in the flowable composition should typically depend on the desired properties of the controlled release implant as described in detail below. Preferably, the flowable composition includes about 10 wt. % to about 90 wt. % or more preferably about 30 wt. % to about 70 wt. % of an organic liquid.

The solubility of the biodegradable thermoplastic polymers in the various organic liquids should differ depending upon their crystallinity, their hydrophilicity, hydrogen-bonding, and molecular weight. Lower molecular-weight polymers should normally dissolve more readily in the organic liquids than high-molecular-weight polymers. As a result, the concentration of a thermoplastic polymer dissolved in the various organic liquids should differ depending upon type of polymer and its molecular weight. Moreover, the higher molecular-weight thermoplastic polymers should tend to give higher solution viscosities than the low-molecular-weight materials.

When the organic liquid forms part of the flowable composition, it functions to enable easy, non-surgical placement of the sustained release delivery system into living tissue. It also facilitates transformation of the flowable composition to an in situ formed implant. Although it is not meant as a limitation of the invention, it is believed that the transformation of the flowable composition is the result of the dissipation of the organic liquid from the flowable composition into the surrounding body fluid and tissue and the infusion of body fluid from the surrounding tissue into the flowable composition. It is believed that during this transformation, the thermoplastic polymer and organic liquid within the flowable composition partition into regions rich and poor in polymer.

For the flowable composition, the concentration of the thermoplastic polymer in the organic liquid should range from about 0.01 g per mL of organic liquid to a saturated concentration. Typically, the saturated concentration should be in the range of about 80 to about 95 wt. % solids or about 4 gm per mL to about 5 gm per mL of organic liquid, assuming that the organic liquid weighs approximately 1 gm per mL.

For polymers that tend to coagulate slowly, a solvent mixture can be used to increase the coagulation rate. In essence, one liquid component of the solvent mixture is a good solvent for the polymer, and the other liquid component of the solvent mixture is a poorer solvent or a non-solvent. The two liquids are mixed at a ratio such that the polymer is still soluble but precipitates with the slightest increase in the amount of non-solvent, such as water in a physiological environment. By necessity, the solvent system should be miscible with both the polymer and water. An example of such a binary solvent system is the use of N-methyl-2-pyrrolidone and ethanol. The addition of ethanol to the N-methyl-2-pyrrolidone/polymer solution increases its coagulation rate.

For the formed implant, the presence of the organic liquid can serve to provide the following properties: plasticization, moldability, flexibility, increased or decreased homogeneity, increased or decreased release rate for the bioactive agent, leaching, promotion or retardation of body fluid influx into the implant, patient comfort, compatibility of thermoplastic polymer and bioactive agent, and the like. Generally the concentration of organic liquid in the formed implant may range from about 0.001 wt. % to as much as about 30 wt. %. Generally, the concentration should be less than an amount that would cause reversion of the formed implant into a flowable composition. Also, the organic liquid may preferentially be chosen so as to display less than substantial ability to dissolve the thermoplastic polymer.

The pliability of the implant can be substantially maintained throughout its life if additives such as the organic liquid are maintained in the implant. Such additives also can act as a plasticizer for the thermoplastic polymer and at least in part may remain in the implant. One such additive having these properties is an organic liquid of low water solubility to water insolubility. Such an organic liquid providing these pliability and plasticizing properties may be included in the delivery system as the sole organic liquid or may be included in addition to an organic liquid that is moderately to highly water soluble.

Organic liquids of low water solubility or water insolubility, such as those forming aqueous solutions of no more than about 5% by weight in water, can function as a pliability, plasticizing component, and in addition can act as the solvating component for the flowable composition embodiment. Such organic liquids can act as plasticizers for the thermoplastic polymer. When the organic liquid has these properties, it is a member of a subgroup of organic liquids termed "plasticizer." The plasticizer influences the pliablity and moldability of the implant composition such that it is rendered more comfortable to the patient when implanted. Moreover, the plasticizer has an effect upon the rate of sustained release of risperidone, a metabolite, or a prodrug thereof such that the rate can be increased or decreased according to the character of the plasticizer incorporated into the implant composition. In general, the organic liquid acting as a plasticizer is believed to facilitate molecular movement within the solid or gel thermoplastic matrix. The plasticizing capability enables polymer molecules of the matrix to move relative to each other so that pliability and easy moldability are provided. The plasticizing capability also enables easy movement of risperidone, a metabolite, or a prodrug thereof so that in some situations, the rate of sustained release is either positively or negatively affected.

High Water Solubility Organic Liquids

A moderate to highly water soluble organic liquid can be generally used in the flowable composition, especially when pliability should not be an issue after formation of the implant. Use of the highly water soluble organic liquid should provide an implant having the physical characteristics of an implant made through direct insertion of the flowable composition.

Use of a moderate to highly water soluble organic liquid in flowable composition should facilitate intimate combination and mixture of the other components therein. It should promote solid or gel homogeneity and pliability of an ex vivo formed implant so that such an implant can be readily inserted into appropriate incisions or trocar placements in tissue.

Useful, highly water soluble organic liquids include, for example, substituted heterocyclic compounds such as N-methyl-2-pyrrolidone (NMP) and 2-pyrrolidone; $(C_2-C_{10})$alkanoic acids such as acetic acid and lactic acid, esters of hydroxy acids such as methyl lactate, ethyl lactate, alkyl citrates, and the like; monoesters of polycarboxylic acids such as monomethyl succinate acid, monomethyl citric acid, and the like; ether alcohols such as glycofurol, glycerol formal, isopropylidene glycol, and 2,2-dimethyl-1,3-dioxolone-4-methanol; Solketal; dialkylamides such as dimethylformamide and dimethylacetamide; dimethylsulfoxide (DMSO) and dimethylsulfone; lactones such as epsilon, caprolactone, and butyrolactone; cyclic alkyl amides such as caprolactam; and mixtures and combinations thereof. Preferred organic liquids include, for example, N-methyl-2-pyrrolidone, 2-pyrrolidone, dimethylsulfoxide, ethyl lactate, glycofurol, glycerol formal, and isopropylidene glycol.

Low Water Solubility Organic Liquids/Solvents

As described above, an organic liquid of low or no water solubility (hereinafter low/no liquid) may also be used in the sustained release delivery system. Preferably, a low/no liquid is used when it is desirable to have an implant that remains pliable, is to be extrudable is to have an extended release and the like. For example, the release rate of the biologically active agent can be affected under some circumstances through the use of a low/no liquid. Typically such circumstances involve retention of the organic liquid within the implant product and its function as a plasticizer or rate modifier.

Suitable low or nonsoluble organic liquids include, for example, esters of carbonic acid and aryl alcohols such as benzyl benzoate; $(C_4-C_{10})$alkyl alcohols; $(C_1-C_6)$alkyl$(C_2-C_6)$ alkanoates; esters of carbonic acid and alkyl alcohols such as propylene carbonate, ethylene carbonate, and dimethyl carbonate, alkyl esters of mono-, di-, and tricarboxylic acids, such as 2-ethyoxyethyl acetate, ethyl acetate, methyl acetate, ethyl butyrate, diethyl malonate, diethyl glutonate, tributyl citrate, diethyl succinate, tributyrin, isopropyl myristate, dimethyl adipate, dimethyl succinate, dimethyl oxalate, dimethyl citrate, triethyl citrate, acetyl tributyl citrate, and glyceryl triacetate; alkyl ketones such as methyl ethyl ketone; as well as other carbonyl, ether, carboxylic ester, amide, and hydroxy containing liquid organic compounds having some solubility in water. Propylene carbonate, ethyl acetate, triethyl citrate, isopropyl myristate, and glyceryl triacetate are preferred because of biocompatibility and pharmaceutical acceptance.

Additionally, mixtures of the foregoing high, low, or no solubility organic liquids providing varying degrees of solubility for the matrix forming material can be used to alter the life time, rate of bioactive agent release, and other characteristics of the implant. Examples include a combination of N-methyl-2-pyrrolidone and propylene carbonate, which provides a more hydrophobic solvent than N-methyl-2-pyrrolidone alone, and a combination of N-methyl-2-pyrrolidone and polyethylene glycol, which provides a more hydrophilic solvent than N-methyl-2-pyrrolidone alone.

The organic liquid for inclusion in the composition should be biocompatible. Biocompatible means that as the organic liquid disperses or diffuses from the composition, it does not result in substantial tissue irritation or necrosis surrounding the implant site.

Organic Liquid for the Preferred Flowable Composition

For the preferred flowable composition incorporating a thermoplastic polyester, any suitable polar aprotic organic liquid can be employed, provided that the suitable polar aprotic solvent displays a body fluid solubility within a range of completely soluble in all proportions to very slightly soluble. Suitable polar aprotic organic liquids are disclosed, e.g., in ALDRICH HANDBOOK OF FINE CHEMICALS AND LABORATORY EQUIPMENT, Milwaukee, Wis. (2000) and in U.S. Pat. Nos. 5,324,519, 4,938,763, 5,702,716, 5,744,153, and 5,990,194. A suitable polar aprotic liquid should be able to diffuse over time into body fluid so that the flowable composition coagulates or solidifies. The diffusion may be rapid or slow. It is also preferred that the polar aprotic liquid for the biodegradable polymer be non-toxic and otherwise biocompatible.

The polar aprotic organic liquid is preferably biocompatible. Suitable polar aprotic organic liquid include, for example, those having an amide group, an ester group, a carbonate group, a ketone, an ether, a sulfonyl group, or a combination thereof.

Preferably, the polar aprotic organic liquid comprises N-methyl-2-pyrrolidone, 2-pyrrolidone, N,N-dimethylformamide, dimethyl sulfoxide, propylene carbonate, caprolactam, triacetin, or any combination thereof. More preferably, the polar aprotic organic solvent is N-methyl-2-pyrrolidone.

The solubility of the biodegradable thermoplastic polyesters in the various polar aprotic liquids should differ depending upon their crystallinity, their hydrophilicity, hydrogen-bonding, and molecular weight. Thus, not all of the biodegradable thermoplastic polyesters should be soluble to the same extent in the same polar aprotic organic liquid, but each biodegradable thermoplastic polymer or copolymer should be soluble in its appropriate polar aprotic solvent. Lower molecular-weight polymers should normally dissolve more readily in the liquids than high-molecular-weight polymers. As a result, the concentration of a polymer dissolved in the various liquids should differ depending upon type of polymer and its molecular weight. Conversely, the higher molecular-weight polymers should normally tend to coagulate or solidify faster than the very low-molecular-weight polymers. Moreover the higher molecular-weight polymers should tend to give higher solution viscosities than the low-molecular-weight materials.

For example, low-molecular-weight polylactic acid formed by the condensation of lactic acid should dissolve in N-methyl-2-pyrrolidone (NMP) to give about 73% by weight solution which still flows easily through a 23-gauge syringe needle, whereas a higher molecular-weight poly(DL-lactide) (DL-PLA) formed by the additional polymerization of DL-lactide gives the same solution viscosity when dissolved in N-methyl-2-pyrrolidone at about 50% by weight. The higher molecular-weight polymer solution coagulates immediately when placed into water. The low-molecular-weight polymer solution, although more concentrated, tends to coagulate very slowly when placed into water.

It has also been found that solutions containing very high concentrations of high molecular weight polymers sometimes coagulate or solidify slower than more dilute solutions. It is believed that the high concentration of polymer impedes the diffusion of solvent from within the polymer matrix and consequently prevents the permeation of water into the matrix where it can precipitate the polymer chains. Thus, there is an optimum concentration at which the solvent can diffuse out of the polymer solution and water penetrates within to coagulate the polymer.

The concentration and species of the polar aprotic organic liquid for the preferred flowable composition incorporating a thermoplastic polyester should typically depend upon the desired properties of the controlled release implant. For example, the species and amount of biocompatible polar aprotic solvent can influence the length of time in which the risperidone, a metabolite, or a prodrug thereof is released from the controlled release implant.

Specifically, in one embodiment, the flowable composition can be used to formulate a one month delivery system of risperidone, a metabolite, or a prodrug thereof. In such an embodiment, the biocompatible polar aprotic solvent can preferably be N-methyl-2-pyrrolidone and can preferably present in about 30 wt. % to about 70 wt. % of the composition.

Alternatively, in another embodiment, the composition can be used to formulate a three month delivery system of risperidone, a metabolite, or a prodrug thereof. In such an embodiment, the biocompatible polar aprotic solvent can preferably be N-methyl-2-pyrrolidone and can preferably present in about 30 wt. % to about 70 wt. % of the composition.

Risperidone

Risperidone (also known as 4-[2-[4-(6-fluorobenzo[d]isoxazol-3-yl)-1-piperidyl]ethyl]-3-methyl-2,6-diazabicyclo[4.4.0]deca-1,3-dien-5-one and marketed under the trade name RISPERDAL®) is a psychotropic agent belonging to the chemical class of benzisoxazole derivatives. Risperidone, a metabolite, or a prodrug thereof may be administered in its unneutralized basic form, or as a salt of an organic or inorganic acid. Examples include the risperidone, a metabolite, or a prodrug thereof salts wherein the gegenion (counter-ion) is acetate, propionate, tartrate, malonate, chloride, sulfate, bromide, and other pharmaceutically acceptable organic and inorganic acid gegenions.

Risperidone, a metabolite, or a prodrug thereof may be lyophilized prior to use. Typically, the risperidone, a metabolite, or a prodrug thereof may be dissolved in an aqueous solution, sterile filtered, and lyophilized in a syringe. In a separate process, the thermoplastic polymer/organic liquid solution can be filled into second syringe. The two syringes can be coupled together and the contents can be drawn back and forth between the two syringes until the thermoplastic polymer, organic liquid, and the risperidone, a metabolite, or a prodrug thereof are effectively mixed together, forming a flowable composition. The flowable composition can be drawn into one syringe. The two syringes can be disconnected and a needle attached to the syringe containing the flowable composition. The flowable composition can be injected through the needle into the body. The flowable composition can be formulated and administered to a patient as described in, e.g., U.S. Pat. Nos. 5,324,519, 4,938,763, 5,702,716, 5,744,153, and 5,990,194; or as described herein. Once administered, the organic liquid dissipates, the remaining polymer gels or solidifies, and a matrix structure is formed. The organic liquid should dissipate and the polymer should solidify or gel so as to entrap or encase the risperidone, a metabolite, or a prodrug thereof within the matrix.

The release of risperidone, a metabolite, or a prodrug thereof from the implant should follow the same general rules for release of a drug from a monolithic polymeric device. The release of risperidone, a metabolite, or a prodrug thereof can be affected by the size and shape of the implant, the loading of risperidone, a metabolite, or a prodrug thereof within the implant, the permeability factors involving the risperidone, a metabolite, or a prodrug thereof and the particular polymer, and the degradation of the polymer. Depending upon the amount of risperidone, a metabolite, or a prodrug thereof selected for delivery, the above parameters can be adjusted by one skilled in the art of drug delivery to give the desired rate and duration of release.

The amount of risperidone, a metabolite, or a prodrug thereof incorporated into the sustained release delivery system depends upon the desired release profile, the concentration of risperidone, a metabolite, or a prodrug thereof used for a biological effect, and the length of time that the risperidone, a metabolite, or a prodrug thereof has to be released for treatment. There is no upper limit on the amount of risperidone, a metabolite, or a prodrug thereof incorporated into the sustained release delivery system except for that of an acceptable solution or dispersion viscosity for injection through a syringe needle. The lower limit of risperidone, a metabolite, or a prodrug thereof incorporated into the sustained release delivery system is dependent upon the activity of the risperidone, a metabolite, or a prodrug thereof and the length of time needed for treatment. Specifically, in one embodiment, the sustained release delivery system can be formulated to provide a one month release of risperidone, a metabolite, or a prodrug thereof. In such an embodiment, the risperidone, a metabolite, or a prodrug thereof can preferably be present in about 0.5 wt. % to about 50 wt. %, preferably about 1 wt. % to about 30 wt. % of the composition. Alternatively, in another embodiment, the sustained release delivery system can be formulated to provide a three month delivery of risperidone, a metabolite, or a prodrug thereof. In such an embodiment, the risperidone, a metabolite, or a prodrug thereof can preferably be present in about 0.5 wt. % to about 50 wt. %, preferably about 1 wt. % to about 30 wt. % of the composition. The gel or solid implant formed from the flowable composition should release the risperidone, a metabolite, or a prodrug thereof contained within its matrix at a controlled rate until the implant is effectively depleted of risperidone, a metabolite, or a prodrug thereof.

Risperidone is extensively metabolized in the liver. The main metabolic pathway is through hydroxylation of risperidone to 9-hydroxyrisperidone by the enzyme, CYP 2D6. A minor metabolic pathway is through N-dealkylation. The main metabolite, 9-hydroxyrisperidone, has similar pharmacological activity as risperidone. Consequently, the clinical effect of the drug (e.g., the active moiety) results from the combined concentrations of risperidone plus 9-hydroxyrisperidone.

Adjuvants and Carriers

The sustained release delivery system may include, for example, a release rate modifier to alter the sustained release rate of risperidone, a metabolite, or a prodrug thereof from the implant matrix. The use of a release rate modifier may either decrease or increase the release of risperidone, a metabolite, or a prodrug thereof in the range of multiple orders of magnitude (e.g., 1 to 10 to 100), preferably up to a ten-fold change, as compared to the release of risperidone, a metabolite, or a prodrug thereof from an implant matrix without the release rate modifier.

With the addition of a hydrophobic release rate modifier such as hydrophobic ethyl heptanoate, to the sustained release delivery system, and formation of the implant matrix through interaction of the flowable composition and body fluid, the release rate of risperidone, a metabolite, or a prodrug thereof can be slowed. Hydrophilic release rate modifiers such as polyethylene glycol may increase the release of the risperidone, a metabolite, or a prodrug thereof. By an appropriate choice of the polymer molecular weight in combination with an effective amount of the release rate modifier, the release rate and extent of release of a risperidone, a metabolite, or a prodrug thereof from the implant matrix may be varied, for example, from relatively fast to relatively slow.

Useful release rate modifiers include, for example, organic substances which are water-soluble, water-miscible, or water insoluble (i.e., hydrophilic to hydrophobic).

The release rate modifier is preferably an organic compound which is thought to increase the flexibility and ability of the polymer molecules and other molecules to slide past each other even though the molecules are in the solid or highly viscous state. Such an organic compound preferably includes a hydrophobic and a hydrophilic region. It is preferred that a release rate modifier is compatible with the combination of polymer and organic liquid used to formulate the sustained release delivery system. It is further preferred that the release rate modifier is a pharmaceutically-acceptable substance.

Useful release rate modifiers include, for example, fatty acids, triglycerides, other like hydrophobic compounds, organic liquids, plasticizing compounds, and hydrophilic compounds. Suitable release rate modifiers include, for example, esters of mono-, di-, and tricarboxylic acids, such as 2-ethoxyethyl acetate, methyl acetate, ethyl acetate, diethyl phthalate, dimethyl phthalate, dibutyl phthalate, dimethyl adipate, dimethyl succinate, dimethyl oxalate, dimethyl citrate, triethyl citrate, acetyl tributyl citrate, acetyl triethyl citrate, glycerol triacetate, di(n-butyl) sebecate, and the like; polyhydroxy alcohols, such as propylene glycol, polyethylene glycol, glycerin, sorbitol, and the like; fatty acids; triesters of glycerol, such as triglycerides, epoxidized soybean oil, and other epoxidized vegetable oils; sterols, such as cholesterol; alcohols, such as ($C_6$-$C_{12}$) alkanols, 2-ethoxyethanol, and the like. The release rate modifier may be used singly or in combination with other such agents.

Suitable combinations of release rate modifiers include, for example, glycerin/propylene glycol, sorbitol/glycerin, ethylene oxide/propylene oxide, butylene glycol/adipic acid, and the like. Preferred release rate modifiers include, for example, dimethyl citrate, triethyl citrate, ethyl heptanoate, glycerin, and hexanediol.

The amount of the release rate modifier included in the flowable composition should vary according to the desired rate of release of the risperidone, a metabolite, or a prodrug thereof from the implant matrix. Preferably, the sustained release delivery system contains about 0.5 to about 30%, preferably about 5 to about 10%, of a release rate modifier.

Other solid adjuvants may also be optionally combined with the sustained release delivery system to act as carriers, especially isolation carriers. These include, for example, additives or excipients such as a starch, sucrose, lactose, cellulose sugar, mannitol, maltitol, dextran, sorbitol, starch, agar, alginates, chitins, chitosans, pectins, tragacanth gum, gum arabic, gelatins, collagens, casein, albumin, synthetic or semi-synthetic polymers or glycerides, and/or polyvinylpyrrolidone.

Additional adjuvants may include, for example, oils such as peanut oil, sesame oil, cottonseed oil, corn oil, and olive oil as well as esters of fatty acids such as ethyl oleate, isopropyl myristate, fatty acid glycerides, and acetylated fatty acid glycerides. Also included are alcohols, such as, but not limited to, ethanol, isopropyl alcohol, hexadecyl alcohol, glycerol, and propylene glycol. Ethers, such as but not limited to, poly(ethyleneglycol); petroleum hydrocarbons such as mineral oil and petrolatum may also be used in the formulations. Pectins, carbomers, methyl cellulose, hydroxypropyl cellulose, hydroxypropyl methyl cellulose, or carboxymethyl cellulose may also be included. These compounds can serve as isolation carriers by coating the risperidone, a metabolite, or a prodrug thereof thereby preventing its contact with the organic solvent and other ingredients of the flowable composition. As isolation carriers, these compounds also help lower the burst effect associated with the coagulation of the flowable composition in situ.

Optionally, other compounds such as, but not limited to, stabilizers, antimicrobial agents, antioxidants, pH modifiers, bioavailability modifiers, and combinations of these are included. Emulsifiers and surfactants such as fatty acids or a non-ionic surfactants including natural or synthetic polar oil, fatty acid esters, polyol ethers, and mono-, di-, or tri-glycerides may also be included.

The Implant

When the implant is formed, the implant has the physical state of a solid or a gel. The solid embodiments may be rigid so that they cannot be flexed or bent by squeezing them between the fingers or they may be flexible or bendable so that they can be compressed or flexed out of original shape by squeezing between the fingers (i.e., a low amount of force). The gel embodiments may be jelly-like in consistency and should flow under pressure. The thermoplastic polymer functions as a matrix in these embodiments to provide integrity to the single body solid or gel and to enable controlled release of the bioactive agent upon implantation.

The thermoplastic polymer matrix is preferably a solid matrix and especially preferably is microporous. In an embodiment of the microporous solid matrix, there is a core surrounded by a skin. The core preferably contains pores of diameters from about 1 to about 1000 microns. The skin preferably contains pores of smaller diameters than those of the core pores. In addition, the skin pores are preferably of a size such that the skin is functionally non-porous in comparison with the core.

Because all of the components of the implant are biodegradable or can be swept away from the implant site by body fluid and eliminated from the body, the implant eventually disappears. Typically the implant components complete their biodegradation or disappearance after the risperidone, a metabolite, or a prodrug thereof has been typically completely released. The structure of the thermoplastic polymer, its molecular weight, the density and porosity of the implant, and the body location of the implant all affect the biodegradation and disappearance rates.

The implant is typically formed subcutaneously in a patient. It can be molded in place upon injection to provide comfort to the patient. The implant volume typically may be between about 0.25 mL to about 3 mL in size.

Therapeutic Use

Surprisingly, it has been discovered that the sustained release delivery system is more effective in delivering risperidone than the RISPERDAL® CONSTA® product. Specifically, as shown in the Examples below, the blood levels of risperidone obtained with the sustained release delivery system are from about 0 nanograms per milliliter (ng/mL) to about 500 ng/mL.

In general, any disease which may be ameliorated, treated, cured, or prevented by administration of risperidone, a metabolite, or a prodrug thereof or a risperidone analog may be treated by administration of the flowable composition. These diseases relate to mental impairments. The following specific malconditions are exemplary of such diseases. These may all be treated by appropriate, effective administration of a flowable composition formulated to deliver an effective amount of risperidone, a metabolite, or a prodrug thereof. These malconditions include: schizophrenia, bipolar disorder, psychotic depression, obsessive-compulsion disorder, Tourette syndrome, autism spectrum disorders, and the like.

Dosages

The amount of flowable composition administered should typically depend upon the desired properties of the controlled release implant. For example, the amount of flowable composition can influence the length of time in which the risperidone, a metabolite, or a prodrug thereof is released from the controlled release implant. Specifically, in one embodiment, the composition can be used to formulate a one month delivery system of risperidone, a metabolite, or a prodrug thereof. In such an embodiment, about 0.20 mL to about 2.0 mL of the flowable composition can be administered. Alternatively, in another embodiment, the composition can be used to formulate a three month delivery system of risperidone, a metabolite, or a prodrug thereof. In such an embodiment, about 0.75 mL to about 1.0 mL of the flowable composition can be administered.

The amount of risperidone, a metabolite, or a prodrug thereof within the flowable composition and the resulting implant should depend upon the disease to be treated, the length of duration desired, and the bioavailability profile of the implant. Generally, the effective amount should be within the discretion and wisdom of the patient's attending physician. Guidelines for administration include, for example, dose ranges of from about 1 to about 16 milligrams (mg) of risperidone, a metabolite, or a prodrug thereof per day, preferably from about 1 to about 5 milligrams (mg) of risperidone, a metabolite, or a prodrug thereof per day, as applied for schizophrenia, bipolar disorder, psychotic depression, obsessive-compulsion disorder, Tourette syndrome, and autism spectrum disorders. The typical flowable composition effective for such sustained delivery over a 1 month period should contain from about 3 to about 300 mg of risperidone, a metabolite, or a prodrug thereof per ml of total volume of flowable composition. The injection volume should range from about 0.2 to about 2.0 mL per implant. The typical flowable composition effective for such sustained delivery of a 3 month period should contain from about 9 to about 900 mg of risperidone, a metabolite, or a prodrug thereof per ml of total volume of flowable composition. The injection volume should range from 0.75 to about 1.0 mL per implant. The polymer formulation should be the primary factor for obtaining the longer sustained release, as discussed above.

All publications, patents, and patent documents are incorporated by reference herein, as though individually incorporated by reference. The invention should now be illustrated with the following non-limiting examples.

The following Examples employ the ATRIGEL® formulation of poly(lactide-co-glycolide) and N-methyl-2-pyrrolidone in combination with risperidone as the flowable composition.

EXAMPLES

In the following Examples, ATRIGEL®/Risperidone refers to ATRIGEL®/Risperidone formulations; ATRIGEL® is a registered Trademark of QLT-USA, Fort Collins, Colo. The particular form of ATRIGEL® product used in these examples is provided with the examples. Unless otherwise indicated, the ATRIGEL® product is the thermoplastic polymer poly(lactide-co-glycolide) (PLG), the thermoplastic polymer poly(lactide-co-glycolide extended with 1,6-hexane diol) (PLGH), or PLGHp in the organic solvent N-methyl-2-pyrrolidone. RISPERDAL® and RISPERDAL® CONSTA® are registered Trademarks of Janssen, L.P., Titusville, N.J.

The ATRIGEL® drug delivery system is a biodegradable polymeric delivery system that can be injected as a liquid. Upon injection of the formulation, the polymer solidifies encapsulating the drug. As the process of biodegradation begins, the drug is slowly released. The release rate of drugs from this type of delivery system can be controlled by the type and molecular weight of the polymer and drug load of the constituted product. Therefore, the system can be tailored to meet the needs of the patient.

The ATRIGEL® Delivery System is currently used in the Food and Drug Administration approved products ELIGARD™ (one, three, and four-month subcutaneous depot formulations of leuprolide acetate) and ATRIDOX® (doxycycline hyclate applied to the periodontal pocket). Clinical studies and post-marketing experience with these products demonstrate that the ATRIGEL® Delivery System itself is well tolerated and provides consistent, sustained release of the incorporated drug over the designated dosing period.

In addition as demonstrated by the clinical results provided below, the flowable compositions have no lag phase, and continuous therapeutic plasma levels. The 1- and 3-month flowable compositions provide an alternative drug delivery technology that addresses these as well as several other drawbacks of currently marketed RISPERDAL® and RISPERDAL® CONSTA® products.

The advantages of the approach using the flowable composition to solve these problems include: a) a rapid therapeutic response with no lag time; b) a subcutaneous injection that is patient friendly; c) less pain; d) no muscle damage and scarring; e) smaller-gauge needles; f) less volume; g) ease-of-administration; h) quick and easy preparation; i) no clogging of the needle; and j) removable up to eight weeks, unlike preparations using microspheres.

As a result, the flowable compositions provide superior pharmacokinetics and higher bioavailability relative to other known delivery systems providing risperidone. These features represent improvements regardless of the particular application, i.e. any risperidone responsive disease.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

| SOURCES OF MATERIALS | |
|---|---|
| Abbreviation | Chemical Name and Supplier |
| ACN | Acetonitrile<br>Sigma-Aldrich,<br>St. Louis, MO. |
| 50/50 PLG (InV 0.10 dL/g) | Birmingham Polymer, Inc.<br>Birmingham, AL.<br>Lot #5 05-01-1A |
| 50/50 PLGH (InV 0.36 dL/g) | Alkermes, Inc.<br>Cambridge, MA.<br>Lot # 1010-492 |
| 50/50 PLGH (InV 0.18 dL/g) | Boehringer Ingelheim<br>Ridgefield, CT.<br>Lot # 1005072 |
| 75/25 PLG (InV 0.19 dL/g) | Birmingham Polymer, Inc.<br>Birmingham, AL.<br>Lot # D99082 |
| 50/50 PLG (InV 0.33 dL/g) | Boehringer Ingelheim<br>Ridgefield, CT.<br>Lot # 1004925 |
| 50/50 PLG (InV 0.24 dL/g) | Birmingham Polymer, Inc.<br>Birmingham, AL.<br>Lot # 112-99-1 |
| 50/50 PLG (InV 0.19 dL/g) | Boehringer Ingelheim<br>Ridgefield, CT.<br>Lot # 1004925 |
| 50/50 PLGH (InV 0.49 dL/g) | Boehringer Ingelheim<br>Ridgefield, CT.<br>Lot # 290541 |
| 65/35 PLGH (InV 0.20 dL/g) | Alkermes, Inc.<br>Cambridge, MA.<br>Lot # 1291-536 |
| 65/35 PLGH (MW 37 kDa) | QLT USA Inc.<br>Fort Collins, CO.<br>Lot # ALN 1654-34 |
| 75/25 PLGH (InV 0.15 dL/g) | Alkermes, Inc.<br>Cambridge, MA.<br>Lot # 1151-514 |
| 75/25 PLGH (InV 0.24 dL/g) | Alkermes, Inc.<br>Cambridge, MA.<br>Lot # 00-141-150 |
| 75/25 PLGH (InV 0.26 dL/g) | Birmingham Polymer, Inc.<br>Birmingham, AL.<br>Lot # D99140 |
| 80/20 PLGH (MW 42 kDa) | QLT USA Inc.<br>Fort Collins, CO.<br>Lot # 2012-61 |
| 85/15 PLGH (InV 0.27 dL/g) | Advanced Polymer Technology<br>Lot # A140-13 |
| 50/50 PLG/PEG5000 (InV 0.79 dL/g) | Birmingham Polymer, Inc.<br>Birmingham, AL.<br>Lot # D99011 |
| 70/30 PLG/PEG5000 (InV 0.79 dL/g) | Birmingham Polymer, Inc.<br>Birmingham, AL.<br>Lot # D97132 |
| PEG8000-PLG (InV 0.29 dL/g) | QLT USA Inc.<br>Fort Collins, CO.<br>Lot # ALN 1654-76 |
| 3-Hydroxy-2-Naphthoic Acid | Acros Organics<br>Geel, Belgium<br>Lot # 03311 |
| Citric Acid Anhydrous | Fisher Scientific<br>Chicago, IL<br>Lot # 006630 |
| Cholesterol | Sigma-Aldrich,<br>St. Louis, MO.<br>Lot # 02653 |
| EDTA | Ethylenediaminetetraacetic acid<br>Sigma-Aldrich,<br>St. Louis, MO. |
| EL | Ethyl Lactate<br>Sigma-Aldrich,<br>St. Louis, MO. |
| Glacial Acidic Acid | Fisher Scientific<br>Chicago, IL<br>Lot # 002418 |
| Hydrochloric Acid | J T Baker<br>Chicago, IL<br>Lot # V28511 |

-continued

| SOURCES OF MATERIALS | |
|---|---|
| Abbreviation | Chemical Name and Supplier |
| Mannitol | Roquette<br>Lestrem, France<br>RDC # 709609 |
| NMP | N-Methyl-2-Pyrrolidone<br>International Specialty Products<br>Wayne, NJ. |
| Pamoic Acid | Sigma-Aldrich,<br>St. Louis, MO.<br>Lot # 03287 |
| PEI | Polyethyleneimine<br>Sigma-Aldrich,<br>St. Louis, MO. |
| Tartaric Acid<br>Anhydrous | Spectrum<br>Lot # PL0341 |
| Risperidone | Medichem<br>Lot # A010580 |
| RISPERDAL ®<br>CONSTA ® | Janssen, L. P.,<br>Titusville, NJ.<br>Lot # 5NA467 |
| RISPERDAL ®<br>tablets | Janssen, L. P.<br>Titusville, NJ. |

| LIST OF ABBREVIATIONS AND DEFINITION OF TERMS | |
|---|---|
| Abbreviation | Definition |
| 50/50<br>65/35<br>75/25<br>85/15<br>95/5 | Weight ratio of lactide to glycolide in the polymer |
| ATRIGEL ® | General name given to a solution prepared by dissolving poly(lactide-co-glycolide) polymers in a biocompatible solvent (typically NMP) |
| AUC | Area under the plasma concentration-time profile |
| $AUC_{0-24}$ | Area under the plasma concentration-time profile from time 0 to 24 hours post-dose |
| $AUC_{0-inf}$ | Area under the plasma concentration-time profile from time 0 to infinity |
| cP | centiPoise |
| $C_{max}$ | Maximum plasma concentration |
| CV(%) | Coefficient of variation, expressed as a percentage |
| FDA | Food and Drug Administration |
| HPLC | High Performance Liquid Chromatography |
| i.m. | Intramuscular |
| i.v. | Intravenous |
| InV | Inherent Viscosity (dL/g) |
| Ke | Apparent terminal phase rate constant |
| kDa | kilodalton |
| KGy | kiloGray |
| Max | Maximum |
| Mg | Milligram |
| Min | Minimum |
| Min | Minute |
| mL | Milliliter |
| MW | Molecular Weight |
| PBS | Phosphate Buffered Saline |
| PD | Pharmacodynamic |
| PEG | Polyethylene glycol |
| PLA | Polylactide |
| PLG | Poly(lactide-co-glycolide) with methyl end group |
| PLC | Poly(lactide-co-caprolactone) |
| PLGH | Poly(DL-lactide-co-glycolide) with a carboxylic acid end group |
| PLGHp | Poly(DL-lactide-co-glycolide) with a free carboxylic acid group on at least one end of each polymer chain) that has been purified by a solvent/nonsolvent precipitation method. |

-continued

| LIST OF ABBREVIATIONS AND DEFINITION OF TERMS | |
|---|---|
| Abbreviation | Definition |
| PK | Pharmacokinetic |
| PPM | Parts per million |
| RSP | Risperidone |
| RT | Room Temperature |
| s.c. | Subcutaneous |
| SD | Standard deviation |
| SE | Standard error |
| TA | Test Article |
| $T_m$ | Time to maximum plasma concentration level |

Test Procedures

Text Article Preparation Procedure Using PLGH

Preparation of Polymer Solutions

Polymer stock solutions were prepared by weighing a known amount of each polymer solid into individual 20 mL scintillation vials. A known amount of N-methyl-2-pyrrolidone was added to each polymer and the vials were placed on a horizontal jar mill. The vials were rotated overnight to produce a visually clear polymer solution indicating dissolution of the polymer. Sterilization of the polymer solution was accomplished by gamma irradiation.

Preparation of Test Article Syringes

The "B" syringes (male syringes) contained risperidone powder and were prepared by weighing drug powder into 1.25 mL Becton Dickinson (BD) male syringes. The "A" syringes (female syringes) were prepared by weighing ATRIGEL® polymer stock solutions into 1.0 mL female syringes.

Preparation of Test Articles (Reconstituted Formulation) for Injection

Immediately prior to injection, "A" and "B" syringes were coupled and mixed by cycling the contents from one syringe to the other for 90 cycles. The mixed formulation was finally transferred to the male dosing syringe for injection. Some of the formulations were roll mixed. Risperidone and selected ATRIGEL® were weighed into a scintillation vial, and the vial was put on horizontal roller mixer to roll overnight before injection.

Plasma SPE Extraction Procedure for Active Risperidone Plasma Analysis

This procedure was adopted from Price, M., Hoffman, D., *Therapeutic Drug Monitoring*, 19, 333-337 (1997). Bond Elute Certify LRC solid-phase extraction columns were prepared by washing with 6 mL methanol and conditioned with 3 mL 0.1 M sodium phosphate buffer (pH 6). Approximately 1 mL of plasma was loaded onto the wet columns and allowed to filter without vacuum. The columns were washed with 3 mL 1 M acetic acid by pulling vacuum and dried for 5 minutes under vacuum. The columns were washed with 6 mL methanol at low vacuum and dried for about 2 minutes under full vacuum.

The samples were eluted into test tubes with about 2 mL of 3% ammonium hydroxide in ethyl acetate using gravity filtration. The reagent was made fresh daily and sonicated before use. The elutes were evaporated to dryness at 42° C. under a stream of nitrogen gas. The residue was dissolved in 150 μL of 65/35 ammonium acetate/acetonitrile, pH 5.4 by vortexing and shaking on the rotary shaker at about 250 rpm at room temperature for about 10 minutes. An aliquot of the solution was placed in an High Performance Liquid Chromatography vial for High Performance Liquid Chromatography analysis. The sample was analyzed by risperidone High Performance Liquid Chromatography method described below.

Reversed Phase High Performance Liquid Chromatography Method for the Quantization of Risperidone and 9-Hydroxy-Risperidone The High Performance Liquid Chromatography had the following conditions: Mobile Phase: 35:65 acetonitrile: ammonium acetate, pH 5.4; flow rate: 1.5 ml/min; autosampler temperature: room temperature; column temperature: room temperature; detection: 275 nm (UV); total run time: 8 min; injection volume: 20 µL; column: Phenomenex Luna C18 250×4.6 mm, 5 µm; column storage: 70/30 acetonitrile/water; approximate retention time of risperidone: 3 minutes; and approximate retention time of 9-hydroxyrisperidone: 2.4 minutes.

For about 2 liters of 35:65 actonitrile:ammonium acetate, pH 5.4 mobile phase, add about 2.5 g ammonium acetate to 1300 mL of $H_2O$, add 700 mL of acetonitrile, mix to dissolve solids, adjust pH to 5.4±0.1 by adding glacial acetic acid, monitor pH with a calibrated electrode, and degas by sonicating the solution for about 5 minutes.

The standard solution preparation is as follows: standard stock solution was made by dissolving approximately 10 mg risperidone in 10 mL 1:1 acetonitrile/$H_2O$. A series standards ranging from 10 ppm to 800 ppm was diluted with 1:1 acetonitrile/$H_2O$ from the standard stock solution.

Implant Extraction Procedure for Implant Retrieval Study

The retrieved implants and tissue were placed in a −86° C. freezer for at least 1 hour. The frozen samples were lyophilized for at least 4 hours. The dry samples were minced with scissors, which were cleaned after each sample to minimize cross-contamination. The samples were minced until powder-like. Approximately 5 mL of 70:30 dimethylsulfoxide/methanol with 1% polyethyleneimine extraction solvent was added to each sample. The samples were mixed overnight at about 200 rpm at 37° C. on the orbital shaker. The samples were sonicated for 10 minutes. 1.5 mL of the extract was loaded into a 3 mL lure lock syringe and filtered through a 0.2 µm pore size filter into a clean test tube. 1 mL of the filtrate was placed into a clean test tube and 4 mL of 50:50 acetonitrile/$H_2O$ was added. The test tube was vortexed for 30 seconds. About 2 mL of the solution was loaded into a 3 mL lure lock syringe and filtered into an High Performance Liquid Chromatography vial. The solution was analyzed by the risperidone High Performance Liquid Chromatography method.

Example 1

Risperidone Release Kinetics and Pharmacokinetics Studies in Rats

Experimental Procedures

All rat preclinical studies were conducted in Sprague-Dawley rats. Five rats per Test Article per time point were injected either intramuscularly or subcutaneously under full anesthesia in the dorsal thoracic (DT) region with approximately 100 mg of the Test Article, described above.

During the course of the study, the animals were observed for overt toxicity and any existing test site abnormalities, including redness, bleeding, swelling, discharge, bruising and Test Article extrusion at the injection site were observed and recorded. In addition, injection weights were recorded at administration and body weights were taken and recorded at administration and at termination.

At selected time points, five rats per Test Article were anesthetized and bled (about 5 mL) via cardiac puncture. Blood was collected in labeled potassium ethylenediaminetetraacetic acid tubes. The blood was centrifuged for 10 min at 3000 rpm. The plasma fraction was transferred to labeled 5 mL plastic culture tubes and stored at −86° C. The plasma was extracted following the Plasma SPE Extraction Procedure For Active Risperidone Plasma Analysis, described above.

The active risperidone concentrations were analyzed using the Reversed Phase High Performance Liquid Chromatography Method For The Quantization of Risperidone And 9-Hydroxyrisperidone, described above.

The active risperidone plasma concentration was calculated based on both risperidone and 9-hydroxyrisperidone. Since 9-hydroxyrisperidone, the product of biotransformation of risperidone in the liver, has the same pharmacological activity and intensity as parent risperidone, it is typical to combine these two risperidone compounds when monitoring the antischizophrenic therapy of risperidone administration.

After blood collection, the animals were terminated with carbon dioxide and the implants were retrieved. The implants were frozen at −86° C. and lyophilized at least 4 hours. The dried implants were extracted following the implant extraction procedure (see the Implant Extraction Procedure for Implant Retrieval Study, described above), and the risperidone content was analyzed using the Reversed Phase High Performance Liquid Chromatography Method for the Quantization of Risperidone and 9-Hydroxyrisperidone, described above.

Results and Discussion for the 24-Hour Burst Studies

The initial 24-hour risperidone release or burst, from the ATRIGEL® delivery system was of interest to the development program. Eight 24-hour in vivo release studies were performed in rats to ensure control of the burst from the system and to identify formulations that could possibly result in sustained risperidone release for 28-days.

The first 24-hour in vivo release study (EXAMPLE 1.1) was conducted using risperidone freebase and was designed to investigate the role of polymer concentration, polymer inherent viscosity and lactide to glycolide ratio within the polymer. The initial release was found dependent on the polymer concentration (the higher the concentration the lower the risperidone burst), inherent viscosity of the polymer (the higher the inherent viscosity the lower the burst), and the lactide to glycolide ratio (the higher the lactide ratio the lower the burst). The differences between the acid end group and the methyl end group were minor and within standard deviation. This study resulted in identification of ATRIGEL® vehicle containing approximately 40% 50/50 PLGH (InV 0.36) in N-methyl-2-pyrrolidone as possible candidate for further evaluation. See Table 1.

TABLE 1

24-Hour Risperidone Release From ATRIGEL ® Implants

| Formulation | Wt. Risperidone Injected (mg) | Wt. Risperidone Remaining in Implant (mg) | Wt. % Risperidone Released | AVG. Wt. % Released |
|---|---|---|---|---|
| colspan=5 | Group I- 10% Risperidone in 50% 50/50 PLGH (InV 0.18) and 50% NMP | | | |
| | 12.88 | 10.76 | 16.41 | |
| | 12.39 | 11.20 | 9.64 | |
| | 11.85 | 10.06 | 15.14 | 14.69 ± 2.98 |
| | 13.01 | 11.06 | 14.97 | |
| | 11.50 | 9.51 | 17.29 | |
| colspan=5 | Group II- 10% Risperidone in 45% 50/50 PLGH (InV 0.18) and 55% NMP | | | |
| | 12.32 | 10.90 | 11.56 | |
| | 12.64 | 5.77 | 54.35 | |
| | 12.23 | 10.48 | 14.30 | 36.01 ± 21.97 |
| | 11.90 | 4.97 | 58.24 | |
| | 12.14 | 7.09 | 41.58 | |
| colspan=5 | Group III- 10% Risperidone in 40% 50/50 PLGH (InV 0.36) and 60% NMP | | | |
| | 10.97 | 9.21 | 16.04 | |
| | 11.20 | 10.50 | 6.33 | |
| | 12.55 | 11.84 | 5.66 | 6.55 ± 5.71 |
| | 11.87 | 11.76 | 0.91 | |
| | 11.77 | 11.32 | 3.81 | |
| colspan=5 | Group IV- 10% Risperidone in 37% 50/50 PLGH (InV 0.36) and 63% NMP | | | |
| | 11.01 | 9.82 | 10.79 | |
| | 11.89 | 10.50 | 11.73 | |
| | 11.72 | 10.78 | 8.05 | 8.21 ± 3.79 |
| | 12.25 | 12.01 | 2.02 | |
| | 10.95 | 10.02 | 8.48 | |
| colspan=5 | Group V- 10% Risperidone in 50% 65/35 PLGH (InV 0.20) and 50% NMP | | | |
| | 12.26 | 7.72 | 37.02 | |
| | 11.69 | 8.34 | 28.61 | |
| | 12.28 | 5.99 | 51.18 | 31.13 ± 13.47 |
| | 12.15 | 9.55 | 21.42 | |
| | 11.62 | 9.60 | 17.42 | |
| colspan=5 | Group VI- 10% Risperidone in 50% 75/25 PLGH (InV 0.24) and 50% NMP | | | |
| | 12.50 | 10.43 | 16.59 | |
| | 11.37 | 9.94 | 12.52 | |
| | 11.39 | 10.16 | 10.77 | 11.62 ± 3.16 |
| | 11.53 | 10.56 | 8.36 | |
| | 11.72 | 10.57 | 9.85 | |
| colspan=5 | Group VII- 10% Risperidone in 40% 50/50 PLG (InV 0.18) and 60% NMP | | | |
| | 12.41 | 4.83 | 60.80 | |
| | 11.58 | 4.94 | 57.33 | |
| | 12.10 | 5.91 | 51.15 | 53.62 ± 5.19 |
| | 12.01 | 6.15 | 48.77 | |
| | 12.37 | 6.18 | 50.03 | |
| colspan=5 | Group VIII- 10% Risperidone in 40% 50/50 PLG (InV 0.35) and 60% NMP | | | |
| | 11.25 | 10.23 | 9.08 | |
| | 11.41 | 11.00 | 3.59 | |
| | 11.96 | 11.44 | 4.34 | 5.02 ± 3.05 |
| | 11.26 | 11.13 | 1.18 | |
| | 11.23 | 10.46 | 6.89 | |
| colspan=5 | Group IX- 10% Risperidone in 40% 75/25 PLG (InV 0.26) and 60% NMP | | | |
| | 11.50 | 9.97 | 13.26 | |
| | 11.46 | 9.75 | 14.88 | |
| | 11.24 | 10.08 | 10.24 | 11.17 ± 3.50 |
| | 11.40 | 10.06 | 11.72 | |
| | 12.45 | 11.74 | 5.72 | |

The next three in vivo studies (EXAMPLES 1.2, 1.3, and 1.4) were designed to evaluate risperidone salts in the ATRIGEL® delivery system. By forming risperidone salts with anionic counter-ions the physicochemical properties of risperidone were altered, such as the stability and the solubility in N-methyl-2-pyrrolidone and water. Ultimately helping risperidone to be more compatible with the ATRIGEL® delivery system as well as reducing the burst. Table 2 shows the risperidone salts that were investigated.

TABLE 2

| Risperidone salt abbreviation | Anion | Ratio |
|---|---|---|
| RSPCl | Hydrochloric Acid | 1:1 |
| RSPCA | Citric Acid | 1:1 |
| RSP Acetate | Acetic Acid | 1:1 |
| RSP Tartrate | Tartaric Acid | 1:1 |
| RSP Pamoate | Pamoic Acid | 1:1 |
| RSP Naphthoate | Naphthoic Acid | 1:1 |
| RSP DOS | Dioctylsulfosuccinate | 1:1 |

These salts were investigated using the same or similar ATRIGEL® vehicles identified in EXAMPLE 1.1 (approximately 40% 50/50 PLGH (InV 0.36) in N-methyl-2-pyrrolidone). The 24-hour release of these salts ranged from 17 to 78% of the total risperidone in the ATRIGEL® formulation (See Tables 3-5). The pamoate and citrate salt showed the most promise of all the salts investigated, however none of the risperidone salts met the requirement of approximately 10% burst.

TABLE 3

24-Hour Risperidone Release From ATRIGEL ® Implants

| Formulation | Wt. RSP salt Injected (mg) | Wt. RSP Remaining in Implant (mg) | Wt. % RSP Released | AVG. Wt. % Released |
|---|---|---|---|---|
| colspan=5 | Group I- 10% RSPCl in 40% 50/50 PLGH (InV 0.36) and 60% NMP | | | |
| | 9.58 | 3.98 | 58.45 | |
| | 9.13 | 2.93 | 67.87 | |
| | 11.19 | 3.74 | 66.62 | 67.91 ± 6.23 |
| | 11.73 | 2.93 | 75.02 | |
| | 11.72 | 3.33 | 71.59 | |
| colspan=5 | Group II- 10% RSPCl in 37% 50/50 PLGH (InV 0.36) and 63% NMP | | | |
| | 8.32 | 1.46 | 82.45 | |
| | 11.17 | 3.16 | 71.76 | |
| | 10.43 | 2.30 | 77.91 | 78.46 ± 4.11 |
| | 11.35 | 2.17 | 80.88 | |
| | 10.64 | 2.21 | 79.28 | |
| colspan=5 | Group III- 10% RSPCl in 50% 75/25 PLGH (InV 0.15) and 50% NMP | | | |
| | 13.51 | 4.69 | 65.33 | |
| | 11.01 | 3.06 | 72.17 | |
| | 11.03 | 3.08 | 72.05 | 69.38 ± 3.24 |
| | 12.15 | 2.54 | 70.90 | |
| | 12.46 | 4.18 | 66.47 | |
| colspan=5 | Group IV- 10% RSPCl in 40% 75/25 PLGH (InV 0.24) and 60% NMP | | | |
| | 12.30 | 2.71 | 78.00 | |
| | 9.71 | 1.97 | 79.69 | |
| | 11.12 | 2.43 | 78.15 | 74.98 ± 5.08 |
| | 10.87 | 3.43 | 68.41 | |
| | 10.95 | 3.22 | 70.64 | |

TABLE 3-continued

24-Hour Risperidone Release From ATRIGEL® Implants

| Formulation | Wt. RSP salt Injected (mg) | Wt. RSP Remaining in Implant (mg) | Wt. % RSP Released | AVG. Wt. % Released |
|---|---|---|---|---|
| Group V- 10% RSPCl in 34% 50/50 PLGH (InV 0.47) and 66% NMP | | | | |
| | 6.29 | 0.89 | 85.90 | |
| | 8.86 | 0.97 | 89.07 | |
| | 10.41 | 1.45 | 86.07 | 85.88 ± 2.11 |
| | 10.90 | 1.83 | 83.24 | |
| | 11.46 | 1.71 | 85.12 | |
| Group VI- 10% RSPCA in 37% 50/50 PLGH (InV 0.36) and 63% NMP | | | | |
| | 9.46 | 6.00 | 36.61 | |
| | 9.76 | 4.99 | 48.87 | |
| | 11.19 | 8.65 | 22.65 | 30.03 ± 12.51 |
| | 11.77 | 9.03 | 23.27 | |
| | 11.45 | 9.30 | 18.75 | |
| Group VII- 20% RSPCl in 37% 50/50 PLGH (InV 0.36) and 63% NMP | | | | |
| | 9.08 | 1.25 | 86.20 | |
| | 10.08 | 1.80 | 82.13 | |
| | 11.78 | 0.91 | 92.32 | 87.72 ± 4.23 |
| | 14.55 | 1.99 | 86.35 | |
| | 12.22 | 1.03 | 91.58 | |
| Group VIII- 20% RSPCl in 30% 50/50 PLGH (InV 0.36) and 70% NMP | | | | |
| | 10.27 | 1.10 | 89.26 | |
| | 12.33 | 1.01 | 91.80 | |
| | 9.43 | 0.37 | 86.08 | 93.49 ± 3.01 |
| | 10.07 | 0.62 | 93.80 | |
| | 8.94 | 0.31 | 96.49 | |

TABLE 4

24-Hour Risperidone Release From ATRIGEL® Implants

| Formulation | Wt. Risperidone salt Injected (mg) | Wt. Risperidone Remaining in Implant (mg) | Wt. % Risperidone Released | AVG. Wt. % Released |
|---|---|---|---|---|
| Group I- 10% RSPAcetate in 37% 50/50 PLGH (InV 0.36) and 63% NMP | | | | |
| | 8.81 | 5.14 | 41.73 | |
| | 12.16 | 6.88 | 43.44 | |
| | 8.73 | 4.21 | 51.78 | 40.69 ± 7.88 |
| | 11.79 | 7.68 | 34.92 | |
| | 12.34 | 8.45 | 31.57 | |
| Group II- 10% RSPTartrate in 37% 50/50 PLGH (InV 0.36) and 63% NMP | | | | |
| | 10.38 | 3.74 | 63.96 | |
| | 7.97 | 3.41 | 57.17 | |
| | 8.96 | 3.65 | 59.28 | 59.87 ± 2.57 |
| | 9.12 | 3.61 | 60.37 | |
| | 9.90 | 4.06 | 58.56 | |
| Group III- 10% RSPCA Encapsulated in Mannitol (Cast and Grind) in 37% 50/50 PLGH (InV0.36) and 63% NMP | | | | |
| | 10.29 | 5.39 | 47.57 | |
| | 8.19 | 3.50 | 57.29 | |
| | 10.20 | 5.55 | 45.57 | 47.63 ± 6.97 |
| | 9.79 | 6.07 | 38.02 | |
| | 10.19 | 5.12 | 49.71 | |

TABLE 4-continued

24-Hour Risperidone Release From ATRIGEL® Implants

| Formulation | Wt. Risperidone salt Injected (mg) | Wt. Risperidone Remaining in Implant (mg) | Wt. % Risperidone Released | AVG. Wt. % Released |
|---|---|---|---|---|
| Group IV- 10% RSPCA Encapsulated in Mannitol (Lypholized) in 37% 50/50 PLGH (InV 0.36) and 63% NMP | | | | |
| | 8.01 | 4.29 | 46.41 | |
| | 9.53 | 4.27 | 55.18 | |
| | 10.95 | 5.58 | 49.06 | 47.85 ± 4.54 |
| | 12.27 | 6.82 | 44.46 | |
| | 11.56 | 6.46 | 44.16 | |
| Group V- 10% RSPCA in 37% 50/50 PLGH (InV 0.18) and 63% NMP | | | | |
| | 12.11 | 2.18 | 81.97 | |
| | 10.78 | 2.59 | 75.95 | |
| | 9.27 | 4.22 | 54.45 | 72.66 ± 15.52 |
| | 9.36 | 0.79 | 91.56 | |
| | 11.38 | 4.63 | 59.36 | |
| Group VI- 10% RSPCA in 34% 65/35 PLGH (InV 0.19) and 66% NMP | | | | |
| | 10.71 | 3.23 | 69.81 | |
| | 10.31 | 2.79 | 72.91 | |
| | 12.13 | 1.71 | 85.89 | 77.99 ± 6.65 |
| | 10.92 | 2.32 | 78.72 | |
| | 10.53 | 1.83 | 82.60 | |
| Group VII- 10% RSPCA in 34% 75/25 PLGH (InV 0.24) and 66% NMP | | | | |
| | 12.43 | 3.36 | 72.97 | |
| | 8.96 | 2.56 | 71.41 | |
| | 12.31 | 2.40 | 80.53 | 72.86 ± 4.57 |
| | 11.23 | 3.27 | 70.86 | |
| | 11.23 | 3.53 | 68.53 | |
| Group VIII- 10% RSPCA in 34% 85/15 PLGH (InV 0.25) and 66% NMP | | | | |
| | 10.83 | 3.30 | 69.49 | |
| | 11.32 | 3.90 | 65.56 | |
| | 10.35 | 3.46 | 66.56 | 72.44 ± 11.10 |
| | 11.10 | 0.88 | 92.11 | |
| | 10.87 | 3.42 | 68.50 | |

TABLE 5

24-Hour Risperidone Release From ATRIGEL® Implants

| Formulation | Wt. Risperidone salt Injected (mg) | Wt. Risperidone Remaining in Implant (mg) | Wt. % Risperidone Released | AVG. Wt. % Released |
|---|---|---|---|---|
| Group I- 10% RSP in 37% 50/50 PLGH (InV 0.36) and 63% NMP | | | | |
| | 10.68 | 8.89 | 16.79 | |
| | 11.77 | 9.95 | 15.48 | |
| | 10.65 | 8.19 | 23.10 | 20.27 ± 4.01 |
| | 10.84 | 8.15 | 24.80 | |
| | 10.43 | 8.22 | 21.18 | |
| Group II- 10% RSP DOS in 37% 50/50 PLGH (InV 0.36) and 63% NMP | | | | |
| | 10.39 | 8.60 | 17.19 | |
| | 9.33 | 6.61 | 29.19 | |
| | 13.92 | 9.16 | 34.19 | 29.81 ± 7.39 |
| | 10.23 | 6.78 | 33.72 | |
| | 8.12 | 5.30 | 34.76 | |

TABLE 5-continued

24-Hour Risperidone Release From ATRIGEL® Implants

| Formulation | Wt. Risperidone salt Injected (mg) | Wt. Risperidone Remaining in Implant (mg) | Wt. % Risperidone Released | AVG. Wt. % Released |
|---|---|---|---|---|
| Group III- 10% RSP Naphthoate in 37% 50/50 PLGH (InV 0.36) and 63% NMP | | | | |
| | 8.31 | 5.10 | 38.67 | |
| | 9.29 | 5.82 | 37.29 | |
| | 11.95 | 6.36 | 46.79 | 40.42 ± 4.21 |
| | 10.89 | 6.88 | 36.83 | |
| | 10.53 | 6.05 | 42.54 | |
| Group IV- 10% RSP Pamoate in 37% 50/50 PLGH (InV 0.36) and 63% NMP | | | | |
| | 10.64 | 8.94 | 16.02 | |
| | 11.05 | 8.28 | 25.04 | |
| | 8.07 | 6.32 | 21.72 | 17.17 ± 8.54 |
| | 12.17 | 11.80 | 3.05 | |
| | 11.16 | 8.92 | 20.01 | |
| Group V- 10% RSPCA/Cholesterol (1:1) in 37% 50/50 PLGH (InV 0.36) and 63% NMP | | | | |
| | 8.87 | 3.38 | 61.87 | |
| | 10.12 | 3.86 | 61.88 | |
| | 8.93 | 3.54 | 60.39 | 61.28 ± 0.70 |
| | 6.94 | 2.67 | 61.57 | |
| | 8.24 | 3.24 | 60.69 | |
| Group VI- 10% RSPCA in 31.5% 50/50 PLGH (InV 0.36) + 5.5% 50/50 PLGH (InV 0.57) and 63% NMP | | | | |
| | 8.66 | 6.76 | 21.99 | |
| | 11.08 | 8.26 | 25.41 | |
| | 10.95 | 7.63 | 30.28 | 28.61 ± 5.04 |
| | 13.29 | 9.27 | 30.27 | |
| | 12.09 | 7.85 | 35.10 | |
| Group VII- 10% RSPCA in 31.5% 50/50 PLGH (InV 0.36) + 5.5% 50/50 PLGH (InV 0.49) and 63% NMP | | | | |
| | 1.04 | 8.53 | 29.19 | |
| | 11.96 | 8.78 | 26.58 | |
| | 11.38 | 7.62 | 33.00 | 33.70 ± 9.86 |
| | 14.16 | 10.07 | 28.87 | |
| | 10.79 | 5.30 | 50.85 | |
| Group VIII- 10% RSPCA in 2% PEG + 36% 50/50 PLGH (InV 0.36) and 63% NMP | | | | |
| | 10.03 | 5.59 | 44.24 | |
| | 11.02 | 7.20 | 34.66 | |
| | 9.03 | 5.82 | 35.55 | 36.04 ± 8.42 |
| | 9.81 | 5.62 | 42.74 | |
| | 13.14 | 10.12 | 23.02 | |

EXAMPLE 1.5 investigated the addition of excipients to the ATRIGEL® formulation. Excipients such as triethylcitrate, ethylheptanoate, and polyvinylpyrrolidone were added to the ATRIGEL® delivery system to aid in the burst control of risperidone from the ATRIGEL® system. The results of this study indicate that the addition of these excipients did not help control the burst of risperidone to less than 10% (See Table 6).

TABLE 6

24-Hour Risperidone Release From ATRIGEL® Implants

| Formulation | Wt. Risperidone salt Injected (mg) | Wt. Risperidone Remaining in Implant (mg) | Wt. % Risperidone Released | AVG. Wt. % Released |
|---|---|---|---|---|
| Group I: 20% Risperidone in 37% 50/50 PLGH (InV 0.36) and 63% NMP | | | | |
| | 24.37 | 20.07 | 17.64 | |
| | 26.09 | 23.10 | 11.46 | |
| | 19.79 | 17.46 | 11.78 | 13.89 ± 3.79 |
| | 19.59 | 17.58 | 10.25 | |
| | 22.15 | 18.09 | 18.33 | |
| Group II: 10% Risperidone in 44% 50/50 PLGH (InV 0.36) and 56% NMP | | | | |
| | 15.94 | 7.41 | 53.48 | |
| | 7.87 | 4.51 | 42.71 | |
| | 11.00 | 7.57 | 31.15 | 37.00 ± 22.52 |
| | 9.96 | 4.31 | 56.73 | |
| | 9.64 | 9.55 | 0.94 | |
| Group III: 10% Risperidone in 37% 50/50 PLGH (InV 0.36) and 63% NMP | | | | |
| | 15.26 | 12.01 | 21.30 | |
| | 10.07 | 7.79 | 22.65 | |
| | 10.18 | 6.55 | 35.64 | 18.65 ± 12.57 |
| | 11.20 | 9.93 | 11.33 | |
| | 11.76 | 11.49 | 2.31 | |
| Group IV: 10% Risperidone in 37% 50/50 PLGH (InV 0.36) and 63% NMP [Prep'd 1 hr prior to dosing] | | | | |
| | 11.26 | 9.76 | 13.30 | |
| | 10.60 | 9.19 | 13.34 | |
| | 10.11 | 8.64 | 14.51 | 18.05 ± 7.43 |
| | 9.37 | 7.66 | 18.26 | |
| | 11.65 | 8.06 | 30.84 | |
| Group V: 10% Risperidone and 5% triethyl citrate in 37% 50/50 PLGH (InV 0.36) and 63% NMP | | | | |
| | 10.57 | 6.39 | 39.57 | |
| | 9.79 | 4.01 | 59.07 | |
| | 9.93 | 7.12 | 28.27 | 33.30 ± 17.20 |
| | 10.33 | 7.60 | 26.47 | |
| | 10.28 | 8.93 | 13.11 | |
| Group VI: 10% Risperidone and 5% ethyl heptanoate in 37% 50/50 PLGH (InV 0.36) and 63% NMP | | | | |
| | 9.13 | 6.73 | 26.25 | |
| | 8.28 | 5.80 | 29.95 | |
| | 10.08 | 7.62 | 24.37 | 28.24 ± 8.70 |
| | 9.72 | 5.64 | 41.98 | |
| | 10.62 | 8.64 | 18.66 | |
| Group VII: 10% Risperidone and 5% polyvinyl pyrrolidone (PVP) C15 in 37% 50/50 PLGH (InV 0.36) and 63% NMP | | | | |
| | 9.95 | 6.96 | 30.06 | |
| | 8.46 | 5.32 | 37.06 | |
| | 11.49 | 8.11 | 29.47 | 27.99 ± 6.55 |
| | 9.92 | 7.65 | 22.91 | |
| | 9.76 | 7.77 | 20.44 | |
| Group VIII: 10% Risperidone and 3% PVP C30 in 37% 50/50 PLGH (InV 0.36) and 63% NMP | | | | |
| | 9.66 | 7.81 | 19.23 | |
| | 11.73 | 9.09 | 22.53 | |
| | 10.96 | 8.32 | 24.04 | 26.78 ± 15.09 |
| | 9.76 | 8.30 | 15.05 | |
| | 10.91 | 5.12 | 53.06 | |

TABLE 6-continued

24-Hour Risperidone Release From ATRIGEL® Implants

| Formulation | Wt. Risperidone salt Injected (mg) | Wt. Risperidone Remaining in Implant (mg) | Wt. % Risperidone Released | AVG. Wt. % Released |
|---|---|---|---|---|
| Group IX: 10% RSPCA and 10% triethyl citrate in 37% 50/50 PLGH (InV 0.36) and 63% NMP | | | | |
| | 9.45 | 3.98 | 57.90 | |
| | 9.75 | 4.79 | 50.82 | |
| | 13.70 | 4.62 | 66.30 | 54.88 ± 7.71 |
| | 10.24 | 4.76 | 53.47 | |
| | 11.27 | 6.09 | 45.94 | |
| Group X: 10% Risperidone and 10% ethyl heptanoate in 37% 50/50 PLGH (InV 0.36) and 63% NMP | | | | |
| | 8.83 | 5.83 | 33.94 | |
| | 10.14 | 5.55 | 45.23 | |
| | 11.68 | 7.59 | 35.06 | 38.18 ± 4.56 |
| | 10.46 | 6.62 | 36.69 | |
| | 11.11 | 6.67 | 40.00 | |
| Group XI: 10% RSP pamoate (1:1) in 37% 50/50 PLGH (InV 0.36) and 63% NMP | | | | |
| | 9.28 | 4.85 | 47.80 | |
| | 9.72 | 5.49 | 43.51 | |
| | 10.08 | 5.85 | 42.02 | 39.64 ± 12.96 |
| | 11.43 | 5.95 | 47.93 | |
| | 10.63 | 8.83 | 16.93 | |
| Group XII: 10% RSP pamoate (2:1) and 10% ethyl heptanoate in 37% 50/50 PLGH (InV 0.36) and 63% NMP | | | | |
| | 9.68 | 4.92 | 49.20 | |
| | 10.06 | 4.40 | 56.31 | |
| | 11.50 | 5.55 | 51.73 | 54.51 ± 10.78 |
| | 11.75 | 3.30 | 71.90 | |
| | 10.46 | 5.92 | 43.41 | |

Figure 2:
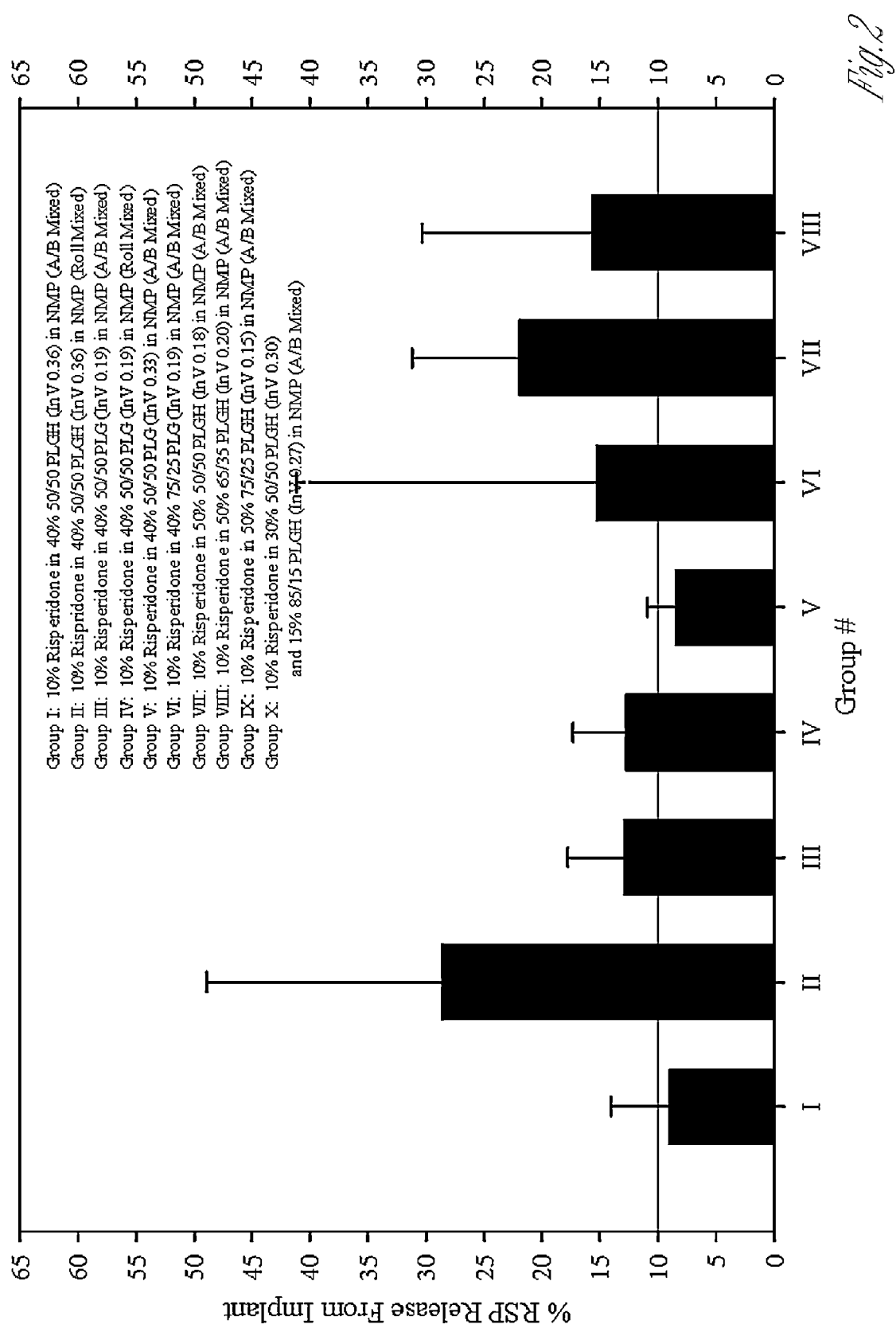
FIG. 2 illustrates the 24-hour release of risperidone from selected ATRIGEL® formulations in rats.

EXAMPLES 1.6 and 1.7 investigated the risperidone freebase without the formation of salts or the addition of excipients administrated subcutaneously. The test articles were selected to again evaluate the effect of polymer concentration, inherent viscosity, and lactide to glycolide ratio. The results of this study agreed well with EXAMPLE 1.1 study results. ATRIGEL® formulations consisting of (1) 40% 50/50 PLGH (InV 0.36) and 60% N-methyl-2-pyrrolidone, (2) 40% 50/50 poly(lactide-co-glycolide) (InV 0.19) and 60% N-methyl-2-pyrrolidone, (3) 40% 50/50 poly(lactide-co-glycolide) (InV 0.33) and 60% N-methyl-2-pyrrolidone, or (4) 40% 65/35 PLGH (InV 0.37) and 60% N-methyl-2-pyrrolidone were found to control the burst of risperidone to approximately 10%. The release of risperidone from ATRIGEL® formulations of EXAMPLES 1.6 and 1.7 are illustrated in FIGS. 1 and 2. The detailed risperidone release data and active plasma concentrations are listed in Tables 7-8 for EXAMPLE 1.6, and in Tables 9-10 for EXAMPLE 1.7.

TABLE 7

24-Hour Risperidone Release From ATRIGEL® Implants

| Formulation | Wt. Risperidone salt Injected (mg) | Wt. Risperidone Remaining in Implant (mg) | Wt. % Risperidone Released | AVG. Wt. % Released |
|---|---|---|---|---|
| Group I: 10% Risperidone in 40% 50/50 PLGH (InV 0.36) and 60% NMP (A/B Mixed) | | | | |
| | 13.72 | 13.89 | −1.26 | |
| | 10.08 | 9.71 | 3.72 | |
| | 9.23 | 8.62 | 6.62 | 4.89 ± 4.69 |
| | 11.18 | 9.89 | 11.56 | |
| | 14.11 | 13.58 | 3.80 | |
| Group II: 10% Risperidone in 40% 50/50 PLGH (InV 0.36) and 60% NMP (Roll Mixed) | | | | |
| | 18.30 | 17.05 | 6.80 | |
| | 15.34 | 14.20 | 7.47 | |
| | 12.79 | 11.90 | 7.01 | 7.13 ± 0.38 |
| | 12.45 | 11.61 | 6.79 | |
| | 14.39 | 13.30 | 7.59 | |
| Group III: 10% Risperidone in 40% 50/50 PLG (InV 0.19) and 60% NMP (A/B Mixed) | | | | |
| | 10.26 | 9.65 | 5.98 | |
| | 9.60 | 8.84 | 7.96 | |
| | 11.36 | 5.10 | 55.08 | 9.05 ± 2.91 |
| | 10.42 | 9.44 | 9.39 | |
| | 10.72 | 9.34 | 12.88 | |
| Group IV: 10% Risperidone in 40% 50/50 PLG (InV 0.19) and 60% NMP (Roll Mixed) | | | | |
| | 12.97 | 11.71 | 9.70 | |
| | 15.84 | 14.74 | 6.94 | |
| | 12.58 | 11.08 | 11.93 | 9.79 ± 1.94 |
| | 15.50 | 13.76 | 11.20 | |
| | 13.07 | 11.87 | 9.19 | |
| Group V: 10% Risperidone in 40% 50/50 PLG (InV 0.33) and 60% NMP (A/B Mixed) | | | | |
| | 12.20 | 11.30 | 7.38 | |
| | 6.49 | 5.79 | 10.79 | |
| | 8.55 | 7.31 | 14.49 | 9.11 ± 3.53 |
| | 11.20 | 10.41 | 7.07 | |
| | 11.09 | 10.44 | 5.82 | |
| Group VI: 10% Risperidone in 40% 75/25 PLG (InV 0.19) and 60% NMP (A/B Mixed) | | | | |
| | 10.06 | 8.31 | 17.42 | |
| | 9.90 | 8.85 | 10.59 | |
| | 11.09 | 9.85 | 11.18 | 13.33 ± 2.92 |
| | 13.01 | 11.02 | 15.28 | |
| | 11.42 | 10.03 | 12.16 | |
| Group VII: 10% Risperidone in 50% 50/50 PLGH (InV 0.18) and 50% NMP (A/B Mixed) | | | | |
| | 15.93 | 14.04 | 11.84 | |
| | 10.97 | 9.88 | 9.92 | |
| | 9.44 | 7.76 | 17.76 | 12.45 ± 3.20 |
| | 12.52 | 10.92 | 12.74 | |
| | 12.56 | 11.30 | 9.99 | |
| Group VIII: 10% Risperidone in 50% 65/35 PLGH (InV 0.20) and 50% NMP (A/B Mixed) | | | | |
| | 16.99 | 11.11 | 34.60 | |
| | 8.60 | 6.09 | 29.15 | |
| | 10.35 | 7.19 | 30.48 | 30.28 ± 2.65 |
| | 11.75 | 8.52 | 27.51 | |
| | 12.00 | 8.44 | 29.67 | |
| Group IX: 10% Risperidone in 50% 75/25 PLGH (InV 0.15) and 50% NMP (A/B Mixed) | | | | |
| | 14.18 | 9.43 | 33.51 | |
| | 12.62 | 8.77 | 30.52 | |
| | 11.79 | 8.51 | 27.86 | 30.13 ± 2.72 |
| | 9.10 | 6.21 | 31.80 | |
| | 11.42 | 8.34 | 26.97 | |

TABLE 7-continued

24-Hour Risperidone Release From ATRIGEL ® Implants

| Formulation | Wt. Risperidone salt Injected (mg) | Wt. Risperidone Remaining in Implant (mg) | Wt. % Risperidone Released | AVG. Wt. % Released |
|---|---|---|---|---|
| Group X: 10% Risperidone in 30% 50/50 PLGH (InV 0.30), 15% 85/15 PLGH (InV 0.27) and 50% NMP (A/B Mixed) | | | | |
| | 13.37 | 12.03 | 10.06 | |
| | 11.08 | 10.19 | 8.05 | |
| | 9.80 | 8.74 | 10.74 | 11.19 ± 2.49 |
| | 9.74 | 8.32 | 14.64 | |
| | 10.47 | 9.17 | 12.45 | |

TABLE 8

24-Hour Active Risperidone Plasma Concentrations

| Formulation | Total Plasma Concentration (ng/ml) | Mean Plasma Concentration (ng/ml) | Standard Deviation |
|---|---|---|---|
| Group I: 10% Risperidone in 40% 50/50 PLGH (InV 0.36) and 60% NMP (A/B Mixed) | | | |
| | 65.1 | | |
| | 48.4 | | |
| | 48.5 | 59.0 | 12.6 |
| | 55.2 | | |
| | 77.9 | | |
| Group II: 10% Risperidone in 40% 50/50 PLGH (InV 0.36) and 60% NMP (Roll Mixed) | | | |
| | 39.0 | | |
| | 63.2 | | |
| | 43.2 | 48.8 | 9.2 |
| | 49.2 | | |
| | 49.4 | | |
| Group III: 10% Risperidone in 40% 50/50 PLG (InV 0.19) and 60% NMP (A/B Mixed) | | | |
| | 83.6 | | |
| | 70.1 | | |
| | 97.5 | 82.4 | 13.3 |
| | 93.0 | | |
| | 68.0 | | |
| Group IV: 10% Risperidone in 40% 50/50 PLG (InV 0.19) and 60% NMP (Roll Mixed) | | | |
| | 70.7 | | |
| | 74.6 | | |
| | 64.5 | 68.0 | 5.1 |
| | 68.2 | | |
| | 61.7 | | |
| Group V: 10% Risperidone in 40% 50/50 PLG (InV 0.33) and 60% NMP (A/B Mixed) | | | |
| | 64.2 | | |
| | 49.1 | | |
| | 42.8 | 55.9 | 12.0 |
| | 72.1 | | |
| | 51.4 | | |
| Group VI: 10% Risperidone in 40% 75/25 PLG (InV 0.19) and 60% NMP (A/B Mixed) | | | |
| | 102.0 | | |
| | 68.3 | | |
| | 119.3 | 89.7 | 20.6 |
| | 79.0 | | |
| | 79.7 | | |
| Group VII: 10% Risperidone in 50% 50/50 PLGH (InV 0.18) and 50% NMP (A/B Mixed) | | | |
| | 126.7 | | |
| | 91.3 | | |
| | 157.5 | 122.2 | 29.9 |
| | 143.4 | | |
| | 92.3 | | |
| Group VIII: 10% Risperidone in 50% 65/35 PLGH (InV 0.20) and 50% NMP (A/B Mixed) | | | |
| | 521.3 | | |
| | 139.3 | | |
| | 163.3 | 246.3 | 173.0 |
| | 309.2 | | |
| | 98.6 | | |
| Group IX: 10% Risperidone in 50% 75/25 PLGH (InV 0.15) and 50% NMP (A/B Mixed) | | | |
| | 161.4 | | |
| | 117.7 | | |
| | 162.6 | 148.6 | 25.9 |
| | 176.9 | | |
| | 124.6 | | |
| Group X: 10% Risperidone in 30% 50/50 PLGH (InV 0.30), 15% 85/15 PLGH (InV 0.27) and 50% NMP (A/B Mixed) | | | |
| | 69.9 | | |
| | 41.6 | | |
| | 40.7 | 58.7 | 20.1 |
| | 53.7 | | |
| | 87.7 | | |

TABLE 9

24-Hour Risperidone Release From ATRIGEL ® Implants

| Formulation | Wt. Risperidone salt Injected (mg) | Wt. Risperidone Remaining in Implant (mg) | Wt. % Risperidone Released | AVG. Wt. % Released |
|---|---|---|---|---|
| Group I: 10% Risperidone in 40% 50/50 PLGH (InV 0.36) and 60% NMP | | | | |
| | 7.51 | 6.20 | 17.44 | |
| | 10.19 | 9.26 | 9.15 | |
| | 11.80 | 11.22 | 4.90 | 8.96 ± 5.03 |
| | 10.70 | 10.10 | 5.64 | |
| | 13.74 | 12.69 | 7.69 | |
| Group II: 10% Risperidone in 40% 50/50 PLGH (InV 0.45) and 56% NMP | | | | |
| | 15.60 | 8.59 | 44.97 | |
| | 9.27 | 4.90 | 47.15 | |
| | 10.13 | 6.39 | 36.92 | 28.64 ± 20.30 |
| | 13.30 | 11.76 | 11.62 | |
| | 11.17 | 10.88 | 2.53 | |
| Group III: 10% Risperidone in 35% 50/50 PLGH (InV 0.45) and 65% NMP | | | | |
| | 10.92 | 9.60 | 12.09 | |
| | 13.26 | 12.41 | 6.38 | |
| | 10.40 | 8.16 | 21.49 | 12.93 ± 4.87 |
| | 13.02 | 10.85 | 16.68 | |
| | 17.47 | 14.57 | 16.58 | |

TABLE 9-continued

24-Hour Risperidone Release From ATRIGEL ® Implants

| Formulation | Wt. Risperidone salt Injected (mg) | Wt. Risperidone Remaining in Implant (mg) | Wt. % Risperidone Released | AVG. Wt. % Released |
|---|---|---|---|---|
| Group IV: 10% Risperidone in 45% 50/50 PLGH (InV 0.36) and 55% NMP | | | | |
| | 8.10 | 7.25 | 10.43 | |
| | 13.40 | 12.30 | 8.20 | |
| | 11.11 | 9.16 | 17.58 | 12.79 ± 4.56 |
| | 11.74 | 9.64 | 17.83 | |
| | 11.95 | 10.77 | 9.92 | |
| Group V: 10% Risperidone in 40% 65/35 PLGH (InV 0.37) and 60% NMP | | | | |
| | 10.06 | 9.35 | 7.10 | |
| | 12.53 | 11.70 | 6.60 | |
| | 11.59 | 10.81 | 6.72 | 8.48 ± 2.47 |
| | 13.17 | 11.55 | 12.28 | |
| | 16.71 | 15.09 | 9.71 | |
| Group VI: 10% Risperidone in 45% 65/35 PLGH (InV 0.37) and 55% NMP | | | | |
| | 13.07 | 10.27 | 21.42 | |
| | 12.47 | 7.66 | 38.59 | |
| | 12.62 | 7.60 | 39.74 | 15.25 ± 25.93 |
| | 15.14 | 16.19 | −6.88 | |
| | 13.14 | 15.33 | −16.63 | |
| Group VII: 10% Risperidone in 40% 75/25 PLGH (InV 0.45) and 60% NMP | | | | |
| | 8.71 | 6.16 | 29.31 | |
| | 13.01 | 9.18 | 29.41 | |
| | 9.02 | 6.75 | 25.20 | 21.95 ± 9.25 |
| | 10.47 | 8.55 | 18.32 | |
| | 10.81 | 10.00 | 7.50 | |
| Group VIII: 10% Risperidone in 45% 75/25 PLGH (InV 0.45) and 55% NMP | | | | |
| | 9.10 | 5.76 | 36.66 | |
| | 11.49 | 9.93 | 13.57 | |
| | 11.56 | 8.91 | 22.96 | 15.60 ± 14.75 |
| | 12.69 | 11.99 | 5.52 | |
| | 13.48 | 13.58 | −0.74 | |

TABLE 10

24-Hour Active Risperidone Plasma Concentrations

| Formulation | Total Plasma Concentration (ng/ml) | Mean Plasma Concentration (ng/ml) | Standard Deviation |
|---|---|---|---|
| Group I: 10% Risperidone in 40% 50/50 PLGH (InV 0.36) and 60% NMP | | | |
| | 90.9 | | |
| | 66.3 | | |
| | 65.7 | 78.9 | 12.2 |
| | 82.9 | | |
| | 88.9 | | |
| | 89.3 | | |
| Group II: 10% Risperidone in 40% 50/50 PLGH (InV 0.45) and 56% NMP | | | |
| | 89.3 | | |
| | 74.8 | | |
| | 82.1 | 85.1 | 7.7 |
| | 84.2 | | |
| | 95.2 | | |
| Group III: 10% Risperidone in 35% 50/50 PLGH (InV 0.45) and 65% NMP | | | |
| | 82.3 | | |
| | 80.6 | | |
| | 106.3 | 82.7 | 14.0 |
| | 70.3 | | |
| | 74.2 | | |
| Group IV: 10% Risperidone in 45% 50/50 PLGH (InV 0.36) and 55% NMP | | | |
| | 69.1 | | |
| | 55.9 | | |
| | 52.5 | 57.3 | 6.8 |
| | 52.5 | | |
| | 56.2 | | |
| Group V: 10% Risperidone in 40% 65/35 PLGH (InV 0.37) and 60% NMP | | | |
| | 110.4 | | |
| | 113.8 | | |
| | 59.8 | 91.9 | 23.3 |
| | 99.7 | | |
| | 75.8 | | |
| Group VI: 10% Risperidone in 45% 65/35 PLGH (InV 0.37) and 55% NMP | | | |
| | 62.5 | | |
| | 79.8 | | |
| | 70.4 | 71.6 | 7.5 |
| | 66.9 | | |
| | 78.7 | | |
| Group VII: 10% Risperidone in 40% 75/25 PLGH (InV 0.45) and 60% NMP | | | |
| | 85.2 | | |
| | 95.1 | | |
| | 74.2 | 88.0 | 10.6 |
| | Not available | | |
| | 97.3 | | |
| Group VIII: 10% Risperidone in 45% 75/25 PLGH (InV 0.45) and 55% NMP | | | |
| | 95.6 | | |
| | 80.6 | | |
| | 113.9 | 96.2 | 15.1 |
| | 108.7 | | |
| | 82.2 | | |

The final 24-hour in vivo study (EXAMPLES 1.8) investigated the affect of risperidone loading on the release of risperidone. Risperidone was evaluated at about 15% and about 20% weight percentage. It was found that the weight % of risperidone in the formulation had a significant affect on the 24-hour release (See Table 11). From the eight 24-hour in vivo studies conducted several risperidone/ATRIGEL® formulations were identified for further evaluation over a period of 28-days in the rat.

TABLE 11

24-Hour Risperidone Release From ATRIGEL ® Implants

| Formulation | Wt. Risperidone salt Injected (mg) | Wt. Risperidone Remaining in Implant (mg) | Wt. % Risperidone Released | AVG. Wt. % Released |
|---|---|---|---|---|
| Group I: 15% Risperidone in 38% 65/35 PLGH 0.37, 2% 70/30 PLG/PEG5000 0.79 and 60% NMP | | | | |
| | 15.24 | 13.64 | 10.45 | |
| | 14.22 | 13.74 | 3.40 | |
| | 16.91 | 15.02 | 11.21 | 6.37 ± 4.86 |
| | 17.86 | 16.59 | 7.14 | |
| | 17.91 | 17.97 | −0.32 | |
| Group II: 20% Risperidone in 38% 65/35 PLGH 0.37, 2% 70/30 PLG/PEG5000 0.79 and 60% NMP | | | | |
| | 13.96 | 12.31 | 11.80 | |
| | 32.75 | 28.86 | 11.87 | |
| | 20.83 | 19.47 | 6.54 | 7.33 ± 6.03 |
| | 22.19 | 22.40 | −0.91 | |
| | 27.64 | 28.86 | −4.42 | |

Results and Discussion for the 28-Day Rat Studies

Six 28-Day and one 14-Day rat studies were conducted to evaluate the release of risperidone from ATRIGEL® delivery systems. All formulations were injected into rats subcutaneously. The composition of each test article is summarized in Table 12. Review of these studies indicates a number of findings: Risperidone was stable in ATRIGEL® implants for 28 days. Risperidone plasma levels were detectable up to 28 days in the rat. Two lead formulations consisting of 15% (w/w) risperidone suspended in two ATRIGEL® composition were identified. The two ATRIGEL® compositions are: (1) 45% 65/35 PLGH (InV=0.37 dL/g) and 55% N-methyl-2-pyrrolidone; (2) 25% 85/15 PLGH (InV 0.27 dL/g), 20% 50/50 PLGH (InV 0.36 dL/g) and 55% N-methyl-2-pyrrolidone. These two formulations provided an initial burst of about 10% and nearly zero-order release of risperidone over 28 days based on implant retrieval data. The pharmacokinetic profiles of all Test Articles showed maximum active risperidone plasma levels at 24-hours post dosing, and decreased slowly until Day 28. The plasma active risperidone levels of the two lead formulations remained higher than 15 ng/ml at Day 28. The area under the curve from Day 0 to Day 28 ($AUC_{Day\ 0\text{-}28}$) was proportional to risperidone dosage.

TABLE 12

Summary of 28-Day Risperidone Rat Studies

| Study # | Study duration | Test Article |
|---|---|---|
| EXAMPLE 1.9 | 28 Days | 1. 10% Risperidone suspended in 40% 50/50 PLGH (InV 0.36) and 60% NMP<br>2. 10% Risperidone suspended in 35% 50/50 PLGH (InV 0.45) and 65% NMP<br>3. 10% Risperidone suspended in 40% 65/35 PLGH (InV 0.37) and 60% NMP<br>4. 10% Risperidone suspended in 38% 50/50 PLGH (InV 0.36), 2% 70/30 PLG/PEG5000 (InV 0.79) and 60% NMP<br>5. 10% Risperidone suspended in 33% 50/50 PLGH (InV 0.45), 2% 70/30 PLG/PEG5000 (InV 0.79) and 65% NMP<br>6. 10% Risperidone suspended in 38% 65/35 PLGH (InV 0.37), 2% 70/30 PLG/PEG5000 (InV 0.79) and 60% NMP |
| EXAMPLE 1.10 | 28 Days | 1. 10% Risperidone suspended in 38% 65/35 PLGH (InV 0.37), 2% PEG300 and 60% NMP<br>2. 10% Risperidone suspended in 35% 65/35 PLGH (InV 0.37), 5% PEG300 and 60% NMP<br>3. 10% Risperidone suspended in 35% 65/35 PLGH (InV 0.37), 5% 70/30 PLG/PEG5000 (InV 0.79) and 60% NMP<br>4. 10% Risperidone suspended in 40% 75/25 PLGH (InV 0.45) and 60% NMP<br>5. 10% Risperidone suspended in 38% 75/25 PLGH (InV 0.45), 2% 70/30 PLG/PEG5000 (InV 0.79) and 60% NMP<br>6. 10% Risperidone suspended in 40% 85/15 PLGH (InV 0.27) and 60% NMP |
| EXAMPLE 1.11 | 28 Days | 1. 10% Risperidone suspended in 40% 65/35 PLGH (InV 0.37) and 60% NMP<br>2. 20% Risperidone suspended in 40% 65/35 PLGH (InV 0.37) and 60% NMP<br>3. 25% Risperidone suspended in 40% 65/35 PLGH (InV 0.37) and 60% NMP<br>4. 20% Risperidone suspended in 40% 50/50 PLG (InV 0.33) and 60% NMP<br>5. 25% Risperidone suspended in 40% 50/50 PLG (InV 0.33) and 60% NMP |
| EXAMPLE 1.12 | 14 Days | 1. 15% Risperidone suspended in 38% 65/35 PLGH (InV 0.37) and 62% NMP<br>2. 15% Risperidone suspended in 40% 65/35 PLGH (InV 0.37) and 60% NMP<br>3. 15% Risperidone suspended in 42.5% 65/35 PLGH (InV 0.37) and 57.5% NMP<br>4. 15% Risperidone suspended in 45% 65/35 PLGH (InV 0.37) and 55% NMP<br>5. 15% Risperidone suspended in 45% 75/25 PLGH (InV 0.24) and 55% NMP<br>6. 15% Risperidone suspended in 20% 85/15 PLGH (InV 0.29), 20% 50/50 PLGH (InV 0.36) and 60% NMP<br>7. 15% Risperidone suspended in 40% 65/35 PLGH (InV 0.37), 5% PEG8000-PLG and 55% NMP<br>8. 15% Risperidone suspended in 22.2% 85/15 PLGH (InV 0.27), 17.8% 65/35 PLGH (InV 0.37) and 60% NMP |
| EXAMPLE 1.13 | 28 Days | 1. 15% Risperidone suspended in 40% 65/35 PLGH (InV 0.37) and 60% NMP<br>2. 20% Risperidone suspended in 40% 65/35 PLGH (InV 0.37) and 60% NMP<br>3. 15% Risperidone suspended in 45% 65/35 PLGH (InV 0.37) and 55% NMP<br>4. 20% Risperidone suspended in 45% 65/35 PLGH (InV 0.37) and 55% NMP<br>5. 20% Risperidone suspended in 20% 85/15 PLGH (InV 0.27), 20% 50/50 PLGH (InV 0.36) and 60% NMP |

Example 1.9

Figure 3:
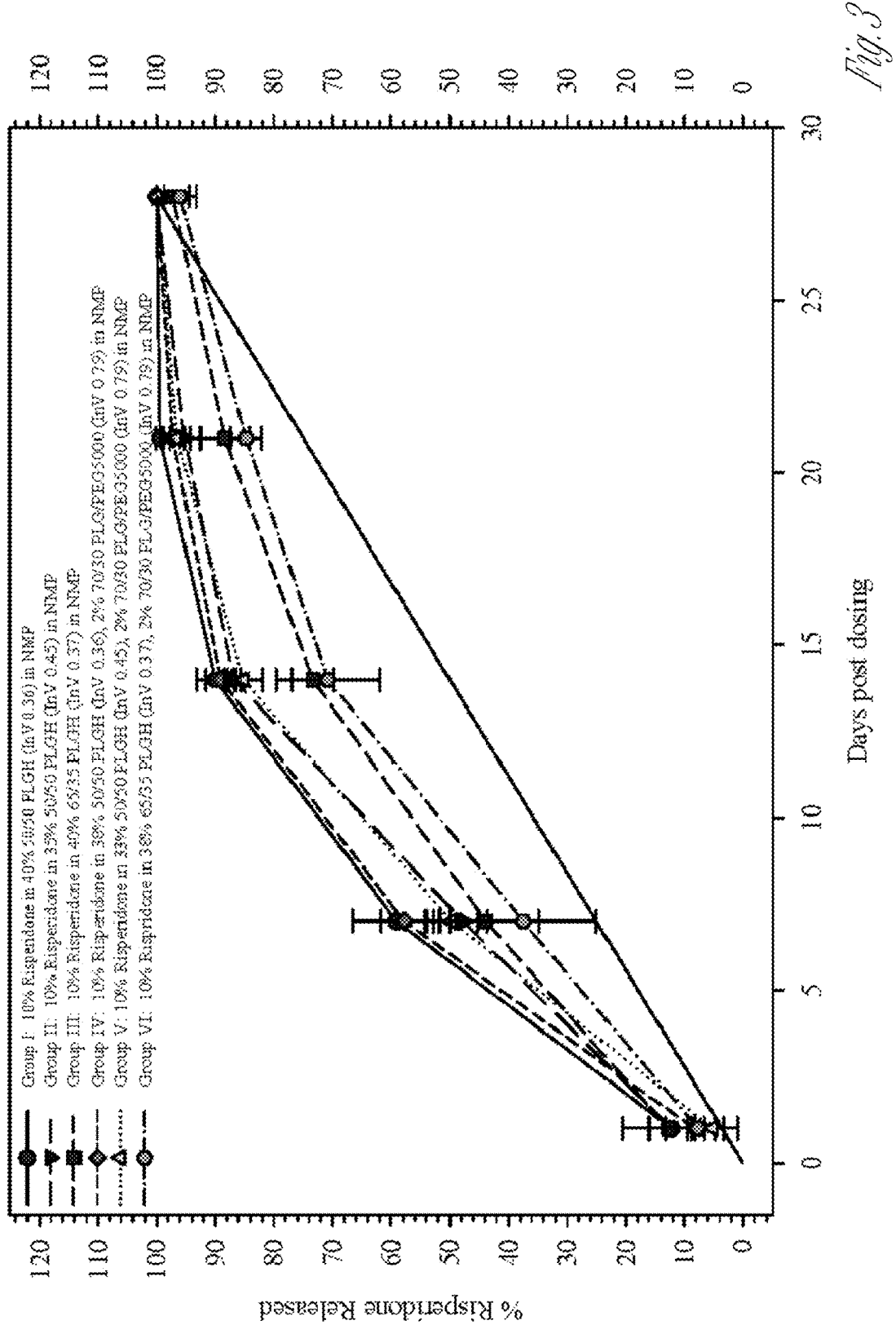
FIG. 3 illustrates the 28-day release of risperidone from selected ATRIGEL® formulations in rats.
Figure 4:
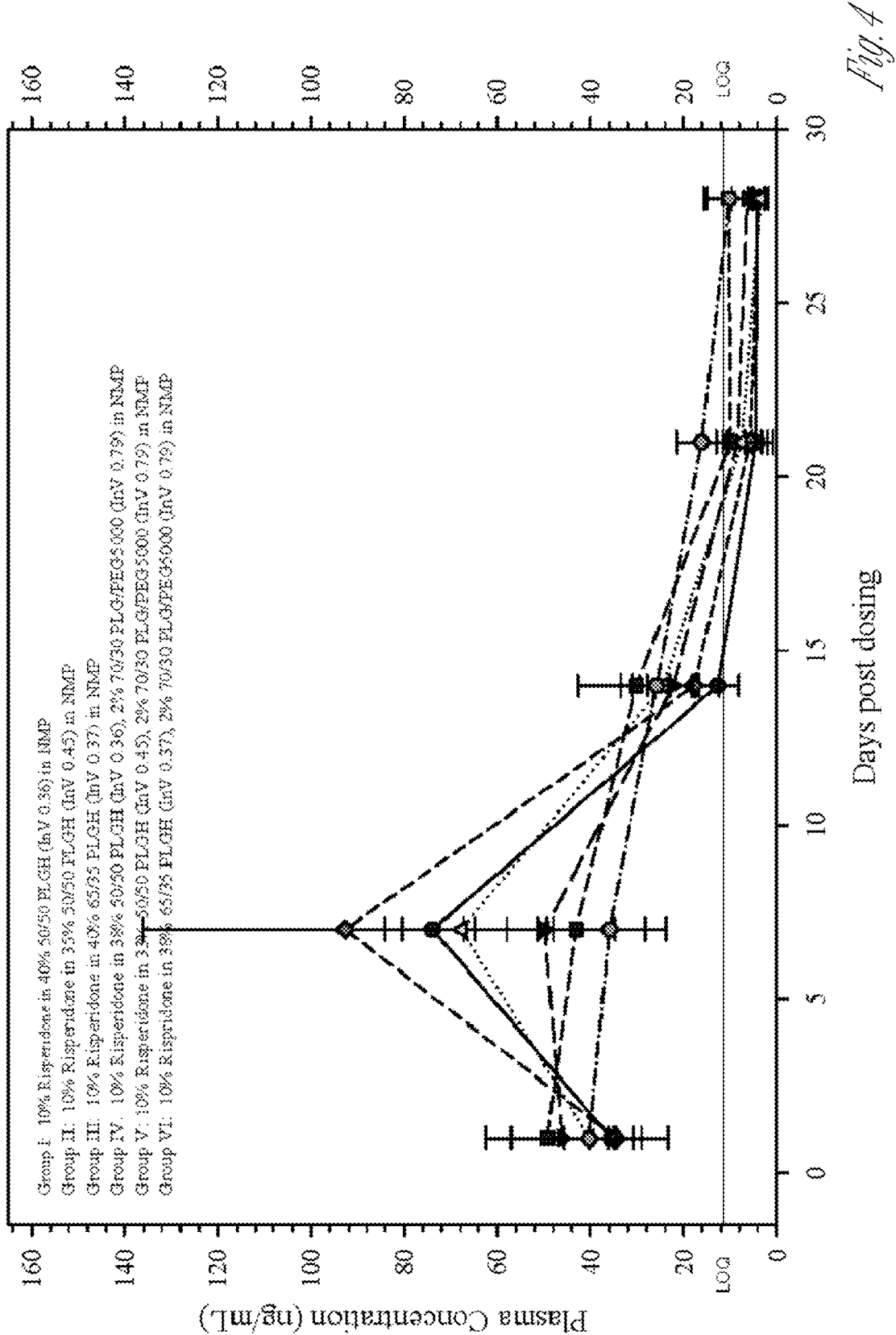
FIG. 4 illustrates the 28-day plasma concentration of active risperidone in rats.

The 28-Day release kinetics and pharmacokinetics of six ATRIGEL®/risperidone formulations containing 10% risperidone were determined in this study. Six ATRIGEL® delivery vehicles prepared with different polymers were compared. The implant retrieval results are summarized in Table 13 and the release profiles are depicted in FIG. 3. The mean active risperidone plasma concentrations are provided in Table 14 and illustrated in FIG. 4.

TABLE 13

28-Day Risperidone Release From ATRIGEL ® Implants

| Test Article | Time Point | % Released | Mean % Released | Standard Deviation |
|---|---|---|---|---|
| Group I: 10% Risperidone in 40% 50/50 PLGH (InV 0.36)/60% NMP | Day 1 | 19.0 | 12.1 | 4.0 |
| | | 10.7 | | |
| | | 9.4 | | |
| | | 12.0 | | |
| | | 9.5 | | |
| | Day 7 | 56.1 | 59.1 | 7.6 |
| | | 61.8 | | |
| | | 62.6 | | |
| | | 47.6 | | |
| | | 67.3 | | |
| | Day 14 | 89.1 | 90.0 | 3.2 |
| | | 91.4 | | |
| | | 91.4 | | |
| | | 93.2 | | |
| | | 84.8 | | |
| | Day 21 | 98.8 | 99.4 | 0.6 |
| | | 100.1 | | |
| | | 99.0 | | |
| | | 99.1 | | |
| | | 100.1 | | |
| | Day 28 | 100.0 | 100.0 | 0.0 |
| | | 100.0 | | |
| | | 100.0 | | |
| | | 100.0 | | |
| | | 100.0 | | |
| Group II: 10% Risperidone in 35%50/50 PLGH (InV 0.45)/65% NMP | Day 1 | 18.4 | 12.3 | 3.6 |
| | | 11.4 | | |
| | | 8.9 | | |
| | | 11.7 | | |
| | | 10.9 | | |
| | Day 7 | 45.0 | 47.7 | 4.1 |
| | | 52.4 | | |
| | | 49.0 | | |
| | | 50.1 | | |
| | | 42.1 | | |
| | Day 14 | 85.1 | 86.8 | 1.1 |
| | | 86.2 | | |
| | | 87.5 | | |
| | | 87.8 | | |
| | | 87.3 | | |
| | Day 21 | 97.3 | 95.2 | 2.5 |
| | | 96.5 | | |
| | | 97.1 | | |
| | | 91.5 | | |
| | | 93.8 | | |
| | Day 28 | 100.0 | 100.0 | 0.0 |
| | | 100.0 | | |
| | | 100.0 | | |
| | | 100.0 | | |
| | | 100.0 | | |
| Group III: 10% Risperidone in 40% 65/35 PLGH (InV 0.37)/60% NMP | Day 1 | 22.3 | 11.8 | 7.1 |
| | | 12.3 | | |
| | | 8.1 | | |
| | | 13.2 | | |
| | | 3.0 | | |
| | Day 7 | 57.1 | 42.2 | 8.6 |
| | | 41.4 | | |
| | | 35.8 | | |
| | | 38.1 | | |
| | | 38.7 | | |
| | Day 14 | 69.1 | 73.0 | 3.2 |
| | | 76.5 | | |
| | | 72.0 | | |
| | | 76.0 | | |
| | | 71.7 | | |
| | Day 21 | 89.0 | 88.1 | 3.6 |
| | | 86.5 | | |
| | | 87.3 | | |
| | | 93.7 | | |
| | | 84.1 | | |
| | Day 28 | 93.6 | 96.0 | 3.6 |
| | | 100.0 | | |
| | | 91.1 | | |
| | | 97.3 | | |
| | | 98.0 | | |
| Group IV: 10% Risperidone in 38% 50/50 PLGH (InV 0.36) + 20% 70/30 PLG/PEG5000 (InV 0.79)/60% NMP | Day 1 | 16.4 | 8.3 | 4.9 |
| | | 6.1 | | |
| | | 7.3 | | |
| | | 8.3 | | |
| | | 3.3 | | |
| | Day 7 | 58.0 | 57.8 | 3.9 |
| | | 64.1 | | |
| | | 54.2 | | |
| | | 57.7 | | |
| | | 54.8 | | |
| | Day 14 | 93.2 | 89.0 | 2.6 |
| | | 89.0 | | |
| | | 87.5 | | |
| | | 86.2 | | |
| | | 89.1 | | |
| | Day 21 | 98.5 | 97.2 | 1.9 |
| | | 93.9 | | |
| | | 98.2 | | |
| | | 97.2 | | |
| | | 98.3 | | |
| | Day 28 | 100.0 | 100.0 | 0.0 |
| | | 100.0 | | |
| | | 100.0 | | |
| | | 100.0 | | |
| | | 100.0 | | |
| Group V: 10% Risperidone in 33% 50/50 PLGH (InV 0.45) + 2% 70/30 PLG/PEG5000 (InV 0.79)/65% NMP | Day 1 | 10.7 | 5.2 | 4.2 |
| | | 7.3 | | |
| | | 4.4 | | |
| | | 4.4 | | |
| | | −0.8 | | |
| | Day 7 | 48.8 | 49.7 | 4.5 |
| | | 43.9 | | |
| | | 54.4 | | |
| | | 47.3 | | |
| | | 54.2 | | |
| | Day 14 | 85.0 | 85.2 | 3.3 |
| | | 89.5 | | |
| | | 84.9 | | |
| | | 86.0 | | |
| | | 80.4 | | |
| | Day 21 | 92.9 | 96.5 | 2.2 |
| | | 96.0 | | |
| | | 98.1 | | |
| | | 96.9 | | |
| | | 98.6 | | |
| | Day 28 | 100.0 | 100.0 | 0.0 |
| | | 100.0 | | |
| | | 100.0 | | |
| | | 100.0 | | |
| | | 100.0 | | |
| Group VI: 10% Risperidone in 38% 65/35 PLGH (InV 0.37) + 2% 70/30 PLG/PEG5000 (InV 0.79)/60% NMP | Day 1 | −26.8 | 7.7 | 18.0 |
| | | −29.0 | | |
| | | 6.9 | | |
| | | 8.4 | | |
| | | −4.5 | | |
| | Day 7 | 43.8 | 37.5 | 12.5 |
| | | 56.1 | | |
| | | 32.4 | | |
| | | 24.6 | | |
| | | 30.7 | | |

TABLE 13-continued

28-Day Risperidone Release From ATRIGEL ® Implants

| Test Article | Time Point | % Released | Mean % Released | Standard Deviation |
|---|---|---|---|---|
| | Day 14 | 63.5 | 70.7 | 8.8 |
| | | 84.9 | | |
| | | 64.8 | | |
| | | 66.7 | | |
| | | 73.8 | | |
| | Day 21 | 87.8 | 84.8 | 2.6 |
| | | 84.1 | | |
| | | 83.3 | | |
| | | 81.6 | | |
| | | 87.1 | | |
| | Day 28 | 95.1 | 96.0 | 2.7 |
| | | 92.7 | | |
| | | 100.0 | | |
| | | 95.2 | | |
| | | 96.9 | | |

TABLE 14

28-Day Active Risperidone Plasma Concentrations

| Test Article | Time Point | Plasma Concentration ng/ml | Mean Concentration ng/ml | Standard Deviation |
|---|---|---|---|---|
| Group I: 10% Risperidone in 40% 50/50 PLGH (InV 0.36)/NMP | Day 1 | 40.0 | 35.5 | 4.7 |
| | | 41.2 | | |
| | | 31.7 | | |
| | | 33.0 | | |
| | | 31.7 | | |
| | Day 7 | 75.0 | 73.9 | 6.6 |
| | | 81.2 | | |
| | | 71.4 | | |
| | | 78.2 | | |
| | | 64.0 | | |
| | Day 14 | 15.1 | 12.7 | 4.6 |
| | | 9.6 | | |
| | | 19.2 | | |
| | | 7.4 | | |
| | | 12.3 | | |
| | Day 21 | 3.5 | 4.4 | 2.3 |
| | | N/A | | |
| | | 6.3 | | |
| | | 6.2 | | |
| | | 1.5 | | |
| | Day 28 | 3.9 | 4.0 | 2.1 |
| | | 2.0 | | |
| | | 6.2 | | |
| | | NDL* | | |
| | | NDL* | | |
| Group II: 10% Risperidone in 35% 50/50 PLGH (InV 0.45)/NMP | Day 1 | 56.9 | 46.1 | 11.0 |
| | | 54.3 | | |
| | | 30.6 | | |
| | | 39.1 | | |
| | | 49.6 | | |
| | Day 7 | 47.0 | 49.8 | 15.0 |
| | | 67.3 | | |
| | | 28.7 | | |
| | | 60.7 | | |
| | | 45.4 | | |
| | Day 14 | 22.2 | 22.2 | 5.5 |
| | | 27.8 | | |
| | | 22.4 | | |
| | | 25.5 | | |
| | | 13.3 | | |
| | Day 21 | 12.3 | 8.4 | 3.2 |
| | | 7.2 | | |
| | | 4.7 | | |
| | | 6.8 | | |
| | | 11.0 | | |
| | Day 28 | 5.7 | 6.2 | 3.5 |
| | | 10.0 | | |
| | | 3.0 | | |
| | | NDL* | | |
| | | NDL* | | |
| Group III: 10% 40% 65/35 PLGH | Day 1 | 46.0 | 49.3 | 13.1 |
| | | 60.8 | | |
| | | 33.8 | | |
| | | 64.7 | | |
| | | 41.4 | | |
| | Day 7 | 31.7 | 43.1 | 14.9 |
| | | 36.5 | | |
| | | 32.3 | | |
| | | 47.7 | | |
| | | 67.2 | | |
| | Day 14 | 30.5 | 30.1 | 12.6 |
| | | 18.9 | | |
| | | 25.7 | | |
| | | 23.9 | | |
| | | 51.4 | | |
| | Day 21 | 7.4 | 9.9 | 3.1 |
| | | 14.5 | | |
| | | 7.3 | | |
| | | 8.7 | | |
| | | 11.5 | | |
| | Day 28 | 17.2 | 10.4 | 5.2 |
| | | 3.6 | | |
| | | 12.9 | | |
| | | 10.7 | | |
| | | 7.6 | | |
| Group IV: 10% 50/50 PLGH (InV PLG/PEG5000 (InV | Day 1 | 29.9 | 34.5 | 5.5 |
| | | 33.2 | | |
| | | 44.0 | | |
| | | 31.7 | | |
| | | 34.0 | | |
| | Day 7 | 64.6 | 92.7 | 43.4 |
| | | 41.8 | | |
| | | 155.6 | | |
| | | 94.9 | | |
| | | 106.4 | | |
| | Day 14 | 12.2 | 17.7 | 5.3 |
| | | 18.9 | | |
| | | 12.7 | | |
| | | 24.8 | | |
| | | 19.9 | | |
| | Day 21 | 1.5 | 5.6 | 4.7 |
| | | 5.2 | | |
| | | 13.3 | | |
| | | 6.1 | | |
| | | 2.2 | | |
| | Day 28 | 3.7 | 3.7 | 0 |
| | | NDL* | | |
| | | NDL* | | |
| | | NDL* | | |
| | | NDL* | | |
| Group V: 10% 50/50 PLGH (InV PLG/PEG5000 (InV | Day 1 | 35.0 | 40.2 | 16.8 |
| | | 69.2 | | |
| | | 38.8 | | |
| | | 29.1 | | |
| | | 28.7 | | |
| | Day 7 | 55.7 | 67.7 | 16.4 |
| | | 47.5 | | |
| | | 86.3 | | |
| | | 68.2 | | |
| | | 80.9 | | |
| | Day 14 | 21.8 | 24.4 | 6.5 |
| | | 22.9 | | |
| | | 26.4 | | |
| | | 16.8 | | |
| | | 34.3 | | |
| | Day 21 | 8.0 | 7.4 | 4.2 |
| | | 6.1 | | |
| | | 8.7 | | |
| | | 12.7 | | |
| | | 1.3 | | |

TABLE 14-continued

28-Day Active Risperidone Plasma Concentrations

| Test Article | Time Point | Plasma Concentration ng/ml | Mean Concentration ng/ml | Standard Deviation |
|---|---|---|---|---|
| | Day 28 | 3.2 | 3.4 | 1.5 |
| | | NDL* | | |
| | | NDL* | | |
| | | 2.0 | | |
| | | 5.0 | | |
| Group VI: 10% 65/35 PLGH (InV 70/30 PLG/PEG5000 (InV NMP | Day 1 | 49.7 | 36.0 | 5.6 |
| | | 40.1 | | |
| | | 35.8 | | |
| | | 36.2 | | |
| | | 39.3 | | |
| | Day 7 | 28.9 | 35.9 | 12.1 |
| | | 32.3 | | |
| | | 34.9 | | |
| | | 26.7 | | |
| | | 56.9 | | |
| | Day 14 | 25.0 | 25.8 | 7.7 |
| | | 16.1 | | |
| | | 20.8 | | |
| | | 33.0 | | |
| | | 34.0 | | |
| | Day 21 | 9.9 | 16.1 | 5.4 |
| | | 22.0 | | |
| | | 16.5 | | |
| | | 11.2 | | |
| | | 20.6 | | |
| | Day 28 | 6.4 | 10.2 | 4.8 |
| | | 8.3 | | |
| | | 8.4 | | |
| | | 18.6 | | |
| | | 9.1 | | |

*NDL: No Detectable levels of risperidone or 9-hydroxyrisperidone.

Tissue macroscopic evaluations showed minimal skin irritation in all groups for 28 days. Implants were found to be firm and non-fragmenting when retrieved from rats at time points 1, 4, 7, 14, 21, and 28 days post dosing.

This implant retrieval study showed that all formulations released risperidone 5.2% to 12.3% 24-hour post injection, and released risperidone through day 14 (70-90%). Plasma risperidone results from days 21 and 28 were significantly less. Plasma levels of active risperidone diminished to less than 10 ng/mL at day 28 which may be unacceptable.

In conclusion, risperidone/ATRIGEL® formulations prepared with 50/50 PLGH (InV 0.36) polymers released risperidone more quickly than 65/35 PLGH (InV 0.37). Formulations prepared with 65/35 PLGH (InV 0.37)/N-methyl-2-pyrrolidone showed the most promising risperidone release over 28 days. Addition of 2% 70/30 PLG/PEG5000 (InV 0.79) in ATRIGEL® reduced the initial burst.

Example 1.10

Figure 5:
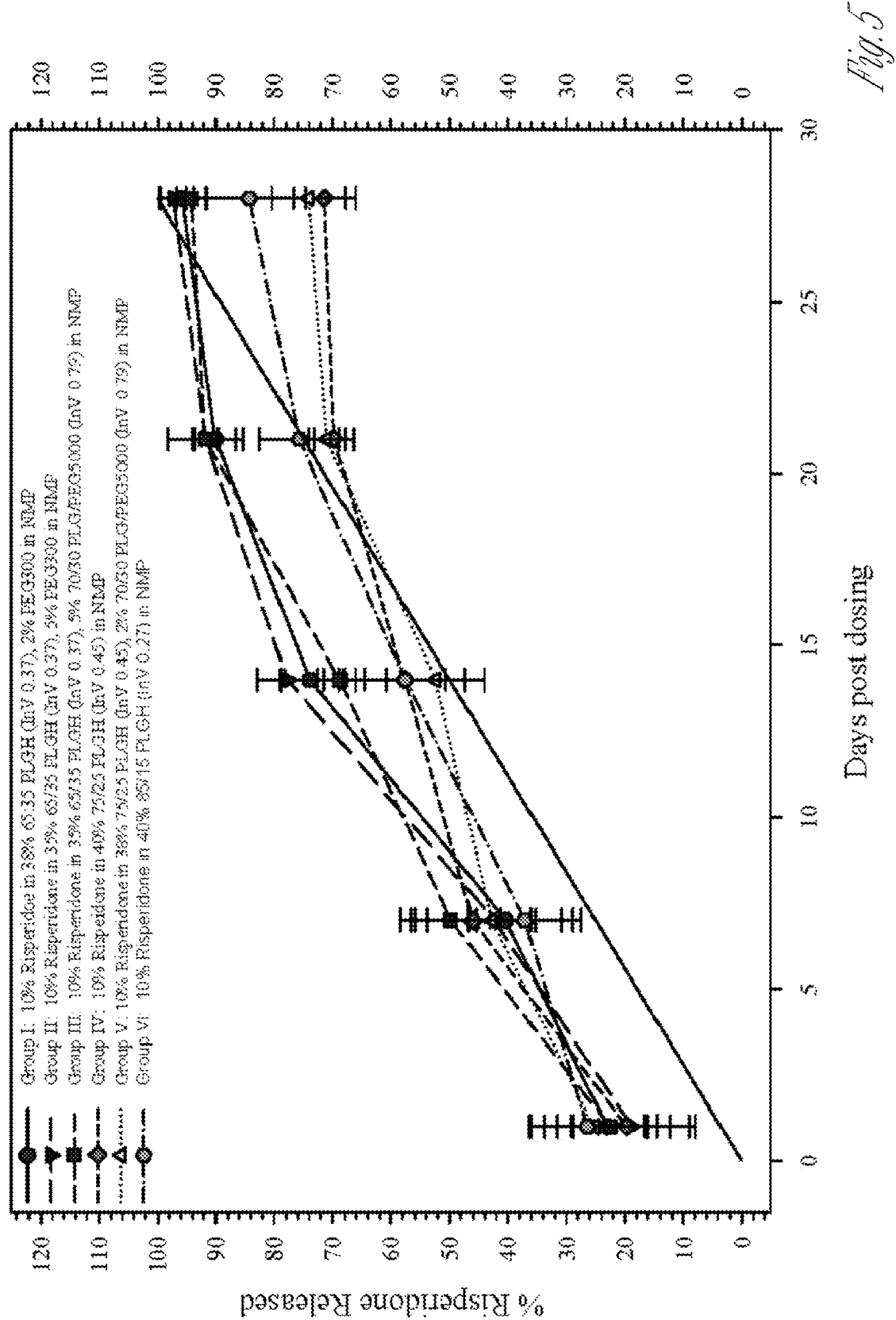
FIG. 5 illustrates the 28-day release of risperidone from selected ATRIGEL® formulations in rats.
Figure 6:
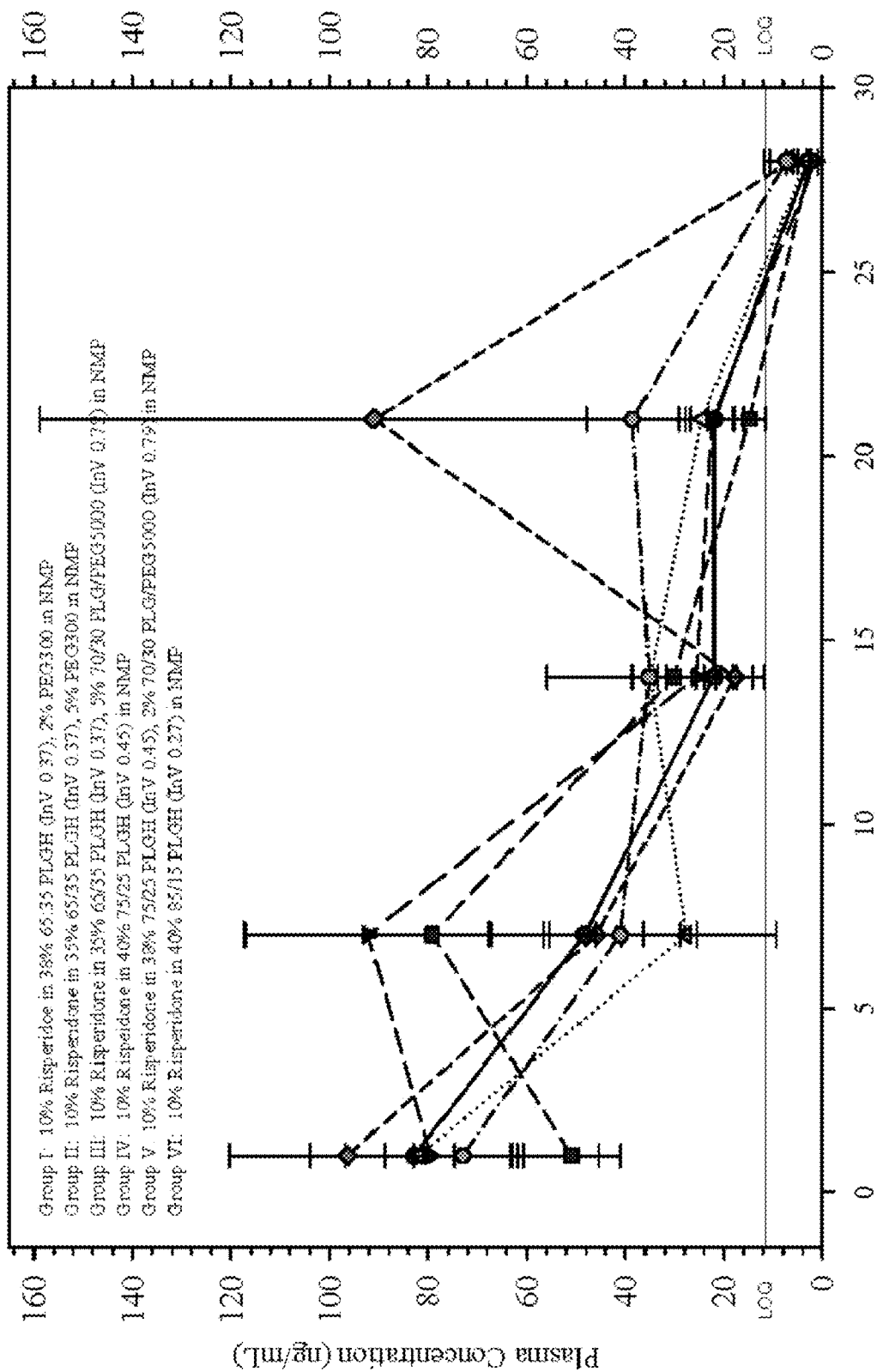
FIG. 6 illustrates the 28-day plasma concentration of active risperidone in rats.

This 28-Day release kinetics and pharmacokinetics study was designed to further investigate the role of polymers in the risperidone release control. Six ATRIGEL®/Risperidone formulations containing 10% risperidone were examined in this study. The first three formulations were focused on 65/35 PLGH (InV 0.37) based on the results of EXAMPLE 1.9. The implant retrieval results were summarized in Table 15 and the release profiles were depicted in FIG. 5. The mean active risperidone plasma concentrations were provided in Table 16 and illustrated in FIG. 6.

TABLE 15

28-Day Risperidone Release From ATRIGEL® Implants

| Test Article | Time Point | % Released | Mean % Released | Standard Deviation |
|---|---|---|---|---|
| Group I: 10% risperidone in 38% 65/35 PLGH (InV 0.37) + 2% PEG300/NMP | Day 1 | 36.0 | 23.1 | 10.7 |
| | | 17.6 | | |
| | | 19.1 | | |
| | | 32.3 | | |
| | | 10.3 | | |
| | Day 7 | 40.2 | 40.4 | 5.1 |
| | | 41.2 | | |
| | | 46.1 | | |
| | | 32.3 | | |
| | | 42.1 | | |
| | Day 14 | 68.4 | 73.9 | 5.0 |
| | | 76.4 | | |
| | | 68.5 | | |
| | | 77.0 | | |
| | | 78.9 | | |
| | Day 21 | 89.7 | 90.1 | 3.5 |
| | | 92.0 | | |
| | | 95.0 | | |
| | | 87.1 | | |
| | | 86.6 | | |
| | Day 28 | 97.8 | 95.8 | 4.1 |
| | | 88.9 | | |
| | | 95.8 | | |
| | | 96.9 | | |
| | | 99.3 | | |
| Group II: 10% risperidone in 35% 65/35 PLGH (InV 0.37) + 5% PEG300/NMP | Day 1 | 21.5 | 18.8 | 9.9 |
| | | 35.1 | | |
| | | 13.5 | | |
| | | 10.8 | | |
| | | 13.4 | | |
| | Day 7 | 45.4 | 42.4 | 11.5 |
| | | 54.4 | | |
| | | 38.1 | | |
| | | 49.2 | | |
| | | 24.7 | | |
| | Day 14 | 68.7 | 77.7 | 5.2 |
| | | 79.6 | | |
| | | 80.7 | | |
| | | 81.2 | | |
| | | 78.4 | | |
| | Day 21 | 81.9 | 91.8 | 6.4 |
| | | 96.6 | | |
| | | 98.4 | | |
| | | 91.4 | | |
| | | 90.6 | | |
| | Day 28 | 99.0 | 97.3 | 2.2 |
| | | 97.8 | | |
| | | 94.1 | | |
| | | 96.0 | | |
| | | 99.5 | | |
| Group III: 10% Risperidone in 35% 65/35 PLGH (InV 0.37) + 5% 70/30 PLG/PEG5000 (InV 0.79)/NMP | Day 1 | 25.8 | 22.6 | 6.5 |
| | | 30.3 | | |
| | | 24.1 | | |
| | | 19.6 | | |
| | | 13.2 | | |
| | Day 7 | 58.2 | 42.4 | 9.0 |
| | | 41.4 | | |
| | | 35.8 | | |
| | | 38.1 | | |
| | | 38.7 | | |
| | Day 14 | 71.8 | 70.3 | 4.0 |
| | | 68.5 | | |
| | | 76.1 | | |
| | | 65.4 | | |
| | | 69.6 | | |
| | Day 21 | 90.3 | 91.4 | 2.1 |
| | | 93.1 | | |
| | | 89.7 | | |
| | | 89.8 | | |
| | | 94.2 | | |
| | Day 28 | 92.8 | 93.6 | 2.5 |
| | | 91.1 | | |
| | | 91.6 | | |
| | | 96.5 | | |
| | | 96.1 | | |

TABLE 15-continued

28-Day Risperidone Release From ATRIGEL ® Implants

| Test Article | Time Point | % Released | Mean % Released | Standard Deviation |
|---|---|---|---|---|
| Group IV: 10% Risperidone in 40% 75/25 PLGH (InV 0.45)/NMP | Day 1 | 38.1 | 19.7 | 11.8 |
| | | 22.7 | | |
| | | 18.1 | | |
| | | 12.2 | | |
| | | 7.4 | | |
| | Day 7 | 62.7 | 46.0 | 9.9 |
| | | 46.8 | | |
| | | 41.2 | | |
| | | 42.4 | | |
| | | 37.2 | | |
| | Day 14 | 67.3 | 57.7 | 10.4 |
| | | 65.3 | | |
| | | 62.8 | | |
| | | 47.7 | | |
| | | 45.2 | | |
| | Day 21 | 71.0 | 69.8 | 3.3 |
| | | 71.9 | | |
| | | 72.1 | | |
| | | 64.0 | | |
| | | 69.7 | | |
| | Day 28 | 80.1 | 71.4 | 5.3 |
| | | 71.9 | | |
| | | 65.9 | | |
| | | 69.6 | | |
| | | 69.6 | | |
| Group V: 10% risperidone in 38% 75/25 PLGH (InV 0.45) + 2% 70/30 PLG/PEG5000/NMP | Day 1 | 35.7 | 25.3 | 10.8 |
| | | 21.0 | | |
| | | 32.1 | | |
| | | 29.0 | | |
| | | 8.5 | | |
| | Day 7 | 51.4 | 42.8 | 13.9 |
| | | 44.7 | | |
| | | 59.3 | | |
| | | 34.2 | | |
| | | 24.2 | | |
| | Day 14 | 66.0 | 52.4 | 8.4 |
| | | 47.6 | | |
| | | 54.7 | | |
| | | 48.9 | | |
| | | 44.9 | | |
| | Day 21 | 75.4 | 71.0 | 3.1 |
| | | 72.4 | | |
| | | 70.9 | | |
| | | 67.4 | | |
| | | 69.0 | | |
| | Day 28 | 74.7 | 74.1 | 6.3 |
| | | 84.6 | | |
| | | 71.4 | | |
| | | 70.9 | | |
| | | 68.8 | | |
| Group VI: 10% Risperidone in 40% 85/15 PLGH (InV 0.27)/NMP | Day 1 | 36.1 | 16.2 | 9.8 |
| | | 28.0 | | |
| | | 15.8 | | |
| | | 16.6 | | |
| | | 35.4 | | |
| | Day 7 | 35.6 | 37.1 | 9.6 |
| | | 41.9 | | |
| | | 35.2 | | |
| | | 49.4 | | |
| | | 23.4 | | |
| | Day 14 | NA | 57.6 | 6.9 |
| | | 54.1 | | |
| | | 50.2 | | |
| | | 66.0 | | |
| | | 60.1 | | |
| | Day 21 | 86.3 | 75.7 | 6.8 |
| | | 73.3 | | |
| | | 77.1 | | |
| | | 67.6 | | |
| | | 74.2 | | |
| | Day 28 | 78.4 | 84.2 | 9.5 |
| | | 92.5 | | |
| | | 94.9 | | |
| | | 83.2 | | |
| | | 72.1 | | |

TABLE 16

28-Day Active Risperidone Plasma Concentrations

| Test Article | Time Point | Plasma Concentration ng/ml | Mean Concentration ng/ml | Standard Deviation |
|---|---|---|---|---|
| Group I: 10% Risperidone in 38% 65/35 PLGH (InV 0.37) + 2% PEG 300/NMP | Day 1 | 56.9 | 82.8 | 37.4 |
| | | 53.2 | | |
| | | 142.9 | | |
| | | 95.3 | | |
| | | 66.0 | | |
| | Day 7 | 29.2 | 48.2 | 19.4 |
| | | 41.5 | | |
| | | 80.7 | | |
| | | 47.5 | | |
| | | 41.9 | | |
| | Day 14 | 21.1 | 21.9 | 3.7 |
| | | 15.9 | | |
| | | 24.8 | | |
| | | 24.0 | | |
| | | 24.0 | | |
| | Day 21 | 14.8 | 21.9 | 5.9 |
| | | 18.0 | | |
| | | 21.1 | | |
| | | 27.4 | | |
| | | 28.4 | | |
| | Day 28 | 3.9 | 3.0 | 2.1 |
| | | — | | |
| | | 4.2 | | |
| | | 4.1 | | |
| | | −0.1 | | |
| Group II: 10% Risperidone in 35% 65/35 PLGH (InV 0.37) + 5% PEG 300/NMP | Day 1 | 75.4 | 79.4 | 17.4 |
| | | 106.3 | | |
| | | 81.3 | | |
| | | 58.2 | | |
| | | 75.6 | | |
| | Day 7 | 64.9 | 92.2 | 25.0 |
| | | 78.4 | | |
| | | 93.1 | | |
| | | 131.7 | | |
| | | 92.7 | | |
| | Day 14 | — | 25.5 | 8.0 |
| | | 25.8 | | |
| | | 26.4 | | |
| | | 15.1 | | |
| | | 34.6 | | |
| | Day 21 | 21.1 | 22.3 | 4.4 |
| | | 16.9 | | |
| | | 24.2 | | |
| | | 27.2 | | |
| | | — | | |
| | Day 28 | 4.2 | 1.4 | 1.8 |
| | | −0.4 | | |
| | | 0.9 | | |
| | | 2.0 | | |
| | | 0.5 | | |
| Group III: 10% Risperidone in 35% 65/35 PLGH (InV 0.37) + 5% 70/30 PLG/PEG5000 (InV 0.79)/NMP | Day 1 | 37.7 | 50.8 | 9.9 |
| | | 56.1 | | |
| | | 52.2 | | |
| | | 63.3 | | |
| | Day 7 | 31.1 | 79.1 | 38.4 |
| | | 53.3 | | |
| | | 101.8 | | |

TABLE 16-continued

28-Day Active Risperidone Plasma Concentrations

| Test Article | Time Point | Plasma Concentration ng/ml | Mean Concentration ng/ml | Standard Deviation |
|---|---|---|---|---|
| | | 128.2 | | |
| | | 81.0 | | |
| | Day 14 | 22.4 | 30.1 | 8.5 |
| | | 26.9 | | |
| | | 23.3 | | |
| | | 36.9 | | |
| | | 41.3 | | |
| | Day 21 | 19.2 | 14.8 | 3.4 |
| | | 11.0 | | |
| | | 14.6 | | |
| | | 12.2 | | |
| | | 16.9 | | |
| | Day 28 | −0.1 | 2.5 | 3.5 |
| | | 3.4 | | |
| | | −1.5 | | |
| | | 7.4 | | |
| | | 3.0 | | |
| Group IV: 10% Risperidone in 40% 75/25 PLGH (InV 0.45)/NMP | Day 1 | 96.4 | 96.4 | 7.7 |
| | | 103.9 | | |
| | | 91.8 | | |
| | | 103.8 | | |
| | | 86.3 | | |
| | Day 7 | 36.6 | 45.8 | 9.6 |
| | | 37.4 | | |
| | | 58.5 | | |
| | | 43.5 | | |
| | | 52.8 | | |
| | Day 14 | 12.1 | 17.8 | 6.1 |
| | | 20.3 | | |
| | | 13.0 | | |
| | | 16.3 | | |
| | | 27.1 | | |
| | Day 21 | 207.0 | 91.0 | 67.9 |
| | | 83.1 | | |
| | | 36.9 | | |
| | | 80.3 | | |
| | | 47.5 | | |
| | Day 28 | 2.3 | 6.5 | 4.1 |
| | | 10.1 | | |
| | | 11.4 | | |
| | | 5.0 | | |
| | | 3.5 | | |
| Group V: 10% Risperidone in 38% 75/25 PLGH (InV 0.45) + 2% 70/30PLG/PEG5000 (InV 0.79)/NMP | Day 1 | 74.4 | 81.8 | 7.0 |
| | | 82.9 | | |
| | | 86.1 | | |
| | | 75.0 | | |
| | | 90.5 | | |
| | Day 7 | 9.7 | 27.6 | 18.4 |
| | | 11.4 | | |
| | | 44.4 | | |
| | | 23.3 | | |
| | | 49.4 | | |
| | Day 14 | 12.8 | 35.0 | 20.9 |
| | | 19.5 | | |
| | | 61.1 | | |
| | | 52.2 | | |
| | | 29.2 | | |
| | Day 21 | 44.8 | 24.4 | 12.9 |
| | | 12.3 | | |
| | | 29.1 | | |
| | | 18.2 | | |
| | | 17.7 | | |
| | Day 28 | −1.7 | 3.3 | 4.2 |
| | | 3.1 | | |
| | | 0.8 | | |
| | | 5.0 | | |
| | | 9.2 | | |
| Group VI: 10% Risperidone in 40% 85/15 PLGH (InV 0.27)/NMP | Day 1 | 62.4 | 68.8 | 9.9 |
| | | 87.8 | | |
| | | 71.4 | | |
| | | 66.2 | | |
| | | 77.1 | | |
| | Day 7 | 41.4 | 41.0 | 15.6 |
| | | 64.8 | | |
| | | 29.0 | | |
| | | 25.1 | | |
| | | 44.5 | | |
| | Day 14 | — | 35.1 | 3.3 |
| | | 36.0 | | |
| | | 30.9 | | |
| | | 34.7 | | |
| | | 38.7 | | |
| | Day 21 | 34.2 | 38.5 | 9.4 |
| | | 36.8 | | |
| | | 26.2 | | |
| | | 45.1 | | |
| | | 50.2 | | |
| | Day 28 | 0.7 | 7.2 | 4.5 |
| | | 5.0 | | |
| | | 12.7 | | |
| | | 8.3 | | |
| | | 9.2 | | |

Tissue macroscopic evaluations showed minimal skin irritation in all groups for 28 days. Implants were found to be firm and non-fragmenting when retrieved from rats at 1, 4, 7, 14, 21, and 28 days post dosing.

The implant retrieval study showed the initial risperidone release of all formulations ranged from 18-26% and released 50-75% of the risperidone dose at day 14. Risperidone release at day 28 ranged from 71-98% of total dose. Plasma concentration of active risperidone at day 1 ranged from 50-96 ng/ml and was less than 10 ng/mL at day 28 for all groups.

The addition of PEG 300 or 5% 70/30 PLG/PEG5000 (InV 0.79) to the 65/35 PLGH (InV 0.37) based ATRIGEL® delivery system increased the 24-hour burst of risperidone as compared with EXAMPLE 1.9, but had no affect on the release rate after initial burst (Group I, II, and III). The 75/25 PLGH (InV 0.45) and 85/15 PLGH (InV 0.27) polymers did not demonstrate a 10% initial burst, but did afford a linear and slow risperidone release.

Example 1.11

Figure 7:
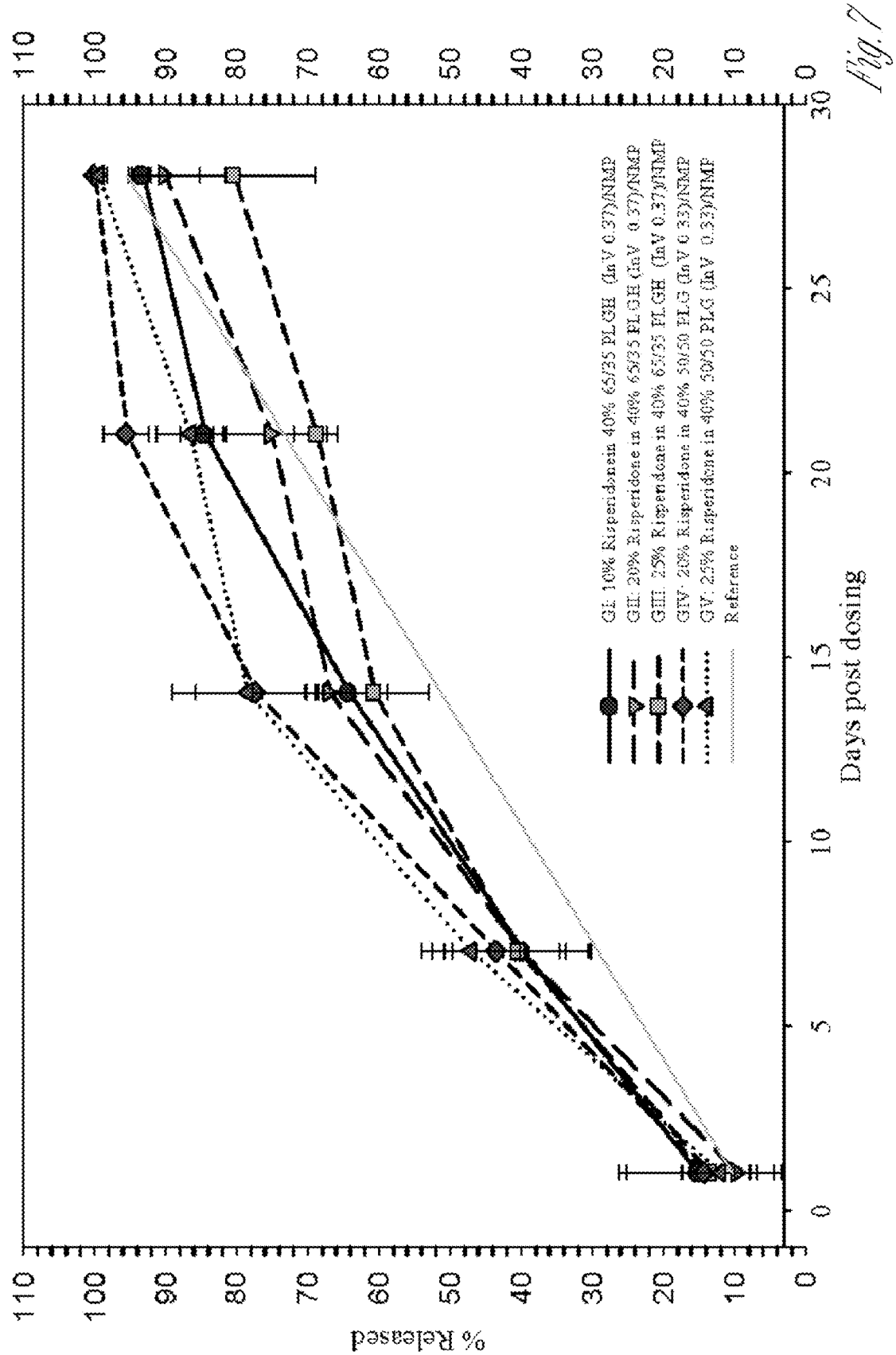
FIG. 7 illustrates the 28-day release of risperidone from selected ATRIGEL® formulations in rats.
Figure 8:
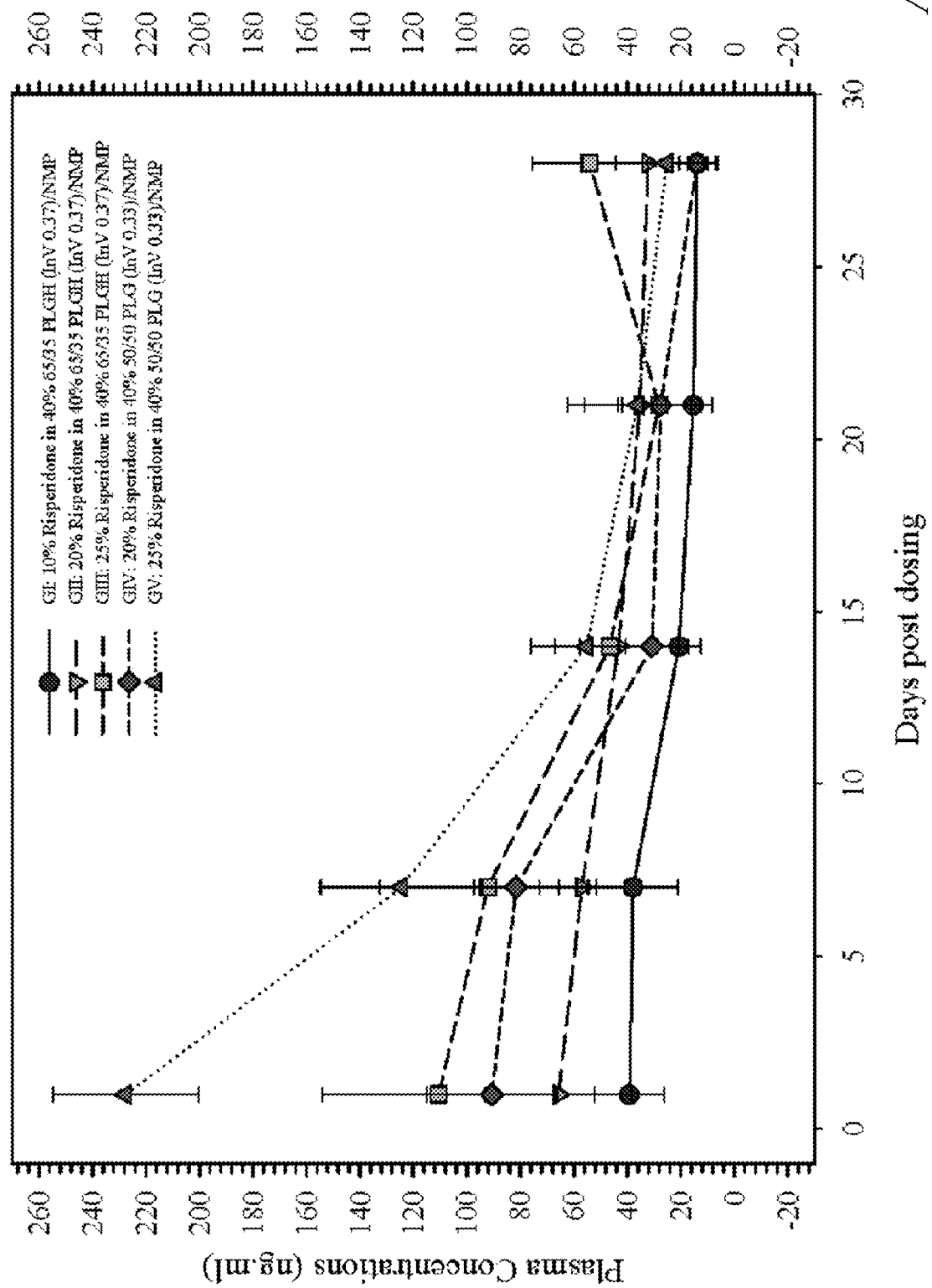
FIG. 8 illustrates the 28-day plasma concentration of active risperidone in rats.

The effects of risperidone loading were investigated in this 28-day release kinetics and pharmacokinetics study using 65/35 PLGH (InV 0.37) and 50/50 poly(lactide-co-glycolide) (InV 0.33) polymers. The implant retrieval results were summarized in Table 17 and the release profiles were shown in FIG. 7. The mean active risperidone plasma concentrations were presented in Table 18 and illustrated in FIG. 8.

TABLE 17

28-Day Risperidone Release From ATRIGEL ® Implants

| Test Article | Time Point | % Released | Mean % Released | Standard Deviation |
|---|---|---|---|---|
| Group I: 10% Risperidone in 40% 65/35 PLGH (InV 0.37)/60% NMP | Day 1 | 26.4 | 15.0 | 10.9 |
| | | 22.1 | | |
| | | 16.5 | | |
| | | 11.9 | | |
| | | −1.8 | | |
| | Day 7 | 50.2 | 39.6 | 6.3 |
| | | 35.3 | | |
| | | 34.4 | | |

TABLE 17-continued

28-Day Risperidone Release From ATRIGEL ® Implants

| Test Article | Time Point | % Released | Mean % Released | Standard Deviation |
|---|---|---|---|---|
| | | 37.9 | | |
| | | 40.2 | | |
| | Day 14 | 62.9 | 64.0 | 5.7 |
| | | 62.8 | | |
| | | 55.7 | | |
| | | 69.8 | | |
| | | 69.0 | | |
| | Day 21 | 78.9 | 84.3 | 3.2 |
| | | 85.5 | | |
| | | 83.8 | | |
| | | 87.1 | | |
| | | 86.1 | | |
| | Day 28 | 94.5 | 93.0 | 1.3 |
| | | 91.2 | | |
| | | 93.2 | | |
| | | 94.0 | | |
| | | 92.2 | | |
| Group II: 20% Risperidone in 40% 65/35 PLGH (InV 0.37)/60% NMP | Day 1 | 9.8 | 9.5 | 3.0 |
| | | 14.3 | | |
| | | 9.3 | | |
| | | 7.4 | | |
| | | 6.7 | | |
| | Day 7 | 52.9 | 39.8 | 9.6 |
| | | 42.9 | | |
| | | 28.6 | | |
| | | 42.1 | | |
| | | 32.4 | | |
| | Day 14 | 62.8 | 66.7 | 3.3 |
| | | 70.8 | | |
| | | 66.9 | | |
| | | 68.9 | | |
| | | 64.2 | | |
| | Day 21 | 80.8 | 74.9 | 8.0 |
| | | 82.7 | | |
| | | 67.4 | | |
| | | 65.2 | | |
| | | 78.5 | | |
| | Day 28 | 96.6 | 89.8 | 5.0 |
| | | 91.3 | | |
| | | 90.3 | | |
| | | 88.2 | | |
| | | 82.8 | | |
| Group III: 25% Risperidone in 40% 65/35 PLGH (InV 0.37)/60% NMP | Day 1 | 10.3 | 13.4 | 3.7 |
| | | 15.9 | | |
| | | 9.6 | | |
| | | 18.2 | | |
| | | 13.1 | | |
| | Day 7 | 49.5 | 40.1 | 10.3 |
| | | 47.1 | | |
| | | 40.1 | | |
| | | 40.7 | | |
| | | 23.2 | | |
| | Day 14 | 60.8 | 60.4 | 7.7 |
| | | 47.3 | | |
| | | 63.6 | | |
| | | 67.6 | | |
| | | 62.8 | | |
| | Day 21 | 98.5 | 80.3 | 16.4 |
| | | 97.7 | | |
| | | 69.4 | | |
| | | 70.8 | | |
| | | 65.1 | | |
| | Day 28 | 78.7 | 80.1 | 11.6 |
| | | 93.1 | | |
| | | 87.8 | | |
| | | 62.6 | | |
| | | 78.3 | | |
| Group IV: 20% Risperidone in 40% 50/50 PLG (InV 0.33)/60% NMP | Day 1 | 17.2 | 14.0 | 10.9 |
| | | 1.8 | | |
| | | 30.8 | | |
| | | 12.2 | | |
| | | 8.2 | | |
| | Day 7 | 37.1 | 43.2 | 9.0 |
| | | 40.5 | | |
| | | 59.1 | | |
| | | 39.6 | | |
| | | 39.9 | | |
| | Day 14 | 72.6 | 76.9 | 8.5 |
| | | 73.5 | | |
| | | 68.8 | | |
| | | 90.5 | | |
| | | 79.3 | | |
| | Day 21 | 91.4 | 95.1 | 3.2 |
| | | 95.8 | | |
| | | 97.6 | | |
| | | 98.6 | | |
| | | 92.3 | | |
| | Day 28 | 99.4 | 99.7 | 0.3 |
| | | 99.9 | | |
| | | 99.4 | | |
| | | 99.9 | | |
| | | 99.7 | | |
| Group V: 25% Risperidone in 40% 50/50 PLG (InV 0.33)/60% NMP | Day 1 | 13.4 | 11.7 | 4.1 |
| | | 9.6 | | |
| | | 18.1 | | |
| | | 8.1 | | |
| | | 9.2 | | |
| | Day 7 | 41.8 | 46.7 | 6.9 |
| | | 46.0 | | |
| | | 38.5 | | |
| | | 54.2 | | |
| | | 53.1 | | |
| | Day 14 | 79.6 | 78.1 | 10.6 |
| | | 89.6 | | |
| | | 64.9 | | |
| | | 69.8 | | |
| | | 86.4 | | |
| | Day 21 | 88.4 | 86.1 | 4.7 |
| | | 85.8 | | |
| | | 91.4 | | |
| | | 78.7 | | |
| | | 86.2 | | |
| | Day 28 | 98.5 | 98.9 | 1.1 |
| | | 98.3 | | |
| | | 100.0 | | |
| | | 100.0 | | |
| | | 97.6 | | |

TABLE 18

28-Day Active Risperidone Plasma Concentrations

| Test Article | Time Point | Plasma Concentration ng/ml | Mean Concentration ng/ml | Standard Deviation |
|---|---|---|---|---|
| Group I: 10% Risperidone in 40% 65/35 PLGH (InV 0.37)/60% NMP | Day 1 | 59.1 | 39.2 | 13.0 |
| | | 22.8 | | |
| | | 40.3 | | |
| | | 35.9 | | |
| | | 38.0 | | |
| | Day 7 | 30.5 | 37.8 | 16.8 |
| | | 67.3 | | |
| | | 27.5 | | |
| | | 28.5 | | |
| | | 35.0 | | |
| | Day 14 | 13.0 | 20.7 | 8.1 |
| | | 17.4 | | |
| | | 34.0 | | |
| | | 17.0 | | |
| | | 22.0 | | |
| | Day 21 | 18.6 | 15.3 | 2.6 |
| | | 16.0 | | |
| | | 15.8 | | |
| | | 14.5 | | |
| | | 11.4 | | |

TABLE 18-continued

28-Day Active Risperidone Plasma Concentrations

| Test Article | Time Point | Plasma Concentration ng/ml | Mean Concentration ng/ml | Standard Deviation |
|---|---|---|---|---|
| | Day 28 | 12.4 | 13.8 | 3.8 |
| | | 13.3 | | |
| | | 18.5 | | |
| | | 8.5 | | |
| | | 16.3 | | |
| Group II: 20% Risperidone in 40% 65/35 PLGH (InV 0.37)/NMP/60% NMP | Day 1 | 97.1 | 65.7 | 27.4 |
| | | 37.3 | | |
| | | 48.1 | | |
| | | 53.1 | | |
| | | 92.9 | | |
| | Day 7 | 61.0 | 56.9 | 15.8 |
| | | 36.3 | | |
| | | 45.1 | | |
| | | 67.1 | | |
| | | 74.8 | | |
| | Day 14 | 64.7 | 43.3 | 14.5 |
| | | 24.5 | | |
| | | 38.5 | | |
| | | 44.6 | | |
| | | 44.1 | | |
| | Day 21 | 16.6 | 35.3 | 27.0 |
| | | 24.7 | | |
| | | 82.5 | | |
| | | 20.8 | | |
| | | 31.9 | | |
| | Day 28 | 16.2 | 32.3 | 20.0 |
| | | 16.6 | | |
| | | 24.3 | | |
| | | 63.2 | | |
| | | 41.0 | | |
| Group III: 25% Risperidone in 40% 65/35 PLGH (InV 0.37)/NMP | Day 1 | 98.6 | 110.5 | 43.5 |
| | | 125.8 | | |
| | | 47.9 | | |
| | | 112.3 | | |
| | | 167.8 | | |
| | Day 7 | 104.0 | 92.1 | 40.5 |
| | | 49.9 | | |
| | | 63.5 | | |
| | | 89.2 | | |
| | | 153.8 | | |
| | Day 14 | 26.1 | 46.5 | 29.5 |
| | | 34.1 | | |
| | | 98.4 | | |
| | | 33.4 | | |
| | | 40.3 | | |
| | Day 21 | 9.9 | 28.2 | 15.6 |
| | | 17.1 | | |
| | | 26.3 | | |
| | | 46.9 | | |
| | | 40.7 | | |
| | Day 28 | 72.6 | 54.0 | 21.7 |
| | | 27.5 | | |
| | | 34.5 | | |
| | | 61.8 | | |
| | | 73.7 | | |
| Group IV: 20% Risperidone in 40% 50/50 PLG (InV 0.33)/NMP | Day 1 | 115.2 | 90.6 | 24.4 |
| | | 115.2 | | |
| | | 86.2 | | |
| | | 59.7 | | |
| | | 76.5 | | |
| | Day 7 | 89.2 | 81.5 | 15.8 |
| | | 69.3 | | |
| | | 105.8 | | |
| | | 70.8 | | |
| | | 72.5 | | |
| | Day 14 | 25.2 | 30.8 | 9.8 |
| | | 18.6 | | |
| | | 39.2 | | |
| | | 28.7 | | |
| | | 42.1 | | |
| | Day 21 | 45.5 | 27.5 | 14.5 |
| | | 32.2 | | |
| | | 26.4 | | |
| | | 5.3 | | |
| | | 28.3 | | |
| | Day 28 | 17.5 | 13.8 | 6.8 |
| | | 13.8 | | |
| | | 5.8 | | |
| | | 9.1 | | |
| | | 23.0 | | |
| Group V: 25% Risperidone in 40% 50/50 PLG (InV 0.33)/NMP/60% NMP | Day 1 | 246.5 | 227.5 | 27.3 |
| | | 215.6 | | |
| | | 197.0 | | |
| | | 213.8 | | |
| | | 264.5 | | |
| | Day 7 | 102.4 | 124.4 | 30.3 |
| | | 84.2 | | |
| | | 144.2 | | |
| | | 134.0 | | |
| | | 157.4 | | |
| | Day 14 | 48.6 | 55.2 | 12.1 |
| | | 58.5 | | |
| | | 70.4 | | |
| | | 38.5 | | |
| | | 60.2 | | |
| | Day 21 | 71.2 | 36.1 | 19.9 |
| | | 21.7 | | |
| | | 29.6 | | |
| | | 29.6 | | |
| | | 28.3 | | |
| | Day 28 | 19.1 | 25.2 | 19.1 |
| | | 25.2 | | |
| | | 16.5 | | |
| | | 7.8 | | |
| | | 57.5 | | |

Tissue macroscopic evaluations showed minimal skin irritation in all groups. Implants were found to be firm and non-fragmenting when retrieved from rats at time points of 1, 4, 7, 14, 21, and 28 days post dosing.

The test articles in this study showed a 9.5±3.0% (Group II) to 15.0±10.9% (Group I) release of risperidone 24 hours post injection and risperidone release ranged from 80.1±11.6% to 99.7±0.3% at day 28 as indicated by the implant retrieval study. Group II, 20% risperidone suspended in 40% 65/35 PLGH (InV 0.37)/60% N-methyl-2-pyrrolidone demonstrated the best release of risperidone over 28 days. The maximum active risperidone plasma concentrations ($C_{max}$) were reached 24 hours post injection for all groups. The active risperidone plasma concentrations decreased and remained at higher than 13.8 ng/ml over 28 days.

In conclusion, formulations containing 10% to 25% risperidone in a delivery system prepared with 40% 65/35 PLGH (InV 0.37) and 60% N-methyl-2-pyrrolidone gave low initial 24-hour burst and sustained risperidone release for 28 days. The 20% load formulation appeared to show the best-controlled risperidone release for 28 days. The ATRIGEL® delivery system based on 65/35 PLGH (InV 0.37) demonstrated better control on the risperidone release compared to 50/50 poly(lactide-co-glycolide) (InV 0.33) over 28 days. There was a correlation between the rat plasma active risperidone concentrations implant risperidone release data. The slower the release rate decline, the higher the active risperidone plasma concentration at Day 14 to 28. The $AUC_{Day\ 0-28}$ was proportional to risperidone dosage.

Example 1.14

Figure 9:
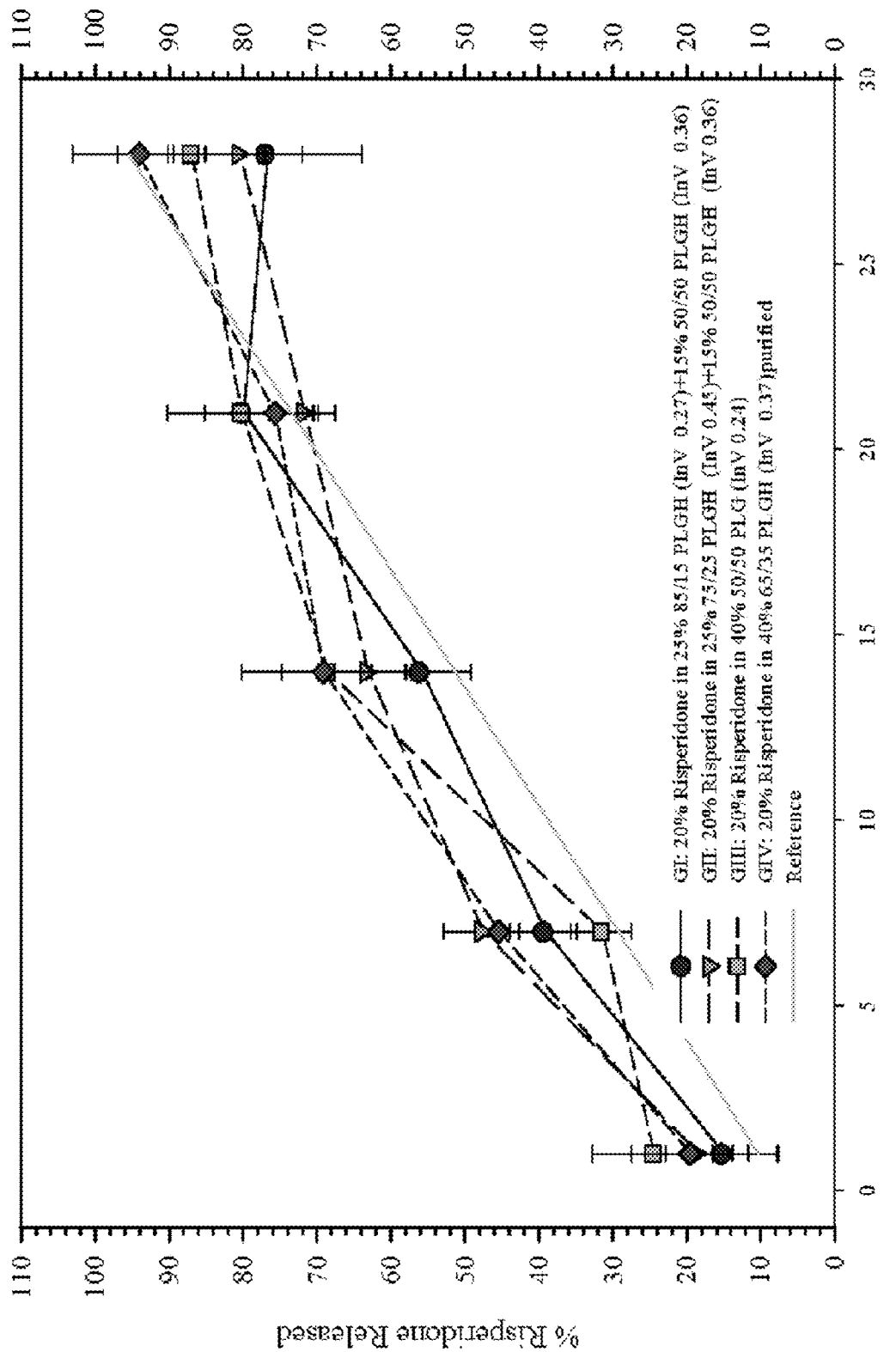
FIG. 9 illustrates the 28-day release of risperidone from selected ATRIGEL® formulations in rats.
Figure 10:
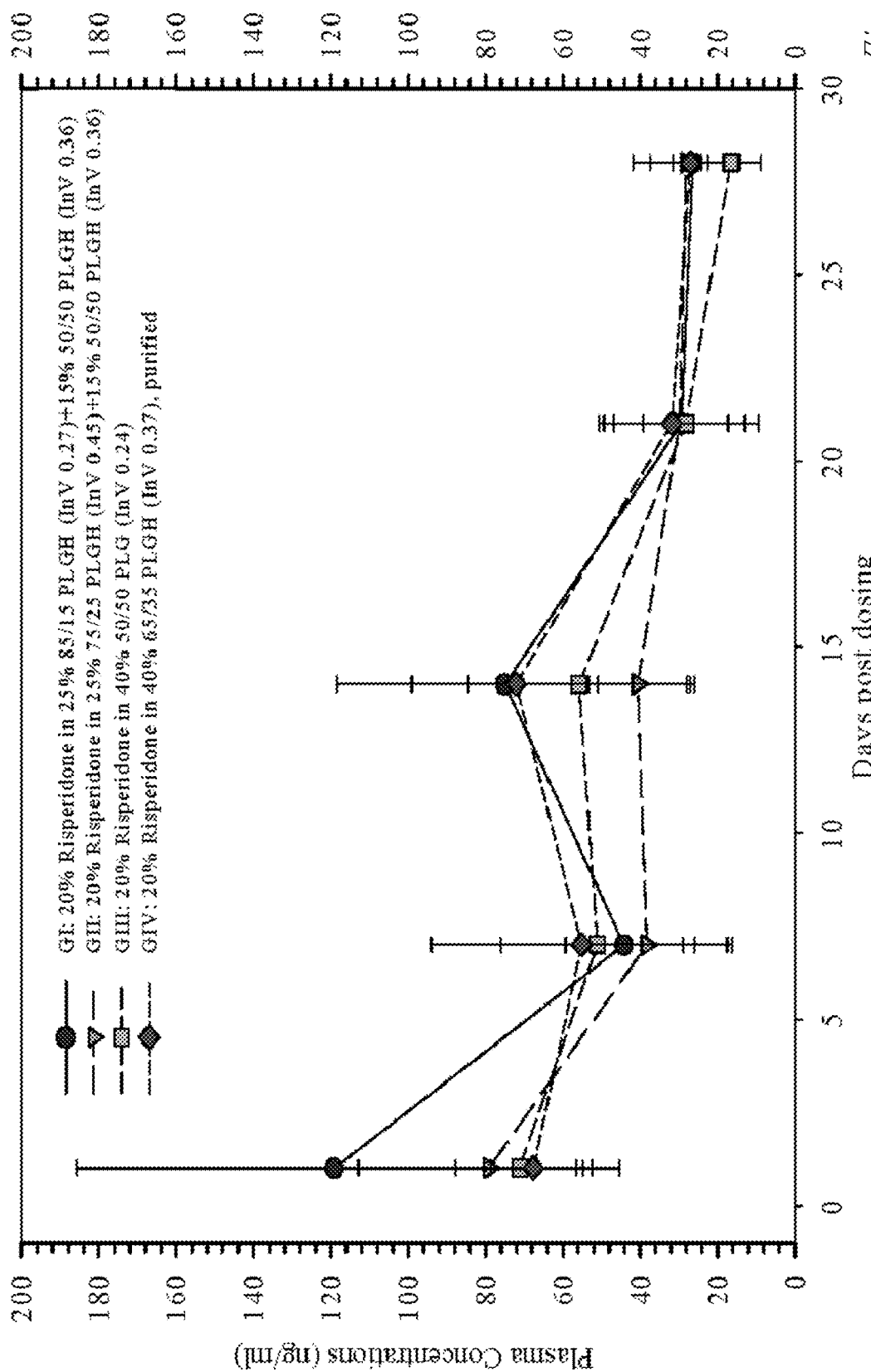
FIG. 10 illustrates the 28-day plasma concentration of active risperidone in rats.

Four ATRIGEL®/Risperidone formulations containing 20% risperidone were evaluated in this release kinetics and pharmacokinetics study. The best formulation (Group II) in EXAMPLE 1.11 was further investigated by using purified 65/35 PLGH (InV 0.37). The effect of blending 15% 50/50 PLGH (InV 0.36) into slow release polymer 85/15 PLGH (InV 0.27) or 75/25 PLGH (InV 0.45) was also investigated. The implant retrieval results were summarized in Table 19 and the release profiles were depicted in FIG. 9. The mean active risperidone plasma concentrations were provided in Table 20 and illustrated in FIG. 10.

TABLE 19

28-Day Risperidone Release From ATRIGEL ® Implants

| Test Article | Time Point | % Released | Mean % Released | Standard Deviation |
|---|---|---|---|---|
| Group I: 20% Risperidone in 25% 85/15 PLGH (InV 0.27) + 15% 50/50 PLGH (InV 0.36)/60% NMP | Day 1 | 26.7 17.4 10.5 13.4 7.1 | 15.0 | 7.5 |
| | Day 7 | 42.7 35.6 39.6 39.8 30.7 | 37.7 | 4.6 |
| | Day 14 | 55.1 64.5 50.0 48.2 61.3 | 55.8 | 7.0 |
| | Day 21 | 81.6 85.1 73.4 98.2 79.2 | 83.5 | 9.3 |
| | Day 28 | 85.3 62.8 66.0 75.0 94.0 | 76.6 | 13.1 |
| Group II: 20% Risperidone in 25% 75/25 PLGH (InV 0.45) + 15% 50/50 PLGH (InV 0.36)/60% NMP | Day 1 | 25.4 18.8 17.3 18.8 11.8 | 18.4 | 4.8 |
| | Day 7 | 54.0 45.0 44.6 39.7 48.6 | 46.4 | 5.3 |
| | Day 14 | 67.0 60.7 66.9 66.9 53.3 | 63.0 | 6.0 |
| | Day 21 | 66.6 72.3 78.0 67.2 71.8 | 71.2 | 4.6 |
| | Day 28 | 84.0 76.4 75.1 72.3 93.8 | 80.3 | 8.7 |
| Group III: 20% Risperidone in 40% 50/50 PLG (InV 0.24)/60% NMP | Day 1 | 30.2 15.2 27.3 16.0 32.7 | 24.3 | 8.1 |
| | Day 7 | 34.4 26.1 24.6 30.4 33.4 | 29.8 | 4.3 |
| | Day 14 | 70.3 60.5 74.3 73.2 63.4 | 68.3 | 6.1 |
| | Day 21 | 87.7 66.3 88.1 73.1 84.9 | 80.0 | 9.8 |
| | Day 28 | 100.1 73.3 90.6 82.6 86.6 | 86.6 | 9.9 |
| Group IV: 20% Risperidone in 40% 65/35 PLGH (InV 0.37) purified/60% NMP | Day 1 | 32.3 15.0 20.9 14.2 13.7 | 19.2 | 7.9 |
| | Day 7 | 44.7 43.7 43.7 43.2 44.3 | 43.9 | 0.6 |
| | Day 14 | 80.4 78.2 62.7 68.7 53.5 | 68.7 | 11.1 |
| | Day 21 | 78.4 81.1 71.9 77.5 66.8 | 75.1 | 5.7 |
| | Day 28 | 98.8 99.8 79.5 100.0 90.0 | 93.6 | 8.9 |

TABLE 20

28-Day Active Risperidone Plasma Concentrations

| Test Article | Time Point | % Released | Mean % Released | Standard Deviation |
|---|---|---|---|---|
| Group I: 20% Risperidone in 25% 85/15 PLGH (InV 0.27) + 15% 50/50 PLGH (InV 0.36)/NMP | Day 1 | 117.9 95.1 58.7 232.2 91.7 | 119.1 | 66.6 |
| | Day 7 | 59.4 60.7 28.6 41.6 30.5 | 44.2 | 15.3 |
| | Day 14 | 98.9 85.7 81.9 73.3 35.2 | 75.0 | 24.1 |
| | Day 21 | 58.5 41.0 20.6 14.8 11.4 | 29.3 | 20.0 |
| | Day 28 | 44.1 18.1 17.6 30.0 22.3 | 26.4 | 11.1 |

TABLE 20-continued

28-Day Active Risperidone Plasma Concentrations

| Test Article | Time Point | % Released | Mean % Released | Standard Deviation |
|---|---|---|---|---|
| Group II: 20% Risperidone in 25% 75/25 PLGH (InV 0.45) + 15% 50/50 PLGH (InV 0.36)/NMP | Day 1 | 105.1<br>51.5<br>116.1<br>37.5<br>85.4 | 79.1 | 33.8 |
| | Day 7 | 22.1<br>28.6<br>74.4<br>36.8<br>29.8 | 38.3 | 20.8 |
| | Day 14 | 58.2<br>49.9<br>29.2<br>31.2<br>34.5 | 40.6 | 12.7 |
| | Day 21 | 52.8<br>39.6<br>15.7<br>29.4<br>11.6 | 29.8 | 17.0 |
| | Day 28 | 24.8<br>Lost sample<br>15.2<br>47.7<br>24.3 | 28.0 | 13.9 |
| Group III: 20% Risperidone in 40% 50/50 PLG (InV 0.24)/NMP | Day 1 | 75.2<br>52.6<br>94.5<br>75.5<br>58.1 | 71.2 | 16.5 |
| | Day 7 | 34.0<br>29.0<br>70.2<br>85.0<br>36.9 | 51.0 | 25.0 |
| | Day 14 | 35.7<br>68.8<br>18.1<br>66.5<br>89.9 | 55.8 | 28.6 |
| | Day 21 | 33.3<br>34.6<br>38.9<br>22.4<br>11.9 | 28.2 | 11.0 |
| | Day 28 | 22.8<br>19.3<br>18.8<br>18.6<br>2.9 | 16.5 | 7.8 |
| Group IV: 20% Risperidone in 40% 65/35 PLGH (InV 0.37) purified/NMP | Day 1 | 76.6<br>55.5<br>67.7<br>57.5<br>80.5 | 67.6 | 11.1 |
| | Day 7 | 104.8<br>19.7<br>89.4<br>31.5<br>30.3 | 55.1 | 39.0 |
| | Day 14 | 133.6<br>109.2<br>33.1<br>36.6<br>47.8 | 72.1 | 46.2 |
| | Day 21 | 20.8<br>13.6<br>50.8<br>53.6<br>20.1 | 31.8 | 18.9 |
| | Day 28 | 20.4<br>30.3<br>Lost sample<br>28.2<br>29.0 | 27.0 | 4.5 |

Tissue macroscopic evaluations showed minimal skin irritation in all groups. Retrieved implants were found to be firm and non-fragmenting when retrieved from rats at 1, 4, 7, 14, 21, and 28 days post dosing.

The test articles in this study showed a 15.0±7.5% (Group I) to 24.3±8.1% (Group III) risperidone release at 24 hours post injection and 76.6±13.1% to 93.6±8.9% release at day 28 as indicated by the implant retrieval study. The maximum active risperidone plasma concentrations ($C_{max}$) were reached 24 hours post injection for all groups and ranged from 67-119 ng/ml. The active risperidone plasma concentrations decreased and remained at higher than 16.5 ng/ml over 28 days.

In conclusion, all Test Articles provided sustained release of risperidone over 28 days, and showed 16.5 ng/ml or higher active risperidone plasma concentrations in the course of the study. Purification of 65/35 PLGH (InV 0.37) increased the initial release of risperidone, but did not affect the release after Day 1 as compared with EXAMPLE 1.11. Blending 50/50 PLGH (InV 0.36) into 85/15 PLGH (InV 0.27) showed promising risperidone release from day 1 to day 28.

Example 1.15

Figure 11:
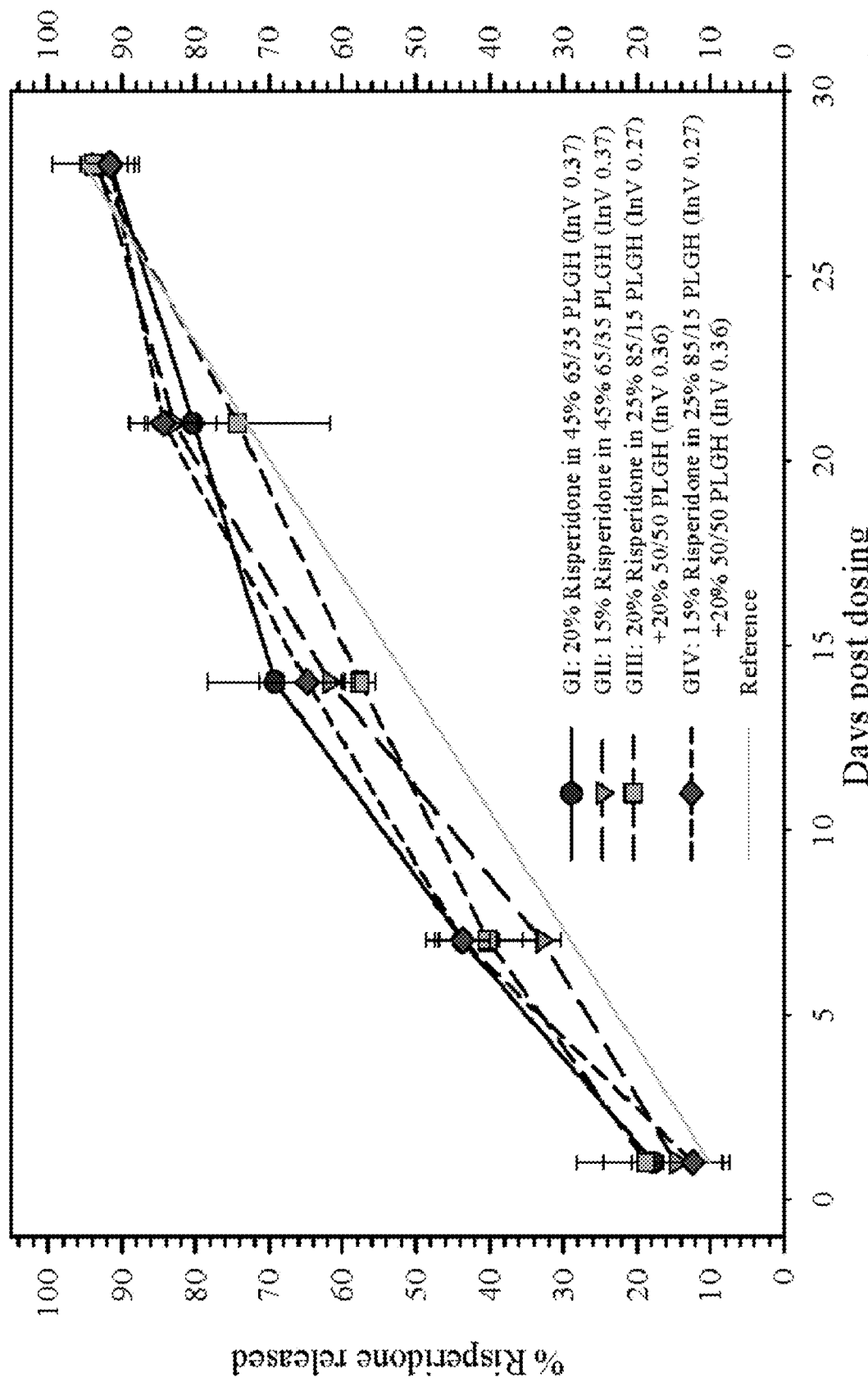
FIG. 11 illustrates the 28-day release of risperidone from selected ATRIGEL® formulations in rats.
Figure 12:
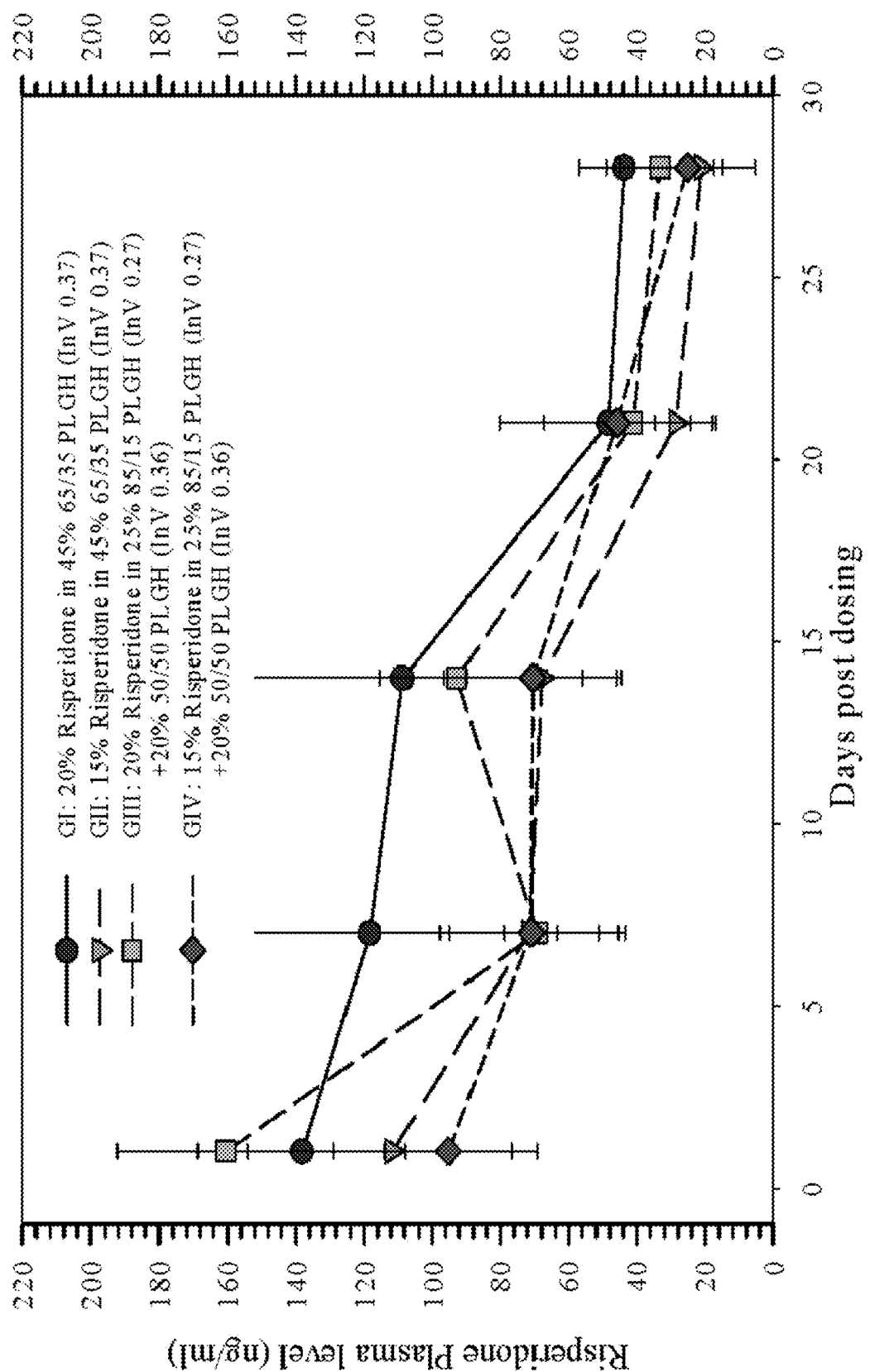
FIG. 12 illustrates the 28-day plasma concentration of active risperidone in rats.

A 28-day release study was conducted focusing on two selected ATRIGEL® delivery systems with 15% and 20% risperidone loading. The two selected systems were: (1) 45% 65/35 PLGH (InV 0.37)/55% N-methyl-2-pyrrolidone and (2) 25% 85/15 PLGH (InV 0.27)+20% 50/50 PLGH (InV 0.36)/55% N-methyl-2-pyrrolidone. The increased polymer loading was formulated to decrease the initial risperidone release. The implant retrieval results were summarized in Table 21 and the release profiles were depicted in FIG. 11. The mean active risperidone plasma concentrations were presented in Table 22 and illustrated in FIG. 12.

TABLE 21

28-Day Risperidone Release From ATRIGEL® Implants

| Test Article | Time Point | % Released | Mean % Released | Standard Deviation |
|---|---|---|---|---|
| Group I: 20% Risperidone in 45% 65/35 PLGH (InV 0.37)/NMP | Day 1 | 41.4<br>29.0<br>21.3<br>16.0<br>4.5 | 22.4 | 13.9 |
| | Day 7 | 42.6<br>48.7<br>48.7<br>37.9<br>40.4 | 43.7 | 4.9 |
| | Day 14 | 65.4<br>68.2<br>84.5<br>67.7<br>59.9 | 69.1 | 9.2 |

TABLE 21-continued

28-Day Risperidone Release From ATRIGEL ® Implants

| Test Article | Time Point | % Released | Mean % Released | Standard Deviation |
|---|---|---|---|---|
| | Day 21 | 77.7 | 80.2 | 3.1 |
| | | 81.6 | | |
| | | 76.8 | | |
| | | 80.5 | | |
| | | 84.4 | | |
| | Day 28 | 90.6 | 91.6 | 2.5 |
| | | 88.2 | | |
| | | 91.3 | | |
| | | 94.8 | | |
| | | 93.1 | | |
| Group II: 15% Risperidone in 45% 65/35 PLGH (InV 0.37)/NMP | Day 1 | 19.2 | 14.6 | 6.2 |
| | | 12.1 | | |
| | | 21.5 | | |
| | | 14.2 | | |
| | | 5.9 | | |
| | Day 7 | 34.5 | 32.8 | 2.6 |
| | | 33.6 | | |
| | | 31.3 | | |
| | | 29.2 | | |
| | | 35.6 | | |
| | Day 14 | 69.8 | 61.7 | 6.2 |
| | | 64.9 | | |
| | | 62.8 | | |
| | | 55.9 | | |
| | | 55.0 | | |
| | Day 21 | 85.1 | 82.8 | 3.5 |
| | | 80.1 | | |
| | | 87.7 | | |
| | | 79.4 | | |
| | | 81.8 | | |
| | Day 28 | 93.3 | 93.2 | 2.2 |
| | | 94.3 | | |
| | | 93.1 | | |
| | | 89.7 | | |
| | | 95.5 | | |
| Group III: 20% Risperidone in 25% 85/15 PLGH (InV 0.27) + 20% 50/50 PLGH (InV 0.36)/55% NMP | Day 1 | 12.2 | 18.7 | 5.7 |
| | | 17.7 | | |
| | | 24.5 | | |
| | | 24.7 | | |
| | | 14.3 | | |
| | Day 7 | 42.7 | 40.1 | 6.7 |
| | | 49.9 | | |
| | | 40.0 | | |
| | | 32.4 | | |
| | | 35.7 | | |
| | Day 14 | 60.5 | 57.5 | 2.1 |
| | | lost | | |
| | | 56.5 | | |
| | | 55.8 | | |
| | | 57.2 | | |
| | Day 21 | 59.7 | 74.2 | 12.6 |
| | | 77.9 | | |
| | | 64.1 | | |
| | | 91.4 | | |
| | | 77.8 | | |
| | Day 28 | 86.2 | 93.7 | 5.6 |
| | | 98.7 | | |
| | | 89.9 | | |
| | | 95.0 | | |
| | | 98.9 | | |
| Group IV: 15% Risperidone in 25% 85/15 PLGH (InV 0.27) + 20% 50/50 PLGH (InV 0.36)/55% NMP | Day 1 | 11.5 | 12.3 | 4.0 |
| | | 10.9 | | |
| | | 17.6 | | |
| | | 14.5 | | |
| | | 7.0 | | |
| | Day 7 | 42.0 | 43.6 | 3.7 |
| | | 43.2 | | |
| | | 39.9 | | |
| | | 43.2 | | |
| | | 49.7 | | |
| | Day 14 | 65.2 | 64.8 | 6.6 |
| | | 63.4 | | |
| | | 65.5 | | |
| | | 55.6 | | |
| | | 74.0 | | |
| | Day 21 | 88.4 | 84.2 | 4.7 |
| | | 79.0 | | |
| | | 79.4 | | |
| | | 87.9 | | |
| | | 86.6 | | |
| | Day 28 | 89.4 | 91.5 | 4.0 |
| | | 98.5 | | |
| | | 88.7 | | |
| | | 90.9 | | |
| | | 90.2 | | |

TABLE 22

28-Day Active Risperidone Plasma Concentrations

| Test Article | Time Point | Plasma Concentration ng/ml | Mean Concentration ng/ml | Standard Deviation |
|---|---|---|---|---|
| Group I: 20% Risperidone in 45% 65/35 PLGH (InV 0.37)/NMP | Day 1 | 130.0 | 138.1 | 30.4 |
| | | 95.0 | | |
| | | 132.3 | | |
| | | 159.3 | | |
| | | 173.9 | | |
| | Day 7 | 56.8 | 118.2 | 66.9 |
| | | * | | |
| | | 208.1 | | |
| | | 79.8 | | |
| | | 128.0 | | |
| | Day 14 | 32.5 | 108.6 | 52.9 |
| | | 172.2 | | |
| | | 95.1 | | |
| | | 100.9 | | |
| | | 142.2 | | |
| | Day 21 | 39.7 | 48.4 | 31.8 |
| | | 21.8 | | |
| | | * | | |
| | | * | | |
| | | 83.6 | | |
| | Day 28 | 36.0 | 43.7 | 13.1 |
| | | 32.8 | | |
| | | 65.8 | | |
| | | 39.2 | | |
| | | 44.7 | | |
| Group II: 15% Risperidone in 45% 65/35 PLGH (InV 0.37)/NMP | Day 1 | 126.2 | 111.6 | 42.3 |
| | | 130.3 | | |
| | | 70.7 | | |
| | | 66.0 | | |
| | | 165.1 | | |
| | Day 7 | * | 71.5 | 26.1 |
| | | 40.7 | | |
| | | 94.5 | | |
| | | 91.7 | | |
| | | 59.0 | | |
| | Day 14 | 90.6 | 67.8 | 21.9 |
| | | 52.4 | | |
| | | 80.4 | | |
| | | 78.0 | | |
| | | 37.8 | | |
| | Day 21 | 30.1 | 28.6 | 10.8 |
| | | 39.6 | | |
| | | 17.4 | | |
| | | 17.7 | | |
| | | 38.3 | | |
| | Day 28 | 17.4 | 21.0 | 5.9 |
| | | 20.8 | | |
| | | 13.3 | | |
| | | 27.3 | | |
| | | 26.0 | | |

TABLE 22-continued

28-Day Active Risperidone Plasma Concentrations

| Test Article | Time Point | Plasma Concentration ng/ml | Mean Concentration ng/ml | Standard Deviation |
|---|---|---|---|---|
| Group III: 20% Risperidone in 25% 85/15 PLGH (InV 0.27) + 20% 50/50 PLGH (InV 0.36)/55% NMP | Day 1 | 113.7<br>174.4<br>169.5<br>183.9<br>* | 160.4 | 31.7 |
| | Day 7 | 39.7<br>109.0<br>71.1<br>54.7<br>70.8 | 69.1 | 25.8 |
| | Day 14 | 122.0<br>111.2<br>77.3<br>71.3<br>81.8 | 92.7 | 22.4 |
| | Day 21 | 46.6<br>*<br>46.6<br>37.2<br>33.5 | 41.0 | 6.7 |
| | Day 28 | 60.8<br>25.1<br>25.2<br>22.5<br>31.7 | 33.1 | 15.9 |
| Group IV: 15% Risperidone in 25% 85/15 PLGH (InV 0.27) + 20% 50/50 PLGH (InV 0.36)/55% NMP | Day 1 | 100.5<br>104.6<br>*<br>107.9<br>67.6 | 95.1 | 18.6 |
| | Day 7 | 65.7<br>81.0<br>lost sample<br>64.4<br>72.7 | 70.9 | 7.7 |
| | Day 14 | 79.6<br>80.4<br>24.2<br>80.3<br>87.7 | 70.4 | 26.0 |
| | Day 21 | 23.9<br>79.9<br>31.9<br>46.8<br>45.8 | 45.7 | 21.5 |
| | Day 28 | 26.0<br>0.0<br>55.7<br>23.9<br>20.1 | 25.1 | 19.9 |

The test articles in this study showed a 12.3±4.0% (Group IV) to 17.7±6.9% (Group I) risperidone release at 24 hours post injection and a 91.5±4.0% to 93.7±5.6% release at day 28 as indicated by the implant retrieval study. All Test Articles showed linear release of risperidone over 28 days. The maximum active risperidone plasma concentrations ($C_{max}$) were reached 24 hours post injection for all groups and ranged from 95.1 to 160.4 ng/ml. The active risperidone plasma concentrations decreased and remained greater than 13.8 ng/ml over 28 days.

In conclusion, formulations based on 45% 65/35 PLGH (InV 0.37) and 55% N-methyl-2-pyrrolidone, using a lower risperidone load (15%) formulation appeared to show better overall release of drug than 20% risperidone load. Formulations using a 25% 85/15 PLGH (InV 0.27) plus 20% 50/50 PLGH (InV 0.36) and 55% N-methyl-2-pyrrolidone, with a 15% risperidone load appeared to control risperidone release better than 20%. No major risperidone release differences were obtained between these two ATRIGEL® formulations. The area under the curve ($AUC_{Day\ 0-28}$) of all four formulations was proportional to risperidone dosage.

Example 1.12

Eight Test Articles with 15% risperidone loading were evaluated in this 14-Day release kinetics and pharmacokinetics study. The affect of 38% to 45% polymer (65/35 PLGH (InV 0.37)) concentration on the risperidone release was evaluated. The implant retrieval results were summarized in Table 23 and the mean active risperidone plasma concentrations were provided in Table 24.

TABLE 23

28-Day Risperidone Release From ATRIGEL® Implants

| Test Article | Time Point | % Released | Mean % Released | Standard Deviation |
|---|---|---|---|---|
| Group I: 15% Risperidone in 38% 65/35 PLGH (InV 0.37)/62% NMP | Day 1 | 21.9<br>14.5<br>24.7<br>13.0<br>29.2 | 20.7 | 6.9 |
| | Day 14 | 72.8<br>74.9<br>67.8<br>82.2<br>68.1 | 73.1 | 5.9 |
| Group II: 15% Risperidone in 40% 65/35 PLGH (InV 0.37)/60% NMP | Day 1 | 22.3<br>18.5<br>21.8<br>12.9<br>11.5 | 17.4 | 5.0 |
| | Day 14 | 76.2<br>85.0<br>80.8<br>80.2<br>63.7 | 77.2 | 8.2 |
| Group III: 15% Risperidone in 42.5% 65/35 PLGH (InV 0.37)/57.5% NMP | Day 1 | 18.0<br>10.9<br>12.1<br>15.4<br>15.2 | 14.3 | 2.8 |
| | Day 14 | 76.0<br>76.5<br>72.0<br>77.3<br>67.1 | 73.8 | 4.3 |
| Group IV: 15% Risperidone in 45% 65/35 PLGH (InV 0.37)/55% NMP | Day 1 | 11.3<br>20.9<br>16.5<br>10.2<br>7.7 | 13.3 | 5.3 |
| | Day 14 | 62.3<br>69.5<br>67.8<br>65.1<br>69.8 | 66.9 | 3.2 |
| Group V: 15% Risperidone in 45% 75/25 PLGH (InV 0.24)/55% NMP | Day 1 | 36.1<br>25.8<br>8.5<br>14.8<br>24.9 | 22.0 | 10.7 |
| | Day 14 | 78.9<br>75.4<br>87.2<br>69.7<br>91.8 | 80.6 | 8.9 |
| Group VI: 15% Risperidone in 20% 85/15 PLGH (InV 0.27) + 20% 50/50 PLGH (InV 0.36)/60% NMP | Day 1 | 18.4<br>10.2<br>6.3<br>7.4<br>29.7 | 14.4 | 9.8 |
| | Day 14 | 86.1<br>59.6 | 75.6 | 9.7 |

TABLE 23-continued

28-Day Risperidone Release From ATRIGEL ® Implants

| Test Article | Time Point | % Released | Mean % Released | Standard Deviation |
|---|---|---|---|---|
| | | 76.3 | | |
| | | 78.4 | | |
| | | 77.7 | | |
| Group VII: 15% Risperidone in 40% 65/35 PLGH (InV 0.37) + 5% PEG8000-PLG (InV 0.27)/55% NMP | Day 1 | 8.2 | 11.4 | 6.6 |
| | | 11.9 | | |
| | | 9.7 | | |
| | | 22.3 | | |
| | | 5.0 | | |
| | Day 14 | 66.8 | 73.3 | 7.4 |
| | | 76.5 | | |
| | | 67.6 | | |
| | | 84.7 | | |
| | | 70.7 | | |
| Group VIII: 15% Risperidone in 22.2% 85/15 PLGH (InV 0.27) + 17.8% 65/35 PLGH (InV 0.37)/60% NMP | Day 1 | 11.4 | 10.8 | 2.9 |
| | | 9.1 | | |
| | | 11.4 | | |
| | | 15.0 | | |
| | | 7.2 | | |
| | Day 14 | 66.0 | 68.7 | 4.8 |
| | | 63.7 | | |
| | | 69.0 | | |
| | | 68.6 | | |
| | | 76.4 | | |

TABLE 24

28-Day Active Risperidone Plasma Concentrations

| Test Article | Time Point | Plasma Concentration ng/ml | Mean Concentration ng/ml | Standard Deviation |
|---|---|---|---|---|
| Group I: 15% Risperidone in 38% 65/35 PLGH (InV 0.37)/62% NMP | Day 1 | 111.4 | 78.7 | 23.4 |
| | | 56.8 | | |
| | | 94.5 | | |
| | | 60.9 | | |
| | | 69.8 | | |
| | Day 14 | 43.3 | 22.0 | 22.7 |
| | | 2.9 | | |
| | | 2.9 | | |
| | | 49.6 | | |
| | | 11.6 | | |
| Group II: 15% Risperidone in 40% 65/35 PLGH (InV 0.37)/60% NMP | Day 1 | 48.2 | 69.3 | 26.6 |
| | | 53.6 | | |
| | | 64.6 | | |
| | | 64.9 | | |
| | | 115.0 | | |
| | Day 14 | 22.0 | 42.9 | 15.8 |
| | | 44.9 | | |
| | | 66.4 | | |
| | | 39.5 | | |
| | | 41.7 | | |
| Group III: 15% Risperidone in 42.5% 65/35 PLGH (InV 0.37)/57.5% NMP | Day 1 | 69.1 | 62.4 | 15.6 |
| | | 46.6 | | |
| | | 46.5 | | |
| | | 82.7 | | |
| | | 67.0 | | |
| | Day 14 | 13.8 | 51.6 | 29.7 |
| | | 73.6 | | |
| | | 36.7 | | |
| | | 88.5 | | |
| | | 45.6 | | |
| Group IV: 15% Risperidone in 45% 65/35 PLGH (InV 0.37)/55% NMP | Day 1 | 48.5 | 53.5 | 3.6 |
| | | 51.0 | | |
| | | 55.2 | | |
| | | 57.2 | | |
| | | 55.6 | | |
| | Day 14 | 30.5 | 41.5 | 11.6 |
| | | 34.6 | | |
| | | 48.4 | | |
| | | 58.5 | | |
| | | 35.8 | | |
| Group VI: 15% Risperidone in 20% 85/15 PLGH (InV 0.27) + 20% 50/50 PLGH (InV 0.36)/60% NMP | Day 1 | 69.4 | 81.4 | 22.9 |
| | | 105.2 | | |
| | | 107.2 | | |
| | | 60.7 | | |
| | | 64.4 | | |
| | Day 14 | 32.8 | 35.4 | 9.8 |
| | | 48.6 | | |
| | | 30.1 | | |
| | | 23.6 | | |
| | | 41.8 | | |
| Group VII: 15% Risperidone in 40% 65/35 PLGH (InV 0.37) + 5% PEG8000-PLG (InV 0.27)/55% NMP | Day 1 | 48.9 | 69.2 | 25.5 |
| | | 60.1 | | |
| | | 106.2 | | |
| | | 84.1 | | |
| | | 46.6 | | |
| | Day 14 | 29.8 | 54.8 | 20.4 |
| | | 78.3 | | |
| | | 43.4 | | |
| | | 49.6 | | |
| | | 72.9 | | |
| Group VIII: 15% Risperidone in 22.2% 85/15 PLGH (InV 0.27) + 17.8% 65/35 PLGH (InV 0.37)/60% NMP | Day 1 | 45.0 | 56.7 | 21.1 |
| | | 53.7 | | |
| | | 88.4 | | |
| | | 63.6 | | |
| | | 32.6 | | |
| | Day 14 | 45.1 | 47.4 | 18.5 |
| | | 76.0 | | |
| | | 29.1 | | |
| | | 33.9 | | |
| | | 52.9 | | |

The macroscopic evaluation showed that the tissue reaction were mostly unremarkable throughout the study. All implants were firm and non-fragmenting at day 1 and 14. One implant from Group VIII, day 14, was slightly mottled in coloration.

The implant retrieval data showed that the eight test articles released 10.8±2.9% (Group VIII) to 22.0±10.7% (Group V) risperidone at 24 hours post injection and 66.9±3.2% (Group IV) to 80.6±8.9% (Group V) at 14 days post injection. Group IV displayed the best release rate of risperidone in this study with 13.3±5.3% release at Day 1 and 66.9±3.2% release at day 14. The test article used for Group IV was 15% risperidone suspended in a delivery system prepared with 45% 65/35 PLGH (InV 0.37) and 55% N-methyl-2-pyrrolidone. The active risperidone plasma concentrations of all groups except Group V were analyzed. The active risperidone plasma concentrations ranged from 53.5±3.6 (Group IV) to 81.4±22.9 ng/ml (Group V) at 24 hours post injection and 22.0±22.7 (Group I) to 54.8±20.4 ng/ml (Group VII) at 14 days post injection.

In conclusion, the concentration of the polymer in ATRIGEL® delivery system appears to be a factor in controlling the release of risperidone. The 24-hour initial release of risperidone decreased with the increase of the polymer concentration. A correlation was obtained between the rat plasma concentrations of active risperidone and implant release data. The higher the 24-hour release of risperidone, the higher the active risperidone concentration in plasma.

Example 1.13

The final 28-Day release and pharmacokinetic study was conducted to confirm the findings in previous studies. In addition, the best combination of risperidone and polymer loading were evaluated. None or minimal skin irritation was confirmed again in this study. All implants were firm and non-fragmenting from day 1 to day 28.

Figure 13:
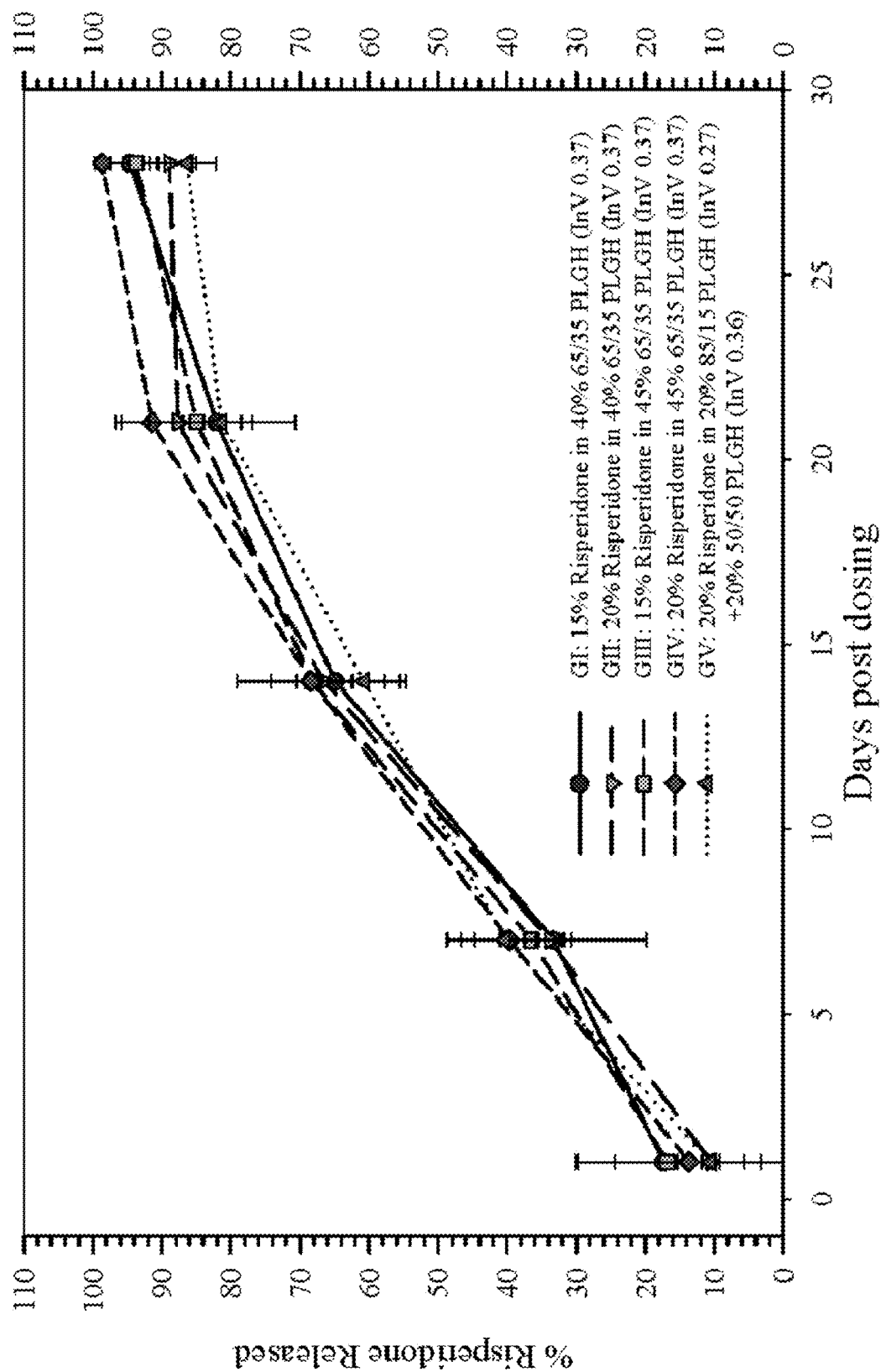
FIG. 13 illustrates the 28-day release of risperidone from selected ATRIGEL® formulations in rats.
Figure 14:
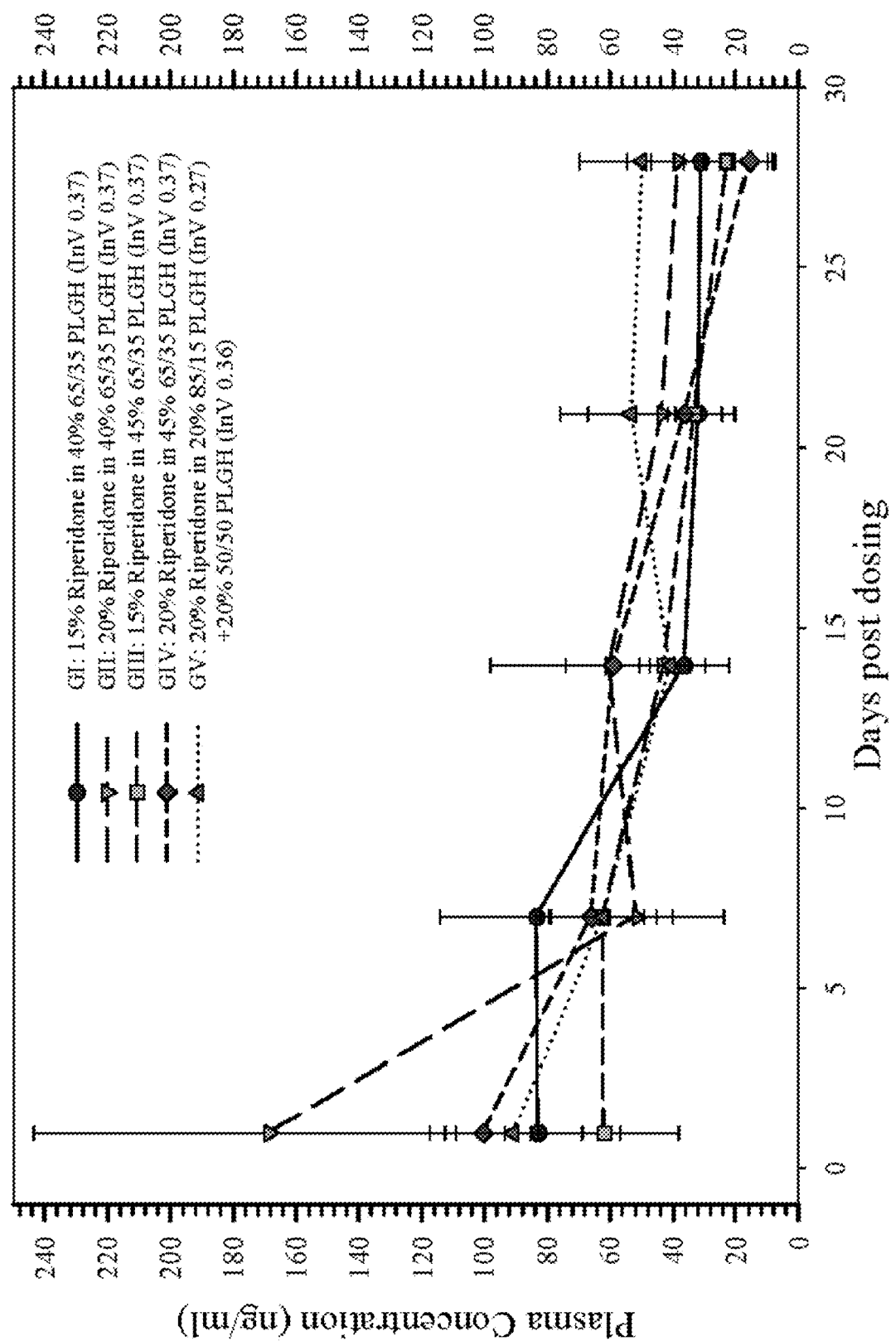
FIG. 14 illustrates the 28-day plasma concentration of active risperidone in rats.

Overall, all formulations showed similar linear sustained release of risperidone during the 28-day study. The implant retrieval study showed 10.5% (Groups II and V) to 17.3±7.0% (Group I) risperidone release of all the Test Articles at 24 hours post injection and a 86.3±4.1% (Group V) to 98.6±1.0% (Group IV) release at day 28. The maximum active risperidone plasma concentrations ($C_{max}$) were reached 24 hours post injection for all groups and ranged from 62.1 (Group III) to 168.9 ng/ml (Group II). The active risperidone plasma concentrations decreased and remained at greater than 15.8 ng/ml (Group IV) over 28 days for all groups. Groups II and V showed the best release profile up to day 21, but showed very slow risperidone release between day 21 to day 28. On the other hand, the plasma concentrations of these groups at day 21 and day 28 were greater than 30 ng/ml, which was inconsistent with the implant release data. The data from this study compared to the previous release and pharmacokinetic data in EXAMPLES 1.11, 1.14, and 1.15, demonstrated that the risperidone release from this formulation was still remarkable, and the pharmacokinetic data were reliable. The implant retrieval results were summarized in Table 25 and the release profiles were depicted in FIG. 13. The mean active plasma risperidone concentrations were presented in Table 26 and illustrated in FIG. 14.

TABLE 25

28-Day Risperidone Release From ATRIGEL ® Implants

| Test Article | Time Point | % Released | Mean % Released | Standard Deviation |
|---|---|---|---|---|
| Group I: 15% Risperidone in 40% 65/35 PLGH (InV 0.37)/60% NMP | Day 1 | 28.9 | 17.3 | 7.0 |
| | | 16.6 | | |
| | | 17.3 | | |
| | | 12.3 | | |
| | | 11.3 | | |
| | Day 7 | 10.2 | 33.3 | 13.4 |
| | | 40.1 | | |
| | | 44.2 | | |
| | | 36.2 | | |
| | | 35.7 | | |
| | Day 14 | 52.3 | 64.9 | 9.3 |
| | | 76.2 | | |
| | | 69.9 | | |
| | | 66.7 | | |
| | | 59.2 | | |
| | Day 21 | 84.4 | 82.1 | 5.1 |
| | | 79.0 | | |
| | | 79.7 | | |
| | | 77.3 | | |
| | | 89.9 | | |
| | Day 28 | 93.4 | 94.6 | 3.9 |
| | | 99.7 | | |
| | | 97.6 | | |
| | | 91.2 | | |
| | | 91.0 | | |
| Group II: 20% Risperidone in 40% 65/35 PLGH (InV 0.37)/60% NMP | Day 1 | 18.5 | 10.5 | 4.9 |
| | | 7.0 | | |
| | | 10.7 | | |
| | | 10.1 | | |
| | | 6.2 | | |
| | Day 7 | 35.5 | 33.8 | 2.1 |
| | | 33.7 | | |
| | | 32.4 | | |
| | | 36.3 | | |
| | | 31.2 | | |
| | Day 14 | 66.9 | 66.5 | 4.0 |
| | | 67.3 | | |
| | | 59.9 | | |
| | | 70.8 | | |
| | | 67.7 | | |
| | Day 21 | 74.9 | 87.7 | 9.1 |
| | | 83.8 | | |
| | | 87.3 | | |
| | | 96.7 | | |
| | | 96.0 | | |
| | Day 28 | 85.3 | 88.9 | 3.9 |
| | | 91.1 | | |
| | | 90.6 | | |
| | | 93.2 | | |
| | | 84.2 | | |
| Group III: 15% Risperidone in 45% 65/35 PLGH (InV 0.37)/60% NMP | Day 1 | 26.6 | 16.7 | 13.5 |
| | | 21.2 | | |
| | | 29.4 | | |
| | | 9.7 | | |
| | | −3.2 | | |
| | Day 7 | 39.5 | 36.5 | 4.5 |
| | | 39.5 | | |
| | | 40.3 | | |
| | | 31.6 | | |
| | | 31.5 | | |
| | Day 14 | 68.4 | 68.2 | 5.9 |
| | | 70.0 | | |
| | | 76.2 | | |
| | | 66.7 | | |
| | | 59.8 | | |
| | Day 21 | 84.2 | 84.9 | 6.5 |
| | | 88.7 | | |
| | | 88.9 | | |
| | | 73.9 | | |
| | | 89.0 | | |
| | Day 28 | 95.6 | 93.7 | 2.0 |
| | | 96.0 | | |
| | | 92.0 | | |
| | | 93.0 | | |
| | | 91.8 | | |
| Group IV: 20% Risperidone in 45% 65/35 PLGH (InV 0.37)/60% NMP | Day 1 | 32.8 | 13.6 | 16.1 |
| | | 26.1 | | |
| | | 12.6 | | |
| | | 3.3 | | |
| | | −6.7 | | |
| | Day 7 | 49.7 | 39.6 | 9.0 |
| | | 38.0 | | |
| | | 47.3 | | |
| | | 27.6 | | |
| | | 35.7 | | |
| | Day 14 | 66.2 | 68.4 | 10.8 |
| | | 78.7 | | |
| | | 80.3 | | |
| | | 56.4 | | |
| | | 60.2 | | |
| | Day 21 | 92.6 | 91.4 | 4.5 |
| | | 97.3 | | |
| | | 93.1 | | |
| | | 85.6 | | |
| | | 88.5 | | |
| | Day 28 | 98.9 | 98.6 | 1.0 |
| | | 98.7 | | |
| | | 96.8 | | |
| | | 99.0 | | |
| | | 99.5 | | |
| Group V: 20% Risperidone in 20% 85/15 PLGH (InV 0.27) + 20% 50/50 PLGH (InV 0.36)/60% NMP | Day 1 | 12.2 | 10.5 | 1.3 |
| | | 9.5 | | |
| | | 9.2 | | |
| | | 10.0 | | |
| | | 11.6 | | |
| | Day 7 | 35.6 | 40.2 | 4.4 |
| | | 36.7 | | |
| | | 46.1 | | |
| | | 43.2 | | |
| | | 39.5 | | |
| | Day 14 | 59.7 | 60.7 | 6.1 |
| | | 64.4 | | |
| | | 52.1 | | |

TABLE 25-continued

28-Day Risperidone Release From ATRIGEL® Implants

| Test Article | Time Point | % Released | Mean % Released | Standard Deviation |
|---|---|---|---|---|
| | | 59.0 | | |
| | | 68.4 | | |
| | Day 21 | 79.5 | 81.3 | 10.6 |
| | | 74.6 | | |
| | | 81.9 | | |
| | | 98.9 | | |
| | | 71.6 | | |
| | Day 28 | 91.9 | 86.3 | 4.1 |
| | | 80.5 | | |
| | | 85.7 | | |
| | | 88.0 | | |
| | | 85.4 | | |

TABLE 26

28-Day Active Risperidone Plasma Concentrations

| Test Article | Time Point | Plasma Concentration ng/ml | Mean Concentration ng/ml | Standard Deviation |
|---|---|---|---|---|
| Group I: 15% Risperidone in 40% 65/35 PLGH (InV 0.37)/60% NMP | Day 1 | 66.1 | 83.2 | 26.4 |
| | | 67.7 | | |
| | | 127.9 | | |
| | | 67.6 | | |
| | | 86.8 | | |
| | Day 7 | 43.7 | 83.7 | 30.9 |
| | | 66.5 | | |
| | | 108.4 | | |
| | | 80.3 | | |
| | | 119.8 | | |
| | Day 14 | 47.2 | 36.5 | 6.7 |
| | | 33.7 | | |
| | | 29.9 | | |
| | | 33.4 | | |
| | | 38.5 | | |
| | Day 21 | 20.9 | 32.0 | 7.6 |
| | | 39.1 | | |
| | | 28.8 | | |
| | | 32.3 | | |
| | | 38.7 | | |
| | Day 28 | 58.1 | 31.2 | 23.4 |
| | | 8.0 | | |
| | | 12.7 | | |
| | | 23.1 | | |
| | | 53.9 | | |
| Group II: 20% Risperidone in 40% 65/35 PLGH (InV 0.37)/60% NMP | Day 1 | 271.4 | 168.9 | 75.2 |
| | | 124.7 | | |
| | | 152.5 | | |
| | | 80.9 | | |
| | | 215.0 | | |
| | Day 7 | 24.7 | 51.9 | 28.1 |
| | | 63.6 | | |
| | | 18.9 | | |
| | | 74.0 | | |
| | | 78.5 | | |
| | Day 14 | 42.0 | 60.3 | 38.0 |
| | | 37.1 | | |
| | | 45.9 | | |
| | | 127.8 | | |
| | | 48.9 | | |
| | Day 21 | 38.8 | 43.7 | 23.6 |
| | | 22.2 | | |
| | | 39.3 | | |
| | | 84.0 | | |
| | | 34.1 | | |
| | Day 28 | 39.1 | 38.5 | 8.9 |
| | | 29.9 | | |
| | | 51.2 | | |
| | | 30.4 | | |
| | | 41.8 | | |

TABLE 26-continued

28-Day Active Risperidone Plasma Concentrations

| Test Article | Time Point | Plasma Concentration ng/ml | Mean Concentration ng/ml | Standard Deviation |
|---|---|---|---|---|
| Group III: 15% Risperidone in 45% 65/35 PLGH (InV 0.37)/60% NMP | Day 1 | 50.2 | 62.1 | 23.6 |
| | | 38.9 | | |
| | | 98.7 | | |
| | | 71.6 | | |
| | | 51.1 | | |
| | Day 7 | 68.7 | 62.4 | 16.7 |
| | | 80.3 | | |
| | | 71.4 | | |
| | | 53.8 | | |
| | | 37.9 | | |
| | Day 14 | 39.2 | 43.1 | 8.0 |
| | | 52.0 | | |
| | | 39.5 | | |
| | | 33.9 | | |
| | | 51.1 | | |
| | Day 21 | 41.9 | 33.3 | 8.7 |
| | | 28.1 | | |
| | | 26.8 | | |
| | | 26.1 | | |
| | | 43.5 | | |
| | Day 28 | 19.7 | 22.7 | 14.0 |
| | | 47.3 | | |
| | | 13.2 | | |
| | | 16.6 | | |
| | | 16.6 | | |
| Group IV: 20% Risperidone in 45% 65/35 PLGH (InV 0.37)/55% NMP | Day 1 | 116.8 | 100.6 | 17.3 |
| | | 90.8 | | |
| | | 112.0 | | |
| | | 108.4 | | |
| | | 75.2 | | |
| | Day 7 | 64.9 | 66.2 | 16.5 |
| | | 43.3 | | |
| | | 73.0 | | |
| | | 88.4 | | |
| | | 61.5 | | |
| | Day 14 | 51.6 | 59.1 | 15.5 |
| | | 50.5 | | |
| | | 86.5 | | |
| | | 56.1 | | |
| | | 51.0 | | |
| | Day 21 | 21.6 | 36.5 | 15.7 |
| | | 19.5 | | |
| | | 42.3 | | |
| | | 42.9 | | |
| | | 56.5 | | |
| | Day 28 | 17.8 | 15.8 | 5.5 |
| | | 12.5 | | |
| | | 22.3 | | |
| | | 18.0 | | |
| | | 8.3 | | |
| Group V: 20% Risperidone in 20% 85/15 PLGH (InV 0.27) + 20% 50/50 PLGH (InV 0.36)/60% NMP | Day 1 | 84.0 | 100.7 | 28.6 |
| | | 77.0 | | |
| | | 139.0 | | |
| | | 123.7 | | |
| | | 79.7 | | |
| | Day 7 | 72.4 | 62.4 | 22.0 |
| | | 89.8 | | |
| | | 46.4 | | |
| | | 34.4 | | |
| | | 69.0 | | |
| | Day 14 | 32.6 | 41.2 | 6.5 |
| | | 41.6 | | |
| | | 43.1 | | |
| | | 50.3 | | |
| | | 38.4 | | |
| | Day 21 | 69.0 | 43.7 | 22.6 |
| | | 9.9 | | |
| | | 36.6 | | |
| | | 45.1 | | |
| | | 57.9 | | |
| | Day 28 | 24.1 | 50.2 | 19.8 |
| | | 41.3 | | |
| | | 51.8 | | |

TABLE 26-continued

28-Day Active Risperidone Plasma Concentrations

| Test Article | Time Point | Plasma Concentration ng/ml | Mean Concentration ng/ml | Standard Deviation |
|---|---|---|---|---|
| | | 78.1 | | |
| | | 55.8 | | |

In conclusion, 15% risperidone dose formulations gave lower 24-hour initial burst. Polymer loading of 40% or 45% appeared to have minimal effect on the overall release of risperidone, but did have a large impact on the syringeability of the reconstituted formulations. However, the higher the drug and polymer load, the more difficult the injection. The higher the drug loading, the smaller the injection volume. A 15% risperidone loading in the total formulation and 45% polymer loadings in the ATRIGEL® delivery system appears to be a better formulation choice. The pharmacokinetic data in this study generally supported the implant retrieval results.

Example 2

Pharmacokinetics Studies in Rabbits

The purpose of this study was to determine and compare the pharmacokinetic profiles of risperidone/ATRIGEL® formulation and RISPERDAL® CONSTA® formulations. The previous risperidone/ATRIGEL® formulation studies evaluated in rats resulted in selecting a 15% risperidone suspended in 45% 65/35 PLGHp (37 kDa)/N-methyl-2-pyrrolidone formulation for further development. The selected formulation was evaluated in two rabbit preclinical studies conducted in New Zealand White rabbits. The two studies were EXAMPLES 2.1 and 2.2. Five or ten rabbits per Test Article were injected subcutaneously with a full dose of the test article containing 30, 60, or 120 mg risperidone.

At selected time points, five or ten rabbits per Test Article were bled (about 3 mL) via marginal ear vein. Blood was collected in labeled potassium EDTA tubes. The blood was centrifuged for 10 min at 3000 rpm. The plasma fraction was transferred to labeled 5 mL plastic culture tubes and stored at −86° C. The plasma was extracted following the Plasma SPE Extraction Procedure For Active Risperidone Plasma Analysis, described above. The active risperidone concentrations were analyzed using the Plasma SPE Extraction Procedure For Active Risperidone Plasma Analysis, described above. The active risperidone plasma concentration was calculated based on both risperidone and 9-hydroxyrisperidone.

On the last day of the study, the rabbits were anesthetized, bled via cardiac puncture and promptly euthanized. The test sites were immediately dissected and evaluated for macroscopic tissue reactions. Implants were removed and physically debrided of tissue, and precipitation characteristics documented. Representative photographs were taken of the test sites.

Personnel evaluated injection sites at each time point for any abnormalities including redness, bleeding, swelling, discharge, bruising, and test article extrusion. Additionally, personnel observed animals post administration for signs of overt toxicity for the duration of the study.

The two studies indicated that (1) all doses of the Risperidone/ATRIGEL® formulation showed an initial burst of risperidone within the first 8 hours post dosing and the second maximum plasma concentration ($C_{max}$) of active risperidone was reached at day 7 to 9 for 60 and 120 mg dose formulations, (2) the area under the curve (AUC) was dose proportional for all three doses, (3) the active risperidone plasma concentration exceeded 25 ng/mL through Day 35 in all three doses and the plasma levels fell below 25 ng/mL at Day 42 and were near 0 at day 50, (4) at one hour post injection, the 50 mg RISPERDAL® CONSTA® showed plasma concentrations greater than 25 ng/mL, the plasma risperidone concentrations decreased to near zero until Day 22 when the plasma risperidone concentration exceeded 100 ng/mL, plasma risperidone concentrations decreased to 12 ng/mL at Day 35 and decreased to near zero at days 42 through 50, (5) the $AUC_{Day\ 0-50}$ of 30 mg Risperidone/ATRIGEL® was comparable to 50 mg RISPERDAL® CONSTA®, and (6) the Pharmacokinetic profiles of all three doses were repeatable.

Example 2.3

A pharmacokinetics study in rabbits was conducted to evaluate the previous data obtained from the 28-day rat studies. The Risperidone/ATRIGEL® formulation chosen from the rat studies was 15% risperidone suspended in 45% 65/35 PLGH (37 kDa) and 55% N-methyl-2-pyrrolidone. The subcutaneous doses in the rabbit were 30, 60, and 120 mg risperidone from this formulation. The injection volumes into the rabbit were 0.2, 0.4, and 0.8 mL. A positive control of 50 mg RISPERDAL® CONSTA® (2 mL IM injection) was also used in this study. The study duration was 50 days with blood collection at 1, 2, 6, 12 hours, and 1, 3, 7, 14, 22, 28, 35, 42, and 45 days via marginal ear vein. At day 50, after blood collection by cardiac puncture the animal was euthanized and the implant was removed for determination of risperidone remaining in the implant. The plasma was extracted following the Plasma SPE Extraction Procedure For Active Risperidone Plasma Analysis, described above. The active risperidone concentrations were analyzed using the Reversed Phase High Performance Liquid Chromatography Method For The Quantization of Risperidone And 9-Hydroxyrisperidone, described above. The active risperidone concentrations at each time point were listed in Table 27.

TABLE 27

50-Day Active Risperidone Plasma Concentrations

| Test Article | Time Point | Plasma Concentration ng/ml | Mean Concentration ng/ml | Standard Deviation |
|---|---|---|---|---|
| Group I: 50 mg RISPERDAL ® CONSTA ® | Day 0.04 | 39.5 | 35.7 | 11.5 |
| | | 49.7 | | |
| | | 23.5 | | |
| | | 41.6 | | |
| | | 24.0 | | |
| | Day 0.08 | 22.6 | 24.2 | 7.0 |
| | | 34.2 | | |
| | | 17.7 | | |
| | | 28.2 | | |
| | | 18.2 | | |
| | Day 0.25 | 9.2 | 9.6 | 2.9 |
| | | 14.4 | | |
| | | 8.5 | | |
| | | 9.2 | | |
| | | 6.8 | | |
| | Day 0.5 | 0.2 | 3.0 | 2.0 |
| | | 4.9 | | |
| | | 2.5 | | |
| | | 4.9 | | |
| | | 2.3 | | |
| | Day 1 | 0.2 | 2.7 | 1.5 |
| | | 3.2 | | |

TABLE 27-continued

50-Day Active Risperidone Plasma Concentrations

| Test Article | Time Point | Plasma Concentration ng/ml | Mean Concentration ng/ml | Standard Deviation |
|---|---|---|---|---|
| | | 3.5 | | |
| | | 3.8 | | |
| | | 2.9 | | |
| | Day 3 | 14.3 | 8.3 | 3.6 |
| | | 8.2 | | |
| | | 5.8 | | |
| | | 8.2 | | |
| | | 5.0 | | |
| | Day 7 | 3.5 | 4.3 | 1.6 |
| | | 4.7 | | |
| | | 5.8 | | |
| | | 5.6 | | |
| | | 2.0 | | |
| | Day 14 | 0.2 | 5.1 | 3.5 |
| | | 8.4 | | |
| | | 8.4 | | |
| | | 3.5 | | |
| | | 5.1 | | |
| | Day 22 | 77.3 | 102.5 | 25.7 |
| | | 136.5 | | |
| | | 101.1 | | |
| | | 119.1 | | |
| | | 78.6 | | |
| | Day 28 | 27.8 | 58.1 | 25.7 |
| | | 63.8 | | |
| | | 94.4 | | |
| | | 64.8 | | |
| | | 39.8 | | |
| | Day 35 | 11.9 | 15.8 | 3.8 |
| | | 14.8 | | |
| | | 21.9 | | |
| | | 13.9 | | |
| | | 16.6 | | |
| | Day 42 | 32.5 | 108.6 | 52.9 |
| | | 172.2 | | |
| | | 95.1 | | |
| | | 100.9 | | |
| | | 142.2 | | |
| | Day 45 | 10.3 | 2.1 | 4.6 |
| | | 0.0 | | |
| | | 0.0 | | |
| | | 0.0 | | |
| | | 0.0 | | |
| | Day 45 | 10.3 | 2.1 | 4.6 |
| | | 0.0 | | |
| | | 0.0 | | |
| | | 0.0 | | |
| | | 0.0 | | |
| | Day 50 | 0.0 | 1.7 | 3.8 |
| | | 0.0 | | |
| | | 0.0 | | |
| | | 0.0 | | |
| | | 8.4 | | |
| Group II: 120 mg Risperidone (15% Risperidone in 45% 65/35PLGHp(InV 0.37) and 55% NMP) | Day 0.04 | 98.8 | 103.5 | 23.4 |
| | | 79.3 | | |
| | | 137.3 | | |
| | | 115.7 | | |
| | | 86.7 | | |
| | Day 0.08 | 134.2 | 166.6 | 35.7 |
| | | 184.2 | | |
| | | 220.5 | | |
| | | 152.4 | | |
| | | 141.6 | | |
| | Day 0.25 | 134.2 | 107.3 | 18.3 |
| | | 86.2 | | |
| | | 115.2 | | |
| | | 97.6 | | |
| | | 103.5 | | |
| | Day 0.5 | 112.7 | 95.2 | 10.3 |
| | | 94.0 | | |
| | | 86.1 | | |
| | | 93.1 | | |
| | | 90.2 | | |
| | Day 1 | 109.6 | 84.1 | 30.7 |
| | | 41.4 | | |
| | | 111.5 | | |
| | | 94.9 | | |
| | | 63.2 | | |
| | Day 3 | 92.7 | 55.4 | 24.0 |
| | | 34.5 | | |
| | | 38.0 | | |
| | | 65.2 | | |
| | | 46.4 | | |
| | Day 7 | 151.0 | 344.0 | 334.8 |
| | | 110.1 | | |
| | | 906.7 | | |
| | | 400.0 | | |
| | | 152.3 | | |
| | Day 14 | 184.0 | 142.9 | 49.4 |
| | | 82.5 | | |
| | | 113.5 | | |
| | | 132.7 | | |
| | | 201.7 | | |
| | Day 22 | 36.1 | 42.8 | 17.8 |
| | | 27.1 | | |
| | | 34.8 | | |
| | | 42.8 | | |
| | | 73.0 | | |
| | Day 28 | 36.3 | 48.7 | 8.5 |
| | | 43.4 | | |
| | | 54.3 | | |
| | | 54.0 | | |
| | | 55.4 | | |
| | Day 35 | 11.9 | 22.8 | 11.6 |
| | | 39.6 | | |
| | | 27.2 | | |
| | | 23.3 | | |
| | | 11.9 | | |
| | Day 42 | 0.0 | 1.6 | 3.6 |
| | | 0.0 | | |
| | | 0.0 | | |
| | | 8.1 | | |
| | Day 45 | 0.0 | 0.0 | 0.0 |
| | | 0.0 | | |
| | | 0.0 | | |
| | | 0.0 | | |
| | | 0.0 | | |
| | Day 50 | 0.0 | 1.6 | 3.5 |
| | | 0.0 | | |
| | | 0.0 | | |
| | | 0.0 | | |
| | | 7.9 | | |
| Group III: 60 mg Risperidone (15% Risperidone in 45% 65/35PLGHp(InV 0.37) and 55% NMP) | Day 0.04 | 56.7 | 77.6 | 17.8 |
| | | 85.2 | | |
| | | 62.9 | | |
| | | 82.5 | | |
| | | 100.6 | | |
| | Day 0.08 | 108.6 | 88.5 | 18.0 |
| | | 102.7 | | |
| | | 63.5 | | |
| | | 80.8 | | |
| | | 87.0 | | |
| | Day 0.25 | 98.8 | 86.1 | 25.5 |
| | | 119.2 | | |
| | | 57.5 | | |
| | | 63.7 | | |
| | | 91.2 | | |
| | Day 0.5 | 85.5 | 82.5 | 21.7 |
| | | 112.7 | | |
| | | 51.7 | | |
| | | 79.7 | | |
| | | 82.9 | | |
| | Day 1 | 64.6 | 61.0 | 22.7 |
| | | 77.0 | | |
| | | 36.4 | | |

TABLE 27-continued

50-Day Active Risperidone Plasma Concentrations

| Test Article | Time Point | Plasma Concentration ng/ml | Mean Concentration ng/ml | Standard Deviation |
|---|---|---|---|---|
|  |  | 87.8 |  |  |
|  |  | 39.4 |  |  |
|  | Day 3 | 36.7 | 30.9 | 8.6 |
|  |  | 37.3 |  |  |
|  |  | 19.6 |  |  |
|  |  | 37.1 |  |  |
|  |  | 23.7 |  |  |
|  | Day 7 | 97.9 | 106.3 | 42.4 |
|  |  | 152.3 |  |  |
|  |  | 105.0 |  |  |
|  |  | 41.5 |  |  |
|  |  | 134.5 |  |  |
|  | Day 14 | 57.4 | 79.3 | 44.6 |
|  |  | 157.8 |  |  |
|  |  | 67.9 |  |  |
|  |  | 47.4 |  |  |
|  |  | 66.1 |  |  |
|  | Day 22 | 37.5 | 30.3 | 8.5 |
|  |  | 32.2 |  |  |
|  |  | 19.7 |  |  |
|  |  | 38.9 |  |  |
|  |  | 23.2 |  |  |
|  | Day 28 | 37.5 | 46.3 | 17.9 |
|  |  | 34.8 |  |  |
|  |  | 37.0 |  |  |
|  |  | 44.6 |  |  |
|  |  | 77.7 |  |  |
|  | Day 35 | 29.4 | 28.7 | 7.1 |
|  |  | 36.5 |  |  |
|  |  | 17.9 |  |  |
|  |  | 32.9 |  |  |
|  |  | 26.5 |  |  |
|  | Day 42 | 20.2 | 5.6 | 8.8 |
|  |  | 0.0 |  |  |
|  |  | 0.0 |  |  |
|  |  | 7.7 |  |  |
|  |  | 0.0 |  |  |
|  | Day 45 | 0.0 | 0.0 | 0.0 |
|  |  | 0.0 |  |  |
|  |  | 0.0 |  |  |
|  |  | 0.0 |  |  |
|  |  | 0.0 |  |  |
|  | Day 50 | 0.0 | 3.1 | 4.2 |
|  |  | 7.9 |  |  |
|  |  | 0.0 |  |  |
|  |  | 0.0 |  |  |
|  |  | 7.6 |  |  |
| Group IV: 30 mg Risperidone (15% Risperidone in 45% 65/35PLGHp(InV 0.37) and 55% NMP) | Day 0.04 | 81.4 | 60.0 | 17.9 |
|  |  | 73.6 |  |  |
|  |  | 52.1 |  |  |
|  |  | 56.9 |  |  |
|  |  | 36.3 |  |  |
|  | Day 0.08 | 88.1 | 72.4 | 19.5 |
|  |  | 96.5 |  |  |
|  |  | 57.7 |  |  |
|  |  | 68.7 |  |  |
|  |  | 50.8 |  |  |
|  | Day 0.25 | 73.1 | 60.8 | 16.1 |
|  |  | 79.1 |  |  |
|  |  | 56.5 |  |  |
|  |  | 57.7 |  |  |
|  |  | 37.8 |  |  |
|  | Day 0.5 | 86.5 | 58.2 | 20.7 |
|  |  | 71.6 |  |  |
|  |  | 45.1 |  |  |
|  |  | 52.8 |  |  |
|  |  | 35.0 |  |  |
|  | Day 1 | 96.5 | 55.0 | 32.5 |
|  |  | 83.4 |  |  |
|  |  | 32.1 |  |  |
|  |  | 37.6 |  |  |
|  |  | 25.4 |  |  |
|  | Day 3 | 42.8 | 28.4 | 13.9 |
|  |  | 43.0 |  |  |
|  |  | 21.0 |  |  |
|  |  | 23.2 |  |  |
|  |  | 11.9 |  |  |
|  | Day 7 | 24.2 | 34.0 | 21.1 |
|  |  | 23.3 |  |  |
|  |  | 15.6 |  |  |
|  |  | 68.9 |  |  |
|  |  | 37.9 |  |  |
|  | Day 14 | 27.7 | 61.2 | 47.9 |
|  |  | 141.2 |  |  |
|  |  | 28.3 |  |  |
|  |  | 70.2 |  |  |
|  |  | 38.7 |  |  |
|  | Day 22 | 26.2 | 23.1 | 6.8 |
|  |  | 18.7 |  |  |
|  |  | 13.3 |  |  |
|  |  | 28.6 |  |  |
|  |  | 28.7 |  |  |
|  | Day 28 | 32.5 | 27.1 | 5.5 |
|  |  | 24.7 |  |  |
|  |  | 24.4 |  |  |
|  |  | 33.3 |  |  |
|  |  | 20.8 |  |  |
|  | Day 35 | 20.2 | 21.5 | 2.4 |
|  |  | 23.6 |  |  |
|  |  | 18.8 |  |  |
|  |  | 24.4 |  |  |
|  |  | 20.5 |  |  |
|  | Day 42 | 17.5 | 5.1 | 7.8 |
|  |  | 8.2 |  |  |
|  |  | 0.0 |  |  |
|  |  | 0.0 |  |  |
|  |  | 0.0 |  |  |
|  | Day 45 | 17.6 | 3.5 | 7.9 |
|  |  | 0.0 |  |  |
|  |  | 0.0 |  |  |
|  |  | 0.0 |  |  |
|  |  | 0.0 |  |  |
|  | Day 50 | 16.0 | 4.8 | 7.1 |
|  |  | 7.8 |  |  |
|  |  | 0.0 |  |  |
|  |  | 0.0 |  |  |
|  |  | 0.0 |  |  |

All implants were small or not found at Day 50. The risperidone remaining in implants were analyzed using implant extraction and High Performance Liquid Chromatography method, results were summarized in Table 28.

TABLE 28

Risperidone Release at Day 50 After A Single SC Injection in Rabbits

| Test Article | Time Point | % Risperidone Released | Mean % Risperidone Released | Standard Deviation |
|---|---|---|---|---|
| Group I: 50 mg RISPERDAL ® CONSTA ® | Day 50 | 100 | 100 | 0 |
|  |  | 100 |  |  |
|  |  | 100 |  |  |
|  |  | 100 |  |  |
|  |  | 100 |  |  |
| Group II: 120 mg Risperidone (15% Risperidone in 45% 65/35 PLGHp (InV 0.37)/NMP) | Day 50 | 100 | 100 | 0 |
|  |  | 100 |  |  |
|  |  | 100 |  |  |
|  |  | 100 |  |  |
|  |  | 100 |  |  |

TABLE 28-continued

Risperidone Release at Day 50 After A Single SC Injection in Rabbits

| Test Article | Time Point | % Risperidone Released | Mean % Risperidone Released | Standard Deviation |
|---|---|---|---|---|
| Group III: 60 mg Risperidone (15% Risperidone in 45% 65/35 PLGHp (InV 0.37)/NMP) | Day 50 | 100 100 100 100 100 | 100 | 0 |
| Group IV: 30 mg Risperidone (15% Risperidone in 45% 65/35 PLGHp (InV 0.37)/NMP) | Day 50 | 100 100 100 100 100 | 100 | 0 |

None or minimal skin irritation was confirmed again in this study. All implants were small or not found at Day 50. All doses of the Risperidone/ATRIGEL® formulations showed an initial active risperidone concentration in plasma within the first 4 hours of the 50-day study. The second $C_{max}$ was reached at day 7 for the 60 and 120 mg formulation. The plasma risperidone concentrations were dose proportional. The risperidone concentration exceeded 25 ng/mL through day 35 in this rabbit study. Plasma risperidone concentrations fell below 25 ng/mL at day 42 and were near zero at day 50 for all 3 doses.

At one hour, the 50 mg RISPERDAL® CONSTA® injection showed plasma concentrations greater than 25 ng/mL. The plasma concentrations for this 14-day product decreased to near zero until day 22 when the plasma risperidone concentration exceeded 100 ng/mL. Plasma risperidone concentrations decreased to 12 ng/mL at day 35 and decreased to near zero at days 42 through day 50.

Figure 15:
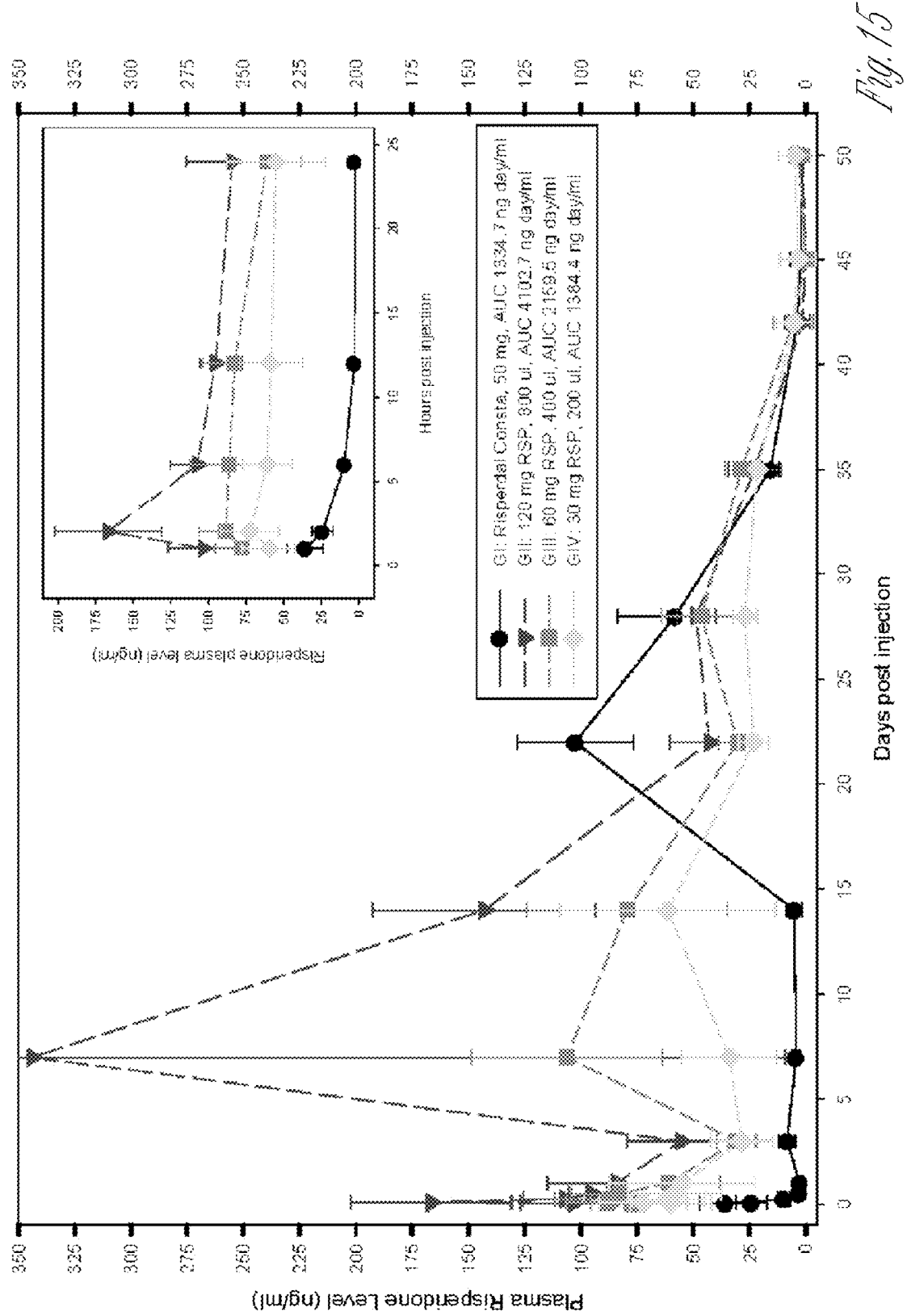
FIG. 15 illustrates the 50-day risperidone/ATRIGEL® pharmacokinetic study in rabbits.

The area under the plasma concentration curve ($AUC_{Day\ 0-50}$) for each formulation, highest plasma risperidone concentration ($C_{max}$), and time ($T_M$) for this rabbit study were shown in Table 29. The pharmacokinetic profiles for all formulations injected in this rabbit study were shown in FIG. 15.

TABLE 29

Pharmacokinetic Parameters for EXAMPLE 2.3

| FORMULATION | $C_{MAX}$ NG/ML | $T_M$ | $AUC_{0-50\ DAYS}$ NG-DAY/ML |
|---|---|---|---|
| 50 MG RISPERDAL ® CONSTA ® | 102.5 | DAY 22 | 1334.7 |
| 120 MG RISPERIDONE/ATRIGEL ® | 344.0 | DAY 7 | 4102.7 |
| 60 MG RISPERIDONE/ATRIGEL ® | 106.3 | DAY 7 | 2159.5 |
| 30 MG RISPERIDONE/ATRIGEL ® | 72.4 | 2 HOURS | 1384.4 |

Example 2.4

A second pharmacokinetic study in rabbits was conducted to confirm the data in the previous 50-day rabbit study (EXAMPLE 2.3). The subcutaneous doses in the rabbit were 30, 60, and 120 mg risperidone in the selected formulation. The injection volumes into the rabbit were 0.2, 0.4, and 0.8 mL. The study duration was 35 days with blood collection at 1, 2, 4, 6, 8, and 12 hours and at 1, 4, 9, 16, 22, and 30 days via marginal ear vein. At day 35, after blood collection by cardiac puncture the animal was euthanized and the implant was removed for determination of risperidone remaining in the implant.

The plasma was analyzed following the Plasma SPE Extraction Procedure For Active Risperidone Plasma Analysis, described above. The active risperidone concentrations were analyzed using the Reversed Phase High Performance Liquid Chromatography Method For The Quantization of Risperidone And 9-Hydroxyrisperidone, described above. Active risperidone concentrations at each time point were listed in Table 30.

TABLE 30

35-Day Active Risperidone Concentrations

| Test Article | Time Point | Plasma Concentration ng/ml | Mean Concentration ng/ml | Standard Deviation |
|---|---|---|---|---|
| Group I: 120 mg Risperidone (15% Risperidone in 45% 65/35PLGHp(InV 0.37) and 55% NMP) | Day 0.02 | 123.1 120.1 91.0 103.3 66.1 | 100.7 | 23.3 |
| | Day 0.04 | 84.8 197.3 165.5 128.6 113.0 | 137.8 | 44.2 |
| | Day 0.08 | 179.9 249.3 250.0 163.4 173.5 | 203.2 | 42.8 |
| | Day 0.16 | 217.8 317.2 262.2 265.7 225.5 | 257.7 | 39.5 |
| | Day 0.25 | 301.4 292.8 309.2 234.3 247.1 | 277.0 | 33.9 |
| | Day 0.33 | 162.7 234.6 345.6 278.9 159.6 | 236.3 | 79.2 |
| | Day 0.5 | 219.2 237.1 203.3 188.1 186.6 | 206.9 | 21.5 |
| | Day 1 | 129.3 111.4 247.7 153.1 105.2 | 149.3 | 58.0 |
| | Day 4 | 111.3 157.1 67.3 97.4 135.8 61.5 73.0 131.0 59.9 88.3 | 98.3 | 34.4 |
| | Day 9 | 209.5 231.4 222.0 225.3 277.5 154.7 210.3 787.7 | 280.7 | 181.5 |

TABLE 30-continued

35-Day Active Risperidone Concentrations

| Test Article | Time Point | Plasma Concentration ng/ml | Mean Concentration ng/ml | Standard Deviation |
|---|---|---|---|---|
| | | 274.9 | | |
| | | 213.6 | | |
| | Day 16 | 120.2 | 149.2 | 54.8 |
| | | 120.2 | | |
| | | 283.4 | | |
| | | 132.6 | | |
| | | 160.0 | | |
| | | 119.3 | | |
| | | 157.3 | | |
| | | 187.4 | | |
| | | 108.9 | | |
| | | 103.1 | | |
| | Day 23 | 86.7 | 78.9 | 22.4 |
| | | 110.4 | | |
| | | 88.2 | | |
| | | 40.5 | | |
| | | 79.7 | | |
| | | 48.8 | | |
| | | 91.5 | | |
| | | 103.5 | | |
| | | 75.2 | | |
| | | 64.2 | | |
| | Day 30 | 28.3 | 30.2 | 14.1 |
| | | 21.7 | | |
| | | 41.8 | | |
| | | 0.0 | | |
| | | 31.5 | | |
| | | 30.7 | | |
| | | 38.5 | | |
| | | 48.5 | | |
| | | 41.9 | | |
| | | 19.4 | | |
| | Day 35 | 0.0 | 4.9 | 9.1 |
| | | 0.0 | | |
| | | 0.0 | | |
| | | 0.0 | | |
| | | 0.0 | | |
| | | 18.9 | | |
| | | 0.0 | | |
| | | 5.5 | | |
| | | 24.6 | | |
| | | 0.0 | | |
| Group II: 60 mg Risperidone (15% Risperidone in 45% 65/35PLGHp(InV 0.37) and 55% NMP) | Day 0.02 | 95.5 | 89.5 | 9.2 |
| | | 98.6 | | |
| | | 79.2 | | |
| | | 94.5 | | |
| | | 79.9 | | |
| | Day 0.04 | 158.2 | 94.6 | 39.4 |
| | | 56.5 | | |
| | | 76.0 | | |
| | | 78.0 | | |
| | | 104.1 | | |
| | Day 0.08 | 105.5 | 168.9 | 45.5 |
| | | 169.9 | | |
| | | 147.6 | | |
| | | 198.5 | | |
| | | 222.9 | | |
| | Day 0.16 | 231.4 | 141.9 | 54.5 |
| | | 96.2 | | |
| | | 107.0 | | |
| | | 153.5 | | |
| | | 121.4 | | |
| | Day 0.25 | 148.1 | 164.7 | 21.1 |
| | | 141.7 | | |
| | | 190.4 | | |
| | | 161.1 | | |
| | | 182.0 | | |
| | Day 0.33 | 169.1 | 152.2 | 43.7 |
| | | 100.4 | | |
| | | 213.2 | | |
| | | 121.7 | | |
| | | 156.9 | | |
| | Day 0.5 | 97.0 | 159.6 | 58.2 |
| | | 128.7 | | |
| | | 171.3 | | |
| | | 149.6 | | |
| | | 251.4 | | |
| | Day 1 | 90.7 | 95.4 | 33.6 |
| | | 55.3 | | |
| | | 139.1 | | |
| | | 73.9 | | |
| | | 117.8 | | |
| | Day 4 | 55.9 | 60.5 | 11.0 |
| | | 69.8 | | |
| | | 51.5 | | |
| | | 60.3 | | |
| | | 55.1 | | |
| | | 58.2 | | |
| | | 66.3 | | |
| | | 49.1 | | |
| | | 53.1 | | |
| | | 85.8 | | |
| | Day 9 | 166.5 | 188.8 | 110.9 |
| | | 215.0 | | |
| | | 142.4 | | |
| | | 119.2 | | |
| | | 110.2 | | |
| | | 140.1 | | |
| | | 285.6 | | |
| | | 463.9 | | |
| | | 125.0 | | |
| | | 119.9 | | |
| | Day 16 | 105.2 | 96.1 | 36.7 |
| | | 101.2 | | |
| | | 131.6 | | |
| | | 94.5 | | |
| | | 168.7 | | |
| | | 68.1 | | |
| | | 69.6 | | |
| | | 98.0 | | |
| | | 33.0 | | |
| | | 91.6 | | |
| | Day 23 | 74.8 | 48.6 | 36.5 |
| | | 27.3 | | |
| | | 66.5 | | |
| | | 35.7 | | |
| | | 133.3 | | |
| | | 42.1 | | |
| | | 34.4 | | |
| | | 48.0 | | |
| | | 0.0 | | |
| | | 23.9 | | |
| | Day 30 | 26.1 | 20.0 | 15.6 |
| | | 0.0 | | |
| | | 40.3 | | |
| | | 23.7 | | |
| | | 18.5 | | |
| | | 21.6 | | |
| | | 0.0 | | |
| | | 41.7 | | |
| | | 0.0 | | |
| | | 27.6 | | |
| | Day 35 | 0.0 | 4.4 | 6.1 |
| | | 10.9 | | |
| | | 0.0 | | |
| | | 13.8 | | |
| | | 0.0 | | |
| | | 13.8 | | |
| | | 0.0 | | |
| | | 0.0 | | |
| | | 0.0 | | |
| | | 5.5 | | |

TABLE 30-continued

35-Day Active Risperidone Concentrations

| Test Article | Time Point | Plasma Concentration ng/ml | Mean Concentration ng/ml | Standard Deviation |
|---|---|---|---|---|
| Group III: 30 mg Risperidone (15% Risperidone in 45% 65/35PLGHp(InV 0.37) and 55% NMP) | Day 0.02 | 51.6 | 70.2 | 14.7 |
| | | 70.5 | | |
| | | 91.4 | | |
| | | 63.1 | | |
| | | 74.4 | | |
| | Day 0.04 | 83.8 | 67.1 | 26.3 |
| | | 53.5 | | |
| | | 34.1 | | |
| | | 101.7 | | |
| | | 62.1 | | |
| | Day 0.08 | 62.4 | 94.5 | 26.2 |
| | | 132.1 | | |
| | | 79.8 | | |
| | | 93.8 | | |
| | | 104.4 | | |
| | Day 0.16 | 141.9 | 113.5 | 39.9 |
| | | 94.3 | | |
| | | 51.8 | | |
| | | 143.3 | | |
| | | 136.3 | | |
| | Day 0.25 | 72.5 | 82.9 | 16.7 |
| | | 97.8 | | |
| | | 94.3 | | |
| | | 91.2 | | |
| | | 58.8 | | |
| | Day 0.33 | 145.5 | 106.5 | 30.7 |
| | | 103.9 | | |
| | | 59.7 | | |
| | | 110.5 | | |
| | | 112.8 | | |
| | Day 0.5 | 84.0 | 85.4 | 14.6 |
| | | 101.7 | | |
| | | 73.5 | | |
| | | 98.8 | | |
| | | 69.1 | | |
| | Day 1 | 88.3 | 76.1 | 21.8 |
| | | 60.9 | | |
| | | 47.8 | | |
| | | 81.0 | | |
| | | 102.3 | | |
| | Day 4 | 43.0 | 53.3 | 27.8 |
| | | 38.3 | | |
| | | 42.8 | | |
| | | 47.0 | | |
| | | 72.7 | | |
| | | 45.5 | | |
| | | 37.8 | | |
| | | 126.1 | | |
| | | 48.2 | | |
| | | 31.5 | | |
| | Day 9 | 136.0 | 88.1 | 38.3 |
| | | 56.6 | | |
| | | 162.0 | | |
| | | 58.6 | | |
| | | 96.1 | | |
| | | 104.1 | | |
| | | 92.5 | | |
| | | 51.6 | | |
| | | 45.7 | | |
| | | 78.3 | | |
| | Day 16 | 28.0 | 51.8 | 16.5 |
| | | 53.3 | | |
| | | 55.9 | | |
| | | 64.5 | | |
| | | 35.6 | | |
| | | 86.3 | | |
| | | 42.9 | | |
| | | 42.9 | | |
| | | 47.3 | | |
| | | 60.9 | | |
| | Day 23 | 0.0 | 24.7 | 15.5 |
| | | 31.1 | | |
| | | 17.4 | | |
| | | 29.7 | | |
| | | 22.0 | | |
| | | 44.9 | | |
| | | 23.8 | | |
| | | 0.0 | | |
| | | 39.3 | | |
| | | 38.8 | | |
| | Day 30 | 0.0 | 19.0 | 8.7 |
| | | 23.2 | | |
| | | 9.0 | | |
| | | 21.9 | | |
| | | 19.7 | | |
| | | 24.8 | | |
| | | 25.2 | | |
| | | 17.2 | | |
| | | 19.2 | | |
| | | 29.8 | | |
| | Day 35 | 0.0 | 2.9 | 6.1 |
| | | 0.0 | | |
| | | 0.0 | | |
| | | 0.0 | | |
| | | 0.0 | | |
| | | 13.2 | | |
| | | 0.0 | | |
| | | 0.0 | | |
| | | 0.0 | | |
| | | 15.5 | | |

All implants were small at Day 35. Implant retrieval data were listed in Table 31.

TABLE 31

Active Risperidone Concentrations

| Test Article | Time Point | % Released | Mean % Released | Standard Deviation |
|---|---|---|---|---|
| Group I: 120 mg Risperidone 15% Risperidone in 45% 65/35 PLGHp (InV 0.37)/NMP) | Day 35 | 100.0 | 99.8 | 0.3 |
| | | 100.0 | | |
| | | 100.0 | | |
| | | 100.0 | | |
| | | 100.0 | | |
| | | 99.2 | | |
| | | 100.0 | | |
| | | 100.0 | | |
| | | 99.4 | | |
| | | 100.0 | | |
| Group II: 60 mg Risperidone (15% Risperidone in 45% 65/35 PLGHp (InV 0.37)/NMP) | Day 35 | 99.7 | 99.8 | 0.3 |
| | | 100.0 | | |
| | | 100.0 | | |
| | | 98.9 | | |
| | | 99.9 | | |
| | | 99.8 | | |
| | | 100.0 | | |
| | | 100.0 | | |
| | | 100.0 | | |
| | | 100.0 | | |
| Group III: 30 mg Risperidone (15% Risperidone in 45% 65/35 PLGHp (InV 0.37)/NMP) | Day 35 | 100.0 | 99.5 | 0.8 |
| | | 99.9 | | |
| | | 99.9 | | |
| | | 99.9 | | |
| | | 100.0 | | |
| | | 99.1 | | |
| | | 99.9 | | |

TABLE 31-continued

Active Risperidone Concentrations

| Test Article | Time Point | % Released | Mean % Released | Standard Deviation |
|---|---|---|---|---|
| | | 99.0 | | |
| | | 99.8 | | |
| | | 97.4 | | |

None or minimal skin irritation was confirmed again in this study. All implants were small at Day 35. All doses of the Risperidone/ATRIGEL® formulations showed an initial burst of plasma risperidone within the first 8 hours of the 35-day study. The risperidone concentrations for each dose were dose dependent and the plasma risperidone profile showed a second burst of risperidone at day 9 in this study for the 60 and 120 mg risperidone doses. The risperidone concentration exceeded 25 ng/mL through day 30 in this rabbit study. Plasma risperidone concentrations fell below 25 ng/mL at day 35 for all 3 doses of risperidone/ATRIGEL®.

Figure 16:
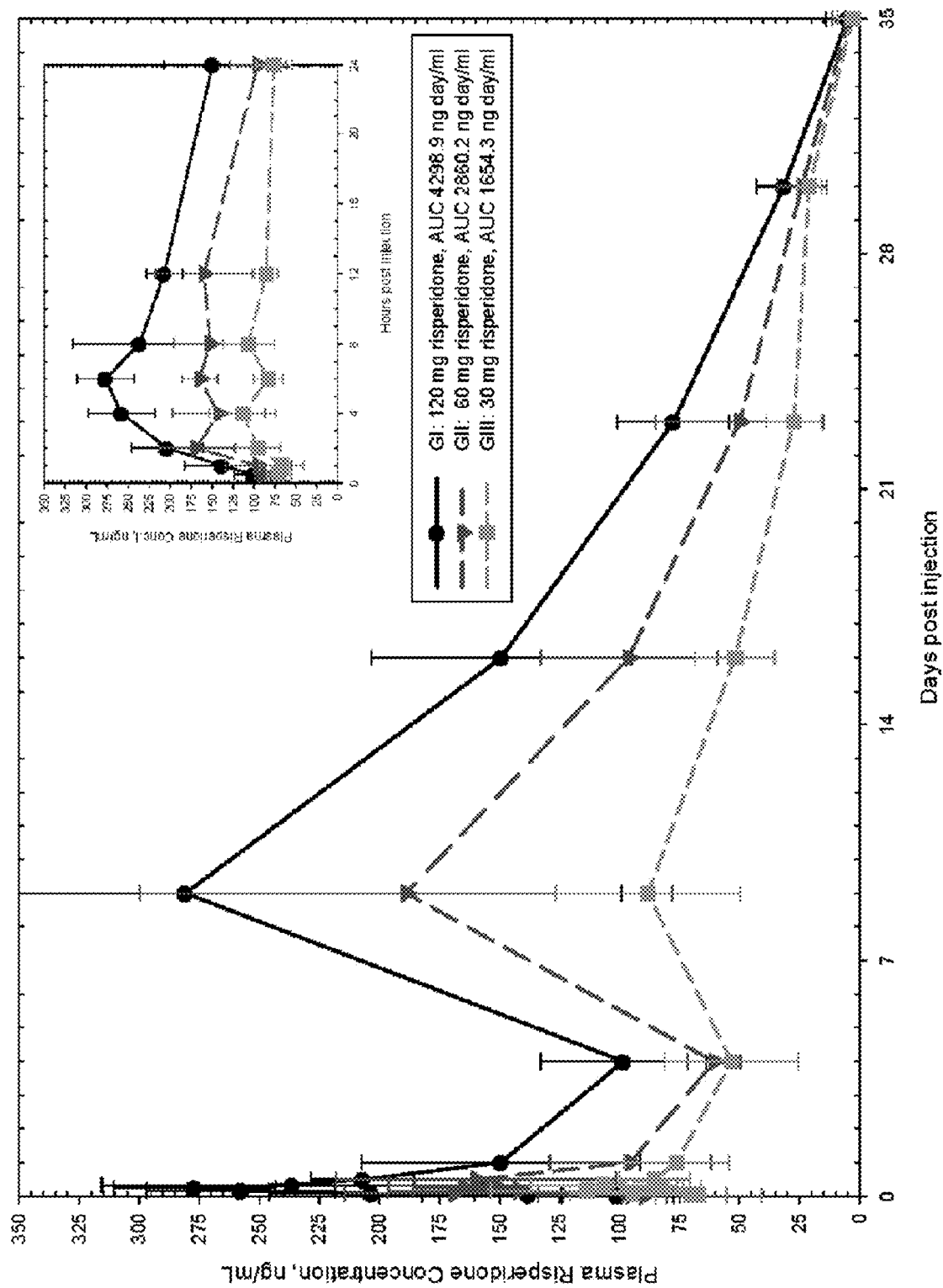
FIG. 16 illustrates the 35-day risperidone/ATRIGEL® pharmacokinetic study in rabbits.

The area under the curve ($AUC_{Day\ 0\text{-}35}$) for each formulation, highest plasma risperidone concentration ($C_{max}$) and time ($T_m$) for this rabbit study were shown in Table 32. The pharmacokinetic profiles for all formulations injected in this rabbit study were shown in FIG. 16.

TABLE 32

Pharmacokinetic Parameters for EXAMPLE 2.4

| FORMULA | $C_{MAX}$ NG/ML | $T_M$ | $AUC_{DAY\ 0\text{-}35}$ NG-DAY/ML |
|---|---|---|---|
| 120 MG RISPERIDONE/ATRIGEL® | 280.7 | DAY 9 | 4298.9 |
| 60 MG RISPERIDONE/ATRIGEL® | 188.8 | DAY 9 | 2860.2 |
| 30 MG RISPERIDONE/ATRIGEL® | 113.5 | 4 HOURS | 1654.4 |

Example 3

Pharmacokinetics and Pharmacodynamics Studies in Dogs

The purpose of this study was to determine the pharmacokinetic profiles of risperidone/ATRIGEL® formulations and to evaluate the anti-emetic effect in dogs. The selected Risperidone/ATRIGEL® formulation was evaluated in EXAMPLE 3 for pharmacokinetic and pharmacodynamic in the dog. This dog preclinical study was conducted in male Beagle Dogs. Six dogs per test article were injected subcutaneous with a full dose of the test article at 30 or 60 mg risperidone. One group was injected with the ATRIGEL® delivery system and one group, under anesthesia, was injected intramuscularly with 2 mL of the RISPERDAL® CONSTA® formulation at 50 mg as negative and positive control respectively. The study duration was 45 days with blood collection at 1, 2, 6, and 8 hours, and 1, 3, 7, 10, 14, 21, 28, 35, 42, and 45 days. The pharmacodynamic study was also conducted at Day 1, 3, 7, 10, 14, 21, 28, 35, 42, and 45.

At specific time points, approximately 2-3 mL of blood was collected in $K_3$EDTA tubes from each dog. The plasma fraction was transferred to labeled 5 mL plastic culture tubes and stored at −86° C. The plasma was extracted following the Plasma SPE Extraction Procedure For Active Risperidone Plasma Analysis, described above. The active risperidone concentrations were analyzed using the Reversed Phase High Performance Liquid Chromatography Method For The Quantization of Risperidone And 9-Hydroxyrisperidone, described above.

The active risperidone plasma concentration was calculated based on both risperidone and 9-hydroxyrisperidone. The active risperidone plasma concentration was calculated based on both risperidone and 9-hydroxyrisperidone and was presented in Table 33.

TABLE 33

45-Day Active Risperidone Concentrations

| Test Article | Time Point | Plasma Concentration ng/ml | Mean Concentration ng/ml | Standard Deviation |
|---|---|---|---|---|
| Group I: RISPERDAL® CONSTA®, 50 mg, IM | Day 0.04 | 5.1 | 7.7 | 2.7 |
| | | 11.8 | | |
| | | 7.8 | | |
| | | 4.4 | | |
| | | 8.6 | | |
| | | 8.3 | | |
| | Day 0.08 | 5.7 | 7.5 | 3.5 |
| | | 8.3 | | |
| | | 11.7 | | |
| | | 2.3 | | |
| | | 10.8 | | |
| | | 6.4 | | |
| | Day 0.25 | 2.9 | 3.3 | 1.9 |
| | | 4.8 | | |
| | | 3.9 | | |
| | | 2.7 | | |
| | | 5.5 | | |
| | | 0.0 | | |
| | Day 0.33 | 2.5 | 2.8 | 1.6 |
| | | 4.0 | | |
| | | 3.6 | | |
| | | 1.9 | | |
| | | 4.5 | | |
| | | 0.0 | | |
| | Day 1 | 0.5 | 0.9 | 0.7 |
| | | 1.3 | | |
| | | 0.6 | | |
| | | 0.9 | | |
| | | 2.1 | | |
| | | 0.0 | | |
| | Day 3 | 0.5 | 2.7 | 3.8 |
| | | 10.0 | | |
| | | 3.8 | | |
| | | 0.5 | | |
| | | 1.1 | | |
| | | 0.0 | | |
| | Day 7 | 2.9 | 2.7 | 2.8 |
| | | 6.8 | | |
| | | 0.0 | | |
| | | 5.1 | | |
| | | 1.2 | | |
| | | 0.0 | | |
| | Day 10 | 0.8 | 8.4 | 16.6 |
| | | 6.0 | | |
| | | 0.0 | | |
| | | 42.0 | | |
| | | 1.4 | | |
| | | 0.0 | | |
| | Day 14 | 2.0 | 11.4 | 21.6 |
| | | 9.2 | | |
| | | 0.4 | | |
| | | 54.9 | | |
| | | 1.7 | | |
| | | 0.5 | | |
| | Day 21 | 33.7 | 43.6 | 24.9 |
| | | 65.6 | | |
| | | 71.3 | | |
| | | 49.2 | | |

TABLE 33-continued

45-Day Active Risperidone Concentrations

| Test Article | Time Point | Plasma Concentration ng/ml | Mean Concentration ng/ml | Standard Deviation |
|---|---|---|---|---|
| | | 39.1 | | |
| | | 2.3 | | |
| | Day 28 | 98.5 | 103.6 | 57.6 |
| | | 112.8 | | |
| | | 92.3 | | |
| | | 56.8 | | |
| | | 210.4 | | |
| | | 51.0 | | |
| | Day 35 | 35.0 | 50.9 | 70.0 |
| | | 43.7 | | |
| | | 0.0 | | |
| | | 12.8 | | |
| | | 190.3 | | |
| | | 23.7 | | |
| | Day 42 | 0.0 | 11.6 | 25.7 |
| | | 5.7 | | |
| | | 0.0 | | |
| | | 0.0 | | |
| | | 63.9 | | |
| | | 0.0 | | |
| | Day 45 | 0.0 | 4.8 | 11.8 |
| | | 0.0 | | |
| | | 0.0 | | |
| | | 0.0 | | |
| | | 28.8 | | |
| | | 0.0 | | |
| Group II: 45% 65/35 PLGH (InV 0.37) and 55% NMP | Day 0.04 | 0.0 | 0.9 | 1.2 |
| | | 0.0 | | |
| | | 2.6 | | |
| | | 0.0 | | |
| | | 2.3 | | |
| | | 0.4 | | |
| | Day 0.08 | 0.0 | 0.0 | 0.0 |
| | | 0.0 | | |
| | | 0.0 | | |
| | | 0.0 | | |
| | | 0.0 | | |
| | | 0.0 | | |
| | Day 0.25 | 0.0 | 0.0 | 0.0 |
| | | 0.0 | | |
| | | 0.0 | | |
| | | 0.0 | | |
| | | 0.0 | | |
| | | 0.0 | | |
| | Day 0.33 | 0.0 | 0.0 | 0.0 |
| | | 0.0 | | |
| | | 0.0 | | |
| | | 0.0 | | |
| | | 0.0 | | |
| | | 0.0 | | |
| | Day 1 | 0.0 | 0.0 | 0.0 |
| | | 0.0 | | |
| | | 0.0 | | |
| | | 0.0 | | |
| | | 0.0 | | |
| | | 0.0 | | |
| Group III: 60 mg Risperidone (15% RSP in 45% 65/35 PLGHp (InV 0.37)/NMP) | Day 0.04 | 4.9 | 33.3 | 31.6 |
| | | 2.2 | | |
| | | 28.4 | | |
| | | 54.5 | | |
| | | 85.0 | | |
| | | 24.7 | | |
| | Day 0.08 | 81.2 | 114.1 | 50.9 |
| | | 75.7 | | |
| | | 110.5 | | |
| | | 157.7 | | |
| | | 192.9 | | |
| | | 66.4 | | |
| | Day 0.25 | 84.4 | 106.4 | 65.4 |
| | | 62.4 | | |
| | | 85.5 | | |
| | | 139.6 | | |
| | | 222.6 | | |
| | | 44.0 | | |
| | Day 0.33 | 84.8 | 95.2 | 56.4 |
| | | 63.2 | | |
| | | 122.7 | | |
| | | 74.9 | | |
| | | 193.4 | | |
| | | 32.0 | | |
| | Day 1 | 49.7 | 65.9 | 41.1 |
| | | 41.5 | | |
| | | 64.6 | | |
| | | 77.1 | | |
| | | 140.3 | | |
| | | 22.1 | | |
| | Day 3 | 36.0 | 54.7 | 33.2 |
| | | 52.6 | | |
| | | 44.1 | | |
| | | 79.5 | | |
| | | 105.0 | | |
| | | 11.0 | | |
| | Day 7 | 56.5 | 72.4 | 52.2 |
| | | 70.2 | | |
| | | 62.9 | | |
| | | 58.9 | | |
| | | 171.2 | | |
| | | 14.5 | | |
| | Day 10 | 60.9 | 104.4 | 110.8 |
| | | 134.3 | | |
| | | 25.8 | | |
| | | 55.1 | | |
| | | 316.6 | | |
| | | 33.7 | | |
| | Day 14 | 86.0 | 56.1 | 41.7 |
| | | 83.7 | | |
| | | 11.5 | | |
| | | 38.0 | | |
| | | 107.4 | | |
| | | 10.5 | | |
| | Day 21 | 14.8 | 7.9 | 6.3 |
| | | 15.2 | | |
| | | 2.7 | | |
| | | 6.0 | | |
| | | 8.7 | | |
| | | 0.0 | | |
| | Day 28 | 5.1 | 3.5 | 2.9 |
| | | 7.4 | | |
| | | 2.1 | | |
| | | 1.1 | | |
| | | 5.4 | | |
| | | 0.0 | | |
| | Day 35 | 13.3 | 8.3 | 6.5 |
| | | 11.3 | | |
| | | 11.4 | | |
| | | 0.0 | | |
| | | 13.8 | | |
| | Day 42 | 0.0 | 0.0 | 0.0 |
| | | 0.0 | | |
| | | 0.0 | | |
| | | 0.0 | | |
| | | 0.0 | | |
| | | 0.0 | | |
| | Day 45 | 0.0 | 0.0 | 0.0 |
| | | 0.0 | | |
| | | 0.0 | | |
| | | 0.0 | | |

TABLE 33-continued

45-Day Active Risperidone Concentrations

| Test Article | Time Point | Plasma Concentration ng/ml | Mean Concentration ng/ml | Standard Deviation |
|---|---|---|---|---|
| | | 0.0 | | |
| | | 0.0 | | |
| Group IV: 30 mg Risperidone (15% RSP in 45% 65/35 PLGHp (InV 0.37)/NMP) | Day 0.04 | 19.1 | 45.0 | 20.5 |
| | | 35.3 | | |
| | | 32.7 | | |
| | | 50.7 | | |
| | | 77.4 | | |
| | | 55.0 | | |
| | Day 0.08 | 20.7 | 54.0 | 37.6 |
| | | 22.4 | | |
| | | 37.3 | | |
| | | 78.2 | | |
| | | 117.7 | | |
| | | 47.8 | | |
| | Day 0.25 | 16.0 | 45.5 | 32.6 |
| | | 18.3 | | |
| | | 48.3 | | |
| | | 41.3 | | |
| | | 106.2 | | |
| | | 42.7 | | |
| | Day 0.33 | 13.3 | 38.9 | 33.8 |
| | | 9.7 | | |
| | | 41.9 | | |
| | | 28.8 | | |
| | | 102.8 | | |
| | | 36.5 | | |
| | Day 1 | 10.9 | 30.6 | 28.6 |
| | | 13.2 | | |
| | | 34.6 | | |
| | | 16.0 | | |
| | | 86.4 | | |
| | | 22.3 | | |
| | Day 3 | 16.3 | 36.1 | 25.2 |
| | | 6.2 | | |
| | | 44.9 | | |
| | | 26.0 | | |
| | | 76.2 | | |
| | | 46.9 | | |
| | Day 7 | 9.2 | 29.3 | 31.9 |
| | | 6.1 | | |
| | | 14.3 | | |
| | | 24.3 | | |
| | | 91.9 | | |
| | | 30.3 | | |
| | Day 10 | 20.1 | 51.5 | 54.4 |
| | | 4.9 | | |
| | | 32.1 | | |
| | | 77.7 | | |
| | | 150.5 | | |
| | | 23.8 | | |
| | Day 14 | 3.8 | 27.1 | 31.9 |
| | | 5.1 | | |
| | | 38.0 | | |
| | | 9.4 | | |
| | | 86.9 | | |
| | | 19.5 | | |
| | Day 21 | 1.1 | 2.0 | 2.9 |
| | | 0.0 | | |
| | | 0.0 | | |
| | | 0.0 | | |
| | | 3.9 | | |
| | | 7.1 | | |
| | Day 28 | 0.0 | 0.6 | 1.1 |
| | | 0.0 | | |
| | | 2.8 | | |
| | | 0.8 | | |
| | | 0.0 | | |
| | | 0.0 | | |
| | Day 35 | 0.0 | 0.0 | 0.0 |
| | | 0.0 | | |
| | | 0.0 | | |
| | | 0.0 | | |
| | | 0.0 | | |
| | | 0.0 | | |
| | Day 42 | 0.0 | 0.0 | 0.0 |
| | | 0.0 | | |
| | | 0.0 | | |
| | | 0.0 | | |
| | | 0.0 | | |
| | | 0.0 | | |
| | Day 45 | 0.0 | 0.0 | 0.0 |
| | | 0.0 | | |
| | | 0.0 | | |
| | | 0.0 | | |
| | | 0.0 | | |
| | | 0.0 | | |

In the afternoon at the specified time points each dog was injected with apomorphine and was monitored to determine the emetic effect of the drug. A characteristic of risperidone in plasma is the prevention of emesis.

Personnel evaluated injection sites at each time point for any abnormalities including redness, bleeding, swelling, discharge, bruising, and Test Article extrusion. Additionally, personnel observed animals post administration for signs of overt toxicity for the duration of the study.

The plasma was analyzed following the Plasma SPE Extraction Procedure For Active Risperidone Plasma Analysis, described above. The active risperidone concentrations were analyzed using the Reversed Phase High Performance Liquid Chromatography Method For The Quantization of Risperidone And 9-Hydroxyrisperidone, described above. None or minimal skin irritation was confirmed and consistent with the previous rabbit studies.

The two doses of the risperidone/ATRIGEL® formulations showed an initial maximum plasma risperidone concentration within the first 2 hours of the 45-day study. The risperidone concentrations for each dose were dose, dependent and the plasma risperidone profile showed a second burst of risperidone at day 10 (51.0 ng/mL and 104.4 ng/mL) for the 30 and 60 mg risperidone doses. The risperidone concentration exceeded 5 ng/mL through day 21 in this dog study for the 60 mg dose. Plasma risperidone levels were less than 10 ng/mL from day 21 through day 35. There were no detectable risperidone concentrations at day 42 and 45 for the 60 mg risperidone formulation. The plasma risperidone of the 30 mg Risperidone/ATRIGEL® group showed less than 5 ng/mL at day 21 and risperidone concentrations were near zero at days 28 through 45.

The 50 mg RISPERDAL® CONSTA® group (Group I) showed an initial plasma risperidone concentration of 7.7 ng/mL. Plasma risperidone concentrations continued to be at or below this concentration until day 14 when the risperidone concentration in plasma increased to a mean value of 11.4 ng/mL. The highest plasma risperidone concentrations ($C_{max}$) for this product were found at day 28, 104.4 ng/mL. The plasma risperidone concentrations at day 42 decreased to 11.4 ng/mL and at day 45 plasma risperidone was 4.8 ng/mL.

Figure 17:
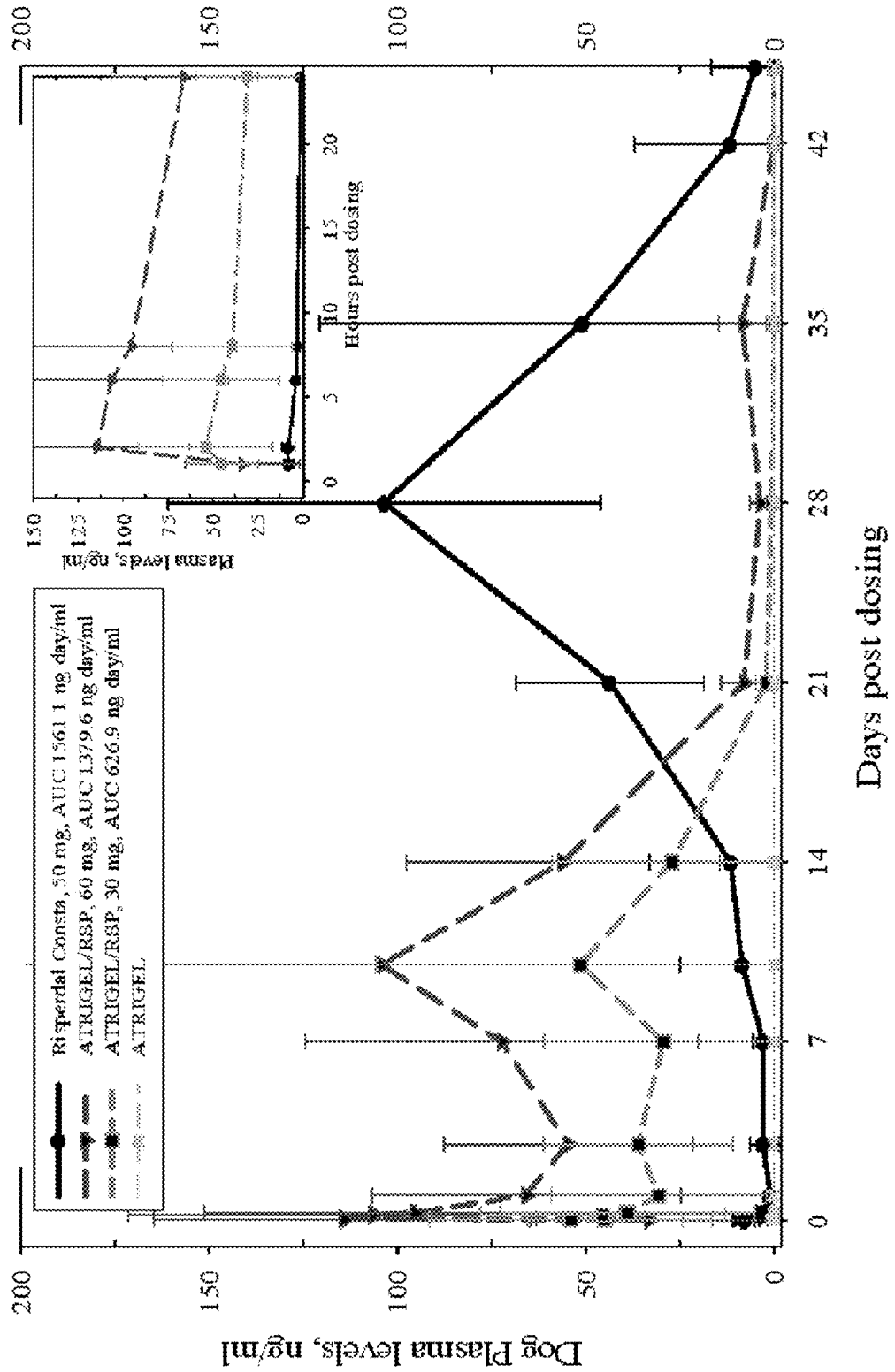
FIG. 17 illustrates the 45-day risperidone/ATRIGEL® pharmacokinetic study in dogs.

The area under the curve. ($AUC_{Day\ 0-45}$) for each formulation, highest plasma risperidone concentration ($C_{max}$) and time ($T_m$) for this dog study were shown in Table 34. The pharmacokinetic profiles for all formulations injected in this dog study were shown in FIG. 17.

TABLE 34

Pharmacokinetic Parameters for EXAMPLE 3.1

| FORMULA | $C_{MAX}$ NG/ML | $T_M$ | $AUC_{DAY\ 0-45}$ NG-DAY/ML |
|---|---|---|---|
| 120 MG RISPERDAL ® CONSTA ® | 103.6 | DAY 28 | 1561.1 |
| 60 MG RISPERIDONE/ATRIGEL ® | 114.1 | 2 HOURS | 1379.6 |
| 30 MG RISPERIDONE/ATRIGEL ® | 54.0 | 2 HOURS | 626.9 |

The pharmacodynamics for risperidone in plasma were measured by the antiemesis effects of risperidone in plasma. At the time points previously described, dogs were injected with an iv administration of apomorphine. After apomorphine administration, the dog was observed for 15 minutes for emesis and the dogs showing emesis were recorded as positive. Results of this testing were recorded in Table 35.

All dogs in the ATRIGEL® group had emesis at all time points. Dogs in the 30 mg dose of Risperidone/ATRIGEL® group showed no emesis through day 21 of the study. At day 28, 33% of the dogs showed an antiemetic effect. Dogs in this group at days 35 through 45 showed a 0-17% antiemetic effect. The 60 mg dose of Risperidone/ATRIGEL® showed no emesis through day 21 and the antiemetic effect was demonstrated in 83% of the dogs at day 28. The antiemetic effect was observed at 50-67% in the dogs in this group from days 35 through 45. The 50 mg dose of RISPERDAL® CONSTA® showed a variable antiemetic effect from day 1 through day 21. The antiemetic effect was 100% for these dogs at days 28 and 35. It decreased at days 42 and 45.

The pharmacokinetic profile for the dogs correlated with the observed anti-emetic effect. Higher plasma risperidone concentrations protected the dogs from emesis. The 30 mg Risperidone/ATRIGEL® formulation showed 100% pharmacodynamic activity through Day 21 and decreased to 33% at Day 28. At time points after Day 28, the antiemetic effect was zero and the plasma risperidone concentrations were not detectable. The 60 mg Risperidone/ATRIGEL® formulation was nearly 100% effective against emesis through Day 28 and showed some activity until the end of the study (Day 45). The RISPERDAL® CONSTA® product had its highest antiemetic activity from days 14 through 35 in this study. At days 42 and 45 the pharmacodynamics activity had decreased.

Example 4

Second Pharmacokinetics and Pharmacodynamics Studies in Dogs

In concern of the low plasma risperidone concentrations and less than 100% antiemetic effect at Day 28 revealed in the dog study of EXAMPLE 3, a second dog pharmacokinetic and pharmacodynamic study (EXAMPLE 4) was conducted to determine if slight modifications to the risperidone/ATRIGEL® delivery system could reduce initial release and increase the duration of drug release. For example, three Risperidone/ATRIGEL® formulations using polymers other than the identified 65/35 PLGHp (37K) were evaluated. The formulations include: (1) 60 mg Risperidone, (15% Risperidone in 45% 75/25 PLGHp (37K)/N-methyl-2-pyrrolidone), (2) 60 mg Risperidone, (15% Risperidone in 45% 80/20 PLGHp (42K)/N-methyl-2-pyrrolidone), and (3) 60 mg Risperidone, (15% Risperidone in 50% 65/35 poly(lactide-co-glycolide) (Dod) (19K)/N-methyl-2-pyrrolidone).

Six male Beagle dogs per test article were injected subcutaneous with a full dose of the test article at 60 mg risperidone. The study duration was 45 days with blood collection at 1, 2, 6, and 8 hours, and 1, 3, 7, 10, 14, 21, 29, 35, 42, and 45 days. The pharmacodynamics study was also conducted at Day 1, 3, 7, 10, 14, 21, 29, 35, 42, and 45. The blood collection/analysis and pharmacodynamic studies were conducted following the same procedures as described in EXAMPLE 3.

Personnel evaluated injection sites at each time point for any abnormalities including redness, bleeding, swelling, discharge, bruising, and Test Article extrusion. Additionally, personnel observed animals post administration for signs of overt toxicity for the duration of the study. None or minimal skin irritation was confirmed and consistent with the previous studies.

All formulations showed an initial maximum plasma risperidone concentration within the first 6 hours of the 45-day study. The plasma risperidone profile showed a second burst of risperidone at Day 10 (70.0 ng/mL and 88.4 ng/mL) for Group I and III respectively. No second burst for Group II. The plasma active risperidone concentrations exceeded 12 ng/ml through Day 29 and maintained detectable risperidone levels at Day 42 and 45 for all the formulations.

Figure 18:
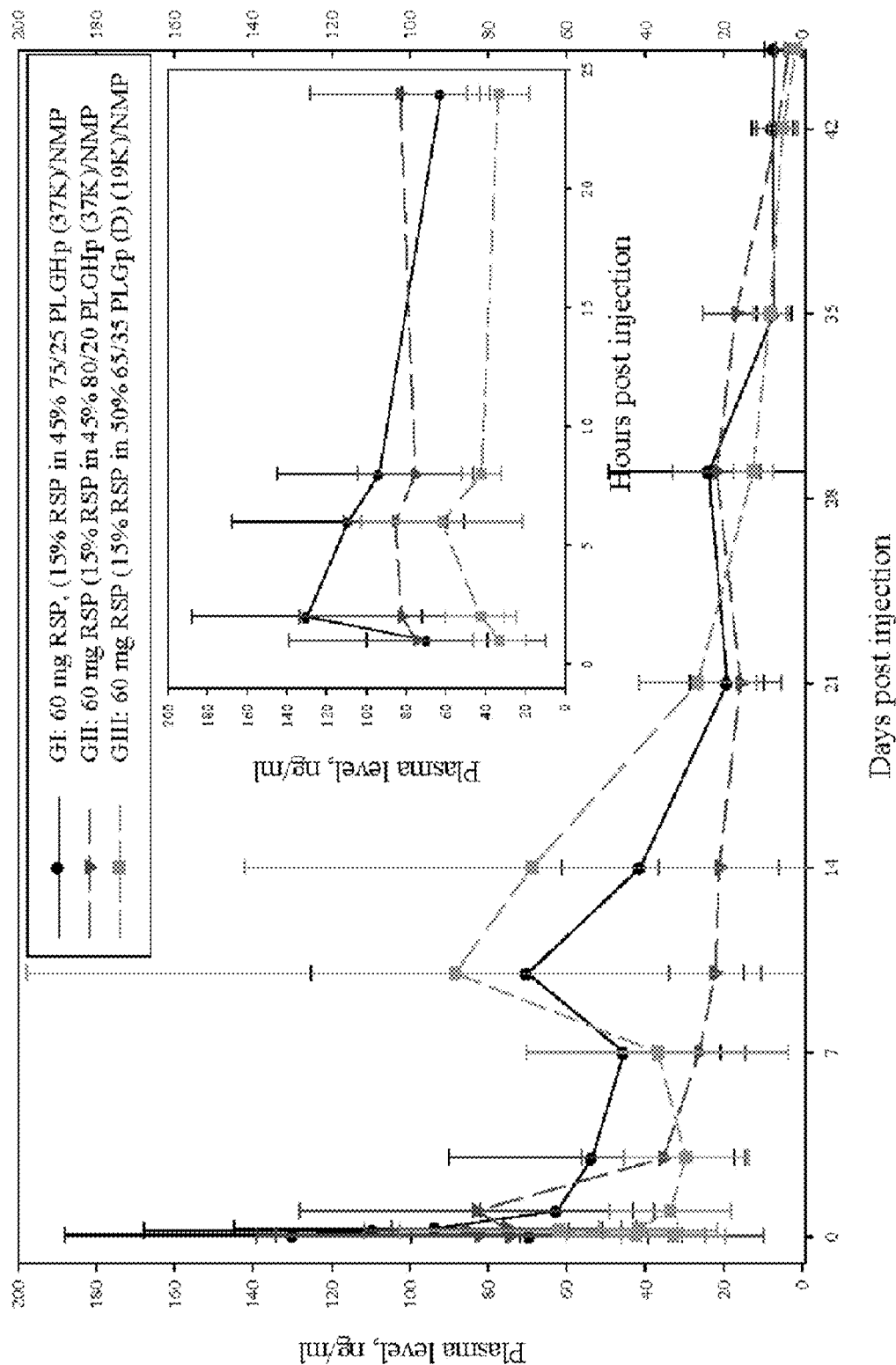
FIG. 18 illustrates the 45-day risperidone/ATRIGEL® pharmacokinetic study in dogs.

The pharmacokinetic profiles for all formulations injected in this dog study were shown in FIG. 18, detailed data presented in Table 36.

TABLE 35

Pharmacodynamics Risperidone/ATRIGEL ® in Dogs
% Dogs Showing Antiemetic Effect using Apomorphine

| TIME DAY | 50 MG RISPERDAL ® CONSTA ® | 30 MG RISPERIDONE/ ATRIGEL ® | 60 MG RISPERIDONE/ ATRIGEL ® | CONTROL ATRIGEL ® |
|---|---|---|---|---|
| 1 | 50% (3/6) | 100% (6/6) | 100% (6/6) | 0% (0/6) |
| 3 | 83% (5/6) | 100% (6/6) | 100% (6/6) | 0% (0/6) |
| 7 | 67% (4/6) | 100% (6/6) | 100% (6/6) | 0% (0/6) |
| 10 | 50% (3/6) | 100% (6/6) | 100% (6/6) | 0% (0/6) |
| 14 | 83% (5/6) | 100% (6/6) | 100% (6/6) | 0% (0/6) |
| 21 | 83% (5/6) | 100% (6/6) | 100% (6/6) | 0% (0/6) |
| 28 | 100% (6/6) | 33% (2/6) | 83% (5/6) | 0% (0/6) |
| 35 | 100% (6/6) | 17% (1/6) | 67% (4/6) | 0% (0/6) |
| 42 | 67% (4/6) | 17% (1/6) | 50% (3/6) | 0% (0/6) |
| 45 | 33% (2/6) | 0% (0/6) | 50% (3/6) | 0% (0/6) |

TABLE 36

45-Day Active Risperidone Concentrations

| Test Article | Time Point | Plasma Concentration ng/ml | Mean Concentration ng/ml | Standard Deviation |
|---|---|---|---|---|
| Group I: 60 mg Risperidone (15% risperidone in 45% 75/25 PLGHp (37K)/NMP) 0.4 ml SC injection | Day 0.04 | 74.9 | 69.3 | 30.3 |
| | | 91.9 | | |
| | | 62.3 | | |
| | | 110.8 | | |
| | | 49.9 | | |
| | | 25.8 | | |
| | Day 0.08 | 116.9 | 129.8 | 58.0 |
| | | 203.6 | | |
| | | 140.9 | | |
| | | 119.6 | | |
| | | 166.1 | | |
| | | 31.4 | | |
| | Day 0.25 | 48.4 | 109.2 | 58.4 |
| | | 165.3 | | |
| | | 165.3 | | |
| | | 109.4 | | |
| | | 136.9 | | |
| | | 29.9 | | |
| | Day 0.33 | 115.6 | 93.4 | 51.2 |
| | | 49.2 | | |
| | | 164.4 | | |
| | | 125.4 | | |
| | | 78.8 | | |
| | | 27.1 | | |
| | Day 1 | 47.3 | 62.4 | 19.5 |
| | | 86.5 | | |
| | | 74.7 | | |
| | | 77.4 | | |
| | | 50.0 | | |
| | | 38.7 | | |
| | Day 3 | 17.2 | 53.5 | 36.4 |
| | | 41.6 | | |
| | | 95.1 | | |
| | | 103.3 | | |
| | | 34.4 | | |
| | | 29.2 | | |
| | Day 7 | 18.6 | 45.3 | 24.7 |
| | | 37.9 | | |
| | | 76.0 | | |
| | | 46.0 | | |
| | | 72.7 | | |
| | | 20.9 | | |
| | Day 10 | 27.2 | 70.0 | 55.1 |
| | | 47.0 | | |
| | | 89.3 | | |
| | | 52.5 | | |
| | | 173.1 | | |
| | | 30.8 | | |
| | Day 14 | 25.6 | 41.3 | 19.8 |
| | | 75.8 | | |
| | | 53.0 | | |
| | | 25.2 | | |
| | | 37.6 | | |
| | | 30.3 | | |
| | Day 21 | 10.9 | 19.0 | 9.3 |
| | | 34.0 | | |
| | | 26.0 | | |
| | | 13.8 | | |
| | | 11.2 | | |
| | | 18.2 | | |
| | Day 29 | 8.0 | 13.4 | 8.9 |
| | | 25.5 | | |
| | | 23.8 | | |
| | | 9.9 | | |
| | | 6.6 | | |
| | | 6.4 | | |
| | Day 35 | 5.5 | 7.2 | 4.2 |
| | | 15.2 | | |
| | | 6.2 | | |
| | | 8.1 | | |
| | | 5.1 | | |
| | | 3.2 | | |
| | Day 42 | 8.1 | 7.5 | 5.1 |
| | | 14.6 | | |
| | | 6.2 | | |
| | | 4.6 | | |
| | | 11.4 | | |
| | | 0.0 | | |
| | Day 45 | 4.5 | 4.7 | 4.1 |
| | | 10.2 | | |
| | | 5.8 | | |
| | | 7.6 | | |
| | | 0.0 | | |
| | | 0.0 | | |
| Group II: 60 mg Risperidone (15% risperidone in 45% 80/20 PLGHp (42K)/NMP) 0.4 ml SC injection | Day 0.04 | 181.3 | 65.3 | 62.1 |
| | | 90.5 | | |
| | | 37.5 | | |
| | | 27.8 | | |
| | | 35.4 | | |
| | | 19.2 | | |
| | Day 0.08 | 168.5 | 75.1 | 49.4 |
| | | 91.9 | | |
| | | 39.4 | | |
| | | 56.2 | | |
| | | 43.0 | | |
| | | 51.5 | | |
| | Day 0.25 | 120.4 | 85.4 | 26.1 |
| | | 85.3 | | |
| | | 53.2 | | |
| | | 72.4 | | |
| | | 112.2 | | |
| | | 69.0 | | |
| | Day 0.33 | 78.6 | 75.2 | 29.3 |
| | | 45.9 | | |
| | | 107.5 | | |
| | | 52.3 | | |
| | | 112.8 | | |
| | | 54.3 | | |
| | Day 1 | 106.0 | 83.0 | 45.2 |
| | | 71.5 | | |
| | | 19.8 | | |
| | | 129.8 | | |
| | | 126.4 | | |
| | | 44.4 | | |
| | Day 3 | 76.1 | 35.3 | 20.8 |
| | | 29.6 | | |
| | | 15.8 | | |
| | | 30.8 | | |
| | | 28.8 | | |
| | | 30.9 | | |
| | Day 7 | 39.6 | 26.1 | 11.6 |
| | | 26.9 | | |
| | | 7.1 | | |
| | | 36.5 | | |
| | | 24.3 | | |
| | | 22.3 | | |
| | Day 10 | 29.4 | 22.1 | 11.8 |
| | | 21.9 | | |
| | | 6.1 | | |
| | | 40.1 | | |
| | | 20.4 | | |
| | | 14.6 | | |
| | Day 14 | 20.3 | 22.6 | 13.9 |
| | | 11.0 | | |
| | | 14.3 | | |
| | | 41.0 | | |
| | | 38.7 | | |
| | | 10.1 | | |

TABLE 36-continued

45-Day Active Risperidone Concentrations

| Test Article | Time Point | Plasma Concentration ng/ml | Mean Concentration ng/ml | Standard Deviation |
|---|---|---|---|---|
| | Day 21 | 20.3 | 15.6 | 10.5 |
| | | 8.1 | | |
| | | 7.6 | | |
| | | 34.8 | | |
| | | 12.9 | | |
| | | 10.1 | | |
| | Day 29 | 17.0 | 21.7 | 11.1 |
| | | 14.1 | | |
| | | 19.2 | | |
| | | 39.5 | | |
| | | 30.5 | | |
| | | 10.1 | | |
| | Day 35 | 17.2 | 16.8 | 8.4 |
| | | 11.1 | | |
| | | 6.7 | | |
| | | 30.0 | | |
| | | 22.6 | | |
| | | 13.2 | | |
| | Day 42 | 10.0 | 6.2 | 5.2 |
| | | 7.1 | | |
| | | 1.2 | | |
| | | 13.7 | | |
| | | 0.0 | | |
| | | 5.5 | | |
| | Day 45 | 7.0 | 3.4 | 3.2 |
| | | 3.4 | | |
| | | 0.0 | | |
| | | 7.1 | | |
| | | 0.0 | | |
| | | 3.1 | | |
| Group III: 60 mg Risperidone (15% risperidone in 50% 65/35 PLGHp (D) (29K)/NMP) 0.4 ml SC injection | Day 0.04 | 35.5 | 32.7 | 13.3 |
| | | 56.1 | | |
| | | 19.1 | | |
| | | 25.4 | | |
| | | 24.1 | | |
| | | 35.9 | | |
| | Day 0.08 | 54.3 | 42.3 | 17.8 |
| | | 66.2 | | |
| | | 20.7 | | |
| | | 40.5 | | |
| | | 23.2 | | |
| | | 48.8 | | |
| | Day 0.25 | 43.0 | 46.5 | 17.5 |
| | | 54.8 | | |
| | | 77.1 | | |
| | | 33.3 | | |
| | | 28.6 | | |
| | | 41.9 | | |
| | Day 0.33 | 55.0 | 41.8 | 10.0 |
| | | 41.0 | | |
| | | 43.4 | | |
| | | 50.3 | | |
| | | 30.8 | | |
| | | 30.5 | | |
| | Day 1 | 61.3 | 33.5 | 15.6 |
| | | 24.8 | | |
| | | 22.9 | | |
| | | 26.7 | | |
| | | 22.4 | | |
| | | 42.8 | | |
| | Day 3 | 42.6 | 29.5 | 15.9 |
| | | 29.0 | | |
| | | 18.8 | | |
| | | 17.8 | | |
| | | 14.7 | | |
| | | 54.3 | | |
| | Day 7 | 25.1 | 36.7 | 33.3 |
| | | 25.8 | | |
| | | 23.2 | | |
| | | 37.5 | | |
| | | 7.0 | | |
| | | 101.8 | | |
| | Day 10 | 72.4 | 88.4 | 109.3 |
| | | 50.5 | | |
| | | 43.2 | | |
| | | 40.3 | | |
| | | 15.7 | | |
| | | 308.5 | | |
| | Day 14 | 82.2 | 68.6 | 73.2 |
| | | 30.8 | | |
| | | 66.1 | | |
| | | 14.4 | | |
| | | 11.8 | | |
| | | 206.4 | | |
| | Day 21 | 32.9 | 26.5 | 15.1 |
| | | 9.5 | | |
| | | 43.6 | | |
| | | 20.2 | | |
| | | 11.0 | | |
| | | 41.9 | | |
| | Day 28 | 12.1 | 12.3 | 4.6 |
| | | 6.7 | | |
| | | 15.9 | | |
| | | 8.2 | | |
| | | 12.0 | | |
| | | 18.9 | | |
| | Day 35 | 6.9 | 8.0 | 4.7 |
| | | 4.8 | | |
| | | 14.6 | | |
| | | 9.8 | | |
| | | 1.3 | | |
| | | 10.6 | | |
| | Day 42 | 3.2 | 4.8 | 3.4 |
| | | 8.8 | | |
| | | 6.7 | | |
| | | 7.5 | | |
| | | 0.0 | | |
| | | 2.9 | | |
| | Day 45 | 0.0 | 1.3 | 2.6 |
| | | 6.5 | | |
| | | 0.0 | | |
| | | 0.0 | | |
| | | 0.0 | | |
| | | 1.5 | | |

The area under the curve ($AUC_{Day\ 0\text{-}45}$) for each formulation, highest plasma risperidone concentration ($C_{max}$) and time ($T_m$) for this dog study were shown in Table 37.

TABLE 37

Pharmacokinetic Parameters for EXAMPLE 4

| TEST ARTICLE | $C_{MAX}$ (NG/ML) | $T_M$ | $AUC_{DAY\ 0\text{-}45}$ (NG-DAY/ML) |
|---|---|---|---|
| GROUP I: 60 MG RISPERIDONE 15% RSP IN 45% 75/25 PLGHP (37K)/NMP | 129.8 | 2 HOURS | 1270.7 |
| GROUP II: 60 MG RISPERIDONE 15% RSP IN 45% 80/20 PLGHP (42K)/NMP | 85.4 | 6 HOURS | 973.3 |
| GROUP IV: 60 MG RISPERIDONE 15% RSP IN 45% 65/35 PLGP(D) (27K)/NMP | 46.5 | 6 HOURS | 1339.1 |

Table 38 showed the pharmacodynamic results of the study. The same dog in Group I threw up on Day 3 and Day 10 in 14-16 minutes after administration of apomorphine, another dog in this group showed emesis on Days 42 and 45, all the other dogs remained healthy through out the study. All dogs showed anti-emesis through Day 45 in Group II except one dog threw up on both Days 42 and 45. These results indicate that formulations Group I and II released risperidone slowly over time and remained at efficacious risperidone levels in dogs over 35 days. Starting from Day 42, active risperidone concentration in some animals (approximately 16.6%) started to drop and could not retain the anti-emetic effect. All dogs in Group III were healthy through Day 29, 3 dogs showed no anti-emesis on Days 35 and 42, and 4 dogs on Day 45 failed to show anti-emesis. These results indicate that Formulation Group III was a one-month formulation which sustained release risperidone at an efficacious level over 29 days. However, Group II showed the best anti-emetic effect through out the study. Overall, all three formulations sustained released efficacious amounts of risperidone over time and showed a minimum efficacy of 29 days.

TABLE 38

Pharmacodynamics Risperidone/ATRIGEL ® in Dogs
% Dogs Showing Antiemetic Effect using Apomorphine

| TIME DAY | 60 MG RISPERIDONE (15% RISPERIDONE IN 45% 75/25 PLGHP (37K)/NMP) | 60 MG RISPERIDONE (15% RISPERIDONE IN 45% 80/20 PLGHP (42K)/NMP) | 60 MG RISPEIRDONE (15% RISPERIDONE IN 50% 65/35 PLG (DOD) (27K)/NMP) |
|---|---|---|---|
| 1 | 100% (6/6) | 100% (6/6) | 100% (6/6) |
| 3 | 83% (5/6) | 100% (6/6) | 100% (6/6) |
| 7 | 100% (6/6) | 100% (6/6) | 100% (6/6) |
| 10 | 83% (5/6) | 100% (6/6) | 100% (6/6) |
| 14 | 100% (6/6) | 100% (6/6) | 100% (6/6) |
| 21 | 100% (6/6) | 100% (6/6) | 100% (6/6) |
| 29 | 100% (6/6) | 100% (6/6) | 100% (6/6) |
| 35 | 100% (6/6) | 100% (6/6) | 50% (3/6) |
| 42 | 83% (5/6) | 83% (5/6) | 50% (3/6) |
| 45 | 83% (1/6) | 83% (5/6) | 33% (2/6) |

Example 5

Third Pharmacokinetics and Pharmacodynamics Studies in Dogs

The purpose of this study was to provide oral vs. risperidone/ATRIGEL® pharmacokinetic data to verify dosing in humans. For example, a Risperidone/ATRIGEL® formulation containing 15% Risperidone suspended in a delivery vehicle of 45% 80/20 PLGHp (42K)/N-methyl-2-pyrrolidone was selected from EXAMPLE 4 and further evaluated in this pharmacokinetic and pharmacodynamic dog study. Three test groups based on this selected formulation delivering 60, 90, or 120 mg risperidone (Group IV, V, and VI) were tested and compared to three control groups, RISPERDAL® Tablets containing 2, 3, or 4 mg risperidone (Group I, II, and III).

Six dogs per test article in this study were injected subcutaneous with approximately 400, 600, and 800 μl of the identified formulation, which delivered approximately 60, 90, and 120 mg of risperidone respectively. Six dogs per control article received an oral tablet daily for 35 days. The study duration was 56 days with blood collection at 1, 2, 4, 6, 8, and 12 hours, and 1, 3, 7, 10, 14, 21, 28, 35, and 42 for all six groups. Blood was also collected on Day 49 and 56 for ATRIGEL® groups. The pharmacodynamics study was conducted at Day 20, 24, 30, and 35. The blood collection/analysis and pharmacodynamic studies were conducted following the same procedures as described in EXAMPLE 3.

Personnel evaluated injection sites at each time point for any abnormalities including redness, bleeding, swelling, discharge, bruising, and Test Article extrusion. Additionally, personnel observed animals post administration for signs of overt toxicity for the duration of the study. None or minimal skin irritation was confirmed and consistent with the previous studies.

Figure 19:
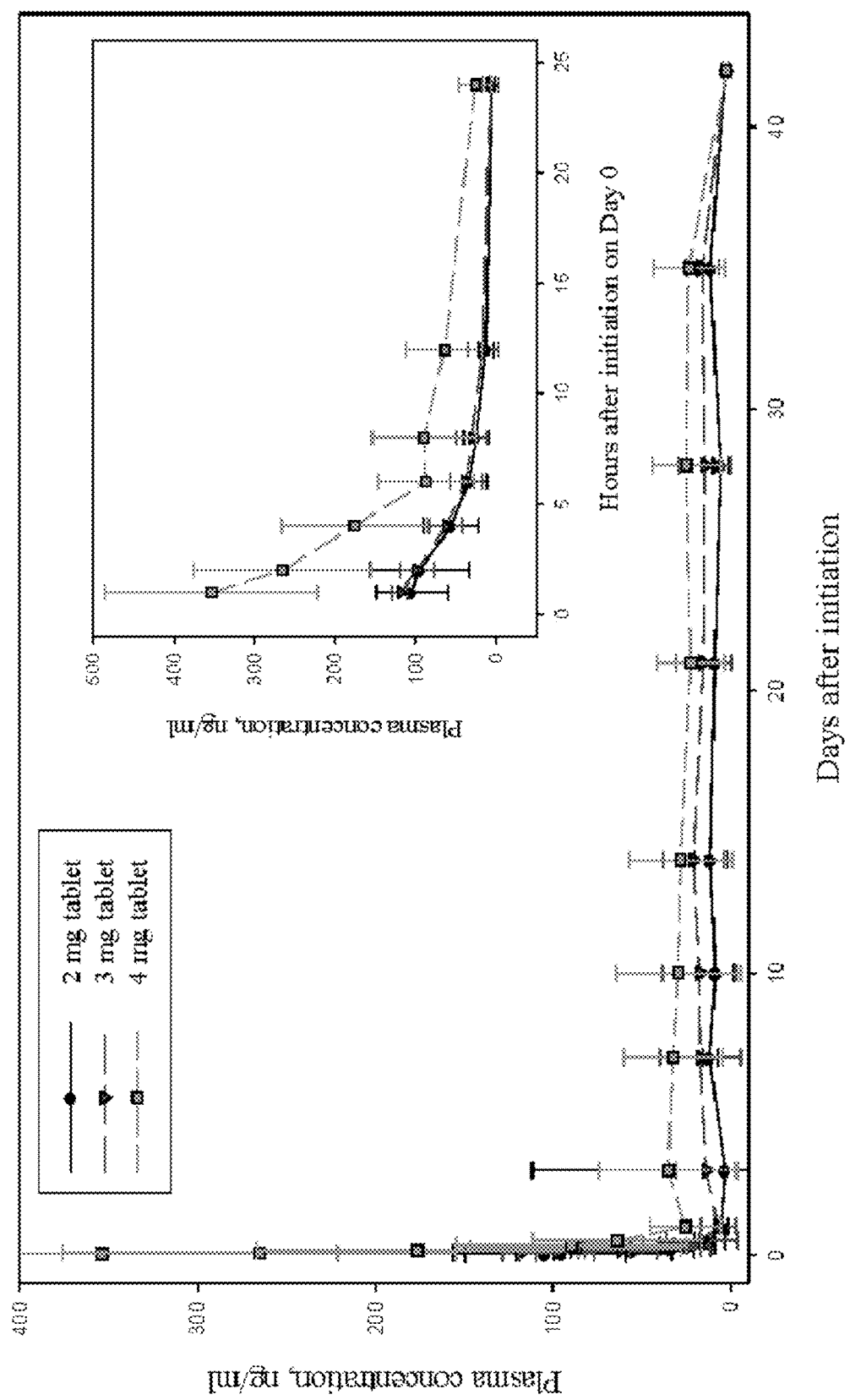
FIG. 19 illustrates the pharmacokinetics of RISPERDAL® tablet daily oral doses of 2 mg, 3 mg, and 4 mg in dogs.

Overall, Groups I to III (RISPERDAL® tablet groups) showed the plasma $C_{max}$ at 1 hour after administration, and reached steady plasma basal levels ($C_{min}$) from Day 7 to Day 35 (FIG. 19 and Table 39). The $C_{min}$ of Group I to III from Day 7 to Day 35 were 9.8, 17.3, and 27.2 ng/ml respectively. Groups I to III showed decreases in plasma risperidone concentration to approximately 3 ng/ml at Day 42 after the last oral dose on Day 35. The plasma risperidone $C_{max}$ levels and basal levels $C_{min}$ for the three groups were determined to be directly dose related.

TABLE 39

45-Day Active Risperidone Concentrations

| Test Article | Time Point | Plasma Concentration ng/ml | Mean Concentration ng/ml | Standard Deviation |
|---|---|---|---|---|
| Group I: RISPERDAL ® tablet, 2 mg oral, daily for 35 days | Day 0.04 | 125.2 | 104.6 | 45.1 |
| | | 34.7 | | |
| | | 157.6 | | |
| | | 130.9 | | |
| | | 111.2 | | |
| | | 68.1 | | |
| | Day 0.08 | 134.6 | 95.2 | 61.4 |
| | | 6.6 | | |
| | | 172.9 | | |
| | | 125.2 | | |
| | | 86.0 | | |
| | | 45.9 | | |
| | Day 0.16 | 76.2 | 55.9 | 34.5 |
| | | 4.4 | | |
| | | 87.7 | | |
| | | 89.4 | | |
| | | 48.4 | | |
| | | 29.3 | | |
| | Day 0.25 | 47.8 | 33.9 | 22.4 |
| | | 0.0 | | |
| | | 45.8 | | |
| | | 60.5 | | |
| | | 32.9 | | |
| | | 16.1 | | |
| | Day 0.33 | 41.4 | 24.8 | 15.6 |
| | | 9.7 | | |
| | | 26.8 | | |
| | | 44.4 | | |
| | | 18.8 | | |
| | | 7.8 | | |
| | Day 0.5 | 16.7 | 12.4 | 8.7 |
| | | 1.6 | | |
| | | 15.0 | | |
| | | 24.8 | | |
| | | 13.0 | | |
| | | 3.4 | | |
| | Day 1 | 9.3 | 5.6 | 3.7 |
| | | 3.2 | | |
| | | 4.7 | | |
| | | 9.5 | | |
| | | 6.7 | | |
| | | 0.0 | | |
| | Day 3 | 10.3 | 3.4 | 4.2 |
| | | 0.0 | | |
| | | **269.2 | | |
| | | 3.2 | | |

TABLE 39-continued

45-Day Active Risperidone Concentrations

| Test Article | Time Point | Plasma Concentration ng/ml | Mean Concentration ng/ml | Standard Deviation |
|---|---|---|---|---|
| | | 3.6 | | |
| | | 0.0 | | |
| | Day 7 | 20.8 | 12.0 | 9.6 |
| | | 22.6 | | |
| | | **159.7 | | |
| | | 10.7 | | |
| | | 6.0 | | |
| | | 0.0 | | |
| | Day 10 | 3.9 | 8.6 | 10.2 |
| | | 27.8 | | |
| | | 2.5 | | |
| | | 11.7 | | |
| | | 5.7 | | |
| | | 0.0 | | |
| | Day 14 | 10.9 | 11.6 | 9.4 |
| | | 24.5 | | |
| | | 2.0 | | |
| | | 15.5 | | |
| | | 16.8 | | |
| | | 0.0 | | |
| | Day 21 | 11.0 | 9.1 | 9.3 |
| | | 23.9 | | |
| | | 1.5 | | |
| | | 15.0 | | |
| | | 3.4 | | |
| | | 0.0 | | |
| | Day 28 | 8.5 | 6.0 | 4.3 |
| | | 10.3 | | |
| | | 2.7 | | |
| | | 10.3 | | |
| | | 4.1 | | |
| | | 0.0 | | |
| | Day 30 1 hour | 12.9 | 69.6 | 67.6 |
| | | 85.2 | | |
| | | 177.1 | | |
| | | 13.7 | | |
| | | * | | |
| | | 58.9 | | |
| | Day 30 2 hour | 6.6 | 45.0 | 44.6 |
| | | 71.6 | | |
| | | 108.9 | | |
| | | 5.8 | | |
| | | * | | |
| | | 31.8 | | |
| | Day 30 4 hour | 5.3 | 37.6 | 36.8 |
| | | 78.4 | | |
| | | 76.7 | | |
| | | 9.2 | | |
| | | * | | |
| | | 18.3 | | |
| | Day 30 6 hour | 4.4 | 31.4 | 32.9 |
| | | 67.7 | | |
| | | 67.0 | | |
| | | 7.9 | | |
| | | * | | |
| | | 9.8 | | |
| | Day 35 | 11.0 | 11.6 | 8.1 |
| | | 25.6 | | |
| | | 6.0 | | |
| | | 15.6 | | |
| | | 8.3 | | |
| | | 3.1 | | |
| | Day 42 | 0.0 | 3.3 | 2.1 |
| | | 4.6 | | |
| | | 3.1 | | |
| | | 6.3 | | |
| | | 3.2 | | |
| | | 2.8 | | |
| Group II: RISPERDAL ® tablet, 3 mg oral, daily for 35 days | Day 0.04 | * | 119.4 | 19.7 |
| | | 117.9 | | |
| | | 132.7 | | |
| | | * | | |
| | | 134.9 | | |
| | | 92.2 | | |
| | Day 0.08 | * | 98.1 | 23.8 |
| | | 119.0 | | |
| | | 81.8 | | |
| | | * | | |
| | | 118.0 | | |
| | | 73.7 | | |
| | Day 0.16 | * | 62.1 | 17.9 |
| | | 76.2 | | |
| | | 41.9 | | |
| | | * | | |
| | | 78.2 | | |
| | | 52.3 | | |
| | Day 0.25 | * | 37.6 | 16.6 |
| | | 59.3 | | |
| | | 19.1 | | |
| | | * | | |
| | | 38.0 | | |
| | | 34.0 | | |
| | Day 0.33 | * | 30.6 | 17.3 |
| | | 38.2 | | |
| | | 13.9 | | |
| | | * | | |
| | | 51.2 | | |
| | | 19.1 | | |
| | Day 0.5 | * | 24.4 | 16.3 |
| | | 35.9 | | |
| | | 5.7 | | |
| | | * | | |
| | | 40.0 | | |
| | | 16.1 | | |
| | Day 1 | * | 10.8 | 8.8 |
| | | 17.4 | | |
| | | 0.0 | | |
| | | * | | |
| | | 18.6 | | |
| | | 7.4 | | |
| | Day 3 | 11.6 | 13.9 | 16.5 |
| | | 43.1 | | |
| | | 0.0 | | |
| | | 4.1 | | |
| | | 22.4 | | |
| | | 2.2 | | |
| | Day 7 | 0.0 | 17.5 | 22.5 |
| | | 58.9 | | |
| | | 0.0 | | |
| | | 25.2 | | |
| | | 14.6 | | |
| | | 6.1 | | |
| | Day 10 | 2.5 | 18.0 | 20.7 |
| | | 55.5 | | |
| | | 0.0 | | |
| | | 26.2 | | |
| | | 15.4 | | |
| | | 8.4 | | |
| | Day 14 | 10.7 | 21.4 | 17.0 |
| | | 52.1 | | |
| | | 12.6 | | |
| | | 30.1 | | |
| | | 15.6 | | |
| | | 7.1 | | |
| | Day 21 | 10.9 | 15.6 | 14.8 |
| | | 40.4 | | |
| | | 0.0 | | |
| | | 25.6 | | |
| | | 10.7 | | |
| | | 6.0 | | |
| | Day 28 | 10.9 | 14.9 | 14.7 |
| | | 40.3 | | |
| | | 0.0 | | |

TABLE 39-continued

45-Day Active Risperidone Concentrations

| Test Article | Time Point | Plasma Concentration ng/ml | Mean Concentration ng/ml | Standard Deviation |
|---|---|---|---|---|
| | | 23.9 | | |
| | | 8.5 | | |
| | | 5.9 | | |
| | Day 30 1 hour | 180.6 | 123.8 | 79.1 |
| | | 249.5 | | |
| | | 94.2 | | |
| | | 25.0 | | |
| | | 104.5 | | |
| | | 88.9 | | |
| | Day 30 2 hour | 157.8 | 110.1 | 71.3 |
| | | 226.2 | | |
| | | 64.1 | | |
| | | 28.1 | | |
| | | 101.1 | | |
| | | 83.4 | | |
| | Day 30 4 hour | 129.5 | 95.3 | 53.0 |
| | | 179.4 | | |
| | | 36.0 | | |
| | | 101.3 | | |
| | | 71.5 | | |
| | | 54.3 | | |
| | Day 30 6 hour | 94.3 | 92.7 | 70.0 |
| | | 163.5 | | |
| | | 11.6 | | |
| | | 186.9 | | |
| | | 63.3 | | |
| | | 36.5 | | |
| | Day 35 | 12.3 | 16.2 | 9.3 |
| | | 25.0 | | |
| | | 3.3 | | |
| | | 28.7 | | |
| | | 16.0 | | |
| | | 11.7 | | |
| | Day 42 | 2.9 | 2.9 | 1.7 |
| | | 5.0 | | |
| | | 3.1 | | |
| | | 3.9 | | |
| | | 0.0 | | |
| | | 2.4 | | |
| Group III: RISPERDAL ® tablet, 4 mg oral, daily for 35 days | Day 0.04 | 348.9 | 353.8 | 132.2 |
| | | 439.4 | | |
| | | 489.7 | | |
| | | * | | |
| | | 347.1 | | |
| | | 143.8 | | |
| | Day 0.08 | 195.0 | 265.3 | 110.6 |
| | | 316.7 | | |
| | | 378.0 | | |
| | | * | | |
| | | 328.6 | | |
| | | 108.2 | | |
| | Day 0.16 | 88.3 | 176.6 | 90.3 |
| | | 240.7 | | |
| | | 272.1 | | |
| | | * | | |
| | | 208.1 | | |
| | | 73.7 | | |
| | Day 0.25 | 33.4 | 87.8 | 59.4 |
| | | 176.2 | | |
| | | 120.7 | | |
| | | * | | |
| | | 55.7 | | |
| | | 52.8 | | |
| | Day 0.33 | 13.6 | 89.9 | 64.5 |
| | | 104.8 | | |
| | | 175.6 | | |
| | | * | | |
| | | 116.1 | | |
| | | 39.2 | | |
| | Day 0.5 | 4.9 | 64.2 | 47.3 |
| | | 75.6 | | |
| | | 123.3 | | |
| | | * | | |
| | | 88.2 | | |
| | | 29.2 | | |
| | Day 1 | 1.8 | 25.9 | 19.9 |
| | | 26.4 | | |
| | | 50.6 | | |
| | | * | | |
| | | 39.3 | | |
| | | 11.5 | | |
| | Day 3 | 0.0 | 35.7 | 38.6 |
| | | 95.8 | | |
| | | 65.6 | | |
| | | 3.4 | | |
| | | 38.7 | | |
| | | 10.7 | | |
| | Day 7 | 0.0 | 32.9 | 27.7 |
| | | 37.6 | | |
| | | 61.2 | | |
| | | 14.1 | | |
| | | 68.7 | | |
| | | 15.5 | | |
| | Day 10 | 0.0 | 29.9 | 34.9 |
| | | 10.1 | | |
| | | 68.4 | | |
| | | 4.0 | | |
| | | 79.7 | | |
| | | 17.2 | | |
| | Day 14 | 1.8 | 28.5 | 29.3 |
| | | 2.1 | | |
| | | 56.0 | | |
| | | 16.7 | | |
| | | 72.6 | | |
| | | 21.7 | | |
| | Day 21 | 1.7 | 22.8 | 18.9 |
| | | 35.4 | | |
| | | 17.3 | | |
| | | 11.5 | | |
| | | 54.2 | | |
| | | 16.7 | | |
| | Day 28 | 0.0 | 25.2 | 19.2 |
| | | 41.0 | | |
| | | 45.9 | | |
| | | 9.5 | | |
| | | 39.3 | | |
| | | 15.7 | | |
| | Day 30 1 hour | 233.1 | 237.7 | 87.7 |
| | | 304.9 | | |
| | | 247.5 | | |
| | | 178.6 | | |
| | | 353.9 | | |
| | | 107.9 | | |
| | Day 30 2 hour | 160.6 | 274.7 | 102.7 |
| | | 311.6 | | |
| | | 369.7 | | |
| | | 310.0 | | |
| | | 363.6 | | |
| | | 132.7 | | |
| | Day 30 4 hour | 75.8 | 208.7 | 97.2 |
| | | 263.3 | | |
| | | 266.0 | | |
| | | 202.9 | | |
| | | 329.0 | | |
| | | 115.0 | | |
| | Day 30 6 hour | 28.6 | 142.5 | 82.5 |
| | | 207.9 | | |
| | | 215.9 | | |
| | | 102.9 | | |
| | | 219.5 | | |
| | | 80.2 | | |

TABLE 39-continued

45-Day Active Risperidone Concentrations

| Test Article | Time Point | Plasma Concentration ng/ml | Mean Concentration ng/ml | Standard Deviation |
|---|---|---|---|---|
| | Day 35 | 0.0 | 23.9 | 20.1 |
| | | 25.5 | | |
| | | 37.7 | | |
| | | 9.2 | | |
| | | 55.1 | | |
| | | 16.1 | | |
| | Day 42 | 0.0 | 2.9 | 2.3 |
| | | 0.0 | | |
| | | 5.2 | | |
| | | 3.2 | | |
| | | 4.8 | | |
| | | 4.0 | | |
| Group IV: 60 mg Risperidone (15% risperidone in 45% 80/20 PLGHp (42K)/NMP) 0.4 ml SC injection | Day 0.04 | 48.8 | 82.8 | 38.7 |
| | | 107.4 | | |
| | | 117.8 | | |
| | | 127.7 | | |
| | | 45.8 | | |
| | | 49.2 | | |
| | Day 0.08 | 55.4 | 95.3 | 39.1 |
| | | 117.0 | | |
| | | 137.0 | | |
| | | 132.4 | | |
| | | 83.0 | | |
| | | 47.1 | | |
| | Day 0.16 | 39.9 | 95.0 | 43.2 |
| | | 105.1 | | |
| | | 144.4 | | |
| | | 125.0 | | |
| | | 111.4 | | |
| | | 43.9 | | |
| | Day 0.25 | 27.2 | 82.6 | 46.1 |
| | | 79.7 | | |
| | | 155.6 | | |
| | | 102.3 | | |
| | | 90.2 | | |
| | | 40.3 | | |
| | Day 0.33 | 27.9 | 75.3 | 43.5 |
| | | 76.7 | | |
| | | 136.2 | | |
| | | 105.1 | | |
| | | 81.4 | | |
| | | 24.6 | | |
| | Day 0.5 | 18.9 | 49.1 | 31.9 |
| | | 23.1 | | |
| | | 98.0 | | |
| | | 72.7 | | |
| | | 55.8 | | |
| | | 26.4 | | |
| | Day 1 | 22.0 | 52.5 | 22.6 |
| | | 45.7 | | |
| | | 78.4 | | |
| | | 71.3 | | |
| | | 65.1 | | |
| | | 32.5 | | |
| | Day 3 | 1.5 | 30.6 | 23.4 |
| | | 30.0 | | |
| | | 66.8 | | |
| | | 47.6 | | |
| | | 21.2 | | |
| | | 16.8 | | |
| | Day 7 | 5.6 | 32.6 | 29.4 |
| | | 21.6 | | |
| | | 88.0 | | |
| | | 40.9 | | |
| | | 20.5 | | |
| | | 18.7 | | |
| | Day 10 | 16.3 | 27.1 | 16.1 |
| | | 34.1 | | |
| | | 56.3 | | |
| | | 20.2 | | |
| | | 23.5 | | |
| | | 12.4 | | |
| | Day 14 | 5.3 | 28.6 | 15.4 |
| | | 31.6 | | |
| | | 49.6 | | |
| | | 30.1 | | |
| | | 37.0 | | |
| | | 17.9 | | |
| | Day 21 | 11.0 | 23.1 | 10.7 |
| | | 24.5 | | |
| | | 29.8 | | |
| | | 27.9 | | |
| | | 36.1 | | |
| | | 9.4 | | |
| | Day 28 | 15.1 | 39.0 | 29.7 |
| | | 22.2 | | |
| | | 20.9 | | |
| | | 47.5 | | |
| | | 94.8 | | |
| | | 33.3 | | |
| | Day 30 1 hour | 25.0 | 37.4 | 24.3 |
| | | 17.9 | | |
| | | 35.2 | | |
| | | 61.5 | | |
| | | 72.2 | | |
| | | 12.7 | | |
| | Day 30 2 hour | 25.2 | 44.9 | 33.3 |
| | | 17.9 | | |
| | | 29.9 | | |
| | | 73.0 | | |
| | | 99.4 | | |
| | | 24.0 | | |
| | Day 30 4 hour | 17.5 | 40.3 | 32.8 |
| | | 19.5 | | |
| | | 19.0 | | |
| | | 82.1 | | |
| | | 83.2 | | |
| | | 20.7 | | |
| | Day 30 6 hour | 23.4 | 34.9 | 25.6 |
| | | 21.4 | | |
| | | 13.7 | | |
| | | 69.7 | | |
| | | 65.5 | | |
| | | 15.7 | | |
| | Day 35 | 12.6 | 21.8 | 13.8 |
| | | 12.4 | | |
| | | 13.7 | | |
| | | 44.1 | | |
| | | 34.1 | | |
| | | 13.9 | | |
| | Day 42 | 16.3 | 20.2 | 6.5 |
| | | 19.0 | | |
| | | 15.8 | | |
| | | 22.3 | | |
| | | 32.3 | | |
| | | 15.3 | | |
| | Day 49 | 16.5 | 14.3 | 3.0 |
| | | 13.3 | | |
| | | 15.7 | | |
| | | 9.7 | | |
| | | 18.0 | | |
| | | 12.3 | | |
| | Day 56 | 8.6 | 11.0 | 3.0 |
| | | 7.7 | | |
| | | 15.1 | | |
| | | 9.0 | | |
| | | 12.2 | | |
| | | 13.3 | | |
| Group V: 90 mg Risperidone (15% risperidone in 45% 80/20 | Day 0.04 | 150.1 | 102.8 | 44.3 |
| | | 55.2 | | |

TABLE 39-continued

45-Day Active Risperidone Concentrations

| Test Article | Time Point | Plasma Concentration ng/ml | Mean Concentration ng/ml | Standard Deviation |
|---|---|---|---|---|
| PLGHp (42K)/NMP 0.6 ml SC injection | | 70.8 | | |
| | | 147.9 | | |
| | | 63.4 | | |
| | | 129.3 | | |
| | Day 0.08 | 185.0 | 116.4 | 54.2 |
| | | 58.6 | | |
| | | 62.4 | | |
| | | 172.8 | | |
| | | 94.6 | | |
| | | 124.7 | | |
| | Day 0.16 | 139.5 | 105.2 | 58.5 |
| | | 61.1 | | |
| | | 47.9 | | |
| | | 204.1 | | |
| | | 74.7 | | |
| | | 103.9 | | |
| | Day 0.25 | 111.8 | 87.3 | 56.5 |
| | | 53.9 | | |
| | | 47.3 | | |
| | | 191.6 | | |
| | | 49.4 | | |
| | | 69.8 | | |
| | Day 0.33 | 88.6 | 76.7 | 55.3 |
| | | 46.5 | | |
| | | 47.8 | | |
| | | 184.2 | | |
| | | 40.8 | | |
| | | 52.5 | | |
| | Day 0.5 | 76.6 | 49.4 | 39.9 |
| | | 21.4 | | |
| | | 21.6 | | |
| | | 118.7 | | |
| | | 27.0 | | |
| | | 30.9 | | |
| | Day 1 | 91.6 | 61.9 | 44.8 |
| | | 40.0 | | |
| | | 27.7 | | |
| | | 139.0 | | |
| | | 24.6 | | |
| | | 48.8 | | |
| | Day 3 | 38.0 | 29.5 | 21.2 |
| | | 13.8 | | |
| | | 12.4 | | |
| | | 66.9 | | |
| | | 14.6 | | |
| | | 31.5 | | |
| | Day 7 | 39.9 | 33.0 | 29.9 |
| | | 13.3 | | |
| | | 10.2 | | |
| | | 89.0 | | |
| | | 13.9 | | |
| | | 31.5 | | |
| | Day 10 | 31.7 | 35.0 | 27.2 |
| | | 28.8 | | |
| | | 7.3 | | |
| | | 86.5 | | |
| | | 19.6 | | |
| | | 36.2 | | |
| | Day 14 | 40.7 | 31.8 | 21.8 |
| | | 25.0 | | |
| | | 10.5 | | |
| | | 71.6 | | |
| | | 20.0 | | |
| | | 23.1 | | |
| | Day 21 | 38.8 | 24.0 | 20.1 |
| | | 17.1 | | |
| | | 13.1 | | |
| | | 57.8 | | |
| | | 7.6 | | |
| | | 9.4 | | |
| | Day 28 | 45.3 | 33.6 | 24.2 |
| | | 33.8 | | |
| | | 15.1 | | |
| | | 74.0 | | |
| | | 27.7 | | |
| | | 5.6 | | |
| | Day 30 1 hour | 41.4 | 36.1 | 26.2 |
| | | 32.5 | | |
| | | 14.5 | | |
| | | 84.4 | | |
| | | 12.2 | | |
| | | 31.4 | | |
| | Day 30 2 hour | 39.2 | 40.8 | 29.8 |
| | | 36.7 | | |
| | | 24.6 | | |
| | | 99.1 | | |
| | | 16.0 | | |
| | | 29.3 | | |
| | Day 30 4 hour | 40.0 | 35.7 | 32.5 |
| | | 29.9 | | |
| | | 17.2 | | |
| | | 97.3 | | |
| | | 4.6 | | |
| | | 25.1 | | |
| | Day 30 6 hour | 42.0 | 33.9 | 31.8 |
| | | 27.9 | | |
| | | 12.0 | | |
| | | 93.5 | | |
| | | 5.2 | | |
| | | 23.1 | | |
| | Day 35 | 50.7 | 37.9 | 25.2 |
| | | 44.1 | | |
| | | 23.5 | | |
| | | 77.4 | | |
| | | 5.1 | | |
| | | 26.8 | | |
| | Day 42 | 56.5 | 33.2 | 26.2 |
| | | 14.1 | | |
| | | 17.6 | | |
| | | 74.4 | | |
| | | 10.2 | | |
| | | 26.7 | | |
| | Day 49 | 37.7 | 22.6 | 20.8 |
| | | 9.4 | | |
| | | 9.9 | | |
| | | 54.8 | | |
| | | 10.5 | | |
| | | 13.3 | | |
| | Day 56 | 20.4 | 18.8 | 8.6 |
| | | 8.8 | | |
| | | 11.7 | | |
| | | 30.6 | | |
| | | 15.2 | | |
| | | 25.8 | | |
| Group VI: 120 mg Risperidone (15% risperidone in 45% 80/20 PLGHp (42K)/NMP), 0.8 ml SC injection | Day 0.04 | 108.1 | 163.6 | 53.9 |
| | | 159.6 | | |
| | | 158.0 | | |
| | | 252.2 | | |
| | | 111.4 | | |
| | | 192.5 | | |
| | Day 0.08 | 130.1 | 180.1 | 64.0 |
| | | 154.4 | | |
| | | 250.5 | | |
| | | 271.3 | | |
| | | 123.9 | | |
| | | 150.3 | | |
| | Day 0.16 | 134.4 | 161.0 | 53.0 |
| | | 146.8 | | |
| | | 229.4 | | |

TABLE 39-continued

45-Day Active Risperidone Concentrations

| Test Article | Time Point | Plasma Concentration ng/ml | Mean Concentration ng/ml | Standard Deviation |
|---|---|---|---|---|
| | | 221.7 | | |
| | | 96.3 | | |
| | | 137.1 | | |
| | Day 0.25 | 117.3 | 133.4 | 50.8 |
| | | 117.7 | | |
| | | 201.8 | | |
| | | 184.3 | | |
| | | 64.0 | | |
| | | 115.3 | | |
| | Day 0.33 | 98.9 | 110.4 | 45.0 |
| | | 86.9 | | |
| | | 175.4 | | |
| | | 148.5 | | |
| | | 49.3 | | |
| | | 103.6 | | |
| | Day 0.5 | 134.8 | 97.7 | 47.9 |
| | | 42.4 | | |
| | | 143.6 | | |
| | | 35.5 | | |
| | | 130.4 | | |
| | | 99.4 | | |
| | Day 1 | 91.5 | 91.3 | 34.3 |
| | | 63.3 | | |
| | | 115.8 | | |
| | | 126.9 | | |
| | | 38.5 | | |
| | | 112.0 | | |
| | Day 3 | 51.2 | 52.1 | 22.4 |
| | | 31.9 | | |
| | | 75.1 | | |
| | | 58.5 | | |
| | | 20.4 | | |
| | | 75.3 | | |
| | Day 7 | 27.8 | 41.3 | 22.5 |
| | | 35.9 | | |
| | | 75.4 | | |
| | | 45.0 | | |
| | | 9.9 | | |
| | | 53.8 | | |
| | Day 10 | 43.1 | 48.6 | 22.9 |
| | | 45.4 | | |
| | | 89.6 | | |
| | | 43.3 | | |
| | | 19.3 | | |
| | | 50.9 | | |
| | Day 14 | 42.3 | 58.6 | 32.2 |
| | | 48.2 | | |
| | | 78.5 | | |
| | | 107.3 | | |
| | | 13.5 | | |
| | | 61.6 | | |
| | Day 21 | 44.2 | 46.6 | 22.1 |
| | | 14.6 | | |
| | | 62.0 | | |
| | | 76.5 | | |
| | | 30.5 | | |
| | | 51.6 | | |
| | Day 28 | 44.0 | 53.7 | 39.6 |
| | | 16.4 | | |
| | | 84.3 | | |
| | | 116.1 | | |
| | | 15.2 | | |
| | | 46.5 | | |
| | Day 30 1 hour | 35.2 | 50.1 | 28.2 |
| | | 26.4 | | |
| | | 91.0 | | |
| | | 78.1 | | |
| | | 23.3 | | |
| | | 47.0 | | |
| | Day 30 2 hour | 35.1 | 60.1 | 36.3 |
| | | 30.9 | | |
| | | 114.9 | | |
| | | 91.8 | | |
| | | 27.1 | | |
| | | 60.6 | | |
| | Day 30 4 hour | 35.8 | 58.5 | 38.7 |
| | | 29.7 | | |
| | | 125.0 | | |
| | | 81.0 | | |
| | | 24.0 | | |
| | | 55.6 | | |
| | Day 30 6 hour | 35.9 | 55.8 | 37.1 |
| | | 21.9 | | |
| | | 117.0 | | |
| | | 78.8 | | |
| | | 23.2 | | |
| | | 57.9 | | |
| | Day 35 | 47.6 | 52.5 | 24.9 |
| | | 26.2 | | |
| | | 94.1 | | |
| | | 53.1 | | |
| | | 29.8 | | |
| | | 64.3 | | |
| | Day 42 | 48.8 | 52.7 | 25.3 |
| | | 22.0 | | |
| | | 57.7 | | |
| | | 71.6 | | |
| | | 27.9 | | |
| | | 88.1 | | |
| | Day 49 | 45.2 | 52.5 | 24.9 |
| | | 19.5 | | |
| | | 54.3 | | |
| | | 74.6 | | |
| | | 17.6 | | |
| | | 41.4 | | |
| | Day 56 | 24.9 | 52.7 | 25.3 |
| | | 21.0 | | |
| | | 33.7 | | |
| | | 23.5 | | |
| | | 13.5 | | |
| | | 29.9 | | |

*These dogs probably spilled the pills they received on that day since no risperidone or 9-OH risperidone was detected at all hourly time points.
**Data not included in mean calculations.

Figure 20:
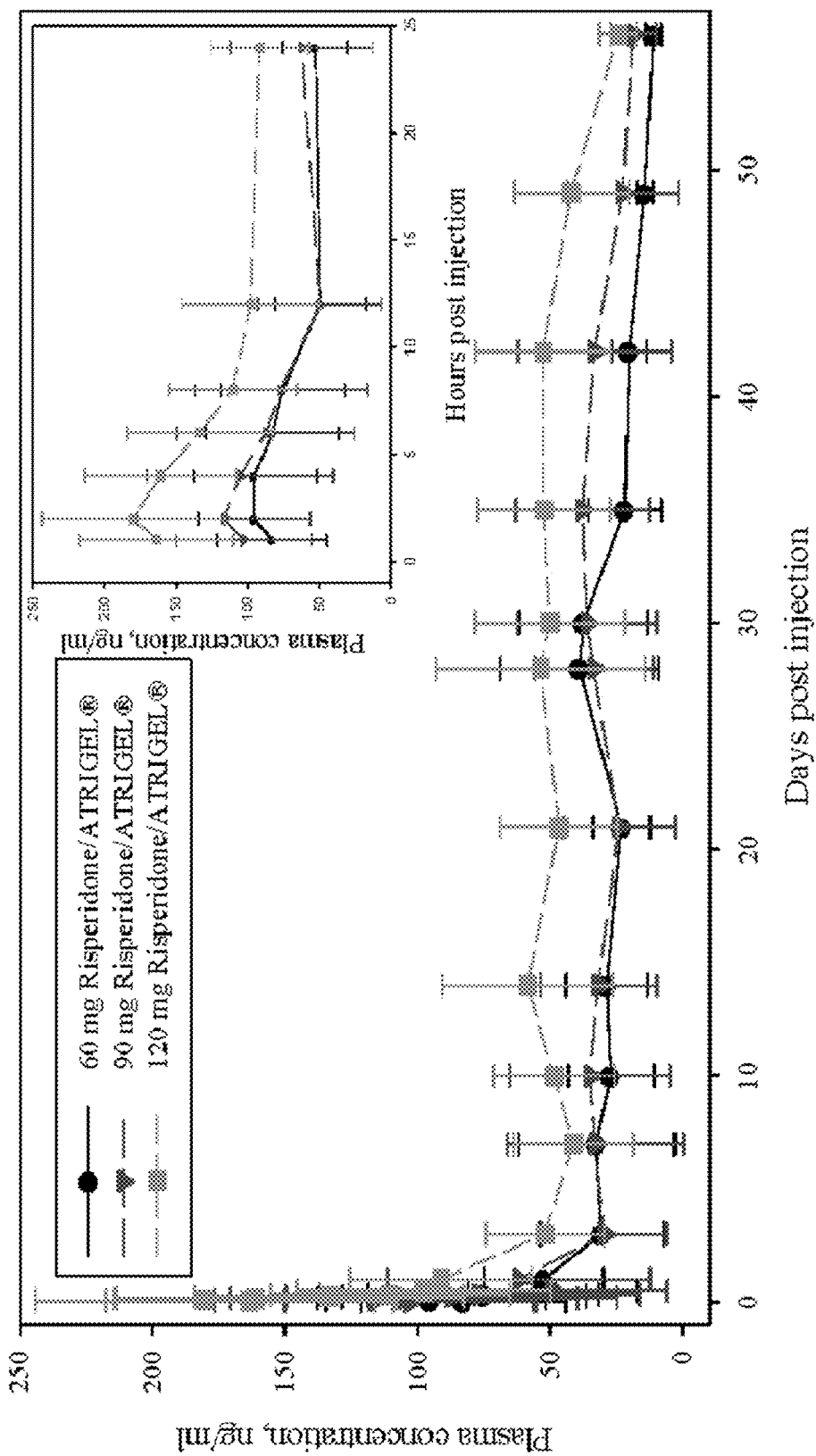
FIG. 20 illustrates the pharmacokinetics of risperidone/ATRIGEL® formulation after subcutaneous into dogs with 60 mg, 90 mg, and 120 mg doses.

Groups IV to VI (Risperidone/ATRIGEL® groups) reached plasma risperidone $C_{max}$ at approximately 2 hours post injection, and reached steady state (Css) in the dog plasma from Day 3 until Day 42 (FIG. 20). The steady state plasma risperidone levels (Css) of Groups IV to VI from Day 3 to Day 42 were 28.9, 32.7, and 50.7 ng/ml, respectively. The plasma risperidone levels decreased slowly from Day 49 to 56 for all three ATRIGEL® groups. The $C_{max}$ and steady state plasma levels (Css) were dose dependent.

Figure 21:
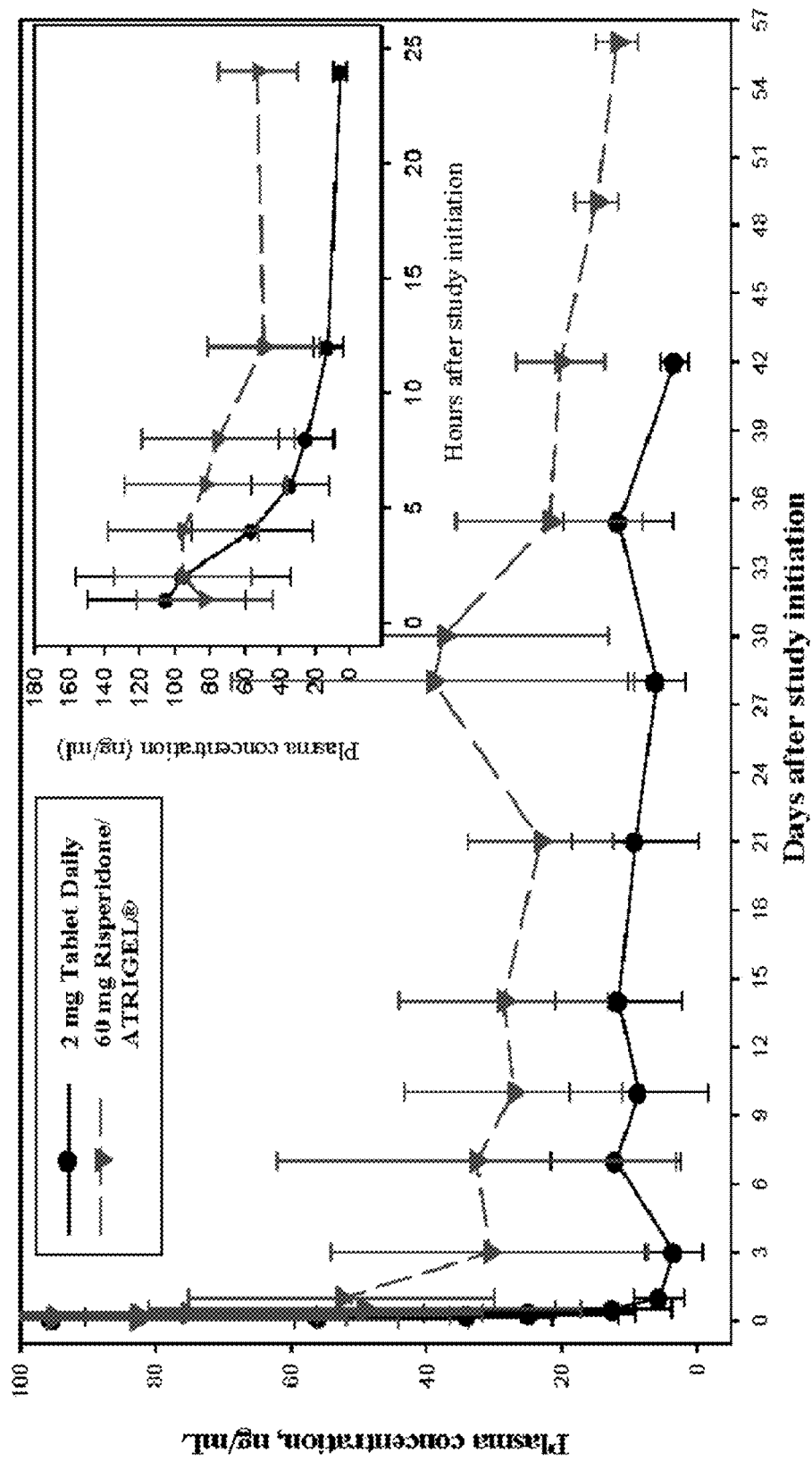
FIG. 21 illustrates the pharmacokinetics comparison between 60 mg risperidone/ATRIGEL® formulation injected subcutaneous into dogs and 2 mg RISPERDAL® tablet daily oral dose.

FIG. 21 showed the pharmacokinetics comparison between Group I (2 mg RISPERDAL® group) and Group IV (60 mg Risperidone/ATRIGEL® JO group). The $C_{max}$ (104.6±45.1 ng/ml) of Group I was higher than that of Group IV (95.3±39.1 ng/ml), however the $C_{min}$ (9.8 ng/ml) was lower than Css of Group IV (28.9 ng/ml) from Day 1 to Day 42, even lower than the concentration at Day 49 (14.3 ng/ml) and Day 56 (11.0 ng/ml). If the $C_{max}$ and $C_{min}$ plasma risperidone levels of the marketed 2 mg RISPERDAL® tablet formulation indicate efficacy for this dose level, this study indicated that the active plasma risperidone concentrations released from the Risperidone/ATRIGEL® formulation meets efficacy requirements throughout 56 days of the study.

Figure 22:
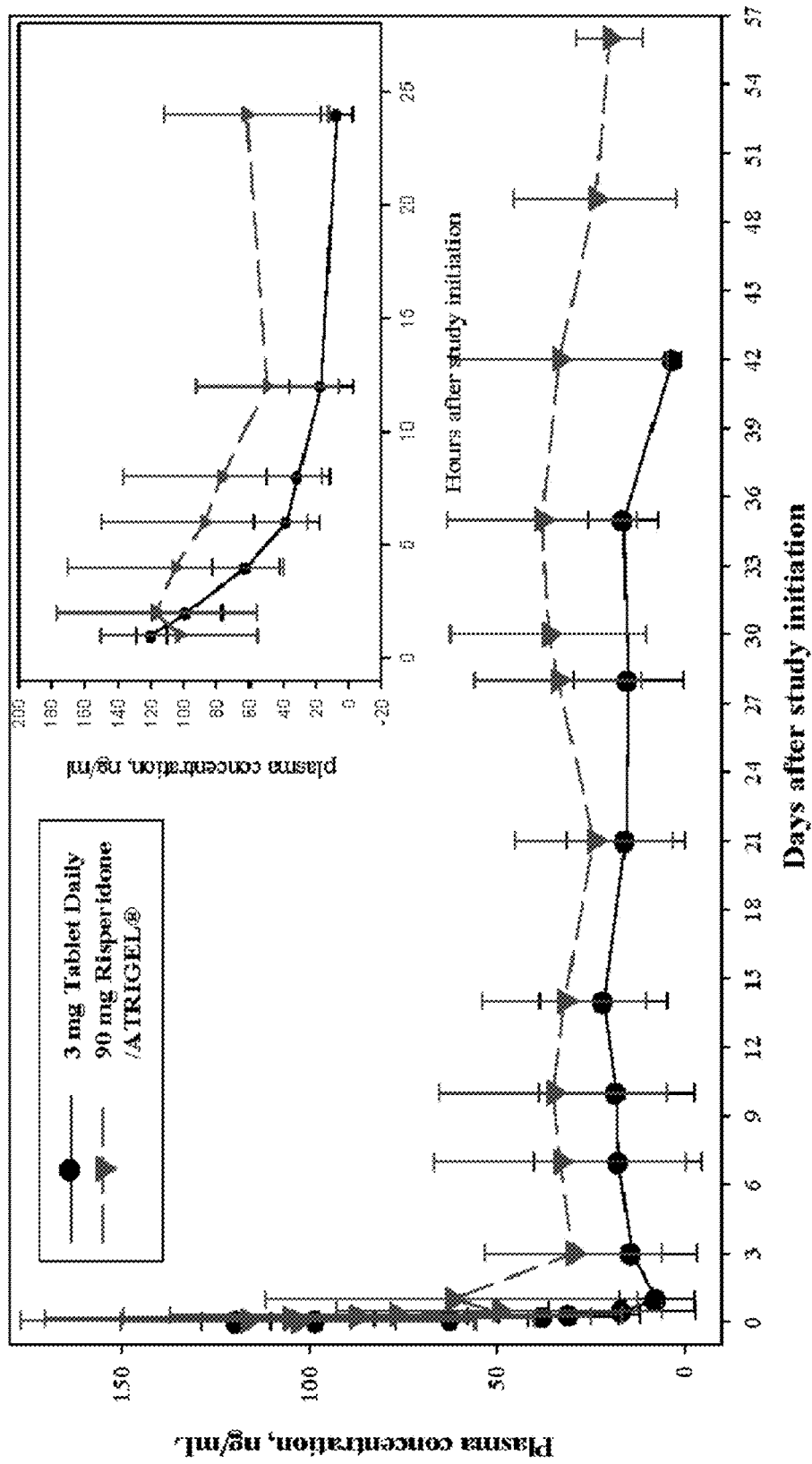
FIG. 22 illustrates the pharmacokinetics comparison between 90 mg risperidone/ATRIGEL® formulation injected subcutaneous into dogs and 3 mg RISPERDAL® tablet daily oral dose.
Figure 23:
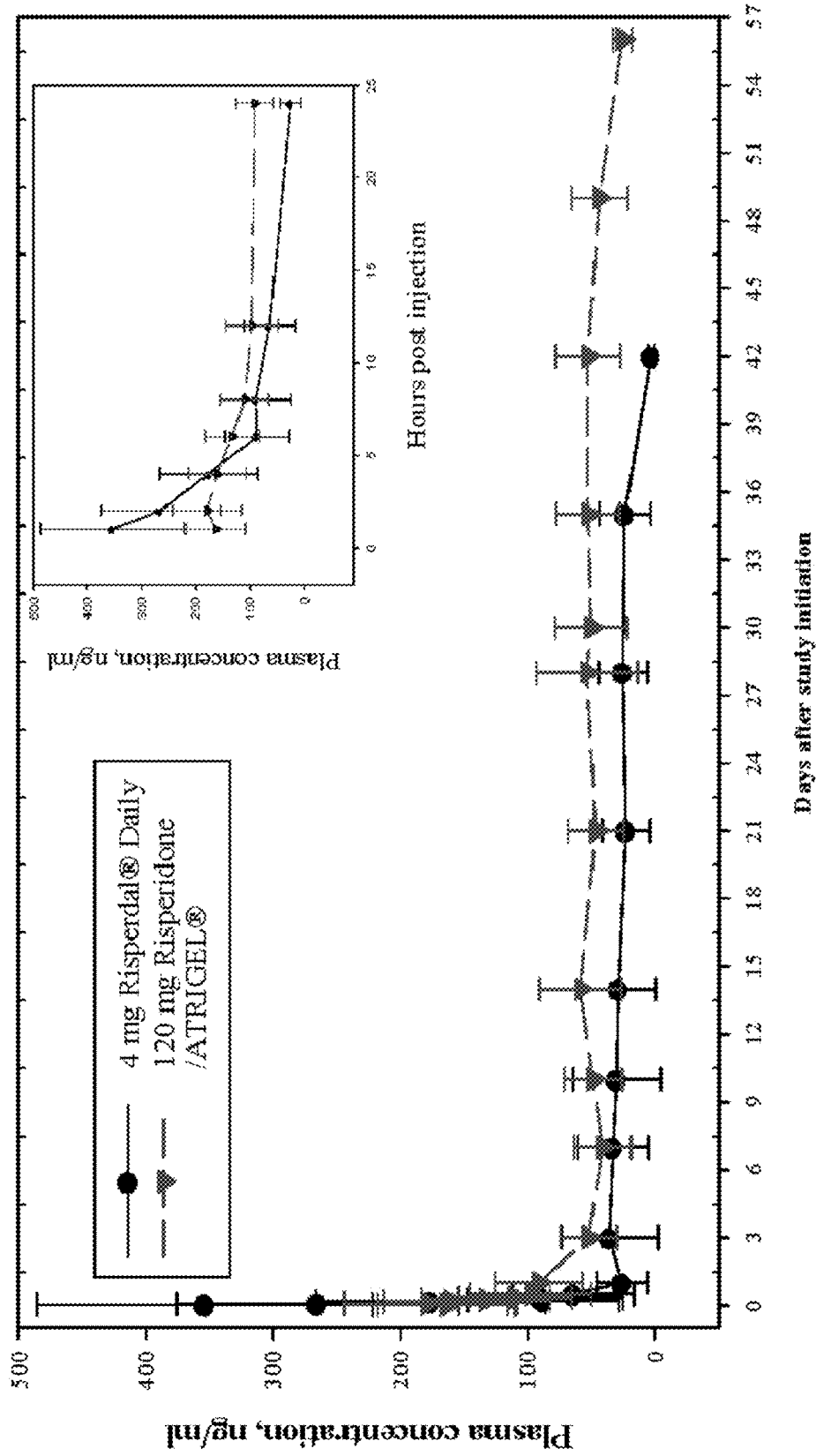
FIG. 23 illustrates the pharmacokinetics comparison between 120 mg risperidone/ATRIGEL® formulation injected subcutaneous into dogs and 4 mg RISPERDAL® tablet daily oral dose.

The same conclusion could be drawn from the comparison between Group II (3 mg RISPERDAL® group) and Group V (90 mg Risperidone/ATRIGEL® group), as well as the comparison between Group III (4 mg RISPERDAL® group) and Group VI (120 mg Risperidone/ATRIGEL® group). The pharmacokinetic data were graphed in FIGS. 22 and 23.

Figure 24:
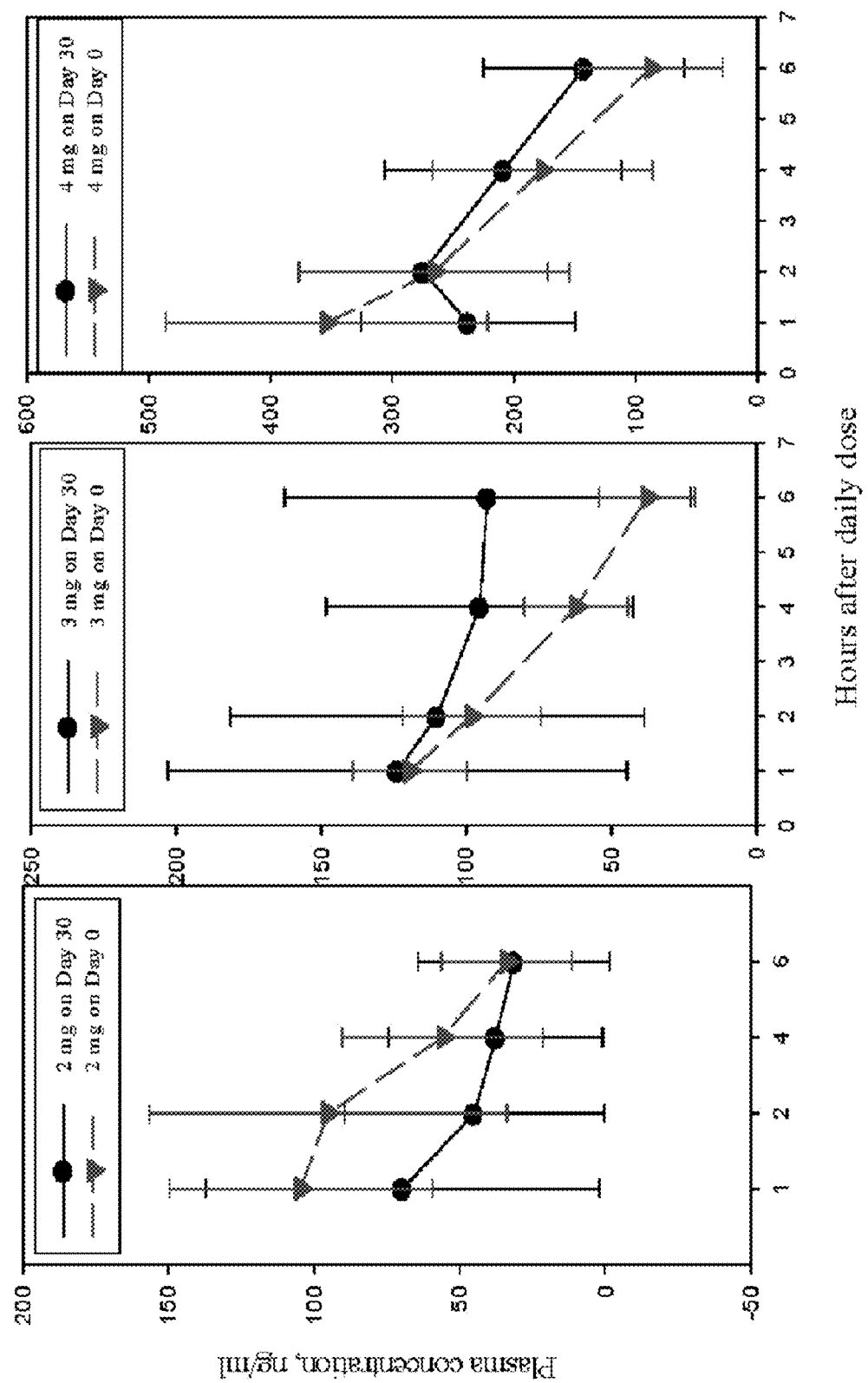
FIG. 24 illustrates the pharmacokinetics on day 0 and day 30 of 2 mg, 3 mg, and 4 mg RISPERDAL® tablet daily oral dose groups.
Figure 25:
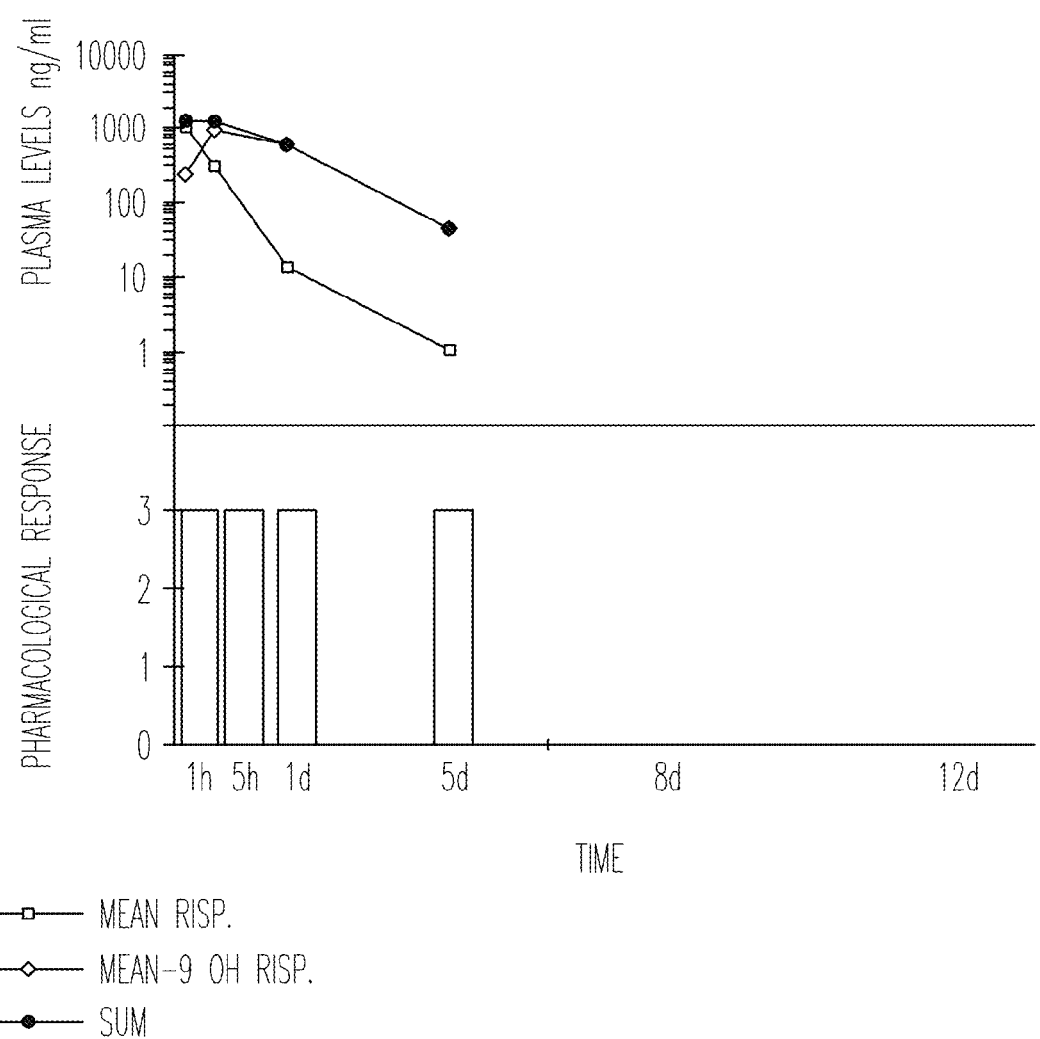
FIG. 25 illustrates the plasma levels of risperidone and the related pharmacological response of risperidone/poly(DL-lactide-co-caprolactone)/ethyl lactate in dogs.
Figure 26:
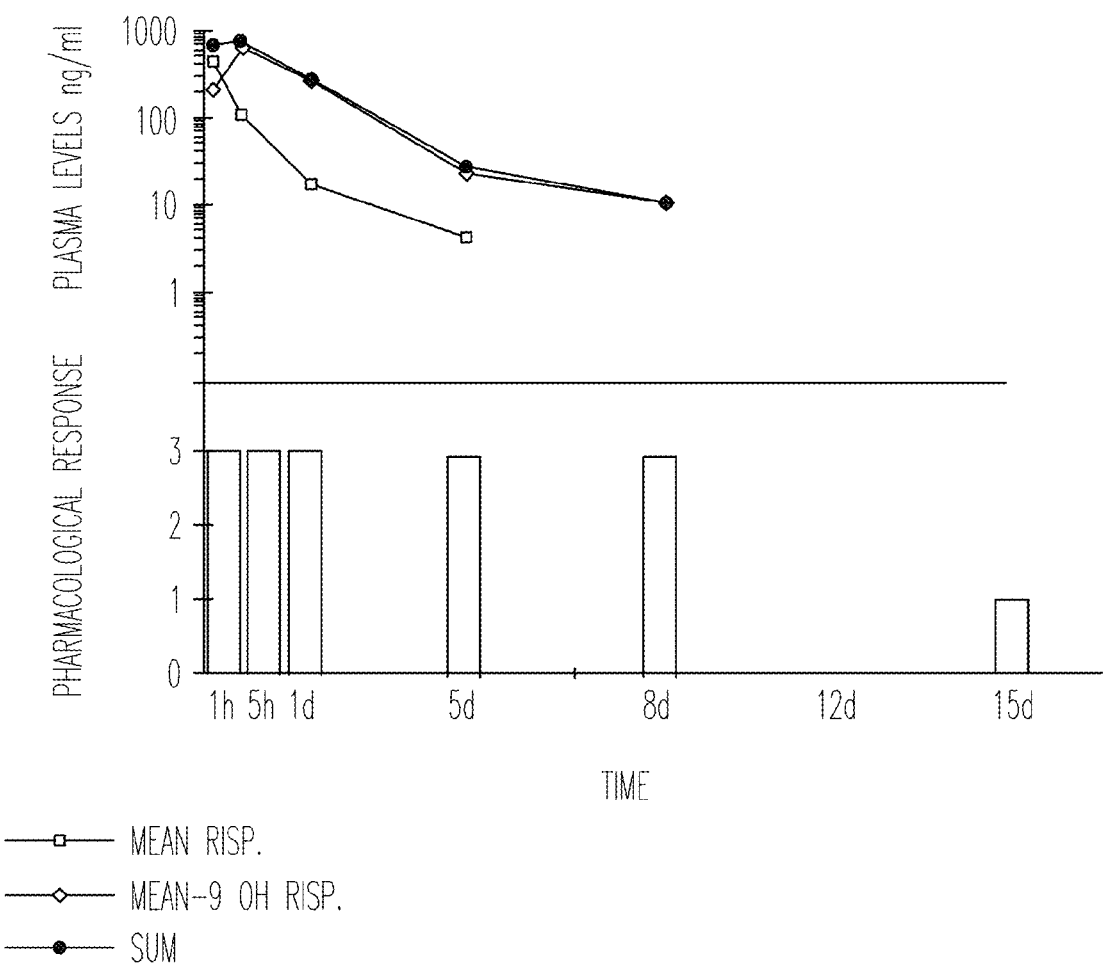
FIG. 26 illustrates the plasma levels of risperidone and the related pharmacological response of risperidone/poly(DL-lactide-co-glycolide)/ethyl lactate in dogs.
Figure 27:
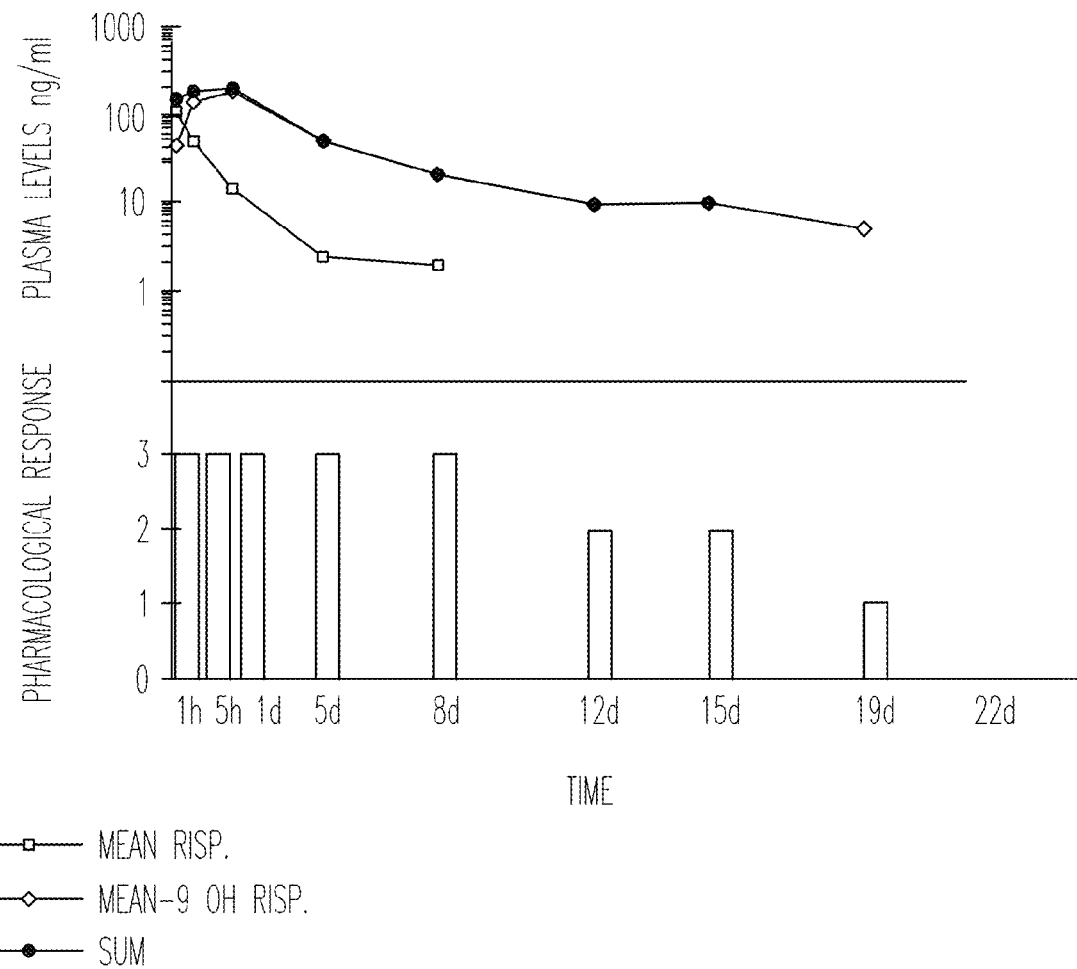
FIG. 27 illustrates the plasma levels of risperidone and the related pharmacological response of risperidone/poly(DL-lactide-co-caprolactone)/N-methyl-2-pyrrolidone in dogs.
Figure 28:
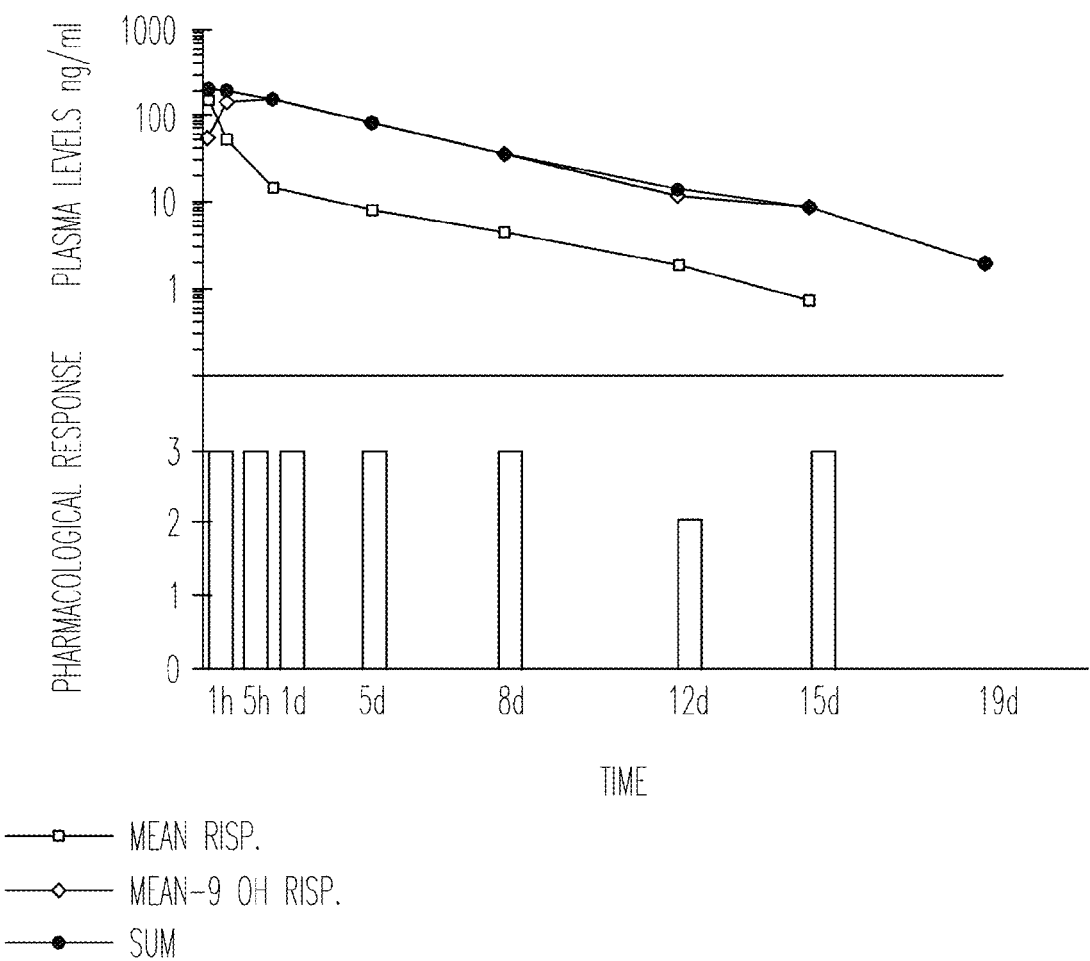
FIG. 28 illustrates the plasma levels of risperidone and the related pharmacological response of risperidone/poly(DL-lactide-co-glycolide)/N-methyl-2-pyrrolidone in dogs.

On Day 30, an additional 6-hour pharmacokinetics study was conducted in all six groups, and the results of Group I to III were compared with 6-hour pharmacokinetic profiles on Day 0 (FIG. 24). For Group I and II, plasma risperidone $C_{max}$ was reached 1 hour after dosing, Group III showed the plasma risperidone $C_{max}$ at 2 hours post dosing. For Group IV to VI, plasma concentrations stayed at steady state level (Css) at all time points. As indicated in FIG. 24, the pharmacokinetic profiles of Groups I to III on Day 30 paralleled the pharmacokinetic profile determined on Day 0.

WinNonlin version 5.0.1 software from PharSight was used in the AUC and t½ calculation in this report. A non-compartmental model with extravascular input for plasma data and linear trapezoidal calculations was used. The total $AUC_{Day\ 0-56}$ of ATRIGEL® groups were calculated based on the mean plasma concentrations obtained at each time point. The total $AUC_{Day\ 0-42}$ of RISPERDAL® groups were predicted using simple addition for 35 days based on the mean pharmacokinetics data on Day 0, and assuming the plasma risperidone concentration reached $C_{min}$ at Day 2. This prediction overestimated the total AUC since the steady state $C_{min}$ was not reached until Day 7 in this study. However, the differences would be acceptable as risperidone is a quick absorption and slow elimination drug. Also the plasma levels on Day 2 to Day 7 were very close to the $C_{min}$, so that the simple addition would not change the pharmacokinetic profiles following each individual daily dosing.

TABLE 41

Pharmacodynamics Risperidone/ATRIGEL ® in Dogs
% Dogs Showing Antiemetic Effect using Apomorphine

| TIME DAY | GROUP I 2 MG RISPERDAL ® | GROUP II 3 MG RISPERDAL ® | GROUP III 4 MG RISPERDAL ® |
|---|---|---|---|
| 20 | 83% (5/6) | 100% (6/6) | 100% (6/6) |
| 24 | 83% (5/6) | 100% (6/6) | 100% (6/6) |
| 30 | 83% (5/6) | 100% (6/6) | 100% (6/6) |
| 35 | 100% (6/6) | 100% (6/6) | 100% (6/6) |

| | GRJOUP IV 60 MG RISPERIDONE/ ATRIGEL ® | GROUP V 90 MG RISPERIDONE/ ATRIGEL ® | GROUP VI 120 MG RISPEIRDONE/ ATRIGEL ® |
|---|---|---|---|
| 20 | 100% (6/6) | 100% (6/6) | 100% (6/6) |
| 24 | 100% (6/6) | 100% (6/6) | 100% (6/6) |
| 30 | 100% (6/6) | 100% (6/6) | 100% (6/6) |
| 35 | 100% (6/6) | 100% (6/6) | 100% (6/6) |

Group IV, the relevant comparison to 2 mg RISPERDAL®, 60 mg Risperidone/ATRIGEL® formulation group remained at efficacious risperidone levels in dogs over 35 days. These results strongly suggested that Risperidone/ATRIGEL® Formulations sustained released risperidone over time and demonstrated better efficacy than relevant comparison tablet groups.

TABLE 40

Pharmacokinetic parameters of each group in EXAMPLE 5

| | $C_{max}$ at Day 0 ng/ml | $T_m$ at Day 0 hours | $C_{24hr}$ at Day 0 ng/ml | $C_{min}$ of RISPERDAL ® groups ng/ml | $C_{ss}$ of ATRIGEL ® groups ng/ml | $AUC_{Day\ 0-1}$ ng · day/ ml | $AUC_{Day\ 0-42}$ ng · day/ ml | $AUC_{Day\ 0-56}$ ng · day/ ml | $t_{1/2}$ day | Dose normalized $NAUC_{Day\ 0-42}$ ng · day/ ml · mg |
|---|---|---|---|---|---|---|---|---|---|---|
| Group I, 2 mg oral tablet | 104.6 | 1 | 5.6 | 9.8 | NA | 26.2 | 1108.4 | NA | 0.44 | 15.8 |
| Group II, 3 mg oral tablet | 119.4 | 1 | 10.4 | 17.3 | NA | 33.8 | 1483.2 | NA | 0.44 | 14.1 |
| Group III, 4 mg oral tablet | 353.8 | 1 | 19.9 | 27.2 | NA | 91.8 | 3378.6 | NA | 0.38 | 24.1 |
| Group IV, 60 mg Risperidone/ ATRIGEL ® | 95.3 | 2 | | NA | 28.9 | 63.1 | 1243.3 | 1417.6 | NA | 20.9 |
| Group V, 90 mg Risperidone/ ATRIGEL ® | 116.4 | 2 | | NA | 32.7 | 69.1 | 1421.5 | 1702.6 | NA | 15.9 |
| Group VI, 120 mg Risperidone/ ATRIGEL ® | 180.1 | 2 | | NA | 50.7 | 111.7 | 2238.9 | 3049.2 | NA | 19.0 |

Table 41 showed the pharmacodynamic results of the study. The emesis study was conducted approximately 5 hours after the daily tablet dose. In Group I, one dog at each time point on Day 20, Day 24, and Day 30 vomited after administration of apomorphine, all the other dogs in Groups II through VI showed anti-emesis through Day 35. These results indicated that 2 mg RISPERDAL® showed marginally efficacy while all the other groups were effective to prevent apomorphine induced emesis.

Overall, all three Risperidone/ATRIGEL® formulations sustained released risperidone into the plasma over time, and maintained steady state plasma risperidone concentrations after the initial burst of risperidone in plasma until Day 42. Furthermore, the plasma levels of risperidone in dogs were effective to maintain dogs free from emesis through Day 35 of the study. In addition, this is the first pre-clinical study to utilize γ-irradiation to produce sterilized risperidone in the B syringe.

Example 6

Comparative Examples Using Non-PLGH Polymers

Solubility of Risperidone in the ATRIGEL® Delivery System Solvents

Risperidone as a dry powder was added to two of the solvents used in the ATRIGEL® Delivery System at various concentrations until the limits of solubility were obtained.

Preparation of Formulations

The various ATRIGEL® formulations evaluated with risperidone were prepared by two methods: (1) weighing specific amounts of risperidone and solvent into glass vials, stirring for approximately five (5) minutes, and adding the biodegradable polymer; and (2) weighing specific amount of biodegradable polymer and solvent into glass vials, stirring until the polymer was dissolved, and adding the amount of risperidone.

In Vitro Formulation Release

Each formulation was run in triplicate with the following protocol: A 5 mL aliquot of phosphate buffered saline (PBS) prepared with 0.02% sodium azide adjusted to pH 7.4 was pipetted into a clean 8 mL amber vial. The vials containing the PBS solution were conditioned at 37° C. for approximately 2 hours in a shaker bath. The vials were removed from the shaker bath and quickly tarred on an analytical balance capable of weighing to an accuracy of 0.1 mg. The formulation to be tested was placed into a 1 ml polypropylene syringe and a sample (30 to 60 mg) was precipitated into the PBS receiving fluid. The vial was reweighed and the amount of formulation weighed into the vial was recorded. The vial was placed into the 37° C. shaker bath with a sealed Teflon cap.

The release solutions were removed after day 1, 2, 3, 5, and 7 days, and at 48 to 72 hour intervals after the first seven days of the release testing. The release solutions were stored at 5° C. until they were analyzed. The remaining PBS solution in each vial was removed by inversion, the vial dried by air, 5 mL of PBS solution was pipetted into the vial and the vial was returned to the shaker bath at 37° C. until the next time interval. A placebo formulation of polymer and the biocompatible solvent was prepared to evaluate interferences in determination of the risperidone by ultraviolet analysis.

Methods of Analysis

The concentration of risperidone in the receiving fluids was determined by ultraviolet spectroscopy at 275 nm. Standards of risperidone were prepared by dissolving approximately 11 mg (nearest 0.1 mg) of risperidone in 100 mL of the PBS solution. Appropriate dilutions were made for a 4 point curve. Linear regression analysis of the standards resulted in a slope of 37.6, a y-intercept of −0.6, and a regression analysis of 0.9999. The standards appear to be stable at 5° C. for approximately 14 days. The limit of detection for the risperidone is 1.6 µg/mL by this method. An ultraviolet scan of a 56.3 µg/mL of risperidone in PBS has a maximum absorption at 276 nm. There is no apparent interferences from the two biocompatible solvents, N-methyl-2-pyrrolidone or ethyl lactate, in the ultraviolet analysis at 275 nm.

An High Performance Liquid Chromatography method for the analysis of risperidone uses an RP18 Hypersil ODS cartridge HP (Hewlett-Packard) with 3 µm particle size. The column was a 10 cm RP18 Hypersil ODS column with 3 µm particle size. The column uses a mobile phase of 65% 0.01M $NH_4H_2PO_4$ brought to pH 8 with diisopropylamine and 35% acetonitrile. The flow rate was 1.5 mL/min and the detection of drug was by ultraviolet spectrophotometry. Retention time for the risperidone was between 2.30 and 2.45 minutes, Analysis of Polymer Formulations for Risperidone Mass balance of the risperidone in the residual polymer after release testing of formulation was performed by dissolving the residual polymer in a 25% acetonitrile/75% methanol solution, diluting to volume with the same solvent and analyzing by ultraviolet spectrophotometry at 275 nm of High Performance Liquid Chromatography. Determination of the risperidone in the original formulation stored at 5° C. was performed by dissolving a known weight of formulation in a solvent mixture of 25% acetonitrile/75% methanol followed by High Performance Liquid Chromatography analysis.

Preparation of Pilot Scale Risperidone Formulations

The polymer/risperidone formulations were prepared for in vivo evaluation in 20 gram batches and for stability/sterilization testing in 100 gram batches. Four formulations at the 20 gram scale were prepared using glass equipment in a class 10,000 clean room area for the in vivo trial. The process of manufacturing used the addition of the risperidone to the solvent on a weight basis. After sufficient stirring (approximately 90 minutes) the polymer was added to the solution or mixture and stirred for 2 to 16 hours. Generally the formulation containing the lactide/glycolide copolymers (PLG) stirred for about 2 hours. Formulations using the lactide/caprolactone copolymers (PLC) stirred up to 16 hours for dissolution of the polymer into the mixture. The formulations were filled into 10 ml polypropylene syringes and capped. All syringes were maintained at 5° C. until resting was initiated.

Eight (8) 100 gram formulations for stability/sterility testing were prepared using a laboratory Ross mixer for preparation. Risperidone concentrations used in these ranged from 5% to 20% by weight. Formulations were prepared in general by adding a known weight of risperidone to the weighed solvent in the Ross mixer bowl. After sufficient mixing time the polymers were added to the mixture or solutions and mixed until the polymer was dissolved. The exception to these standard preparations was the poly(lactide-co-caprolactone) formulations. The poly(lactide-co-caprolactone) polymers have a longer dissolution time. Therefore, it was determined that mixing the poly(lactide-co-caprolactone) polymer with the solvent (N-methyl-2-pyrrolidone or ethyl lactate) 16 to 24 hours prior to formulation preparation was typically used to prepare the risperidone formulations. The risperidone was added to the polymer/solvent solution as a dry powder in all cases where this procedure was used.

After completion of the formulation preparations, the entire mixture or solution was transferred into glass jars until they were prepared for sterility evaluation by gamma radiation and/or stability evaluation at −6°, 5°, and 25° C.

Sterilization of Risperidone/Polymer Formulations

The eight formulations prepared for testing were sterilized in glass vials and gamma resistant polypropylene copolymer syringes using various dose levels of irradiation. In addition to the formulations, risperidone as a dry powder was also sterilized in syringes and glass vials as well as a 5% solution of risperidone in ethyl lactate or N-methyl-2-pyrrolidone. Sterilization of ethyl lactate was also performed.

Animal Studies

Three in vivo studies were conducted with the risperidone/polymer formulations developed in this program. The first study was carried out by injecting four formulations intramuscularly into dogs using 18 gauge needles. The injection volumes of the different formulations were adjusted to give approximately 2.5 mg/kg of risperidone in each animal. Samples of blood were withdrawn from each dog an Day 1 at 0, 1, and 5 hours followed by additional samples taken on Days 2, 5, 8, 12, 15, 19, and 22 if suggested by the apomorphine challenge. In this test, apomorphine is injected at different time intervals and the lack of emesis in the dogs indicates that the plasma levels are above the threshold for antipsychotic activity. The samples of blood are analyzed for risperidone and its major metabolite, 9-hydroxyl risperidone, by High Performance Liquid Chromatography methods.

The second study was also conducted using the same methods described above. In this study, the two most promising formulations by in vitro release data, were tested. The third study was conducted by using four formulations developed for evaluations. In this study, the four formulations were injected intramuscularly into rats. The rats were sacrificed at 6 and 24 hours after injection and on Days 3, 5, and 7. The polymer implants were retrieved, residual tissue was cleaned off the polymer implants, and they were lyophilized. After lyophilization, the polymer implants were ground and extracted with 25/75 acetonitrile/methanol. The extracting solution was filtered and the solutions analyzed for risperidone content by ultraviolet spectroscopy. The percent release of risperidone was calculated based upon the amounts of polymer injected and retrieved.

Results and Discussion

The results and discussion section is organized by the solvent used to develop the liquid ATRIGEL® Delivery System for risperidone.

ATRIGEL® Delivery System with N-Methyl-2-Pyrrolidone as the Biocompatible Solvent Solubility Limits:

The limits of solubility tests showed that risperidone was soluble in N-methyl-2-pyrrolidone up to 5% by weight. Therefore any ATRIGEL® formulation containing the target quantity of risperidone (150 mg=7.5% by weight) would be a suspension. It was also found that the order of addition was of interest for the ATRIGEL® System with N-methyl-2-pyrrolidone. If the risperidone was first dissolved in N-methyl-2-pyrrolidone, followed by the addition of polymer, the formulations were solutions up to 5% by weight risperidone. If the risperidone was added to the already formed polymer solution, the drug was not soluble at the 5% by weight level.

In Vitro Release:

A number of polylactides (PLA), lactide/glycolide copolymers, and lactide/caprolactone copolymers were used with N-methyl-2-pyrrolidone to develop formulations for controlled release of risperidone. The concentration of polymer and the concentration of drug used in these formulations was varied. Also, additives were employed in efforts to affect the release rates. The sixty-three (63) formulations prepared with N-methyl-2-pyrrolidone and evaluated are given in Table 41.

TABLE 41

Polymer Formulations Using N-Methyl-2-Pyrrolidone

| Polymer | % Polymer | % Drug Load | Additives |
|---|---|---|---|
| 50/50 PLG (0.35) | 40 | 5, 10, 20 | None |
| 50/50 PLG (0.35) | 30 | 5, 10, 15, 20 | None |
| 50/50 PLG (0.19) | 25 | 5, 10, 20 | None |
| 50/50 PLG (0.19) | 40 | 10 | None |
| 50/50 PLG (0.52) | 25 | 5, 10, 20 | None |
| 85/15 PLG (0.24) | 25 | 5, 10, 20 | None |
| 65/35 PLG (0.23) | 25 | 5, 10, 20 | None |
| 65/35 PLG (0.41) | 25 | 10, 20 | None |
| 75/25 PLC (0.74) | 40 | 5, 10 | None |
| 50/50 PLC (0.63) | 40 | 5, 10 | None |
| 75/25 PLC (0.74) | 25 | 10, 20 | None |
| 50/50 PLC (0.63) | 25 | 10, 20 | None |
| PLA (0.24) | 40 | 5, 10, 20 | None |
| PLA (0.36) | 40 | 5, 10 | None |
| PLA (0.22) | 30 | 10 | None |
| PLA (0.24) | 25 | 20 | None |

TABLE 41-continued

Polymer Formulations Using N-Methyl-2-Pyrrolidone

| Polymer | % Polymer | % Drug Load | Additives |
|---|---|---|---|
| PLA (0.22) | 25 | 20 | None |
| PLA (2000) | 25 | 20 | None |
| PLA (2000) | 25 | 20 | Lactic acid (0.5, 1.3%) |
| PLA (2000) | 25 | 20 | Ethyl heptanoate (0.5, 1.3%) |
| PLA (2000) | 25 | 20 | Polyethylene glycol (0.5, 1.3%) |
| PLA (2000) | 25 | 20 | Polypropylene carbonate (0.5, 1.3%) |
| PLA (2000) | 25 | 20 | Polyvinyl pyrrolidone (0.5, 1.3%) |
| PLA (2000) | 25 | 20 | Ethanol (0.5, 1.3%) |
| PLA (2000) | 30 | 20 | None |
| PLA (2000) | 20 | 20 | PLG (5%) |
| PLA (2000) | 40 | 10 | None |
| PLA (2000) | 40 | 20 | None |

Polylactide:

Formulations containing risperidone at 5% and 10% by weight in 40% polylactide (IV=0.24 dL/g) and IV=0.36 dL/g) gave a fairly rapid burst of drug in vitro and the drug release slowed considerably such that less than 40% of the total drug was released in 15 days. The 20% risperidone formulation was slightly better in that 50% of the drug was released in 30 days, however, the viscosity of this highly drug-loaded formulation was too high for injectability. A change to lower molecular weight polylactide (MW=2000, IV=0.11 dL/g) and lower polymer concentrations (25%) gave much better in vitro release characteristics. A near zero-order release profile was obtained and approximately 98% of the drug was released in 34 days for this 20% risperidone formulation. The initial burst on Day 1 was 27 µg/mg formulation and the daily release from Day 1 through Day 30 was 3 to 4 µg/mg. Additives such as lactic acid, ethanol, ethyl heptanoate, propylene carbonate, and polyethylene glycol were added to the formulation at 0.5, 1.0 and 3.0% by weight in efforts to decrease the solubility of risperidone in N-methyl-2-pyrrolidone or the water that diffused into the polymer matrix and subsequently reduce the burst effect even further. None of the additives tested had any effect on the initial drug release. However, an increase in the low IV polymer concentration from 25% to 40% showed a significant lowering of the initial burst from the 27 µg/mg observed earlier to 18.8 µg/mg formulation.

PLG:

The poly(lactide-co-glycolide) formulations of risperidone in which the copolymer had a high lactide content (85/15 poly(lactide-co-glycolide) and 65/35 PLG) gave in vitro release profiles similar to that for the polylactide homopolymer with the fairly high initial burst and low levels of sustained release thereafter. The release profiles were obtained with the 58/50 poly(lactide-co-glycolide) materials. Near zero-order release of risperidone was obtained with all formulations and about 78 to about 90% of the drug was released in 30 days. Whereas release from the other polymer formulations slowed after several days, the 50/50 polymers appeared to swell after about seven days and release larger and more constant amounts of risperidone. This effect is shown for the 50/50 poly(lactide-co-glycolide) with IV=0.35 dL/g and for the same polymer with the lower IV=0.19 dL/g.

The near zero-order release rates were obtained with all of the 50/50 poly(lactide-co-glycolide) formulations. These included formulations with 5, 10, and 20% drug and those with 25, 30, and 40% polymer. The differences observed were that the formulations with higher drug loadings and lower polymer concentrations tended to give higher burst levels.

Poly(Lactide-Co-Caprolactone):

The risperidone formulations containing poly(lactide-co-caprolactone) in N-methyl-2-pyrrolidone were similar to those obtained with the polylactide homopolymer in that a fairly high initial burst of drug was observed and the release rate slowed considerably after the first week. This effect is shown for the 10% risperidone formulations and for the 20% risperidone formulations. Although the burst effect was reduced for the same formulations containing 40% polymer, the viscosity of these formulations was too high for suitable injectability.

ATRIGEL® Delivery System with Ethyl Lactate as the Biocompatible Solvent Solubility Limits:

Risperidone was soluble in ethyl lactate up to concentrations of 7.5% by weight. However, when polymer was added to the formulations 5% by weight, the risperidone formulations remained as solutions. In contrast to the results obtained with N-methyl-2-pyrrolidone, the order of addition of polymer and risperidone to ethyl lactate had no effect. All polymer formulations with 5% by weight drug load were solutions. Higher drug loadings in the ATRIGEL® system were suspensions.

In Vitro Release:

As with the N-methyl-2-pyrrolidone studies, a wide-variety of polymers, polymer molecular weights, polymer concentrations, drug loadings, and additives were used to prepare formulations with ethyl lactate as the solvent. Initial efforts were aimed at obtaining formulations that were solutions and which could be injected easily. Later efforts focused upon reducing the initial burst of drug from the polymer formulations. The formulations prepared with ethyl lactate and evaluated are given in Table 42.

TABLE 42

Polymer Formulations Using Ethyl Lactate

| Polymer | % Polymer | % Drug Load | Additives |
| --- | --- | --- | --- |
| 50/50 PLG (0.35) | 40 | 5.0 | None |
| 50/50 PLG (0.35) | 40 | 7.5 | None |
| 50/50 PLG (0.35) | 40 | 10.0 | None |
| 50/50 PLG (0.35) | 20 | 5.0 | None |
| 50/50 PLG (0.35) | 20 | 7.5 | None |
| 50/50 PLG (0.35) | 20 | 10.0 | None |
| 50/50 PLG (0.35) | 40 | 5.0 | None |
| 50/50 PLG (0.19) | 40 | 7.5 | None |
| 50/50 PLG (0.19) | 40 | 10.0 | None |
| 50/50 PLG (0.19) | 30 | 5.0 | None |
| 50/50 PLG (0.19) | 30 | 7.5 | None |
| 50/50 PLG (0.19) | 30 | 10.0 | None |
| 50/50 PLG (0.19) | 20 | 5.0 | None |
| 50/50 PLG (0.19) | 20 | 7.5 | None |
| 50/50 PLG (0.19) | 20 | 10.0 | None |
| 50/50 PLG (0.19) | 30 | 10.0 | None |
| 85/15 PLG (0.24) | 30 | 20.0 | None |
| 85/15 PLG (0.24) | 30 | 10.0 | None |
| 65/35 PLG (0.23) | 30 | 20.0 | None |
| 65/35 PLG (0.23) | 30 | 10.0 | None |
| 50/50 PLG (0.52) | 30 | 20.0 | None |
| 85/15 PLG (0.69) | 30 | 10.0 | None |
| 85/15 PLG (0.69) | 30 | 20.0 | None |
| 65/35 PLG (0.69) | 30 | 10.0 | None |
| 65/35 PLG (0.69) | 30 | 20.0 | None |
| 50/50 PLG (0.35) | 40 | 5.0 | Lactic acid (0.5%) |
| 50/50 PLG (0.35) | 40 | 5.0 | Lactic acid (1.0%) |
| 50/50 PLG (0.35) | 40 | 5.0 | Lactic acid (3.0%) |
| 50/50 PLG (0.35) | 40 | 10.0 | Lactic acid (0.5%) |
| 50/50 PLG (0.35) | 40 | 10.0 | Lactic acid (1.0%) |
| 50/50 PLG (0.35) | 40 | 10.0 | Lactic acid (3.0%) |
| 50/50 PLG (0.35) | 40 | 5.0 | Ethyl heptanoate (0.5%) |
| 50/50 PLG (0.35) | 40 | 5.0 | Ethyl heptanoate (1.0%) |
| 50/50 PLG (0.35) | 40 | 5.0 | Ethyl heptanoate (3.0%) |
| 50/50 PLG (0.35) | 40 | 10.0 | Ethyl heptanoate (0.5%) |
| 50/50 PLG (0.35) | 40 | 10.0 | Ethyl heptanoate (1.0%) |
| 50/50 PLG (0.35) | 40 | 10.0 | Ethyl heptanoate (3.0%) |
| 75/25 PLC (0.74) | 40 | 5.0 | None |
| 75/25 PLC (0.74) | 40 | 7.5 | None |
| 75/25 PLC (0.74) | 40 | 10.0 | None |
| 75/25 PLC (0.74) | 30 | 5.0 | None |
| 75/25 PLC (0.74) | 30 | 7.5 | None |
| 75/25 PLC (0.74) | 30 | 10.0 | None |
| 75/25 PLC (0.74) | 20 | 5.0 | None |
| 75/25 PLC (0.74) | 20 | 7.5 | None |
| 75/25 PLC (0.74) | 20 | 10.0 | None |
| 75/25 PLC (0.74) | 27 | 5.0 | None |
| 75/25 PLC (0.74) | 30 | 20.0 | None |
| PLA (0.24) | 40 | 5.0 | None |
| PLA (0.24) | 40 | 7.5 | None |
| PLA (0.24) | 40 | 10.0 | None |
| PLA (0.37) | 40 | 5.0 | None |
| PLA (0.37) | 40 | 7.5 | None |
| PLA (0.37) | 40 | 10.0 | None |
| PLA (2000) | 25 | 10 | None |
| PLA (2000) | 25 | 20 | None |
| PLA (2000) | 40 | 5.0 | Lactic acid (0.5%) |
| PLA (2000) | 40 | 5.0 | Lactic acid (1.0%) |
| PLA (2000) | 40 | 5.0 | Lactic acid (3.0%) |
| PLA (2000) | 40 | 10.0 | Lactic acid (0.5%) |
| PLA (2000) | 40 | 10.0 | Lactic acid (1.0%) |
| PLA (2000) | 40 | 10.0 | Lactic acid (3.0%) |
| PLA (2000) | 40 | 5.0 | Ethyl heptanoate (0.5%) |
| PLA (2000) | 40 | 5.0 | Ethyl heptanoate (1.0%) |
| PLA (2000) | 40 | 5.0 | Ethyl heptanoate (3.0%) |
| PLA (2000) | 40 | 10.0 | Ethyl heptanoate (0.5%) |
| PLA (2000) | 40 | 10.0 | Ethyl heptanoate (1.0%) |
| PLA (2000) | 40 | 10.0 | Ethyl heptanoate (3.0%) |
| PLA (2000) | 40 | 10.0 | None |
| PLA (2000) | 40 | 10.0 | PLA (0.32) 5% |
| PLA (2000) | 40 | 10.0 | PLA (0.32) 10% |
| PLA (2000) | 40 | 10.0 | PLA (0.32) 15% |
| PLA (2000) | 55 | 10.0 | None |

Polylactide:

The first formulations containing polylactide with IV=0.24 dL/g and IV=0.37 dL/g similar to those obtained with N-methyl-2-pyrrolidone were not encouraging. Neither of these formulations released over 20% of the drug load in the seven days of evaluation and the release rates were not constant. A change to a low molecular weight polylactide (MW=2000, IV=0.11 dL/g) gave much better results in that the release rates were sustained at fairly constant levels for 25 days. However, the initial burst of drug was still relatively high (30-38 µg/mg of formulation). An increase in the polymer concentration reduced the initial burst to 10 µg/mg, and gave nearly constant release of risperidone out to 19 days. The relatively low burst effect is probably due to the higher polymer concentration and the higher drug loading, both changes which decrease the solubility of risperidone in the ethyl lactate solvent. The lactic acid and ethyl heptanoate additives had no effect upon the initial release of drug.

PLG:

Initial trials with risperidone in poly(lactide-co-glycolide) formulations used 5% drug loadings, a 50/50 PLG, and a polymer concentration of 40% by weight. In these formulations, the drug was in solution. However, at 5° C., the risperidone precipitated to form suspensions. A lowering of the polymer concentration to 20% enabled the drug to remain in solution even at 5° C. Any formulation with risperidone levels greater than 5% were suspensions. As expected, the formulations with 20% polymer concentration gave high initial bursts of drug followed by fairly constant release for about 14 days. After that time, the release rates dropped to low levels. The formulations with 40% polymer concentration gave less of an initial burst than the 20% polymer formulations, but the initial release was still relatively high with 15-20% of the drug being released in 24 hours. The remainder of the drug was the released at a fairly constant rate for 30 days. The poly(lactide-co-glycolide) polymers with higher lactide content (65/35-85/15) did not reduce the burst as did slow of the formulations with lactic acid and ethyl heptanoate.

Poly(Lactide-Co-Caprolactone):

The release characteristics of risperidone in these polymers was similar to those obtained for the poly(lactide-co-glycolide) materials. With a 50/50 poly(lactide-co-caprolactone) at 40% polymer concentration and various loads of risperidone, the initial burst of drug was about 13 to about 20% followed by fairly constant release thereafter. However, the cumulative percent of drug released in 30 days was about 75%, a value less than that obtained with the poly(lactide-co-glycolide) materials. An increase in the molecular weight of the poly(lactide-co-caprolactone) polymer from an IV=0.63 dL/g to IV=0.74 dL/g and an increase in the lactide content to 75/25 reduced the initial burst and the cumulative release after 30 days. The 40% polymer formulations were viscous. Therefore the polymer concentration was reduced to 20%. As with the other polymers, the lower concentration of polymer gave formulations with large initial burst of drug and relatively fast release of the remaining drug with some formulations releasing 90% of the drug in 20 days.

In Vivo Release:

First Dog Study

Based upon an evaluation of all the formulations prepared during the first two months of the program, four formulations (EXAMPLES 6-1, 6-2, 6-3, and 6-4) were selected for the first study in dogs. Formulations that gave a variety of release rates were selected as no in vitro to in vivo correlation was available at that time. All of the formulations continue to release risperidone out to 30 days with some giving more of a burst effect than others. The formulations ware also selected to provide two that were solutions in ethyl lactate and two that were suspensions in N-methyl-2-pyrrolidone. The effect of solvent type as well as drug solubility in the solvents was to be evaluated In addition, the formulations consisted of three different polymers with the fourth being the same as one of the others but with a lower molecular weight. Polymer compatibility and possibly degradation rate were also to be evaluated.

The results of the apomorphine challenge in dogs tested with the four formulations are given in Tables 43-44.

TABLE 43

| Group | Formulation (mg eq/gr formulation) | Dog No. | Body Weight (kg) | Dose (mg · kg, im) |
|---|---|---|---|---|
| A | risperidone (50)/PLC/Ethyl Lactate, 18 gauge needle (750 mg form, im) | 1 | 14.5 | 2.6 |
|   |   | 2 | 14.4 | 2.6 |
|   |   | 3 | 14.5 | 2.6 |
| B | risperidone (50)/PLG/Ethyl Lactate, 18 gauge needle (500 mg form, im) | 4 | 11.8 | 2.1 |
|   |   | 5 | 10.3 | 2.4 |
|   |   | 6 | 10.5 | 2.4 |
| C | risperidone (100)/PLC/NMP, 18 gauge needle (250 mg form, im) | 7 | 11.6 | 2.2 |
|   |   | 8 | 13.3 | 1.9 |
|   |   | 9 | 10.9 | 2.3 |
| D | risperidone (100)/PLG/NMP, 18 gauge needle (250 mg form, im) | 10 | 13.7 | 2.7 |
|   |   | 11 | 12.3 | 3.0 |
|   |   | 12 | 14.4 | 2.6 |

TABLE 44

| | \multicolumn{12}{c}{Dose mg/kg} |
|---|---|---|---|---|---|---|---|---|---|---|---|---|
| | A | | | B | | | C | | | D | | |
| | Dog #1 2.6 | Dog #2 2.6 (im) | Dog #3 2.6 | Dog #4 2.1 | Dog #5 2.4 (im) | Dog #6 2.4 | Dog #7 2.2 | Dog #8 1.9 (im) | Dog #9 2.3 | Dog #10 2.7 | Dog #11 3.0 (im) | Dog #12 2.6 |
| 1 hour | + | + | + | + | + | + | + | + | + | + | + | + |
| 5 hour | + | + | + | + | + | + | + | + | + | + | + | + |
| 1 day | + | + | + | + | + | + | + | + | + | + | + | + |
| 4 day | + | + | + | + | + | + | + | + | + | + | + | + |
| 7 day | − | − | − | + | + | + | + | + | + | + | + | + |
| 11 day | − | − | − | − | − | − | + | − | + | + | − | + |
| 14 day | | stop | | − | + | − | + | − | + | + | + | + |
| 18 day | | | | | stop | | − | + | − | − | − | − |
| 21 day | | | | | | | − | − | − | | stop | |
| 25 day | | | | | | | | stop | | | | |

These data show that the formulations with ethyl lactate protected the dogs for 4-7 days. The formulations in N-methyl-2-pyrrolidone showed activity up to 14 days. The results of the pharmacokinetic analysis of the blood samples are given in Tables 45-48 and shown in FIGS. 25-28, respectively.

TABLE 45

Risperidone (50)/Poly(DL-lactide-co-caprolactone)/Ethyl Lactate, 18 gauge needle (750 mg form, im)

| | | R64766 ng/ml | | | | R76477 ng/ml | | | |
|---|---|---|---|---|---|---|---|---|---|
| Day | Time | Dog #1 2.6 (Im) | Dog #2 2.6 (Im) | Dog #3 2.6 | Mean (±SD) | Dog #1 | Dog #2 | Dog #3 | Mean (±SD) |
| 1 | 0 hour | ND | ND | ND | | ND | ND | ND | |
|   | 1 hour | 1404+ | 1108+ | 639+ | 1050 (385.7) | 496+ | 131+ | 83.5+ | 234 (220.0) |
|   | 5 hour | 322+ | 281+ | 286+ | 296 (22.4) | 1502+ | 849+ | 560+ | 970 (482.6) |
| 2 | 24 hour | 14.2+ | 12.3+ | 14.7+ | 14 (1.3) | 829+ | 581+ | 395+ | 602 (217.7) |
| 5 | 96 hour | 3.1+ | ND | ND | 1 (1.8) | 67.4+ | 40.4+ | 28.4+ | 45 (20.0) |
| 8 | 158 hour | ND | ND | ND | | ND | ND | ND | |
| 12 | 264 hour | NS | NS | NS | | NS | NS | NS | |

"+" means protection against apomorphine reduced emesis

TABLE 46

Risperidone (50)/Poly(DL-lactide-co-glycolide)/Ethyl Lactate, 18 gauge needle (500 mg form, im)

| | | R64766 ng/ml | | | | R76477 ng/ml | | | |
|---|---|---|---|---|---|---|---|---|---|
| Day | Time | Dog #4 2.1 (Im) | Dog #5 2.4 (Im) | Dog #6 2.4 | Mean (±SD) | Dog #4 | Dog #5 | Dog #6 | Mean (±SD) |
| 1 | 0 hour | ND | ND | ND | | ND | ND | ND | |
|   | 1 hour | 615+ | 315+ | 382+ | 437 (157.5) | 333+ | 101+ | 177+ | 204 (118.3) |
|   | 5 hour | 115+ | 144+ | 58.3+ | 106 943.60 | 854+ | 455+ | 512+ | 607 (215.8) |
| 2 | 24 hour | 13.3+ | 23.8+ | 15.7+ | 18 (5.5) | 289+ | 250+ | 218+ | 252 (35.6) |
| 5 | 96 hour | 6.2+ | 2.9+ | 4.4+ | 5 (1.7) | 29.7+ | 21.1+ | 21.2+ | 24 (4.9) |
| 8 | 158 hour | ND | ND | ND | | 13.8+ | 10.8+ | 9.0+ | 11 (2.4) |
| 12 | 264 hour | ND | ND | ND | | ND | ND | ND | |
| 15 | 36 hour | ND | ND | ND | | ND | ND | ND | |

"+" means protection against apomorphine reduced emesis

TABLE 47

Risperidone (100)/Poly(DL-lactide-co-caprolactone)/N-methyl-2-pyrrolidone, 18 gauge needle (250 mg form, im)

| | | R64766 ng/ml | | | | R76477 ng/ml | | | |
|---|---|---|---|---|---|---|---|---|---|
| Day | Time | Dog #7 2.62 | Dog #8 1.9 (Im) | Dog #9 2.3 (Im) | Mean (±SD) | Dog #7 | Dog #8 | Dog #9 | Mean (±SD) |
| 1 | 0 hour | ND | ND | ND | | ND | ND | ND | |
|   | 1 hour | 111+ | 108+ | 92.7+ | 104 (9.8) | 48.8+ | 40.3+ | 36.7+ | 43 (5.4) |
|   | 5 hour | 60.7+ | 39.0+ | 39.1+ | 46 (12.5) | 187+ | 113+ | 100+ | 133 (46.9) |
| 2 | 24 hour | 13.8+ | 15.2+ | 12.9+ | 14 (1.2) | 220+ | 174+ | 130+ | 175 (45.0) |
| 5 | 96 hour | 4.4+ | ND | 2.7+ | 2 (2.2) | 71.5+ | 33.1+ | 37.7+ | 47 (21.0) |
| 8 | 158 hour | 2.2+ | ND | 3.6+ | 2 (1.8) | 29.1+ | 9.3+ | 21.7+ | 20 (10.0) |
| 12 | 264 hour | ND | ND | ND | | 15.4+ | ND | 13.2+ | 10 (8.3) |
| 15 | 336 hour | ND | ND | ND | | 20.0+ | ND | 10.3+ | 10 (10.0) |
| 19 | 432 hour | ND | ND | ND | | 7.9 | ND | 7.3+ | 5 (4.4) |
| 22 | 504 hour | ND | ND | ND | | ND | ND | ND | |

"+" means protection against apomorphine reduced emesis

TABLE 48

Risperidone (100)/Poly(DL-lactide-co-glycolide)/N-methyl-2-pyrrolidone, 18 gauge needle (250 mg form, im)

| | | R64766 ng/ml | | | | R76477 ng/ml | | | |
|---|---|---|---|---|---|---|---|---|---|
| Day | Time | Dog #10 2.7 (Im) | Dog #11 3.0 (Im) | Dog #12 2.6 (Im) | Mean (±SD) | Dog #10 | Dog #11 | Dog #12 | Mean (±SD) |
| 1 | 0 hour | ND | ND | ND | | ND | ND | ND | |
|   | 1 hour | 170+ | 96.8+ | 162+ | 143 (40.2) | 62.4+ | 34.4+ | 57.1+ | 51 (14.9) |
|   | 5 hour | 64.9+ | 39.2+ | 43.1+ | 49 (13.9) | 152+ | 98.5+ | 155+ | 139 (35.2) |
| 2 | 24 hour | 17.5+ | 13.2+ | 13.4+ | 15 (2.4) | 146+ | 113+ | 169+ | 143 (28.1) |
| 5 | 96 hour | 9.2+ | 6.3+ | 9.1+ | 8 (1.6) | 80.3+ | 77.0+ | 75.9+ | 78 (2.3) |

TABLE 48-continued

Risperidone (100)/Poly(DL-lactide-co-glycolide)/N-methyl-2-pyrrolidone, 18 gauge needle (250 mg form, im)

| | | R64766 ng/ml | | | | R76477 ng/ml | | | |
|---|---|---|---|---|---|---|---|---|---|
| Day | Time | Dog # 10 2.7 (Im) | Dog # 11 3.0 (Im) | Dog # 12 2.6 (Im) | Mean (±SD) | Dog # 10 | Dog # 11 | Dog # 12 | Mean (±SD) |
| 8 | 158 hour | 6.0+ | 2.7+ | 5.3+ | 5 (1.7) | 30.4+ | 36.4+ | 37.2+ | 35 (3.7) |
| 12 | 264 hour | 3.8+ | 2.1 | ND | 1 (1.9) | 18.8+ | 10.4 | 7.6+ | 12 (5.8) |
| 15 | 336 hour | 2.3+ | ND | ND | 3 (0.4) | 11.4+ | 10.0+ | 5.7+ | 9 (3.0) |
| 19 | 432 hour | ND | ND | ND | | ND | 6.1 | ND | 2 (3.5) |

"+" means protection against apomorphine reduced emesis

These data show that the two formulations with ethyl lactate gave a high initial burst of drug at approximately 800-1400 ng/mL and the plasma levels of dug dropped fairly quickly within one week to where the sum of risperidone and its metabolite were below the minimum level of 10-45 mg/mL needed for activity. The two formulations with N-methyl-2-pyrrolidone gave much less of a burst with plasma levels for the drug and metabolite at approximately 200 ng/mL. The plasma levels were also sustained above the minimum for about 15 to about 19 days showing a much more constant release for these two formulations.

Both the pharmacological (apomorphine challenge) and the pharmacokinetic data correlate fairly well with the in vitro daily release rates for the four formulations. If the in vitro daily release rate in terms of μg of risperidone, released/mg of formulation is multiplied by the quantity (mg) of formulation injected into the dogs, a risperidone release (mg) in the dogs on a daily basis can be predicted. The data suggests the minimum daily dose of risperidone needed in dogs for a biological response is about 0.6 mg. Both of the formulations with ethyl lactate show a large amount of drug calculated to be released in the first day. EXAMPLE 6-1, the poly(lactide-co-caprolactone) polymer formulation, also shows that the quantity of drug released falls below 0.6 mg about Day 4. The biological response obtained with this formulation was for about 4-5 days. The other ethyl lactate formulation (EXAMPLE 6-4) containing the poly(lactide-co-glycolide) polymer maintains the 0.6 mg level out to Day 6. The levels of risperidone fall slightly below this value through Day 16. Biological responses to this formulation were observed through Day 8 with one dog responding at Day 15. The two formulations with N-methyl-2-pyrrolidone maintain the level of risperidone much longer. EXAMPLE 6-2 with poly(lactide-co-caprolactone) maintains the 0.6 mg risperidone level to Day 13. The biological response was obtained for all three dogs at Day 8 with 2 animals responding to Day 15. The poly(lactide-co-glycolide) formulation with N-methyl-2-pyrrolidone was calculated to maintain the 0.6 mg level to Day 20. Biological response was observed at Day 15. This particular polymer degrades quickly in vivo and may have fragmented and released the drug faster than predicted based upon in vitro data.

Second Dog Study

The data from the first study in dogs indicated that formulations with significant reductions in the initial burst of drug would be desired as the maximum tolerated blood level for risperidone and its metabolite was estimated as 75 ng/mL. Above this level, safety concerns about hypertension and other side effects would be major considerations. Of the many formulations tested in vitro, it was found that two appeared to meet the requirement for a low initial burst of risperidone followed by constant release far 38 days. These were the low molecular weight (MW=2000, IV=0.11 dL/g) polylactide formulation with a high concentration of polymer (55%) and the 50/50 poly(lactide-co-glycolide) formulation with an IV=0.35 dL/g. These two formulations were projected to meet the target range of plasma levels for risperidone by a series of calculations based upon the initial in vitro release of drug and the plasma level at one hour from the first four formulations tested in dogs. Thus, if the percent of drug released in 24 hours in vitro is multiplied by the quantity of drug in the formulation, a value for the quantity of drug released initially is obtained. Table 49 gives these values for the first four formulations tested in dogs and the two new formulations proposed for additional studies. Sixteen (16) of these initial in vitro release values for the first four formulations tested in dogs are plotted versus the plasma levels at one hour for risperidone and its 9-hydroxyl metabolite and a curve can be used to obtain a correlation of in vitro to in vivo drug release. When the initial in vitro values for the two new formulations are inserted into the second order polynomial, the estimated plasma levels at one hour are 63.9 ng/mL for the polylactide formulation and 31.1 ng/mL for the poly(lactide-co-glycolide) formulation. These plasma levels fit well within the targeted range of 15-75 ng/mL.

TABLE 49

Calculated Values for Initial Quantity of Risperidone Released from formulations Tested in Dogs

| Number | Description | Quantity of Drug (mg) Released in 24 hours |
|---|---|---|
| EXAMPLE 6-1 | 75/25 PLC (IV = 0.76 dL/g) in ethyl lactate 5% risperidone | 10.13 |
| EXAMPLE 6-2 | 50/50 PLC (IV = 0.63 dL/g) in NMP 10% risperidone | 3.63 |
| EXAMPLE 6-3 | 50/50 PLC (IV = 0.19 dL/g) in NMP 10% risperidone | 4.13 |
| EXAMPLE 6-4 | 50/50 PLC (IV = 0.35 dL/g) in ethyl lactate 5% risperidone | 10.75 |
| EXAMPLE 6-5 | 50/50 PLC (IV = 0.35 dL/g) in NMP 10% risperidone | 1.25 |
| EXAMPLE 6-6 | 55% PLA (MW = 2000; IV = 0.11 dL/g) in ethyl lactate, 10% risperidone | 2.50 |

The two new formulations were prepared and both the pharmacological response (apomorphine challenge) and pharmacokinetic analysis of risperidone plasma levels were to be evaluated. The results were disappointing in that effects were seen for about two weeks for the apomorphine challenge as noted in Tables 50-51. Also, general observation of the animals suggested that a high burst of drug was still being obtained as the animals were heavily sedated during the first four days of the trial. A severe local inflammation resulting in abscesses was noted for the formulation containing ethyl lactate. In addition, the viscosities of the test formulations were judged to be too high for practical use.

TABLE 50

| Group | Formulation (mg eq/gr formulation) | Dog No. | Body Weight (kg) | Dose (mg · kg, im) |
|---|---|---|---|---|
| C | 50/50 PLC (IV = 0.35 dL/g) in NMP 10% risperidone | Dog # 4 | 12.7 | 2.5 |
|   |   | Dog # 5 | 10.6 | 2.6 |
|   |   | Dog # 6 | 11.7 | 2.4 |
| D | 55% PLA (MW = 2000; IV = 0.11 dL/g) in ethyl lactate, 10% risperidone | Dog # 13 | 9.6 | 2.8 |
|   |   | Dog # 14 | 12.8 | 2.5 |
|   |   | Dog # 15 | 8.0 | 2.5 |

TABLE 51

| | Dose mg/kg | | | | | |
|---|---|---|---|---|---|---|
| | C | | | D | | |
| | Dog # 4 | Dog # 5 (im) | Dog # 6 | Dog # 13 | Dog # 14 (im) | Dog # 15 |
| 1 hour | + | + | + | + | + | + |
| 5 hour | + | + | + | + | + | + |
| 1 day | + | + | + | + | + | + |
| 4 day | + | + | + | + | + | + |
| 7 day | + | + | + | + | + | + |
| 11 day | + | + | − | + | + | + |
| 14 day | − | + | − | − | + | + |
| 18 day | − | + | − | − | − | + |
| 21 day | − | + | − | − | − | − |
| 25 day | | stop | | | stop | |

The results from the second dog study were unexpected. No local inflammatory response had been observed previously with the ethyl lactate solvent. The response in this study may have been caused by some degradation of the solvent itself or the combination with the low molecular weight polylactide polymer. The large burst effect noted by the sedation of the dogs (but not confirmed by pharmacokinetic analyses) was also unexpected for these two formulations and prompted an investigation. It was discovered that the method of preparation of the formulations affected the initial release of drug. The release profiles were generated from formulations in which the risperidone, solvent and polymer were mixed together and allowed to equilibrate 24 hours before in vitro testing. The formulation with poly(lactide-co-glycolide) was actually prepared by mixing the risperidone in N-methyl-2-pyrrolidone and adding polymer with stirring until the polymer had dissolved. The polylactide formulation with ethyl lactate was prepared by dissolving the polymer in ethyl lactate and adding risperidone with stirring to obtain adequate mixing. However, because of potential storage stability problems, the two formulations tested in dogs were prepared by dissolving each polymer in the appropriate solvent and placing each polymer solution in a syringe. The risperidone in powder form was weighed into two separate syringes. The four syringes were coupled to a polymer solution syringes and mixed the two materials immediately before use. When the two formulations produced by this method were tested in vitro, the initial release of drug was increased over that shown by the same formulations produced by earlier method. Both formulations prepared by this syringe-mixing method gave almost identical in vitro release rates with the initial burst of drug being about 12% instead of the previous about 5 to about 10% used in the calculations to predict drug plasma levels. At the 72% initial burst, the plasma levels in the dogs would have been predicted to be greater than 200 ng/mL.

Implant Retrieval Study in Rats:

In efforts to reduce the initial burst of drug and to obtain some correlation of in vitro to in vivo release, a study was conducted in rats in which formulations were injected into rats and the solid polymer implant retrieved at various times for analysis of residual polymer. The four formulations tested are given in Table 52.

TABLE 52

| Polymer | Solvent | Drug Loading | Additive |
|---|---|---|---|
| PLA (MW = 2000; IV = 0.11 dL/g), 25% | NMP | 20% | None |
| 50/50 PLG (IV = 0.35 dL/g) 30% | NMP | 10% | None |
| 50/50 PLG (IV = 0.35 dL/g) 40% | EL | 5% | None |
| 50/50 PLG (IV = 0.35 dL/g) 30% | EL | 10% | Ethyl Heptanoate 3% |

The percent drug released based upon residual drug in the implants was determined for each of the formulations. Although the data are highly variable because of the difficulty in retrieving the implants, they show that the formulation with 5% risperidone in ethyl lactate gave a high initial release of drug. The data also show that the initial burst with this formulation can be reduced by the use of the hydrophobic additive, ethyl heptanoate. The data also show that the initial burst is reduced even more with the polylactide and poly(lactide-co-glycolide) formulations in N-methyl-2-pyrrolidone. It should be noted that all of the formulations gave higher drug release in vivo than in the laboratory tests.

Stability and Sterilization Studies:

Because of the difficulties in obtaining formulations with the desired in vivo release characteristics, the stability program with the different formulations was limited to short-term observations. The formulations containing risperidone in N-methyl-2-pyrrolidone were suspensions which were not physically stable as they settled out at all drug loads evaluated in a short time of about two days. In addition, the risperidone/N-methyl-2-pyrrolidone formulations showed color instability problems upon storage at temperatures above 5° C. as they tended to darken with time.

The risperidone/ethyl lactate formulations were more stable than those with N-methyl-2-pyrrolidone. The formulations with 5% drug were solutions but tended to form white crystals at 5° C. storage condition. When warmed back to room temperature, the crystals re-dissolved. Formulations with drug levels above 5% were suspensions which were also physically unstable as they settled out with time. However, the ethyl lactate formulations gave better color stability at 5° C. and room temperature as there was no color change in the formulations after one month at room temperature.

Eight formulations were prepared for gamma irradiation sterilization as were solutions of risperidone (5%) in ethyl lactate and N-methyl-2-pyrrolidone and risperidone alone. The dose level was 30 to 33 KGy for each of the samples.

Upon visual inspection, the syringes and glass vials containing the sterilized risperidone/polymer formulations with N-methyl-2-pyrrolidone were amber to brown in color in comparison to non-sterilized controls which were a yellow color. There was a yellow/beige color observed in the drug itself after sterilization in both the glass vials and syringes. The 5% risperidone formulation in ethyl lactate was yellow compared to its colorless control sample and the 5% risperidone formulation in N-methyl-2-pyrrolidone was brown in comparison to the yellow color observed in the non-radiated controls.

Analysis of the risperidone in the formulations was performed by the High Performance Liquid Chromatography method described above. Syringes and glass vials obtained from the gamma radiation testing were analyzed with the control formulations. The results are reported in Table 53. The isocratic as well as the gradient High Performance Liquid Chromatography methods used to analyze these samples failed to detect any additional compounds. The cause for the color change observed in the syringes and glass vials which were gamma irradiated has not been determined.

TABLE 53

Analysis for Risperidone After Gamma Radiation of Formulations

| Sample | Risperidone Concentration (mg/g) | Gamma Radiation Glass Vials Risperidone (mg/g) | Gamma Radiation Syringes Risperidone (mg/g) |
|---|---|---|---|
| 5% Risperidone/Ethyl Lactate/40% (50/50)PLG | 48.0 | 48.0 | 53.4 |
| 20% Risperidone/NMP/ 25% PLA | 204.1 | 188.3 | 209.7 |
| 10% Risperidone/NMP/ 25% (50/50)PLG | 192.3 | 79.8 | 90.8 |
| 10% Risperidone/NMP/ 30% PLG | 107.5 | 84.4 | 103.2 |
| 5% Risperidone/EL/ 20% PLG | 49.8 | 47.8 | 47.5 |
| 10% Risperidone/NMP/ 25% PLC | 114.6 | 96.3 | 88 |
| 5% Risperidone/EL/ 20% PLG | 52.5 | 57.4 | 55.4 |
| 5% Risperidone/EL/ 27% PLC | 53.1 | 49.3 | 51.8 |

A second series of irradiation experiments were also conducted using different levels of irradiation from 5 KGy to 31 KGy to determine the effect of dose level upon stability. In these experiments, the 50/50 poly(lactide-co-glycolide) polymers with IV=0.35 dL/g and IV=0.49 dL/g were dissolved in N-methyl-2-pyrrolidone at 30% concentration. These were loaded into gamma-irradiation polypropylene syringes and capped. Risperidone powder was also loaded into gamma-resistant polypropylene syringes and cap. The materials were exposed to irradiation at four different levels: 5.8 KGy, 18.3 KGy, 27.9 KGy, and 31 KGy. General observations were that the polymer solution in N-methyl-2-pyrrolidone gradually changed from clear to slightly yellow as the level of irradiation increased. On addition, risperidone which was initially white turned beige at the lowest level of irradiation and the color darkened as the level of irradiation increased.

CONCLUSIONS

The results showed that risperidone could be incorporated into the ATRIGEL® Drug Delivery System and released at controlled rates for sustained periods of time. The formulations in which risperidone was suspended in the liquid polymer delivery system appeared to give the lowest initial drug burst and the most sustained release over time. These formulations were the 50/50 poly(lactide-co-glycolide) in N-methyl-2-pyrrolidone and the low molecular weight polylactide in ethyl lactate. Of the two solvents evaluated, N-methyl-2-pyrrolidone gave the best release characteristics. In general, the use of low molecular weight polymers at relatively high polymer concentrations tended to reduce the initial burst and sustain drug delivery. However, none of the formulations tested in animals were able to reduce the initial plasma concentration of risperidone to safe levels and none were able to sustain a pharmacological effect past about two weeks.

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims.

What is claimed is:

1. An injectable, flowable composition comprising
   (a) about 15 wt % risperidone base in
   (b) about 45 wt % of an 80/20 poly(DL-lactide-co-glycolide) biodegradable thermoplastic polyester with a terminal carboxy group having an average molecular weight of about 10,000 Daltons to about 50,000 Daltons; and
   (c) about 55 wt % of N-methyl-2-pyrrolidone.

2. The composition of claim 1, wherein the flowable composition is subcutaneously injectable.

3. The composition of claim 1, wherein the flowable composition transforms into a solid implant in situ after contact with water, body fluid, or other aqueous medium.

4. The composition of claim 1, wherein the flowable composition produces maximum plasma concentration ($C_{max}$) levels of risperidone within about 6 hours after injection into a patient.

5. The composition of claim 1, wherein the flowable composition produces maximum plasma concentration ($C_{max}$) levels of risperidone within about 2 hours after injection into a patient.

6. The composition of claim 1, wherein the biodegradable thermoplastic polyester has an average molecular weight of about 15,000 Daltons to about 40,000 Daltons.

7. The composition of claim 1, wherein the biodegradable thermoplastic polyester has a polydispersity index of about 1.4 to about 2.0.

* * * * *